United States Patent
Kato et al.

(10) Patent No.: US 10,243,148 B2
(45) Date of Patent: Mar. 26, 2019

(54) AROMATIC AMINE COMPOUND, AND ORGANIC ELECTROLUMINESCENT ELEMENTS INCLUDING THE COMPOUND

(71) Applicant: IDEMITSU KOSAN CO., LTD., Chiyoda-ku (JP)

(72) Inventors: Tomoki Kato, Ichihara (JP); Masahiro Kawamura, Chiba (JP); Masakazu Funahashi, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

(21) Appl. No.: 15/502,572

(22) PCT Filed: Jun. 7, 2016

(86) PCT No.: PCT/JP2016/066975
§ 371 (c)(1),
(2) Date: Feb. 8, 2017

(87) PCT Pub. No.: WO2016/199784
PCT Pub. Date: Dec. 15, 2016

(65) Prior Publication Data
US 2017/0229649 A1   Aug. 10, 2017

(30) Foreign Application Priority Data
Jun. 8, 2015 (JP) ................. 2015-116176

(51) Int. Cl.
*H01L 51/00* (2006.01)
*H01L 51/50* (2006.01)
(Continued)

(52) U.S. Cl.
CPC .......... *H01L 51/006* (2013.01); *C07C 211/61* (2013.01); *C07D 209/86* (2013.01);
(Continued)

(58) Field of Classification Search
CPC ............... H01L 51/006; C07C 211/61
(Continued)

(56) References Cited

U.S. PATENT DOCUMENTS 7,288,617 B2 * 10/2007 Treacher ............ C07C 17/2632
   252/582
8,445,630 B2 * 5/2013 Schafer ................. C08G 61/12
   252/301.16
(Continued)

FOREIGN PATENT DOCUMENTS

JP   2010-132638 A   6/2010
JP   2013-544757 A   12/2013
(Continued)

OTHER PUBLICATIONS

International Search Report dated Aug. 23, 2016 in PCT/JP2016/066975 filed Jun. 7, 2016.
Office Action dated Sep. 18, 2018 in Japanese Patent Application No. 2015-116176 (with English translation), 9 pages.

*Primary Examiner* — Caleb E Henry
(74) *Attorney, Agent, or Firm* — Oblon, McClelland, Maier & Neustadt, L.L.P.

(57) ABSTRACT

A compound represented by formula (1):

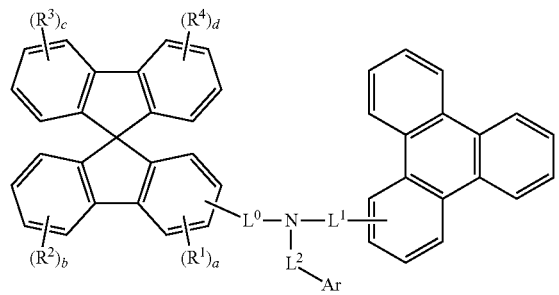

(1)

wherein $R^1$ to $R^4$, a to d, $L^0$ to $L^2$, and Ar are as defined in the description, is a material providing an organic electroluminescence device which can be operated at a low driving voltage and has a long lifetime.

23 Claims, 1 Drawing Sheet

(51) Int. Cl.
  *C07C 211/61* (2006.01)
  *C07D 209/86* (2006.01)
  *C07D 307/91* (2006.01)
  *C07D 333/18* (2006.01)
  *C07D 333/76* (2006.01)

(52) U.S. Cl.
  CPC ......... *C07D 307/91* (2013.01); *C07D 333/18* (2013.01); *C07D 333/76* (2013.01); *H01L 51/0061* (2013.01); *H01L 51/0054* (2013.01); *H01L 51/0056* (2013.01); *H01L 51/0058* (2013.01); *H01L 51/0068* (2013.01); *H01L 51/0072* (2013.01); *H01L 51/0073* (2013.01); *H01L 51/0074* (2013.01); *H01L 51/5012* (2013.01); *H01L 51/5056* (2013.01); *H01L 51/5088* (2013.01)

(58) Field of Classification Search
  USPC .......................................................... 257/40
  See application file for complete search history.

(56) References Cited

U.S. PATENT DOCUMENTS 8,507,901 B2 * 8/2013 Pan ..................... G03G 7/0026
  257/40
8,581,262 B2 * 11/2013 Pan ....................... B82Y 10/00
  257/40
2014/0138632 A1  5/2014 Kim et al.
2015/0155491 A1  6/2015 Mujica-Fernaud et al.

FOREIGN PATENT DOCUMENTS

| | | |
|---|---|---|
| JP | 2014-509306 A | 4/2014 |
| JP | 10-2014-0109058 A | 9/2014 |
| KR | 10-2012-0100031 A | 9/2012 |
| KR | 10-2013-0078749 A | 7/2013 |
| WO | 2015/012618 A1 | 1/2015 |
| WO | WO 2016/013867 A1 | 1/2016 |

* cited by examiner

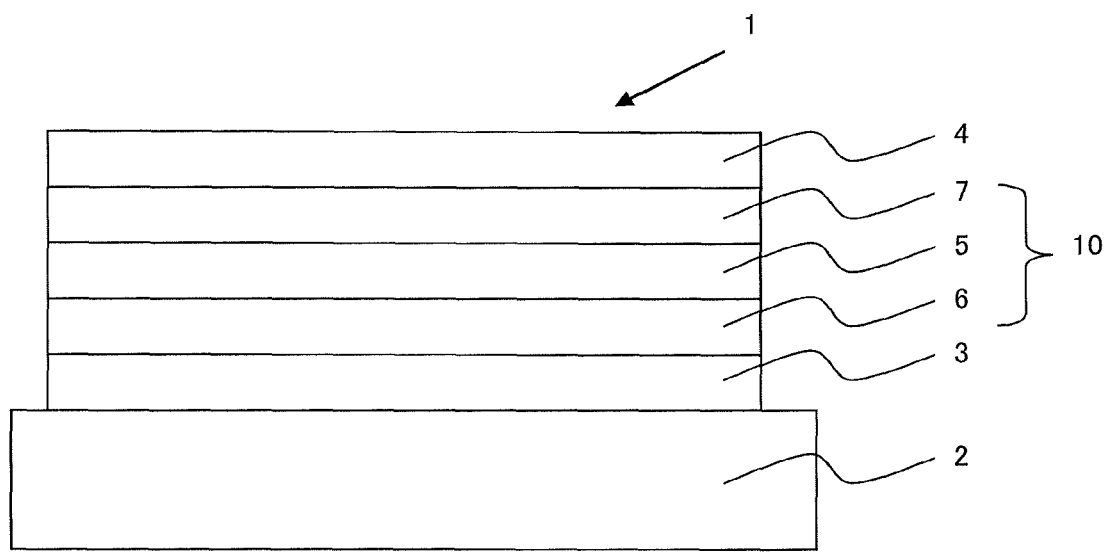

AROMATIC AMINE COMPOUND, AND ORGANIC ELECTROLUMINESCENT ELEMENTS INCLUDING THE COMPOUND

TECHNICAL FIELD

The present invention relates to compounds, materials for organic electroluminescence devices, organic electroluminescence devices, and electronic devices.

BACKGROUND ART

An organic electroluminescence device (also referred to as "organic EL device") generally comprises an anode, a cathode, and an organic thin film layer comprising one or more layers between the anode and the cathode. When a voltage is applied between the electrodes, electrons are injected from the cathode and holes are injected from the anode into a light emitting region. The injected electrons recombine with the injected holes in the light emitting region to form excited states. When the excited state returns to the ground state, the energy is released as light. Therefore, it is important for increasing the efficiency of an organic EL device to develop a compound which transports electrons or holes into a light emitting region efficiently and facilitates the recombination of electrons and holes.

Patent Literature 1 describes an amine compound wherein 9,9'-spirobifluorene, 9,9-dimethylfluorene, and phenanthrene are directly bonded to the same nitrogen atom. Patent Literature 1 describes that this amine compound is suitable as a hole transporting material, but, the performance of an organic EL device comprising this amine compound is not described.

Patent Literature 2 describes an amine compound wherein 9,9'-spirobifluorene, triphenylene having three phenyl substituents, and an arene selected from benzene, naphthalene, 9,9-dimethylfluorene, phenanthrene, etc. are directly bonded to the same nitrogen atom. Patent Literature 2 describes that this amine compound can be used in a light emitting layer or a hole transporting layer, but, the performance of an organic EL device comprising this amine compound is not described.

Patent Literature 3 describes an amine compound wherein a substituted or unsubstituted triphenylene, 9,9-dimethylfluorene, and biphenyl or terphenyl are bonded to the same nitrogen atom. An organic EL device actually produced in the working examples includes the amine compound in a hole transporting layer.

Patent Literature 4 describes an amine compound wherein biphenyl, 9,9-diphenylfluorene, and a triphenylene having a phenyl substituent are bonded to the same nitrogen atom. Patent Literature 4 describes that this amine compound is used in a hole transporting layer, etc., but, the performance of an organic EL device comprising this amine compound is not described.

The amine compounds described in Patent Literatures 1 to 4 are still required to be improved in their performances as organic EL devices, particularly in the driving voltage and the lifetime.

CITATION LIST

Patent Literature

Patent Literature 1: JP 2013-544757A
Patent Literature 2: JP 2010-132638A
Patent Literature 3: JP 2014-509306A
Patent Literature 4: KR 20130078749A

SUMMARY OF INVENTION

Technical Problem

The present invention has been made to solve the above problems and an object thereof is to provide an organic EL device which can be operated at a low driving voltage and has a long lifetime and provide a material of organic EL devices which can realize such an organic El device.

Solution to Problem

As a result of intensive research, the inventors have found that a compound represented by formula (1) provides an organic EL device which can be operated at a low driving voltage and has a long lifetime.

In an aspect, the present invention provides a compound represented by formula (1):

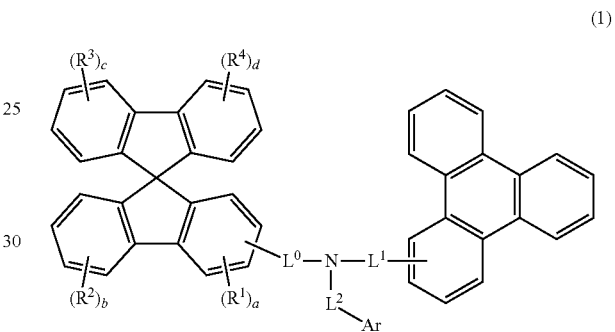

(1)

wherein:
each of $R^1$ to $R^4$ is independently a substituted or unsubstituted alkyl group having 1 to 20 carbon atoms, a substituted or unsubstituted aryl group having 6 to 10 ring carbon atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 10 ring carbon atoms, or a cyano group;
a is an integer of 0 to 3, and each of b, c, and d is independently an integer of 0 to 4, wherein each of $(R^1)_0$, $(R^2)_0$, $(R^3)_0$, and $(R^4)_0$ means that $R^1$, $R^2$, $R^3$, or $R^4$ does not exist, and when a, b, c, or d is an integer of 2 or more, two or three $R^1$'s, two to four $R^2$'s, two to four $R^3$'s, and two to four $R^4$'s may be respectively the same or different, and each of adjacent two R's, adjacent two $R^2$'s, adjacent two $R^3$'s, and adjacent two $R^4$'s may be bonded to each other to form a ring structure;
each of $L^0$ to $L^2$ is independently a single bond, a substituted or unsubstituted arylene group having 6 to 50 ring carbon atoms or a substituted or unsubstituted heteroarylene group having 5 to 50 ring atoms;
Ar is a substituted or unsubstituted aryl group having 6 to 50 ring carbon atoms or a substituted or unsubstituted heteroaryl group having 5 to 50 ring atoms; and
an optional substituent referred to by "substituted or unsubstituted" is at least one group selected from the group consisting of an alkyl group having 1 to 20 carbon atoms, a cycloalkyl group having 3 to 50 ring carbon atoms, an aryl group having 6 to 10 ring carbon atoms, an aralkyl group having 7 to 30 carbon atoms which comprises an aryl group having 6 to 10 ring carbon atoms, an alkoxy group having 1 to 20 carbon atoms, an aryloxy group having 6 to 10 ring carbon atoms, a mono-, di-, or tri-substituted silyl group, wherein the substituent is selected from an alkyl group having 1 to 20 carbon atoms and an aryl group having 6 to 10 ring carbon atoms, a haloalkyl group having 1 to 20 carbon atoms, a haloalkoxy group having 1 to 20 carbon atoms, a halogen atom, a cyano group, and a nitro group.

In another aspect, the present invention provides a material for organic electroluminescence devices which comprises the compound (1).

In still another aspect, the present invention provides an organic electroluminescence device which comprises a cathode, an anode, and an organic thin film layer disposed between the cathode and the anode, wherein the organic thin film layer comprises one or more layers, the organic thin film layer comprises a light emitting layer, and at least one layer of the organic thin film layer comprises the compound (1).

In still another aspect, the present invention provides an electronic device comprising the organic electroluminescence device.

Advantageous Effects of Invention

The organic EL device comprising the compound (1) can be operated at a low driving voltage and has a long lifetime.

BRIEF DESCRIPTION OF DRAWINGS

FIG. 1 is a schematic view showing the structure of the organic EL device in an aspect of the invention.

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The term of "unsubstituted group ZZ" referred to by "substituted or unsubstituted group ZZ" used herein means that no hydrogen atom in the group ZZ is substituted by a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means the number of the carbon atoms included in the atoms which are members forming the ring itself of a compound in which a series of atoms is bonded to form a ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The compound in an aspect of the invention is represented by formula (1) (hereinafter also referred to as "compound (1)"):

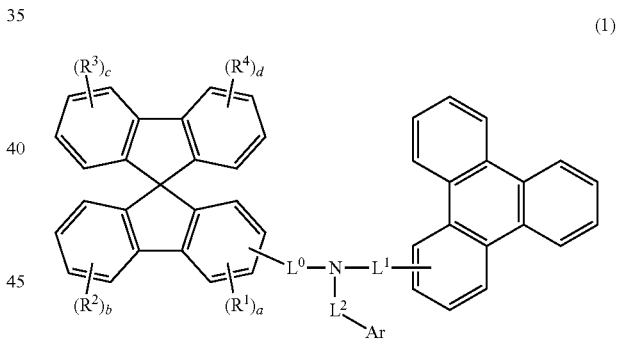

(1)

The compound (1) is preferably represented by any of formulae (1-1) to (1-4):

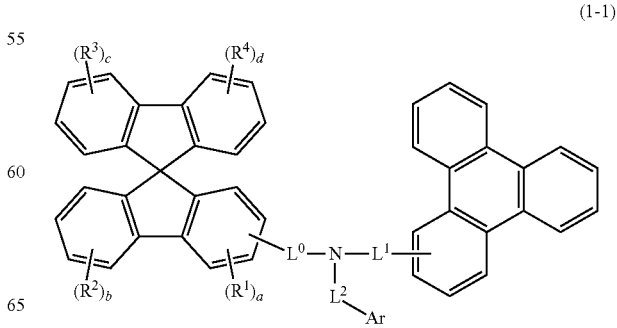

(1-1)

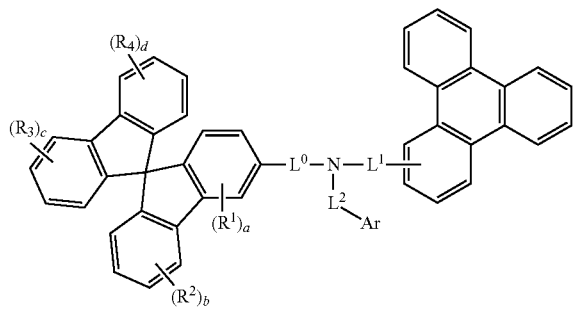
(1-2)
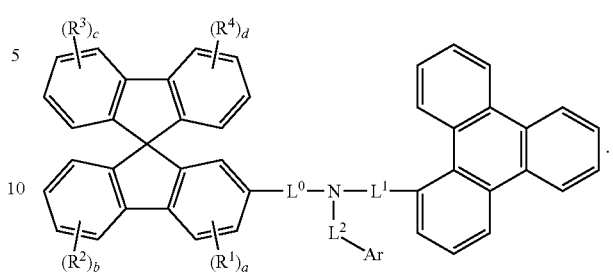
(1-1b)
Formula (1-2) is preferably represented by formula (1-2a) or (1-2b):
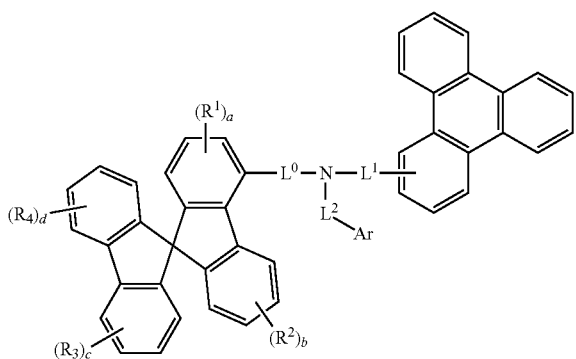
(1-3)
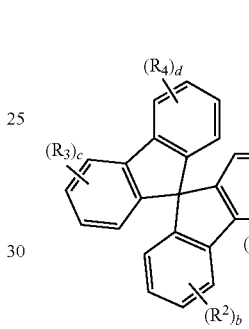
(1-2a)
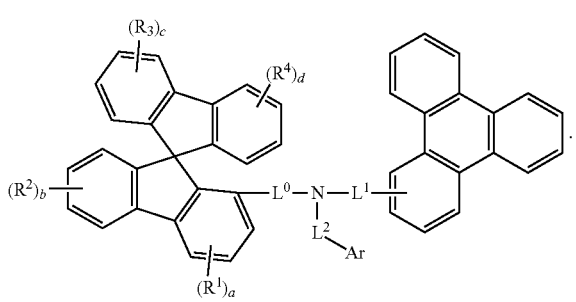
(1-4)
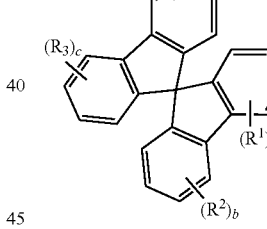
(1-2b)
Formula (1-1) is preferably represented by formula (1-1a) or (1-1b):
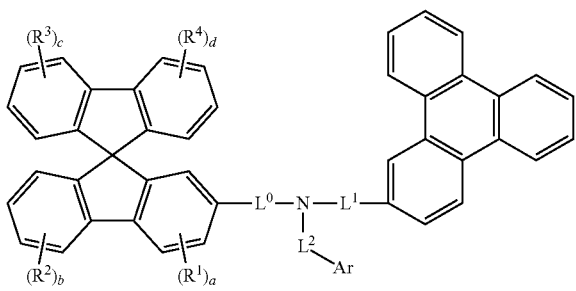
(1-1a)
Formula (1-3) is preferably represented by formula (1-3a) or (1-3b):
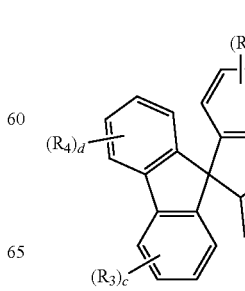
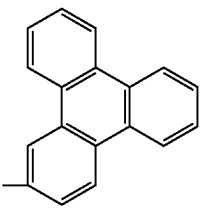
(1-3a)

-continued

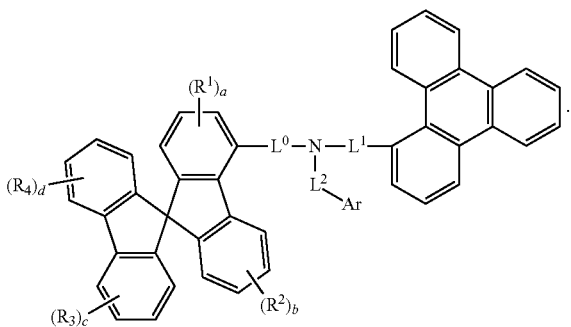
(1-3b)

Formula (1-4) is preferably represented by formula (1-4a) or (1-4b):

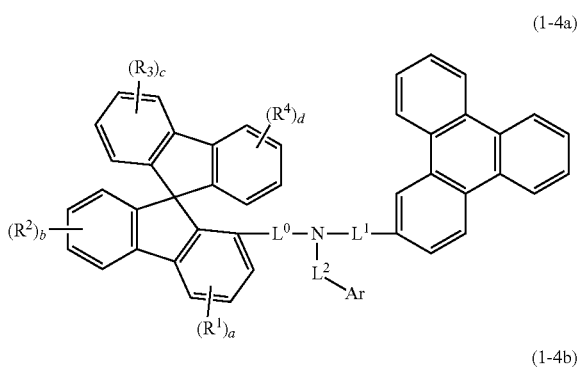
(1-4a)

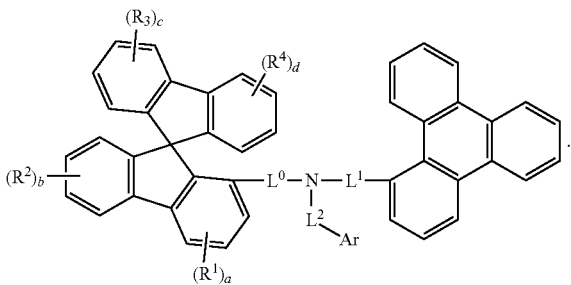
(1-4b)

Each of $R^1$ to $R^4$ is independently a substituted or unsubstituted alkyl group having 1 to 20, preferably 1 to 5, and more preferably 1 to 4 carbon atoms; a substituted or unsubstituted aryl group having 6 to 10, preferably 6 ring carbon atoms; a halogen atom; a substituted or unsubstituted fluoroalkyl group having 1 to 20, preferably 1 to 5, and more preferably 1 to 4 carbon atoms; a substituted or unsubstituted alkoxy group having 1 to 20, preferably 1 to 5, and more preferably 1 to 4 carbon atoms; a substituted or unsubstituted fluoroalkoxy group having 1 to 20, preferably 1 to 5, and more preferably 1 to 4 carbon atoms; a substituted or unsubstituted aryloxy group having 6 to 10, preferably 6 ring carbon atoms; or a cyano group.

Each of $R^1$ to $R^4$ is preferably selected from a substituted or unsubstituted alkyl group having 1 to 20 carbon atoms, a substituted or unsubstituted aryl group having 6 to 10 ring carbon atoms, and a halogen atom.

In the substituted or unsubstituted alkyl group having 1 to 20 carbon atoms, examples of the alkyl group include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups), with a methyl group, an ethyl group, a n-propyl group, an isopropyl group, a n-butyl group, an isobutyl group, a s-butyl group, a t-butyl group, and a pentyl group (inclusive of isomeric groups) being preferred, a methyl group, an ethyl group, a n-propyl group, an isopropyl group, a n-butyl group, an isobutyl group, a s-butyl group, and a t-butyl group being more preferred, and a methyl group and a t-butyl group being still more preferred.

In the substituted or unsubstituted aryl group having 6 to 10 ring carbon atoms, examples of the ary group include a phenyl group and a naphthyl group, with a phenyl group being preferred.

The a halogen atom is a fluorine atom, a chlorine atom, a bromine atom, or an iodine atom, with a fluorine atom being preferred.

In the substituted or unsubstituted fluoroalkyl group having 1 to 20 carbon atoms, examples of the fluoroalkyl group include those obtained by replacing at least one, preferably 1 to 7 hydrogen atoms, or all the hydrogen atoms of the alkyl group having 1 to 20 carbon atoms mentioned above with a fluorine atom or fluorine atoms. Preferred are a heptafluoropropyl group (inclusive of isomeric groups), a pentafluoroethyl group, a 2,2,2-trifluoroethyl group, and a trifluoromethyl group, more preferred are a pentafluoroethyl group, a 2,2,2-trifluoroethyl group, and a trifluoromethyl group, and still more preferred is a trifluoromethyl group.

The substituted or unsubstituted alkoxy group having 1 to 20 carbon atoms is represented by $—OR^{11}$, wherein $R^{11}$ is the substituted or unsubstituted alkyl group having 1 to 20 carbon atoms mentioned above. The alkoxy group is preferably a t-butoxy group, a propoxy group (inclusive of isomeric groups), an ethoxy group, or a methoxy group, more preferably an ethoxy group or a methoxy group, and still more preferably a methoxy group.

The substituted or unsubstituted fluoroalkoxy group having 1 to 20 carbon atoms is represented by $—OR^{12}$, wherein $R^{12}$ is the substituted or unsubstituted fluoroalkyl group having 1 to 20 carbon atoms mentioned above. The fluoroalkoxy group is preferably a heptafluoropropoxy group (inclusive of isomeric groups), a pentafluoroethoxy group, a 2,2,2-trifluoroethoxy group, or a trifluoromethoxy group, more preferably a pentafluoroethoxy group, a 2,2,2-trifluoroethoxy group, or a trifluoromethoxy group, and still more preferably a trifluoromethoxy group.

The substituted or unsubstituted aryloxy group having 6 to 10 ring carbon atoms is represented by $—OR^{13}$, wherein $R^{13}$ is the substituted or unsubstituted aryl group having 6 to 10 ring carbon atoms mentioned above. The aryl group is preferably a phenyl group or a naphthyl group and more preferably a phenyl group.

The subscript a is an integer of 0 to 3, preferably an integer of 0 to 2, and more preferably 0 or 1. Each of b, c, and d is independently an integer of 0 to 4, preferably an integer of 0 to 2, and still more preferably 0 or 1. In an embodiment of the invention, a to d are preferably all 0. In another embodiment of the invention, one to three selected from b, c, and d is/are 1.

When each of a to d is 0, each of $(R^1)_0$, $(R^2)_0$, $(R^3)_0$, and $(R^4)_0$ means that $R^1$, $R^2$, $R^3$, or $R^4$ does not exist, i.e., the benzene ring has no substituent $R^1$, $R^2$, $R^3$ or $R^4$.

When each of a, b, c and d is an integer of 2 or more, two or three $R^1$'s, two to four $R^2$'s, two to four $R^3$'s, and two to four $R^4$'s may be the same or different, respectively. Each pair of adjacent two $R^1$'s, adjacent two $R^2$'s, adjacent two $R^3$'s, and adjacent two $R^4$'s may be bonded to each other to form a ring structure or not bonded to each other thereby failing to form a ring structure. The ring structure is preferably an aromatic hydrocarbon ring or an aromatic heterocyclic ring comprising a ring hetero atom, such as a nitrogen atom, an oxygen atom, and a sulfur atom.

Ar is a substituted or unsubstituted aryl group having 6 to 50, preferable 6 to 24, and more preferably 6 to 12 ring carbon atoms or a substituted or unsubstituted heteroaryl group having 5 to 50, preferable 5 to 24, and more preferably 5 to 18 ring atoms.

Examples of the aryl group in the substituted or unsubstituted aryl group having 6 to 50 ring carbon atoms for Ar include a phenyl group, a biphenylyl group, a terphenylyl group, a biphenylenyl group, a naphthyl group, an acenaphthylenyl group, an anthryl group, a benzanthryl group, an aceanthryl group, a benzophenanthryl group, a triphenylenyl group, a phenalenyl group, a fluorenyl group, a pentacenyl group, a picenyl group, a pentaphenyl group, a pyrenyl group, a chrysenyl group, a benzochrysenyl group, a s-indanyl group, an as-indanyl group, a fluoranthenyl group, and a perylenyl group, with a phenyl group, a biphenylyl group, a terphenylyl group, a naphthyl group, and a fluorenyl group being preferred.

The heteroaryl group of the substituted or unsubstituted heteroaryl group having 5 to 50 ring atoms for Ar comprises 1 to 5, preferably 1 to 3, and more preferably 1 to 2 ring hetero atoms, such as a nitrogen atom, a sulfur atom, and an oxygen atom. Examples of the heteroaryl group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group (a benzothienyl group, the same applies below), an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a naphthobenzofuranyl group, a dibenzothiophenyl group (a dibenzothienyl group, the same applies below), a naphthobenzothiophenyl group (naphthobenzothienyl group, the same applies below), a carbazolyl group (N-carbazolyl group and C-carbazolyl group, the same applies below), a benzocarbazolyl group (benzo-N-carbazolyl group and benzo-C-carbazolyl group, the same applies below), a phenanthridinyl group, an acridinyl group, a phenanthrolinyl group, a phenazinyl group, a phenothiazinyl group, a phenoxazinyl group, and a xanthenyl group. Preferred are a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, a naphthobenzofuranyl group, a dibenzothiophenyl group, a naphthobenzothiophenyl group, a carbazolyl group, and a benzocarbazolyl group. More preferred are a thienyl group, a benzothiophenyl group, a dibenzofuranyl group, a naphthobenzofuranyl group, a dibenzothiophenyl group, a naphthobenzothiophenyl group, a carbazolyl group, and a benzocarbazolyl group.

In a preferred embodiment of the invention, Ar is represented by any of formulae (a) to (n):

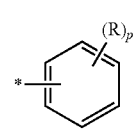

(a)

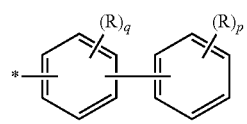

(b)

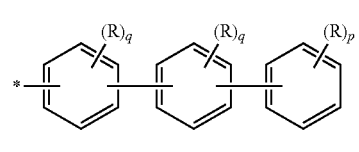

(c)

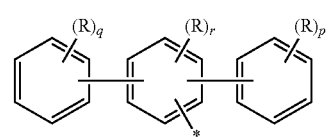

(d)

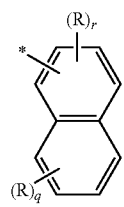

(e)

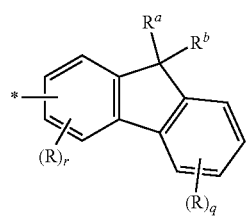

(f)

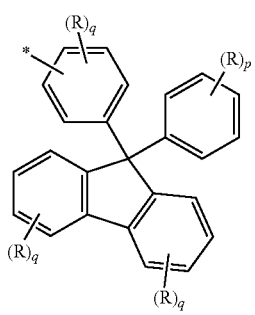

(g)

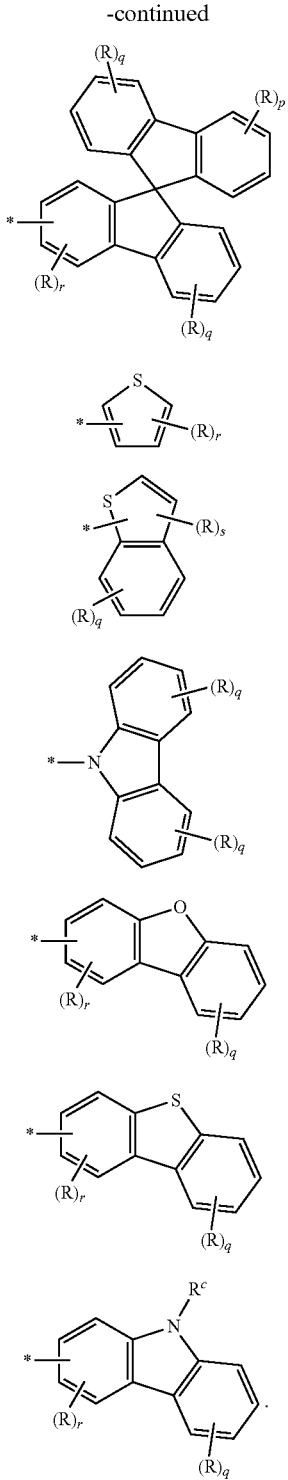

In formulae (a) to (n), * is a bond to L² of formula (1).

In formulae (a) to (n), each R is independently a group selected from the group consisting of a substituted or unsubstituted alkyl group having 1 to 20, preferably 1 to 5, and more preferably 1 to 4 carbon atoms; a substituted or unsubstituted cycloalkyl group having 3 to 50, preferably 3 to 6, and more preferably 5 or 6 ring carbon atoms; a substituted or unsubstituted aryl group having 6 to 10, preferably 6 ring carbon atoms; a substituted or unsubstituted aralkyl group having 7 to 30 carbon atoms which comprises a substituted or unsubstituted aryl group having 6 to 10, preferably 6 ring carbon atoms; a substituted or unsubstituted alkoxy group having 1 to 20, preferably 1 to 5, and more preferably 1 to 4 carbon atoms; a substituted or unsubstituted aryloxy group having 6 to 10, preferably 6 ring carbon atoms; a mono-, di-, or tri-substituted silyl group, wherein the substituent is selected from a substituted or unsubstituted alkyl group having 1 to 20, preferably 1 to 5, and more preferably 1 to 4 carbon atoms and a substituted or unsubstituted aryl group having 6 to 10, preferably 6 ring carbon atoms; a substituted or unsubstituted haloalkyl group having 1 to 20, preferably 1 to 5, and more preferably 1 to 4 carbon atoms; a substituted or unsubstituted haloalkoxy group having 1 to 20, preferably 1 to 5, and more preferably 1 to 4 carbon atoms; a halogen atom; a cyano group; and a nitro group.

In an embodiment of the invention, adjacent two Rs of formulae (a) to (n), preferably formulae (k) to (n) may be bonded to each other to form a benzene ring together with the ring carbon atoms to which adjacent two Rs are bonded.

In another embodiment of the invention, adjacent two Rs are not bonded to each other.

Each R is independently and preferably selected from a substituted or unsubstituted alkyl group having 1 to 20 carbon atoms, a substituted or unsubstituted aryl group having 6 to 10 ring carbon atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 10 ring carbon atoms, and a cyano group.

The details of the groups for R selected from the substituted or unsubstituted alkyl group having 1 to 20 carbon atoms, the substituted or unsubstituted aryl group having 6 to 10 ring carbon atoms, the halogen atom, the substituted or unsubstituted fluoroalkyl group having 1 to 20 carbon atoms, the substituted or unsubstituted alkoxy group having 1 to 20 carbon atoms, the substituted or unsubstituted fluoroalkoxy group having 1 to 20 carbon atoms, and the substituted or unsubstituted aryloxy group having 6 to 10 ring carbon atoms are as described above with respect to $R^1$ to $R^4$.

Examples of the cycloalkyl group of the substituted or unsubstituted cycloalkyl group having 3 to 50 ring carbon atoms for R include a cyclopropyl group, a cyclobutyl group, a cyclopentyl group, a cyclohexyl group, a cycloheptyl group, a cyclooctyl group, and an adamantyl group, with a cyclopentyl group and a cyclohexyl group being preferred.

The substituted or unsubstituted aralkyl group having 7 to 30 carbon atoms which comprises a substituted or unsubstituted aryl group having 6 to 10 ring carbon atoms for R is a group obtained by replacing one hydrogen atom of the substituted or unsubstituted alkyl group having 1 to 20 carbon atoms mentioned above with respect to $R^1$ to $R^4$ with the substituted or unsubstituted aryl group having 6 to 10 ring carbon atoms mentioned above with respect to $R^1$ to $R^4$.

The mono-, di-, or tri-substituted silyl group for R is a silyl group having a substituent selected from the substituted or unsubstituted alkyl group having 1 to 20 carbon atoms and the substituted or unsubstituted aryl group having 6 to 10 ring carbon atoms each mentioned above with respect to $R^1$ to $R^4$. Examples thereof include a trimethylsilyl group, a triethylsilyl group, a t-butyldimethylsilyl group, a propyldimethylsilyl group, an isopropyldimethylsilyl group, a triphenylsilyl group, phenyldimethylsilyl group, a t-butyldiphenylsilyl group, and a tritolylsilyl group.

The haloalkyl group of the substituted or unsubstituted haloalkyl group having 1 to 20 carbon atoms for R is a group obtained by replacing at least one, preferably 1 to 7 hydrogen atoms, or all the hydrogen atoms of the alkyl group having 1 to 20 carbon atoms mentioned above with respect to $R^1$ to $R^4$ with a halogen atom selected from a fluorine atom, a chlorine atom, a bromine atom, and an iodine atom, preferably a fluorine atom. The haloalkyl group is preferably a heptafluoropropyl group (inclusive of isomeric groups), a pentafluoroethyl group, a 2,2,2-trifluoroethyl group, or a trifluoromethyl group, more preferably a pentafluoroethyl group, a 2,2,2-trifluoroethyl group, or a trifluoromethyl group, and still more preferably a trifluoromethyl group.

The substituted or unsubstituted haloalkoxy group having 1 to 20 carbon atoms for R is represented by —$OR^{14}$, wherein $R^{14}$ is the substituted or unsubstituted haloalkyl group having 1 to 20 carbon atoms, preferably the fluoroalkyl group having 1 to 20 carbon atoms, each mentioned above. The haloalkoxy group is preferably a heptafluoropropoxy group (inclusive of isomeric groups), a pentafluoroethoxy group, a 2,2,2-trifluoroethoxy group, or a trifluoromethoxy group, more preferably a pentafluoroethoxy group, a 2,2,2-trifluoroethoxy group, or a trifluoromethoxy group, and still more preferably a trifluoromethoxy group.

In formulae (a) to (n), each p is independently an integer of 0 to 5, preferably an integer of 0 to 3, more preferably 0 or 1, and still more preferably 0. Each q is independently an integer of 0 to 4, preferably an integer of 0 to 2, more preferably 0 or 1, and still more preferably 0. Each r is independently an integer of 0 to 3, preferably 0 to 2, more preferably 0 or 1, and still more preferably 0. Subscript s is 0 or 1, and preferably 0.

When p, q, or r is an integer of 2 or more, two to five Rs, two to four Rs, and two to three Rs may be the same or different, and adjacent two Rs may be bonded to each other to form a ring structure. The ring to be formed by adjacent two Rs together with two ring carbon atoms to which two Rs are bonded is preferably an aromatic hydrocarbon ring and an aromatic heterocyclic ring comprising an ring hetero atom, such as a nitrogen atom, an oxygen atom, and a sulfur atom.

When any one of p to s is 0, $(R)_0$ means that R does not exist, i.e., not substituted by R. In an embodiment of the invention, the group represented by any of formulae (a) to (n) preferably has one or two Rs and more preferably has one R. In another embodiment of the invention, the group represented by any of formulae (a) to (n) does not have R.

In formula (f), each of $R^a$ and $R^b$ is independently a substituted or unsubstituted alkyl group having 1 to 20, preferably 1 to 5, and more preferably 1 to 4 carbon atoms; a substituted or unsubstituted aryl group having 6 to 10, preferably 6 ring carbon atoms; a halogen atom; a substituted or unsubstituted fluoroalkyl group having 1 to 20, preferably 1 to 5, and more preferably 1 to 4 carbon atoms; a substituted or unsubstituted alkoxy group having 1 to 20, preferably 1 to 5, and more preferably 1 to 4 carbon atoms; a substituted or unsubstituted fluoroalkoxy group having 1 to 20, preferably 1 to 5, and more preferably 1 to 4 carbon atoms; a substituted or unsubstituted aryloxy group having 6 to 10, preferably 6 ring carbon atoms; or a cyano group. Two selected from R, $R^a$, and $R^b$ may be bonded to each other to form a ring structure.

Each of $R^a$ and $R^b$ is independently and preferably selected from a substituted or unsubstituted alkyl group having 1 to 20 carbon atoms and a substituted or unsubstituted aryl group having 6 to 10 ring carbon atoms.

The details of the groups for $R^a$ and $R^b$ are the same as the groups mentioned above with respect to $R^1$ to $R^4$.

In formula (n), $R^c$ is a hydrogen atom, a substituted or unsubstituted alkyl group having 1 to 20, preferably 1 to 5, and more preferably 1 to 4 carbon atoms, or a substituted or unsubstituted aryl group having 6 to 10, preferably 6 ring carbon atoms.

$R^c$ is preferably a substituted or unsubstituted alkyl group having 1 to 20 carbon atoms or a substituted or unsubstituted aryl group having 6 to 10 ring carbon atoms, and more preferably a substituted or unsubstituted aryl group having 6 to 10 ring carbon atoms.

The details of the groups for $R^c$ are the same as the groups mentioned above with respect to $R^1$ to $R^4$.

Formula (b) is preferably a 2-, 3-, or 4-biphenylyl group which may have a substituent R.

Formula (c) is preferably a 2-, 3-, or 4-p-terphenylyl group, a 2-, 3-, or 4-m-terphenylyl group, or 2-, 3-, or 4-o-terphenylyl group, each optionally having a substituent R.

Formula (d) is preferably a 2'-p-terphenylyl group, a 2'-, 4'-, or 5'-m-terphenylyl group, or a 4'-o-terphenylyl group, each optionally having a substituent R.

Formulae (b), (c), and (d) are preferably represented by any of formulae (b-1), (b-2), (c-1), (c-2), and (d-1):

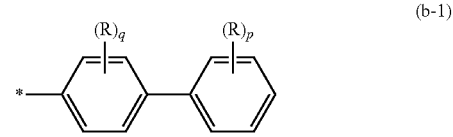

(b-1)

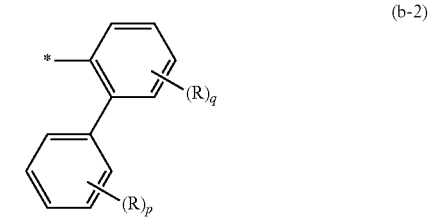

(b-2)

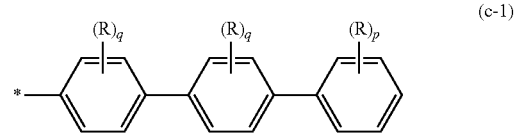

(c-1)

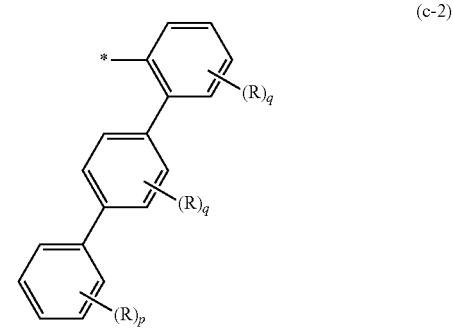

(c-2)

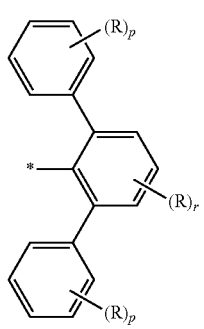

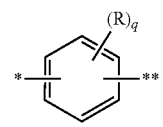

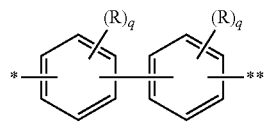

wherein R, p, q, r, and * are as defined above.

Formula (e) is preferably a 1-naphthyl group or a 2-naphthyl group, each optionally having a substituent R.

In formula (f), each $R^a$ and $R^b$ is preferably a methyl group or a phenyl group, or one of $R^a$ and $R^b$ is preferably a methyl group and the other is preferably a phenyl group. The group represented by formula (f) is bonded to $L^2$ of formula (1) via any of the positions 1 to 4, preferably the position 2 or 4 of the fluorene ring.

Formula (g) is preferably a 4-(9-phenylfluorene-9-yl)phenyl group which may have a substituent R.

The group represented by formula (h) is bonded to $L^2$ of formula (1) via any of the positions 1 to 4, preferably the position 2 or 4 of the fluorene ring.

The group represented by formula (i) is bonded to $L^2$ of formula (1) preferably via the position 2 of the thiophene ring.

The group represented by formula (j) is bonded to $L^2$ of formula (1) preferably via the position 2 of the benzothiophene ring.

The group represented by formula (l) is bonded to $L^2$ of formula (1) via any of the positions 1 to 4, preferably the position 2 or 4 of the dibenzofuran ring.

The group represented by formula (m) is bonded to $L^2$ of formula (1) via any of the positions 1 to 4, preferably the position 2 or 4 of the dibenzothiophene ring.

In formula (n), $R^c$ is preferably a phenyl group, and the group represented by formula (n) is bonded to $L^2$ of formula (1) via any of the positions 1 to 4, preferably the position 3 of the carbazole ring.

Each of $L^0$ to $L^2$ is independently a single bond, a substituted or unsubstituted arylene group having 6 to 50, preferable 6 to 24, and more preferably 6 to 12 ring carbon atoms or a substituted or unsubstituted heteroarylene group having 5 to 50, preferable 5 to 24, and more preferably 5 to 18 ring atoms.

The arylene group of the substituted or unsubstituted arylene group having 6 to 50 ring carbon atoms is a group obtained by removing one hydrogen atom from the aryl group having 6 to 50 ring carbon atoms mentioned above with respect to Ar. The heteroarylene group of the substituted or unsubstituted heteroarylene group having 5 to 50 ring atoms is a group obtained by removing one hydrogen atom from the heteroaryl group having 5 to 50 ring atoms mentioned above with respect to Ar.

Each of $L^0$ to $L^2$ is independently and preferably a single bond or a substituted or unsubstituted arylene group having 6 to 50 ring carbon atoms. The substituted or unsubstituted arylene group having 6 to 50 ring carbon atoms is preferably represented by formula (ii) or (iii):

wherein:

R and q are as defined above with respect to formulae (a) to (n);

when $L^0$ is represented by formula (ii) or (iii), one of * and ** is a bond to the spirobifluorene structure, and the other is a bond to the nitrogen atom;

when $L^1$ is represented by formula (ii) or (iii), one of * and ** is a bond to the triphenylene, and the other is a bond to the nitrogen atom; and when $L^2$ is represented by formula (ii) or (iii), one of * and ** is a bond to Ar, and the other is a bond to the nitrogen atom.

Formulae (ii) and (iii) are preferably represented by the following formulae:

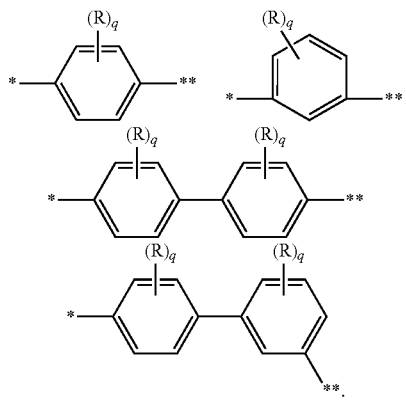

In an embodiment of the invention, preferred is the compound (1) wherein each of $L^0$ to $L^2$ is a single bond and Ar is an aryl group represented by any of formulae (a) to (h).

In another embodiment of the invention, preferred is the compound (1) wherein each of $L^0$ and $L^1$ is a single bond, $L^2$ is a substituted or unsubstituted arylene group having 6 to 50 ring carbon atoms or a substituted or unsubstituted heteroarylene group having 5 to 50 ring atoms, preferably a substituted or unsubstituted arylene group having 6 to 50 ring carbon atoms, and more preferably an arylene group represented by formula (ii) or (iii), and Ar is a heteroaryl group represented by any of formulae (i) to (n).

$L^0$ is bonded to preferably any of the positions 2 to 4, more preferably the position 2 or 4 of the 9,9'-spirobifluorene ring.

$L^1$ is preferably bonded to the position 2 of the triphenylene ring.

The optional substituent referred to by "substituted or unsubstituted" used herein is at least one selected from the group consisting of an alkyl group having 1 to 20, preferably 1 to 5, and more preferably 1 to 4 carbon atoms; a cycloalkyl group having 3 to 50, preferably 3 to 6, and more preferably 5 or 6 ring carbon atoms; an aryl group having 6 to 10 and preferably 6 ring carbon atoms; an aralkyl group which comprises an aryl group having 6 to 10 ring carbon atoms; an alkoxy group having 1 to 20 carbon atoms; an aryloxy group having 6 to 10 and preferably 6 ring carbon atoms; a mono-, di-, or tri-substituted silyl group, wherein the substituent is selected from an alkyl group having 1 to 20 carbon atoms and an aryl group having 6 to 10 ring carbon atoms; a haloalkyl group having 1 to 20 carbon atoms; a haloalkoxy group having 1 to 20 carbon atoms; a halogen atom; a cyano group; and a nitro group. The details of the above optional substituents are the same as those of the corresponding groups mentioned above with respect to R and others.

Examples of the compound (1) are shown below, although not limited thereto.

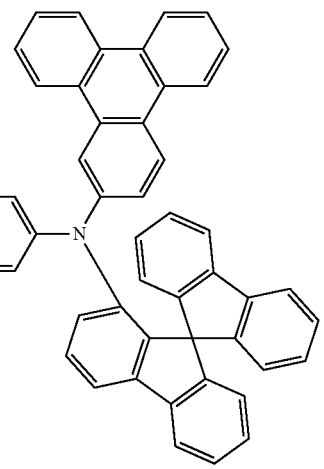

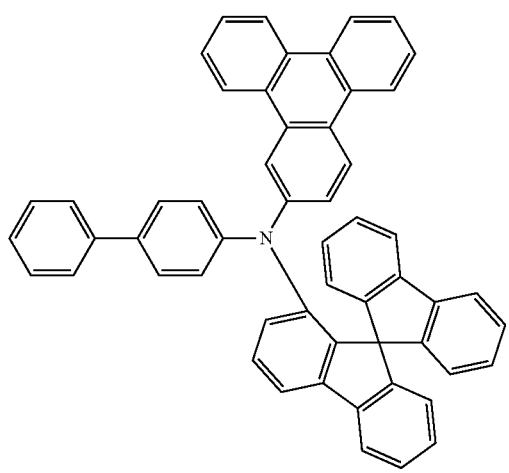

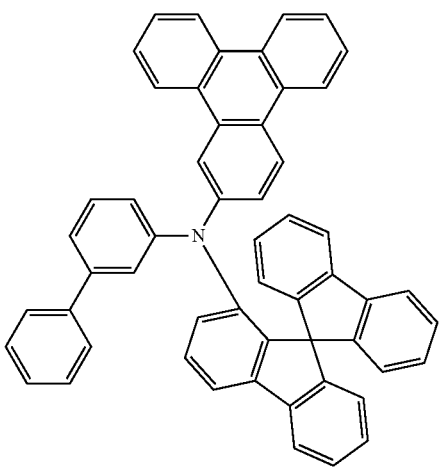

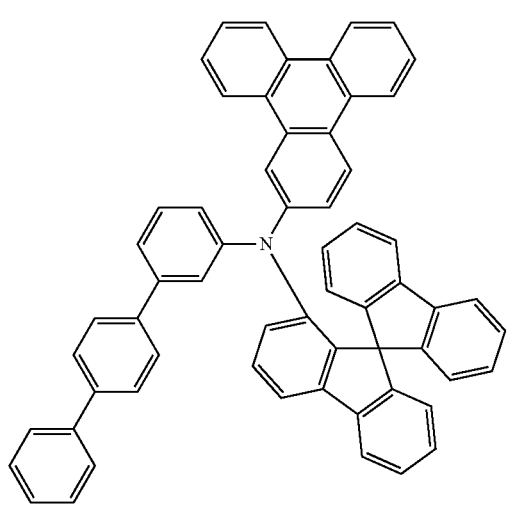

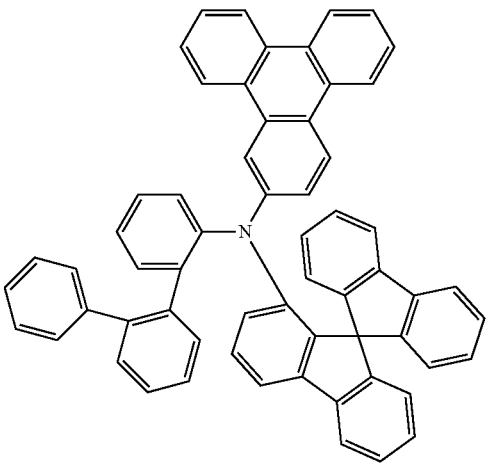

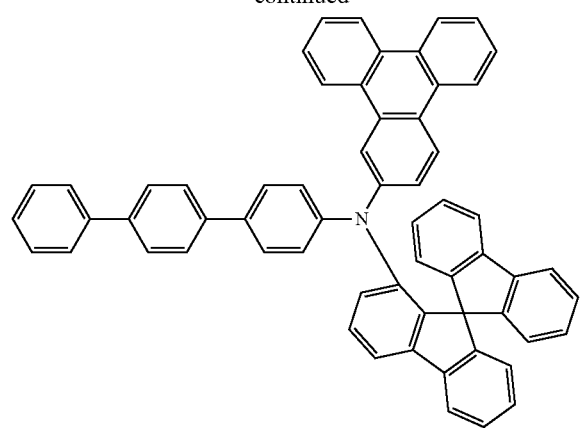
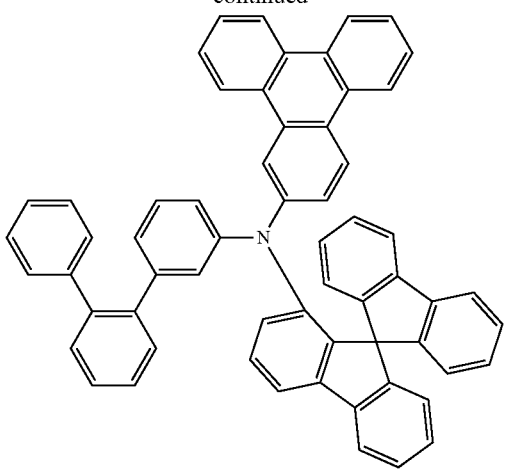
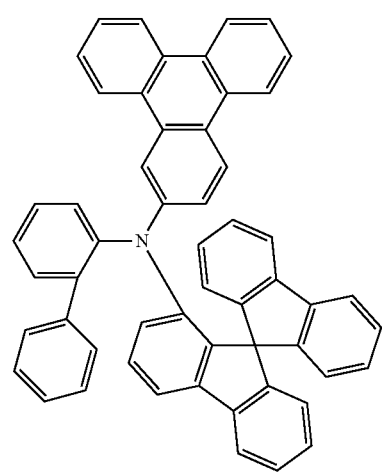
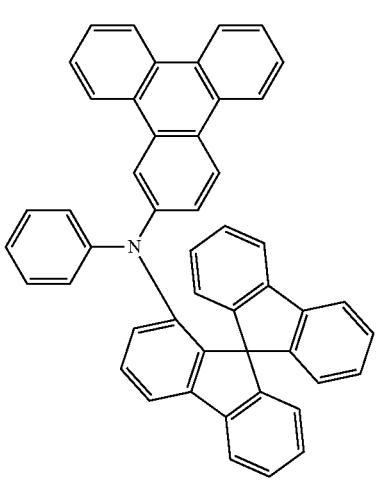
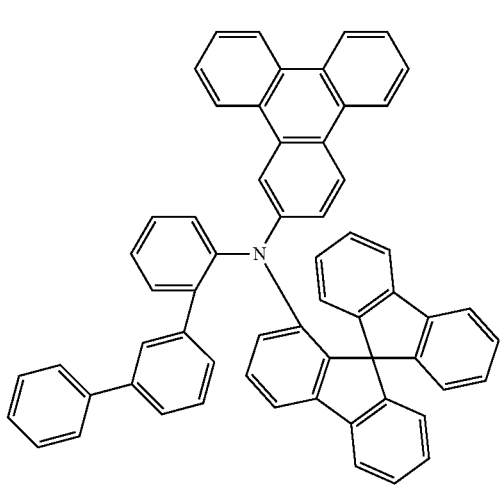
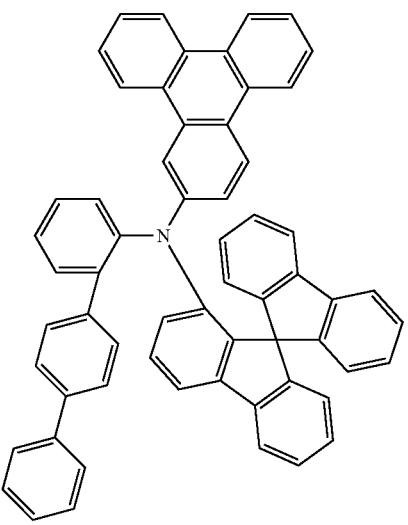

21
-continued
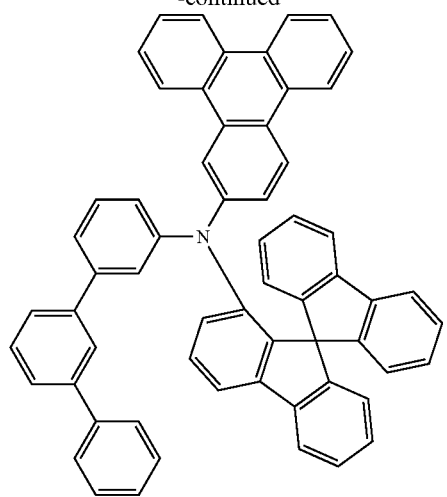
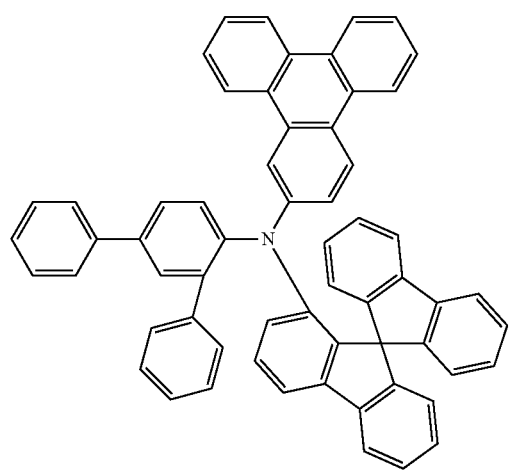
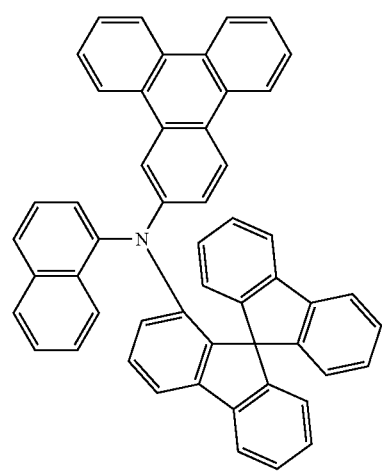
22
-continued
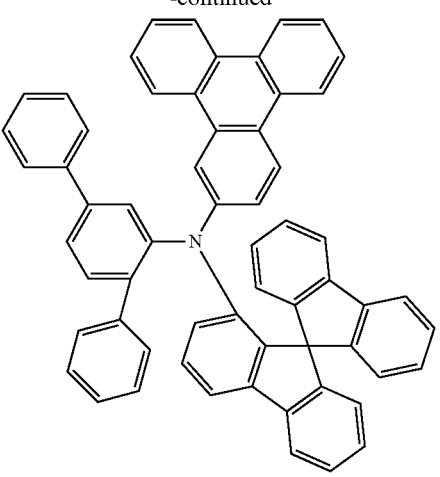
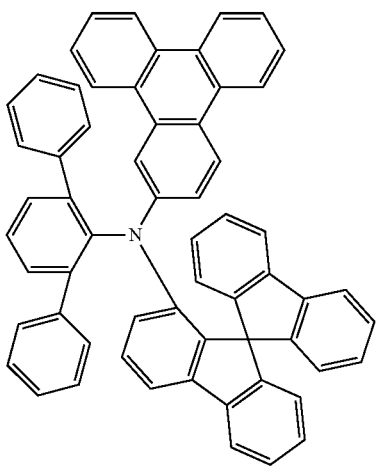

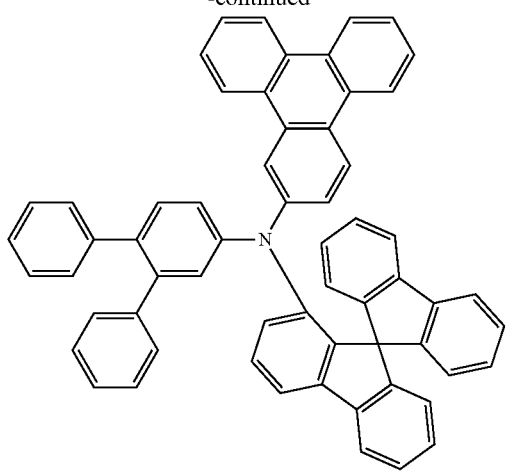
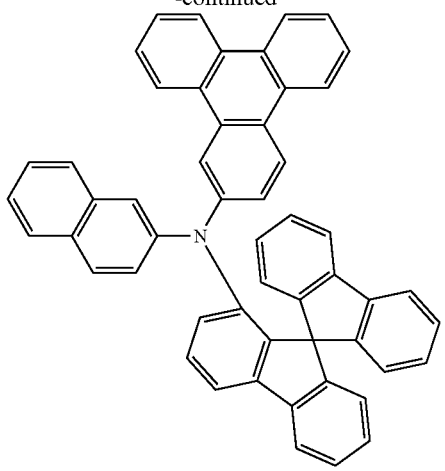
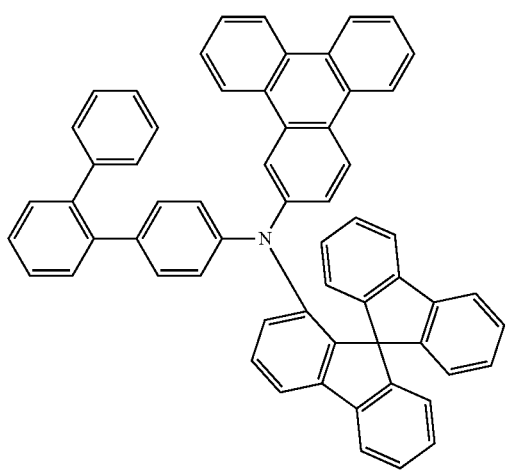
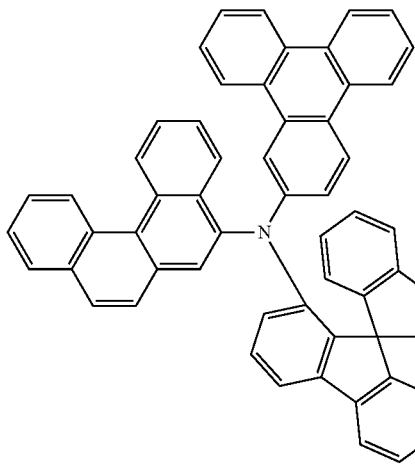
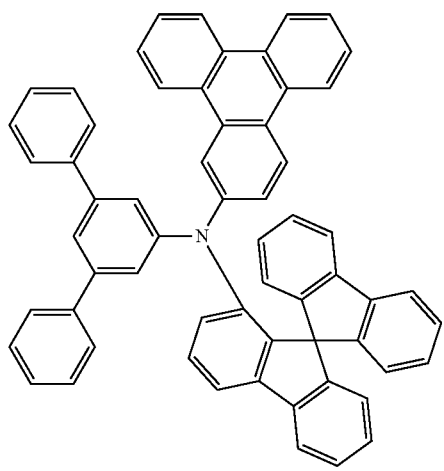
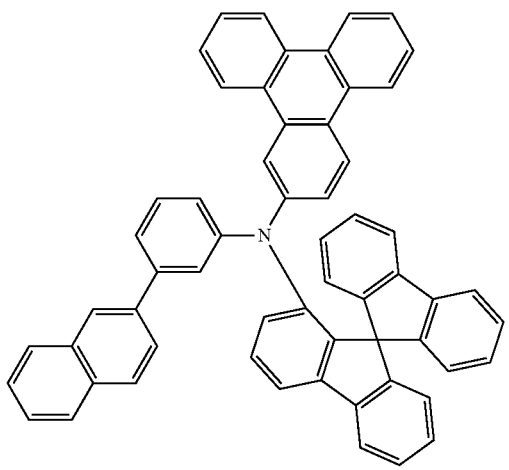

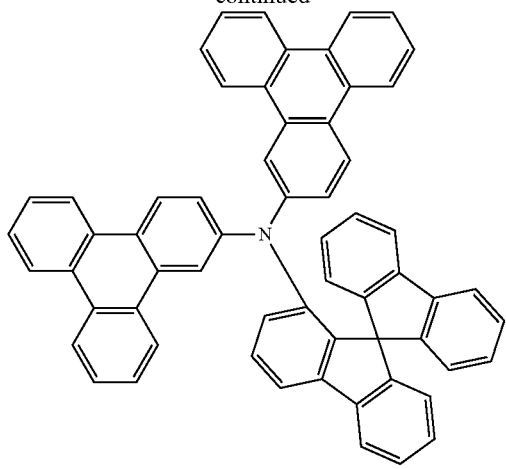
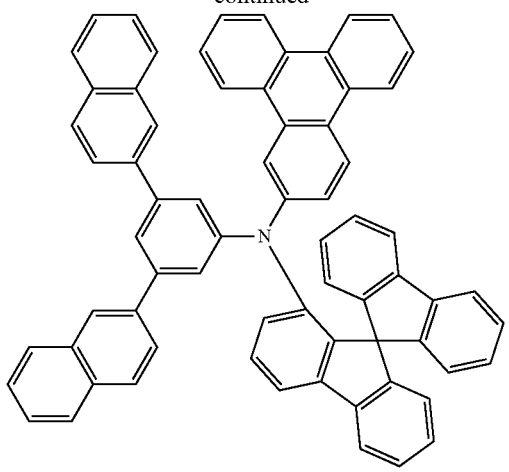
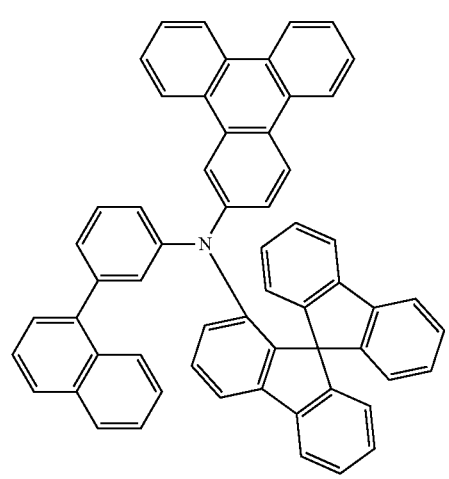
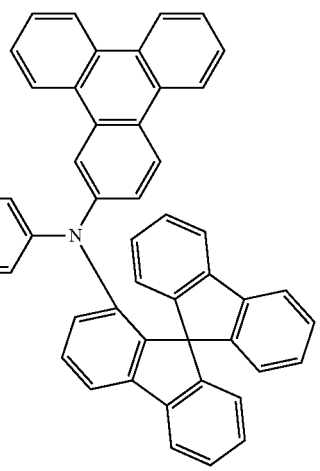
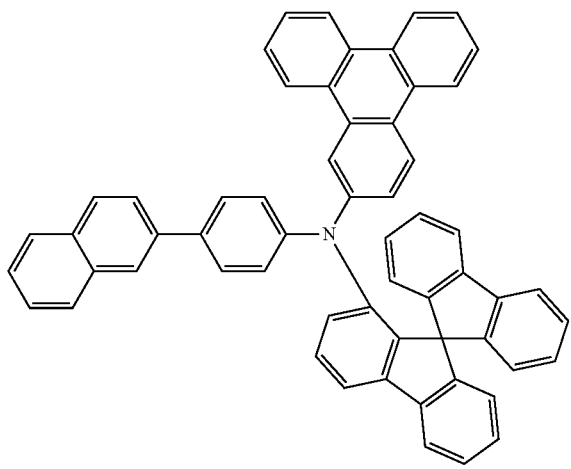
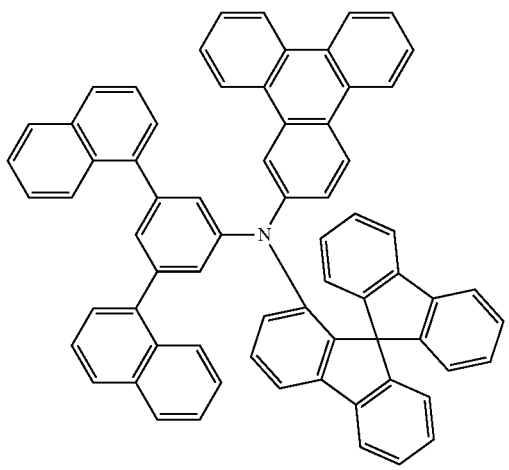

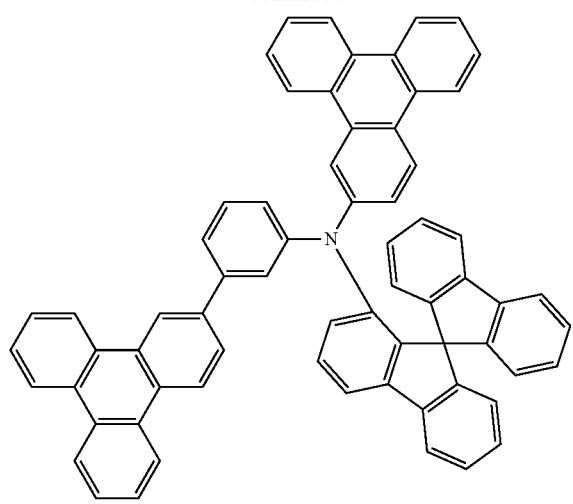
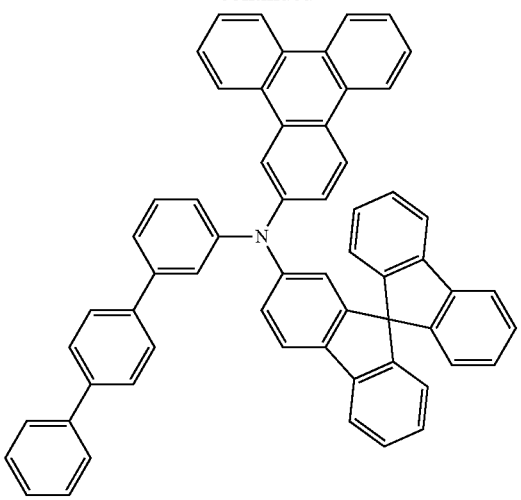
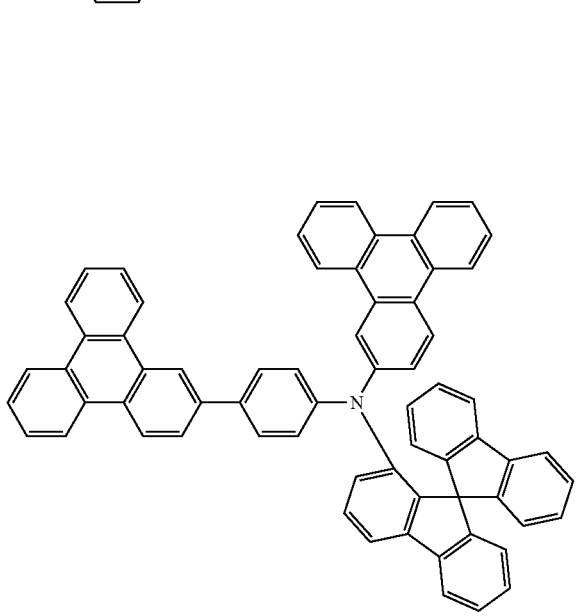
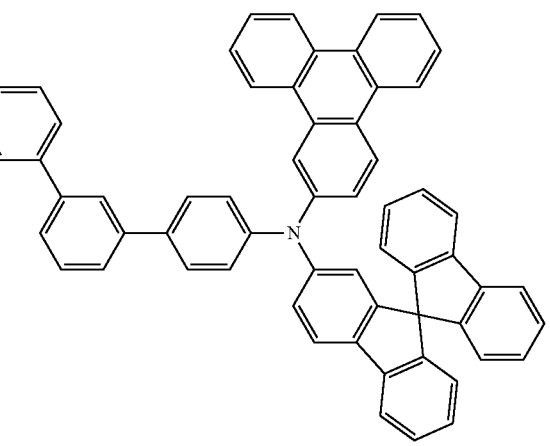
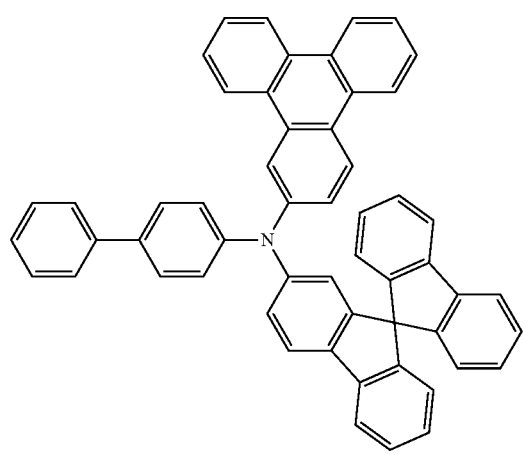
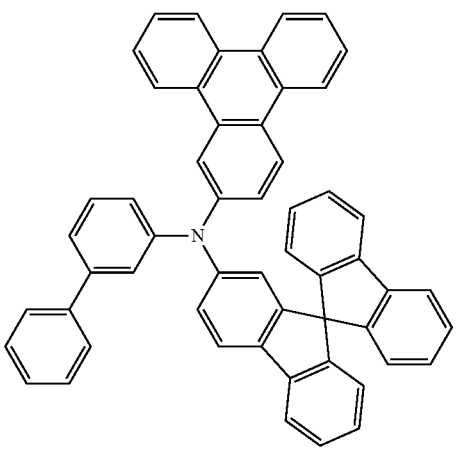

29
-continued
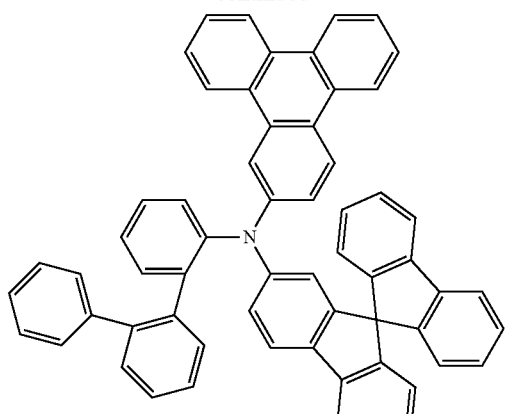
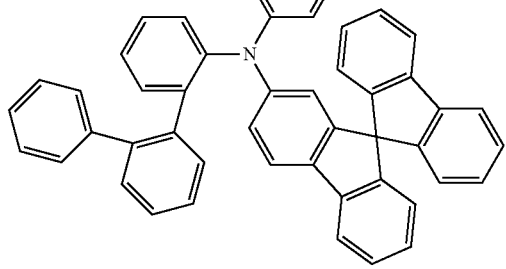
30
-continued
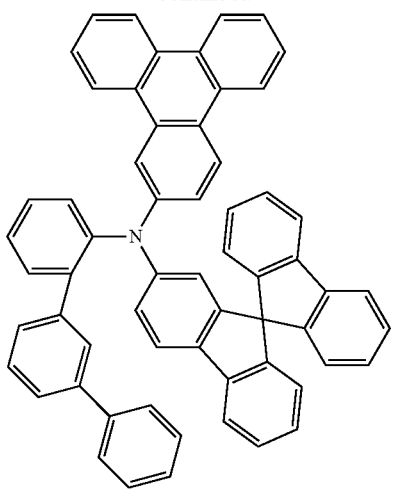
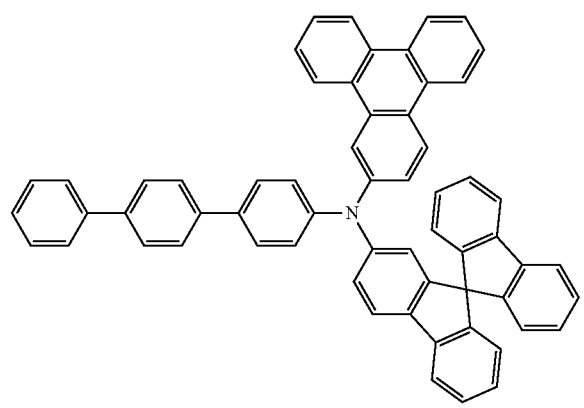
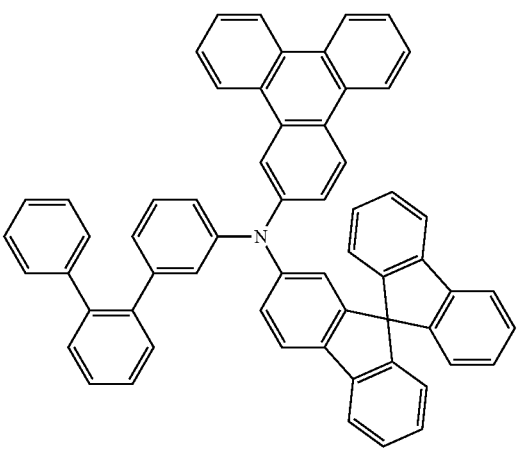
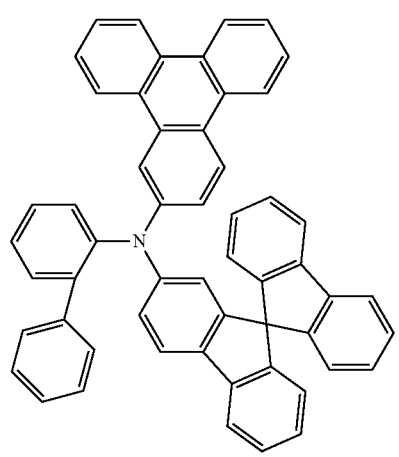
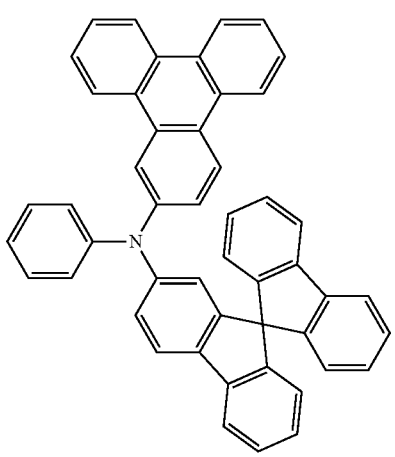

31
-continued
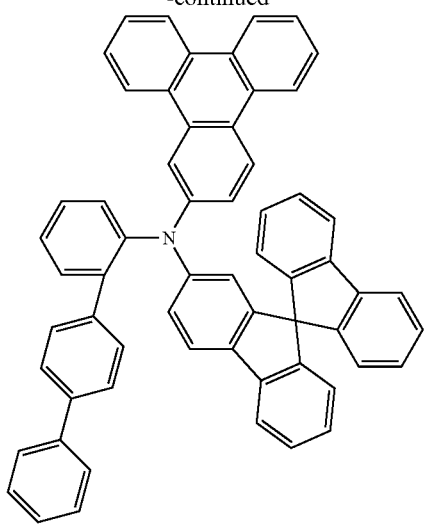
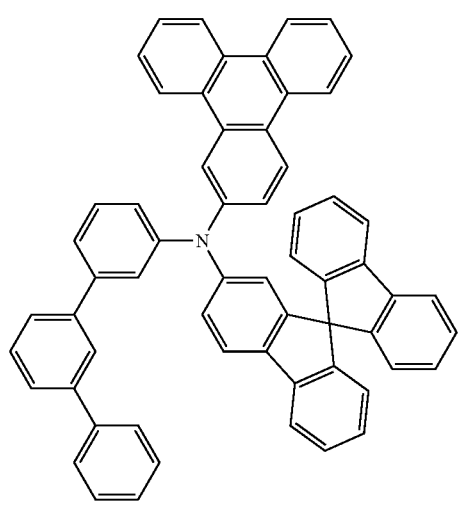
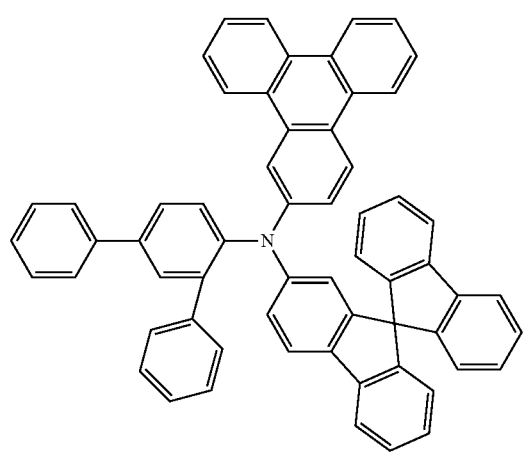
32
-continued
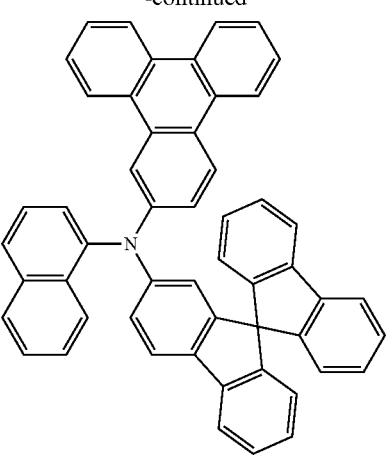
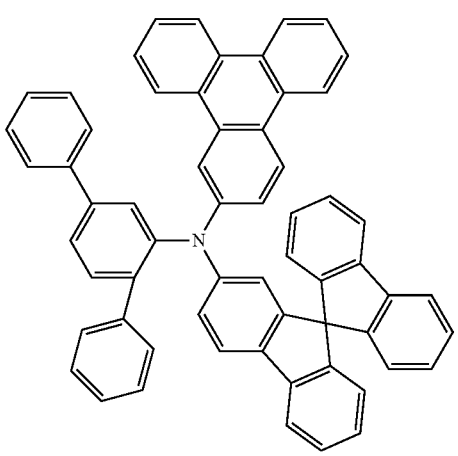
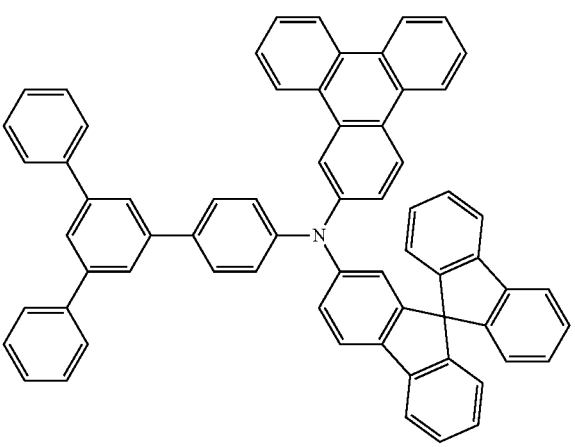

33
-continued
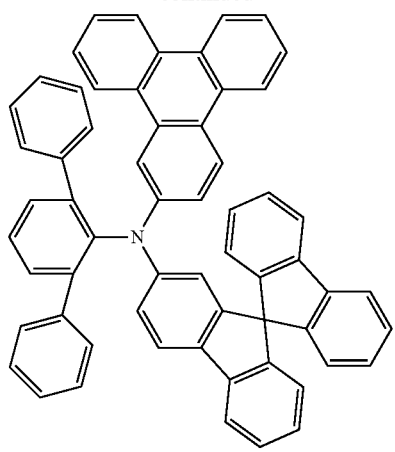
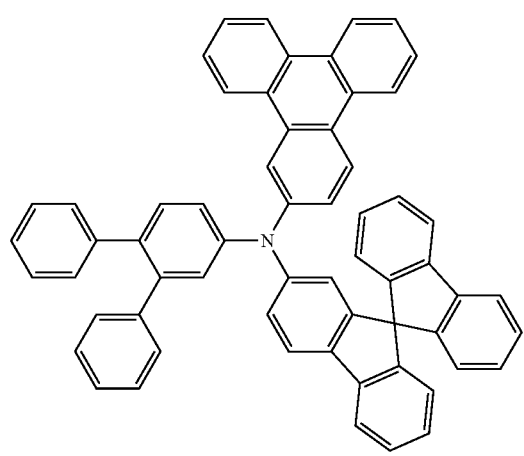
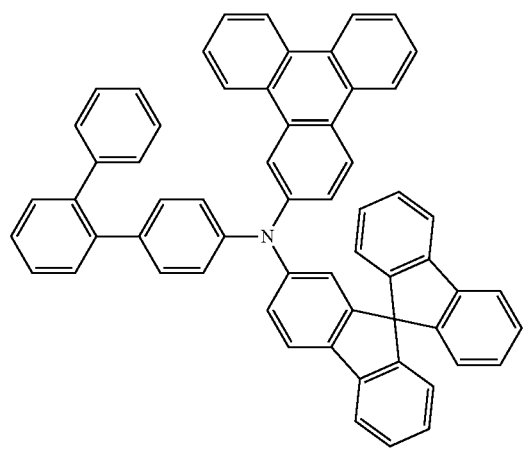
34
-continued
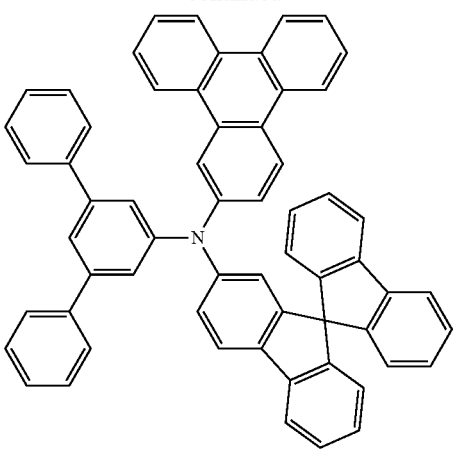
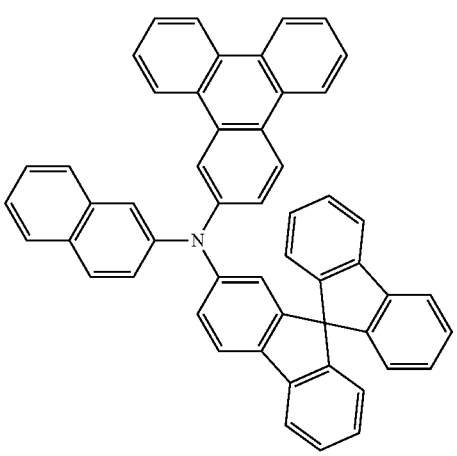
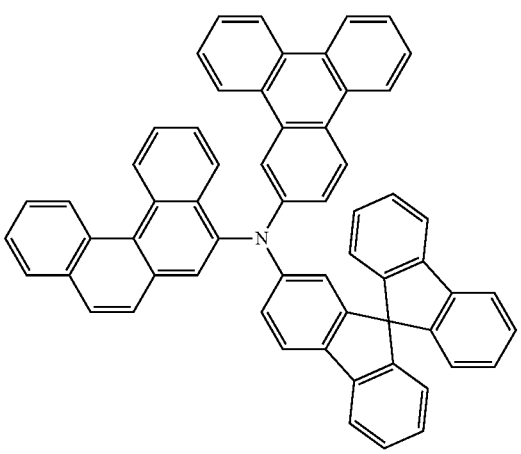

-continued
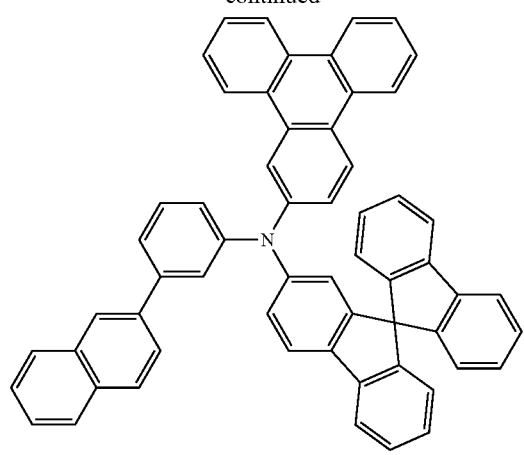
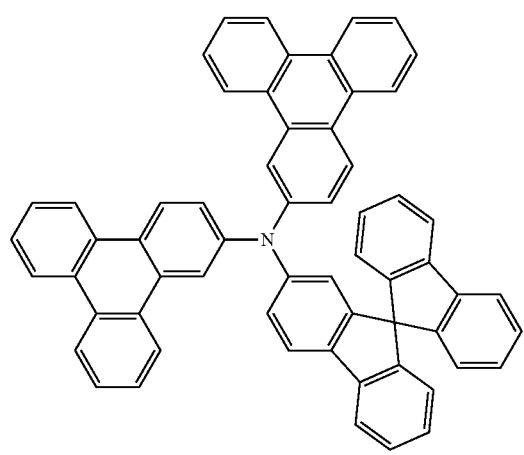
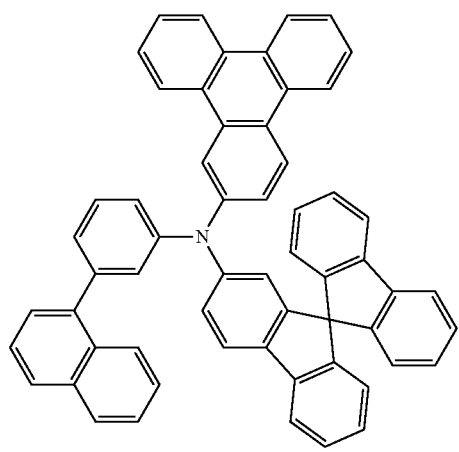
-continued
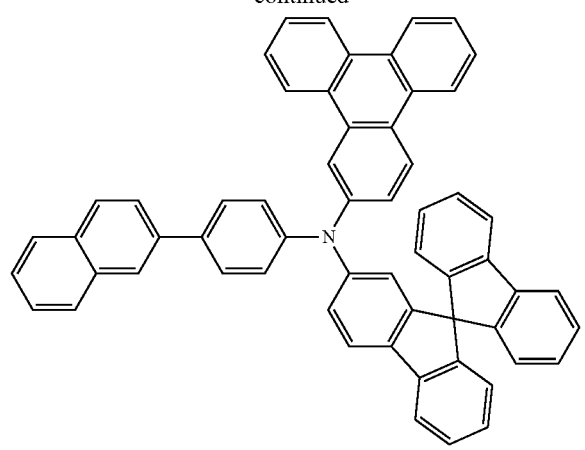
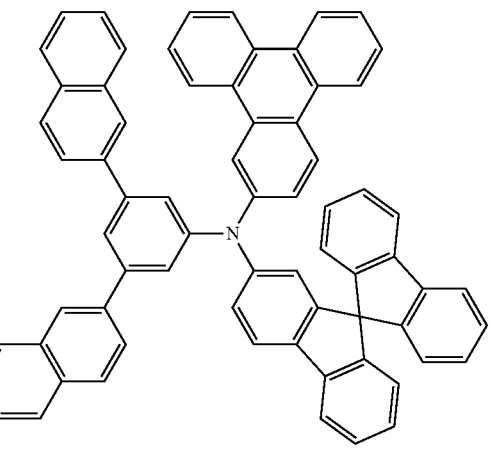
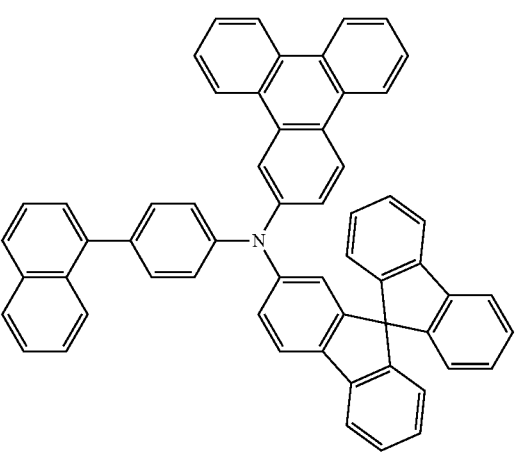

37
-continued
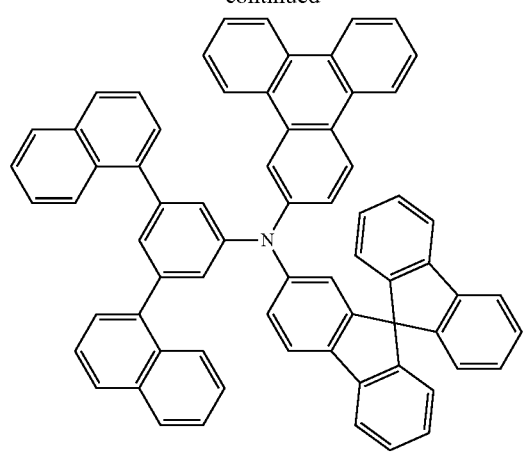
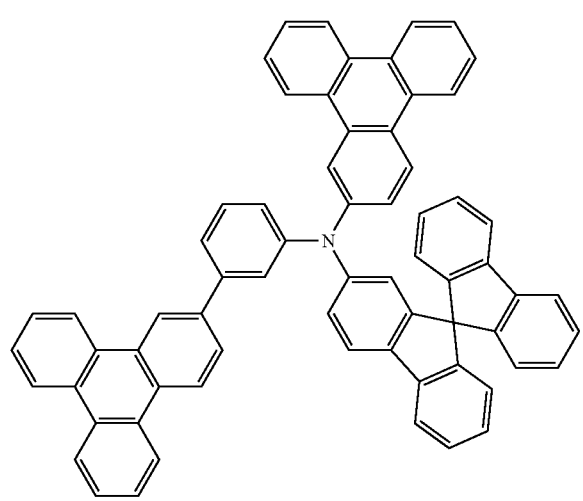
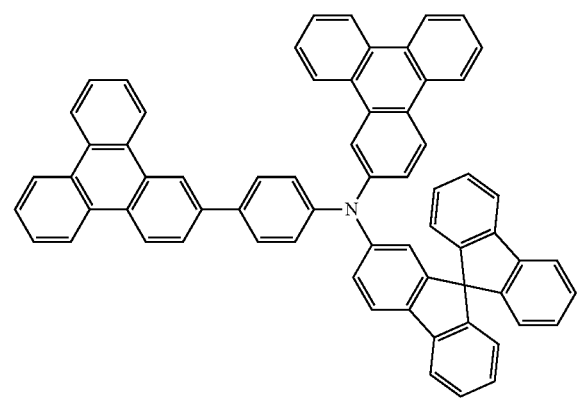
38
-continued
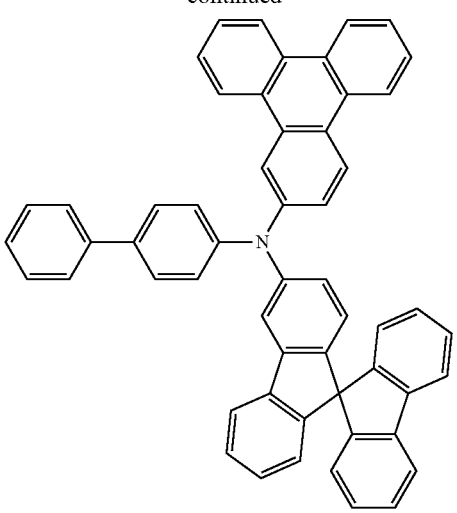
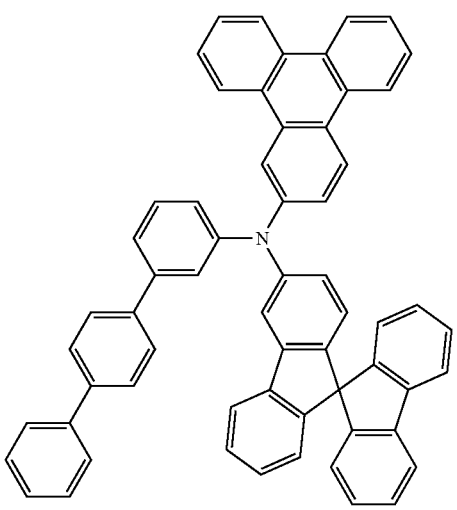
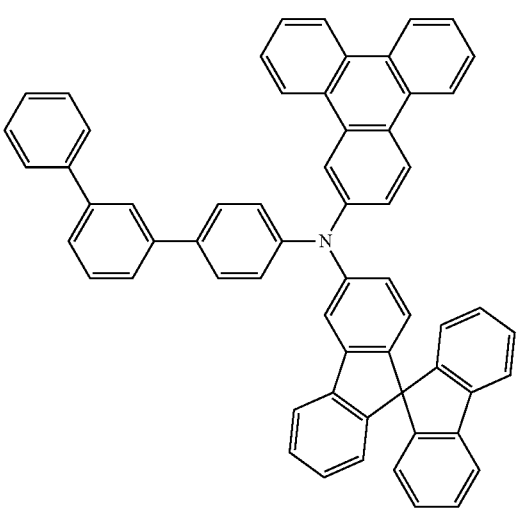

-continued
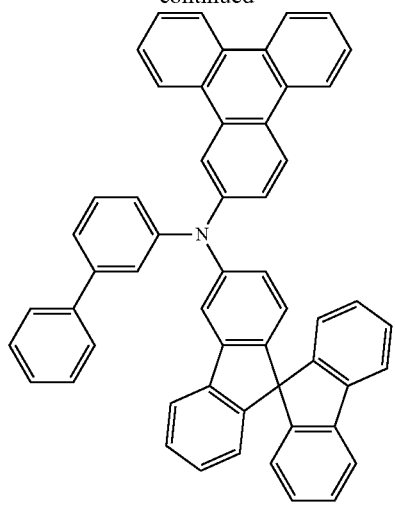
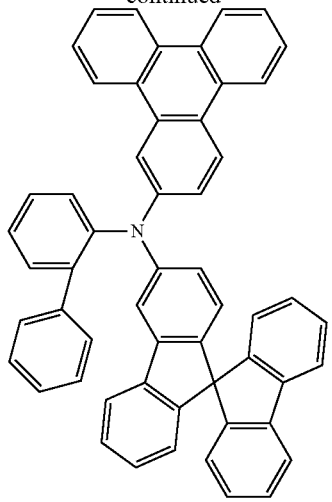
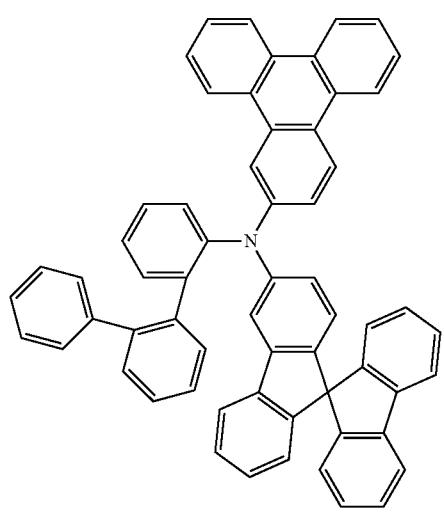
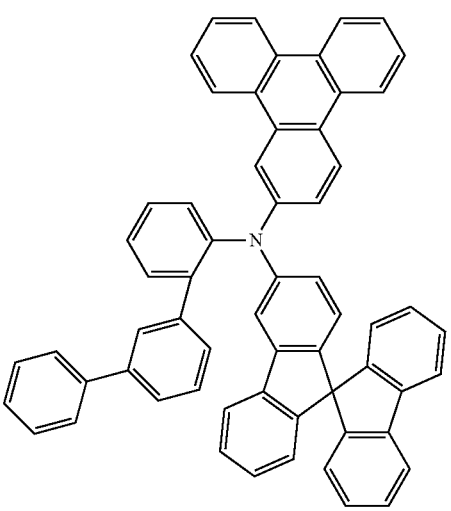
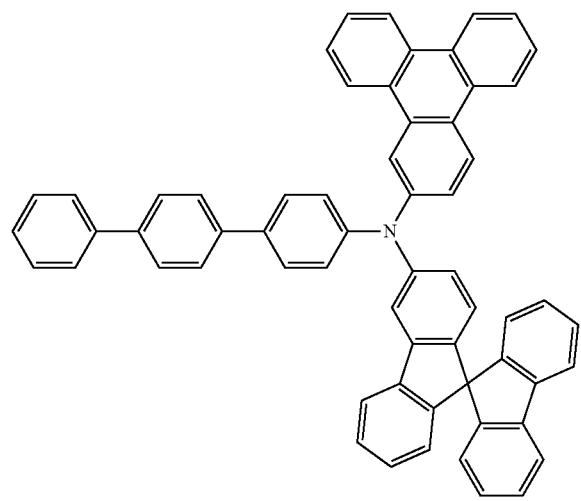
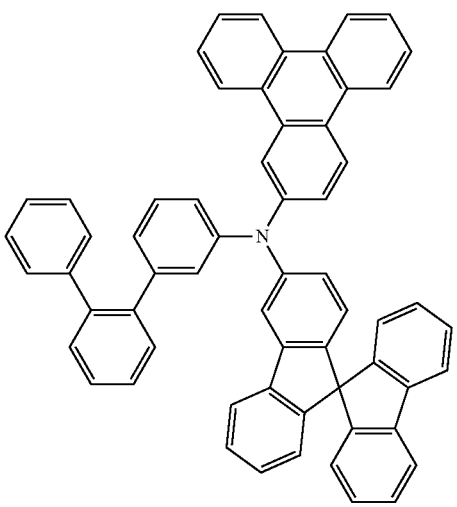

-continued
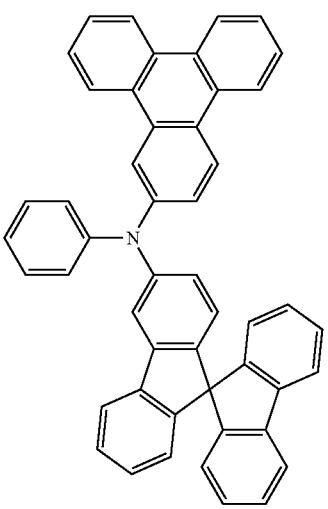
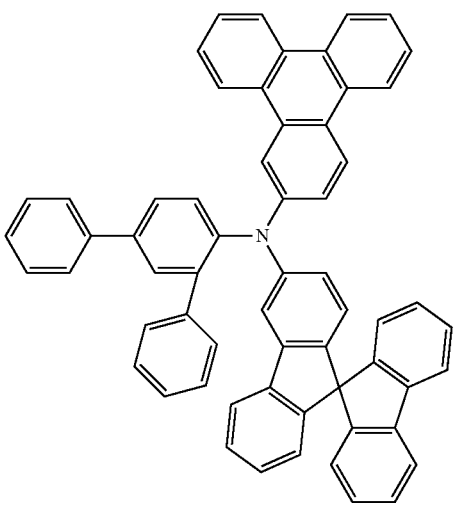
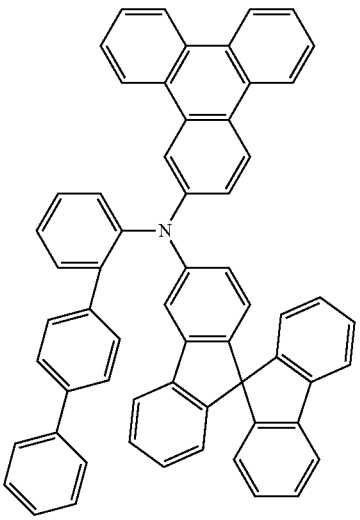
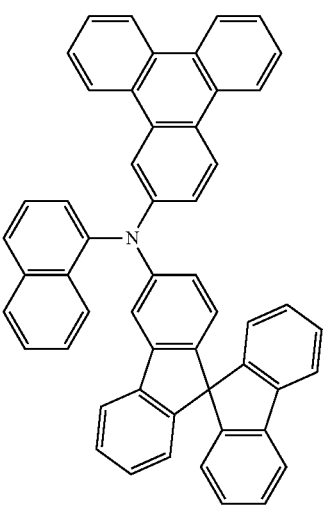
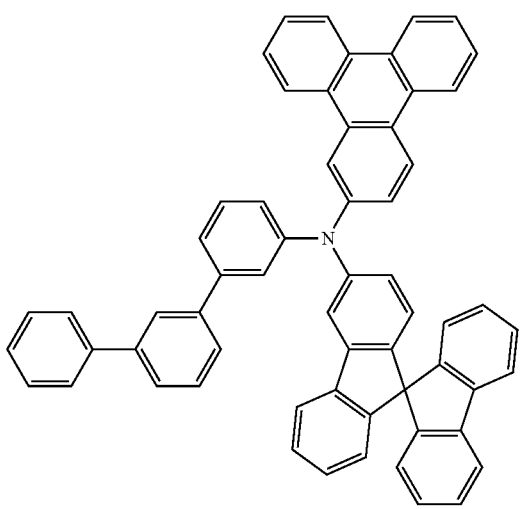
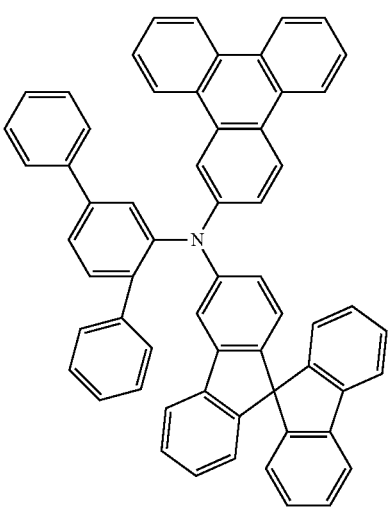

-continued
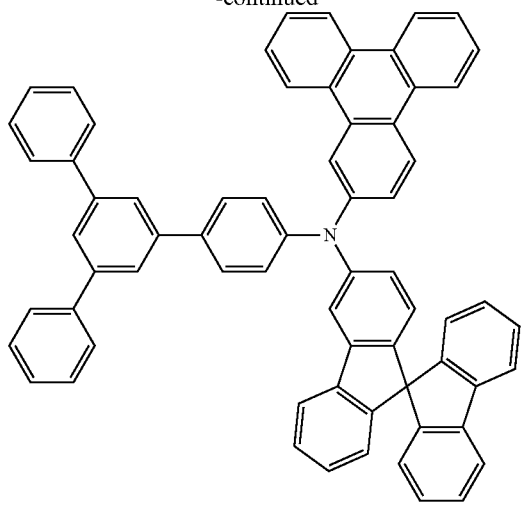
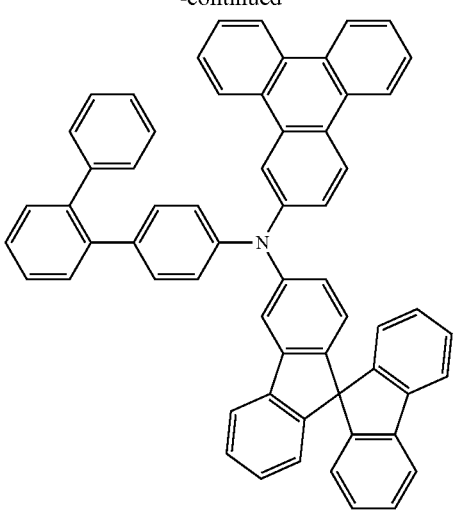
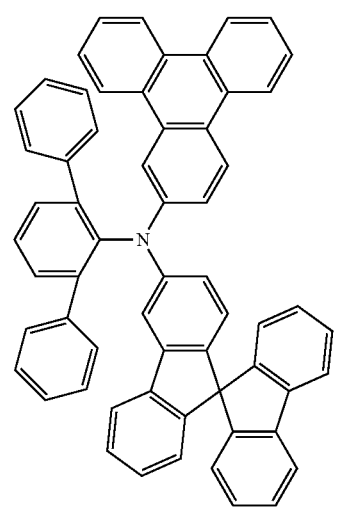
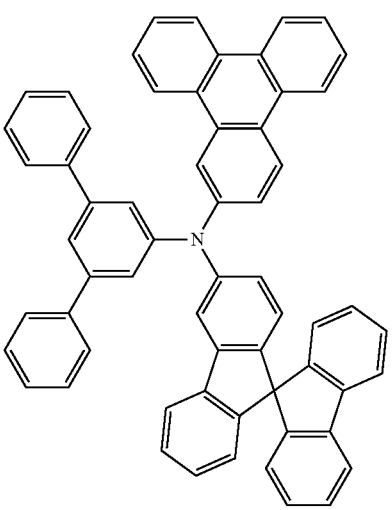
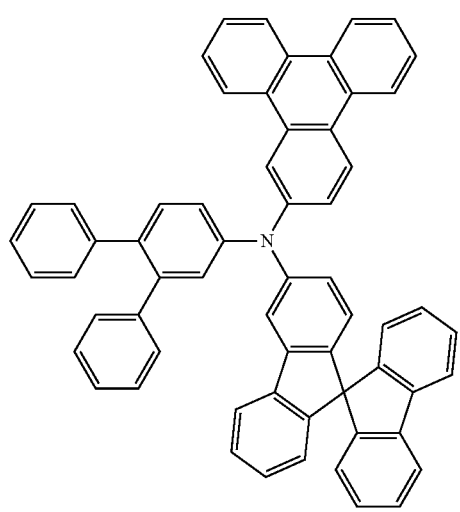
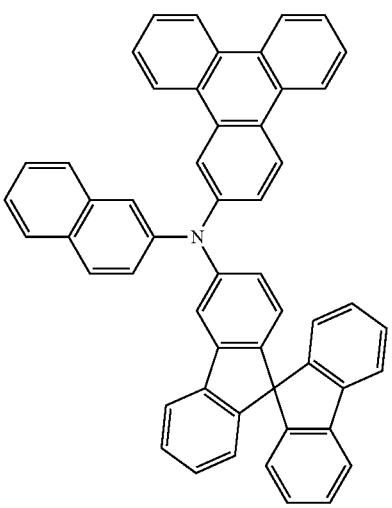

45
-continued
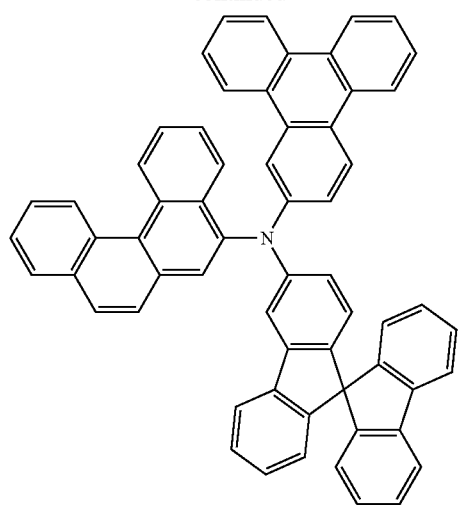
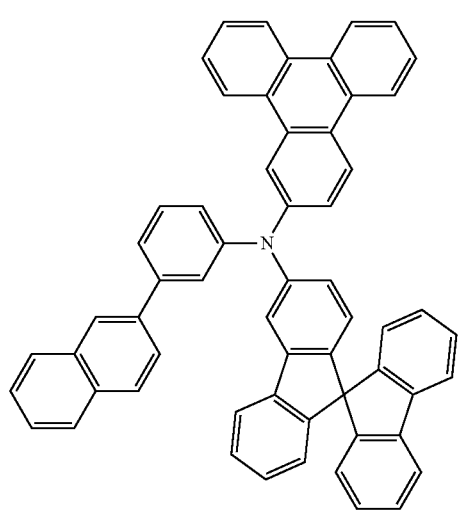
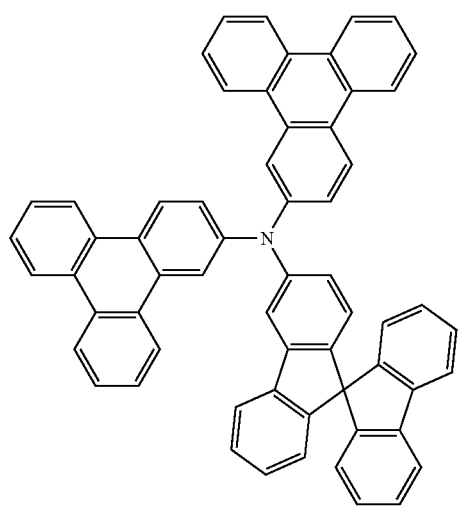
46
-continued
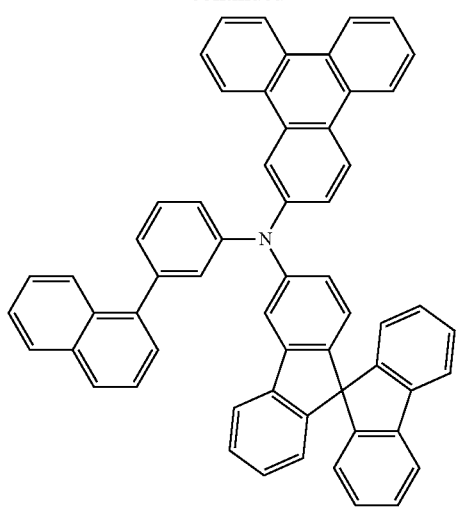
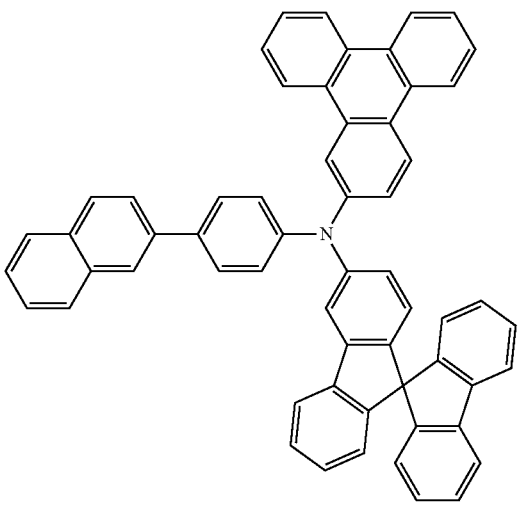
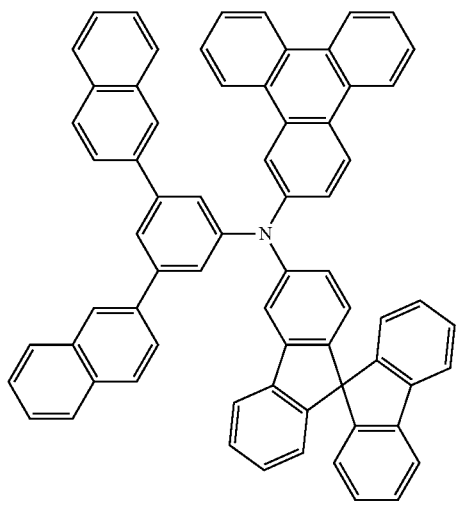

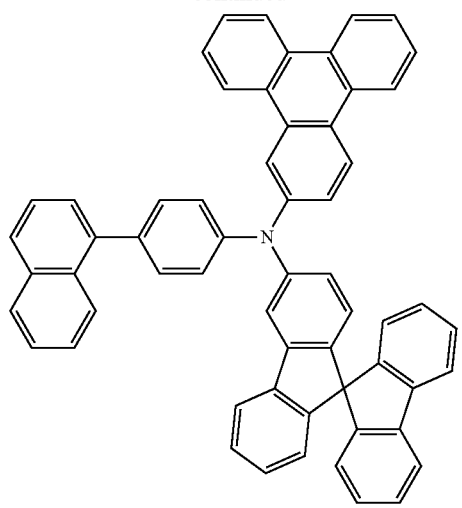
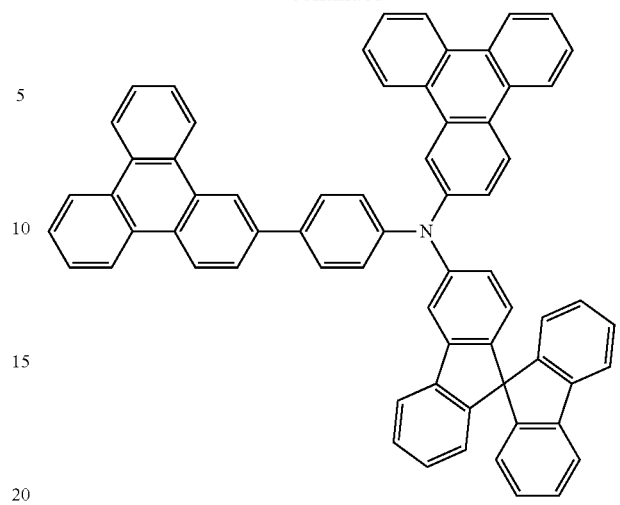

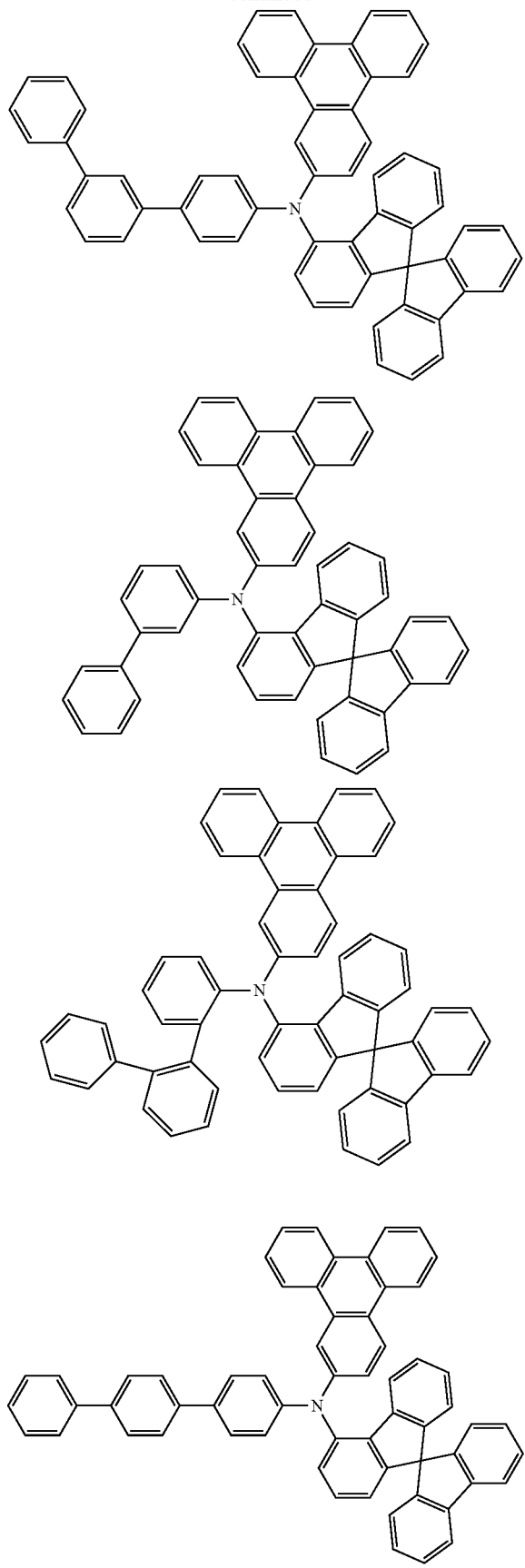
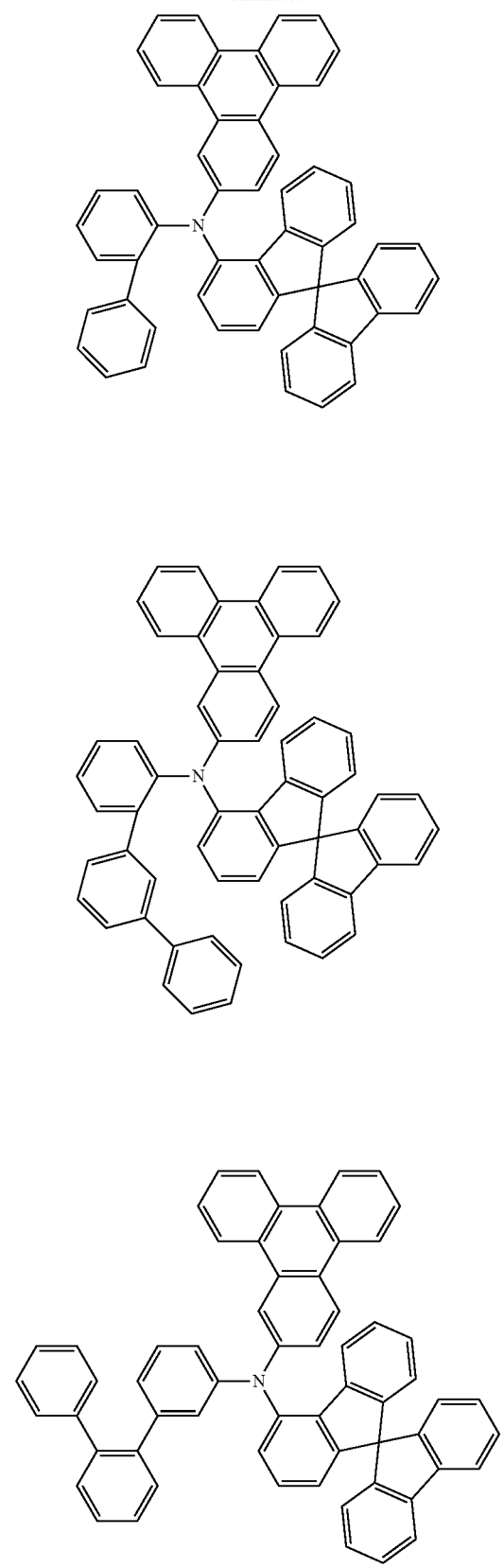

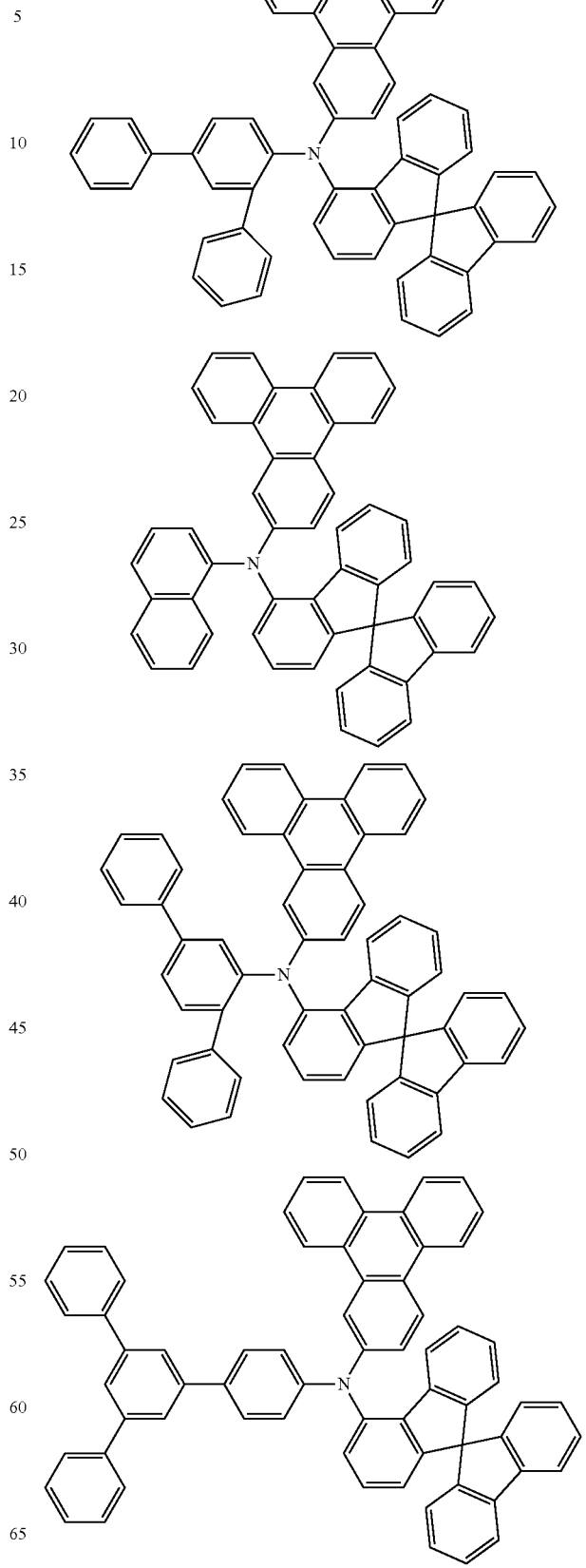

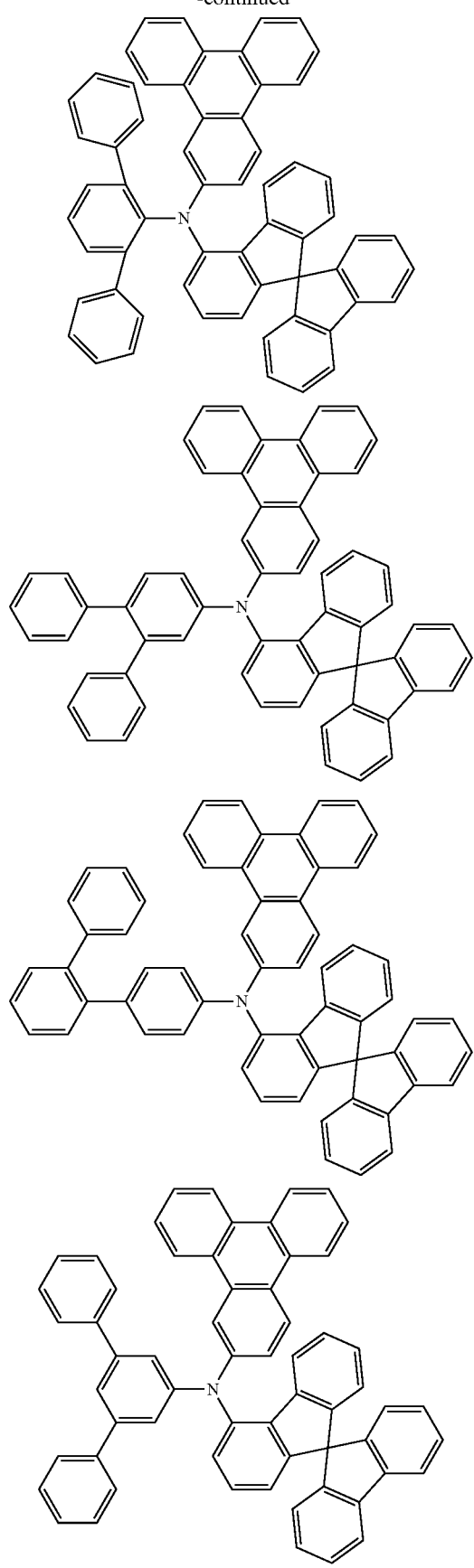
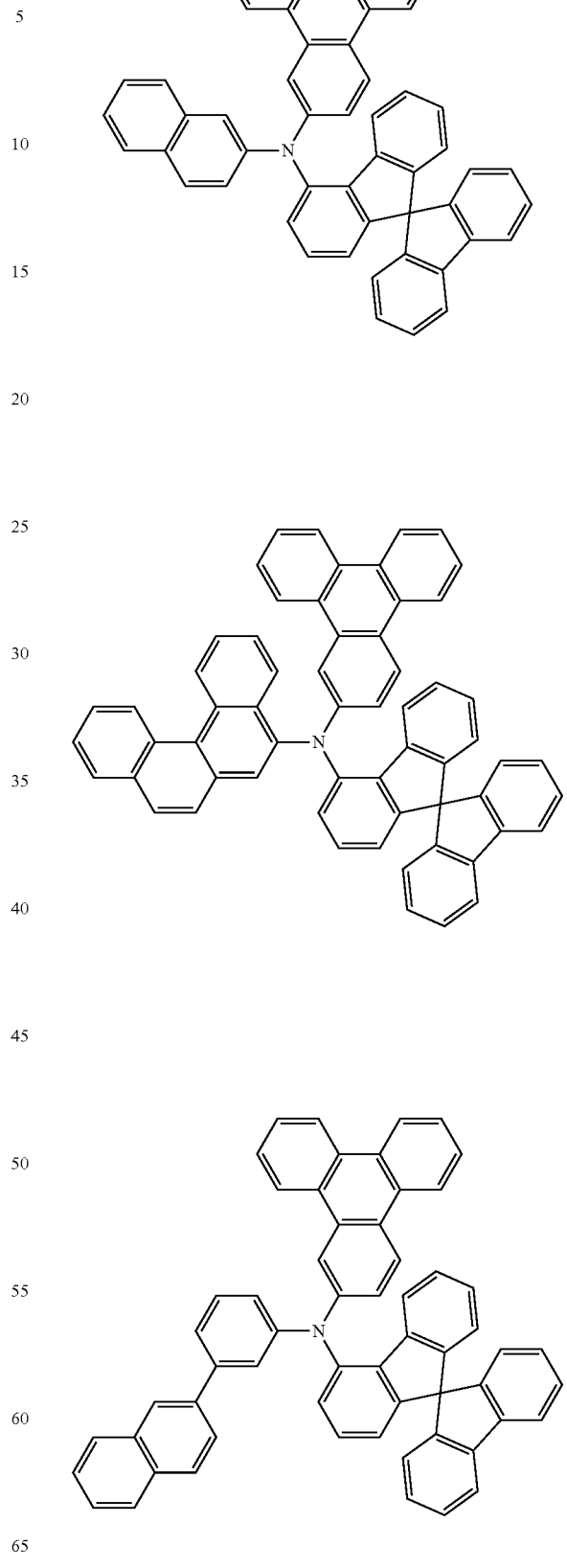

-continued
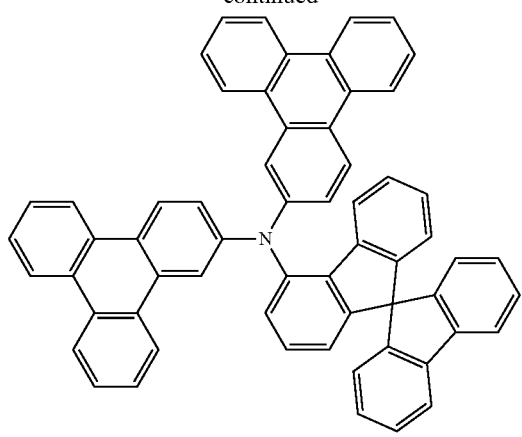
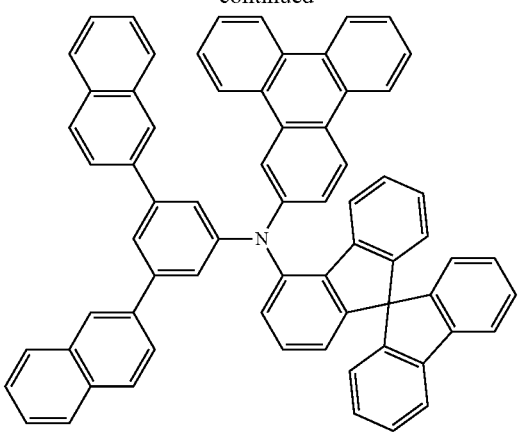
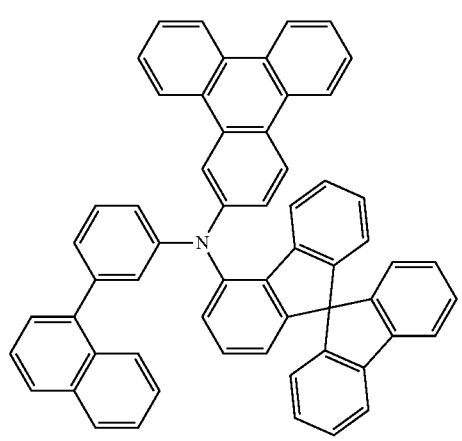
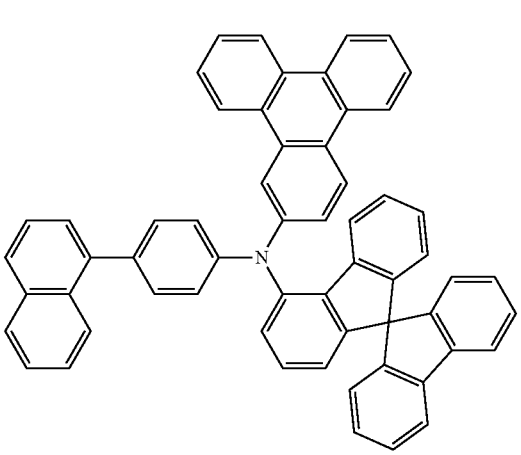
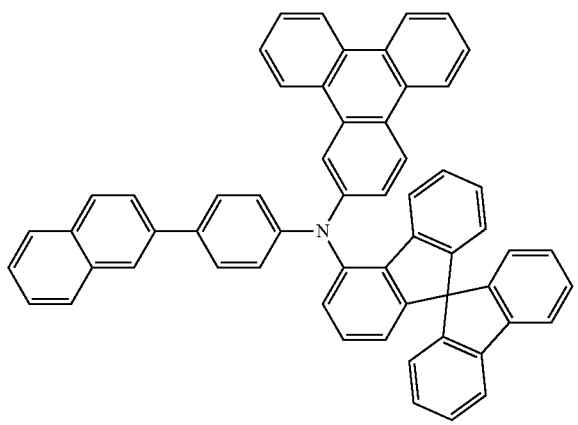
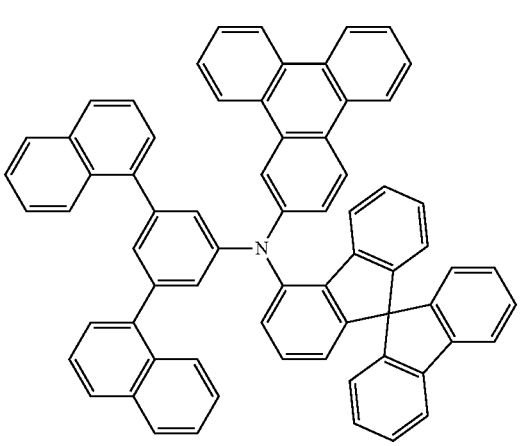

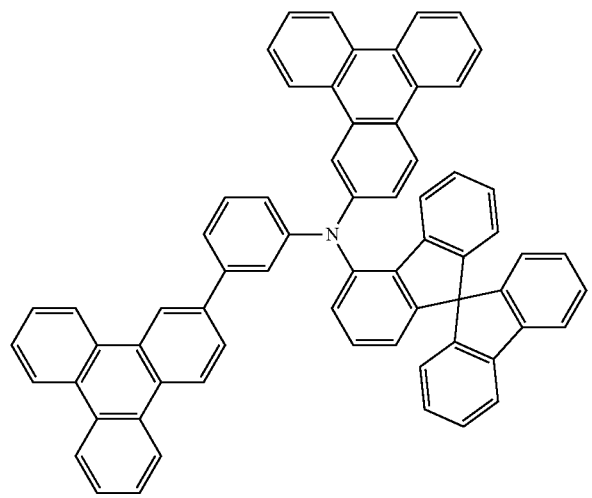
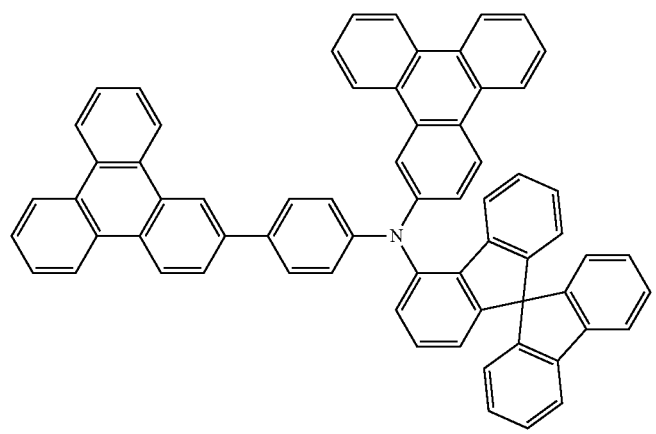
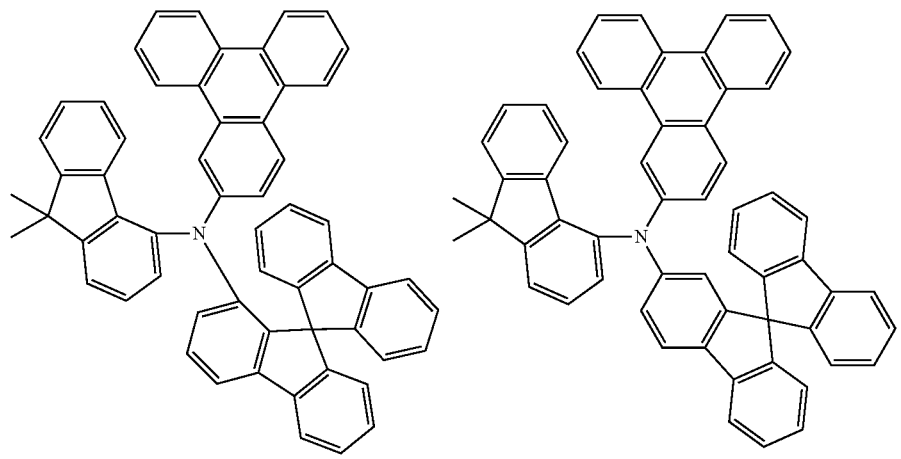

-continued
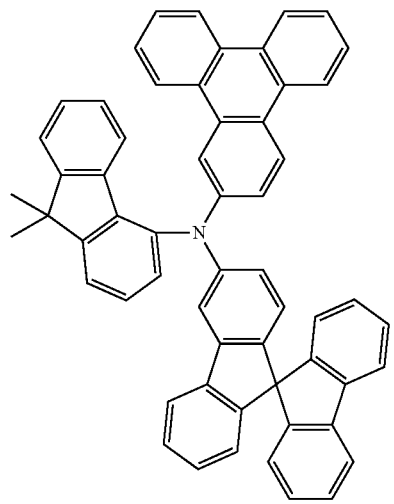
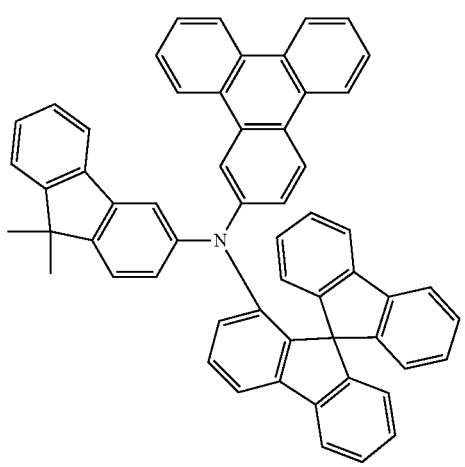
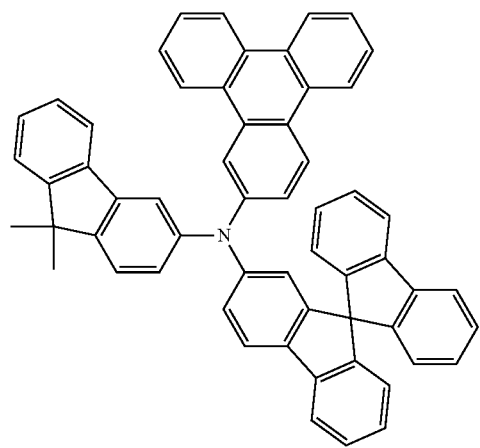
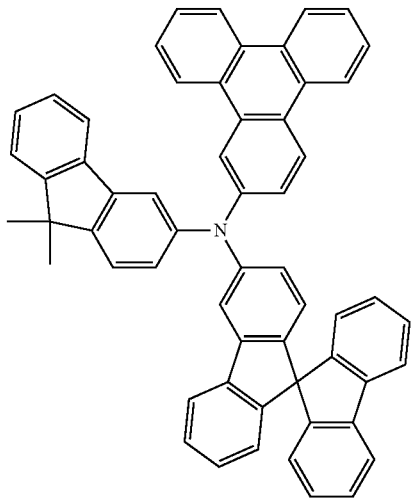
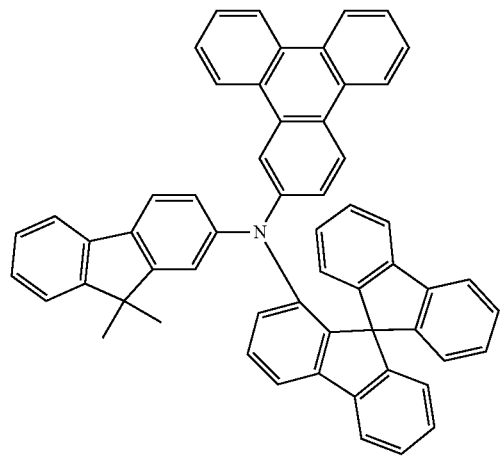
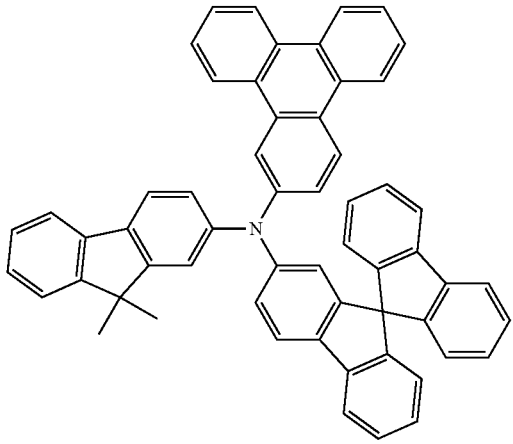

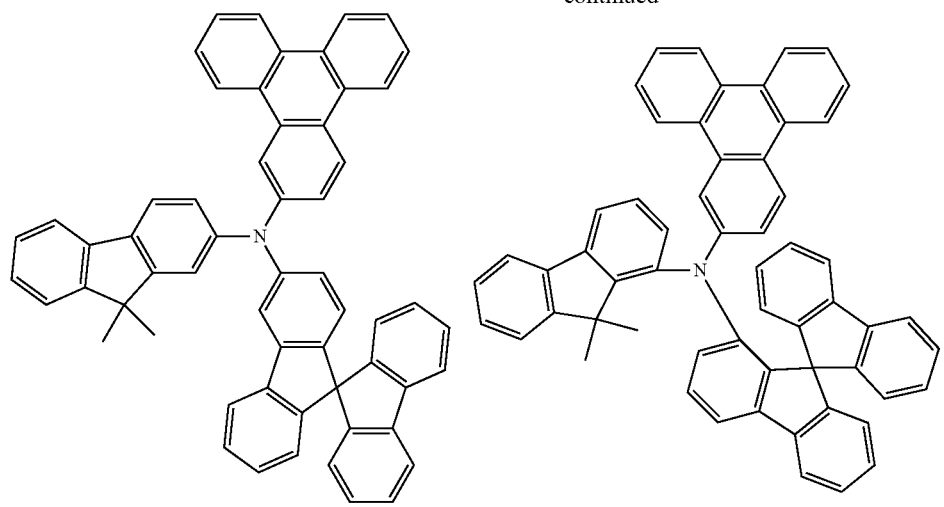
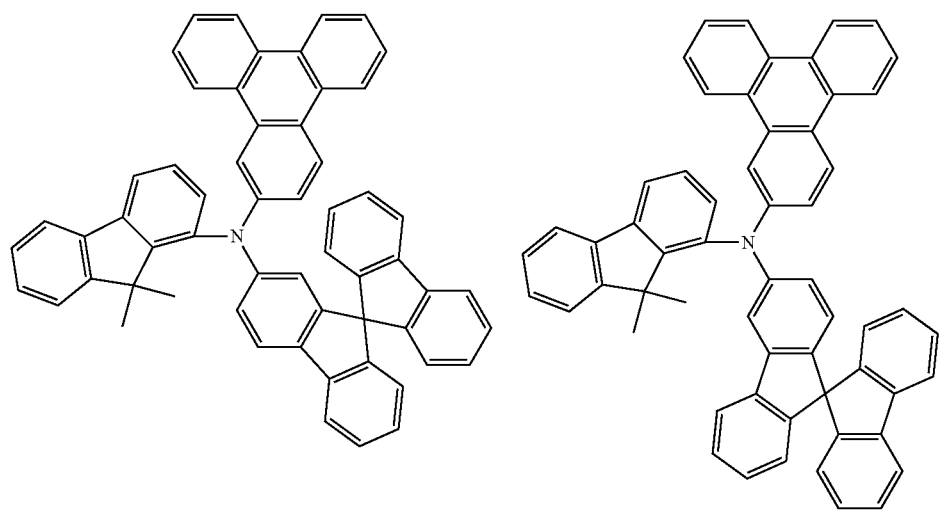
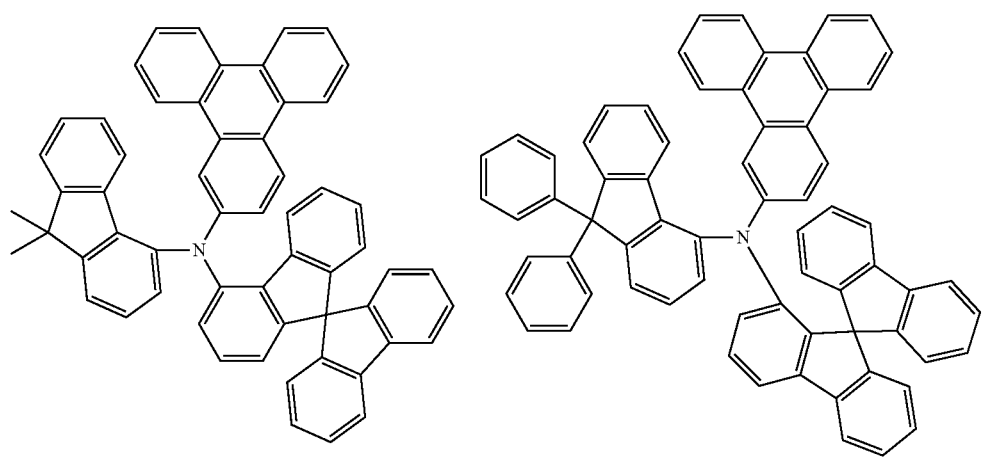

-continued
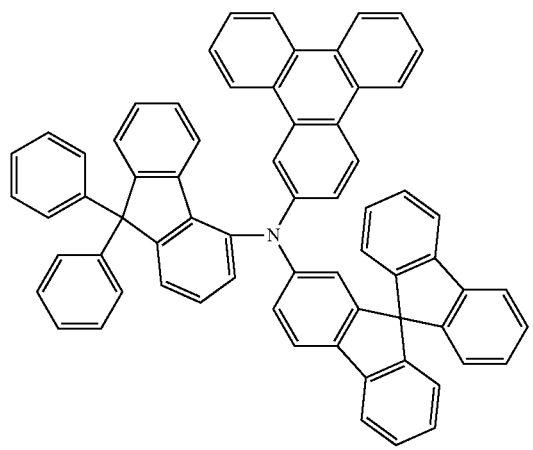
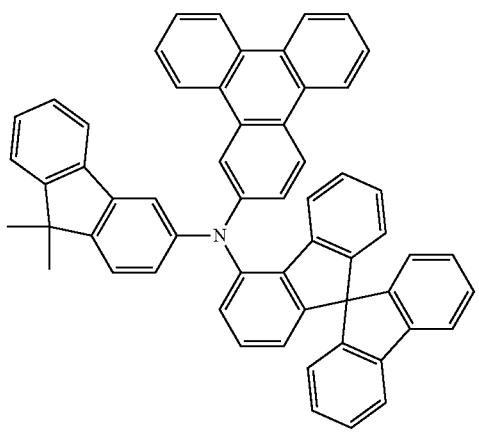
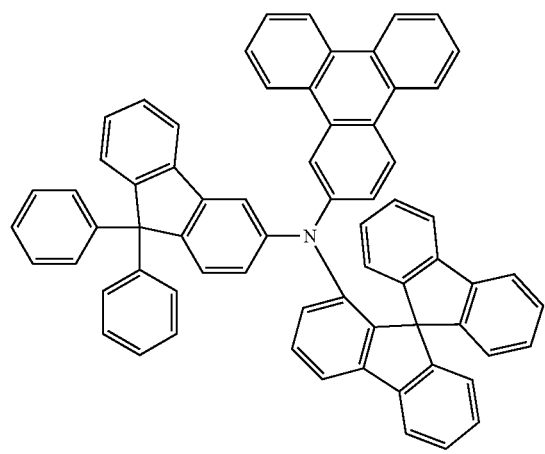
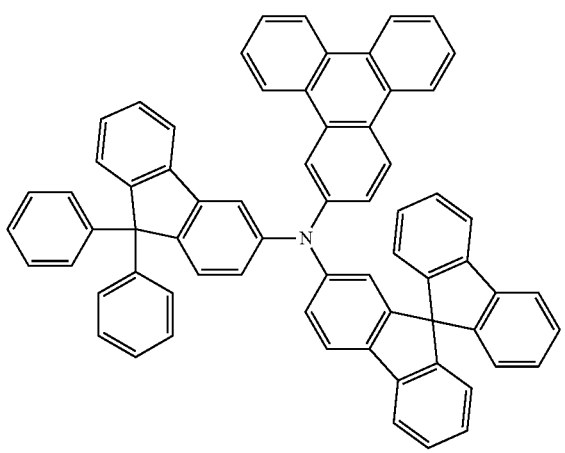
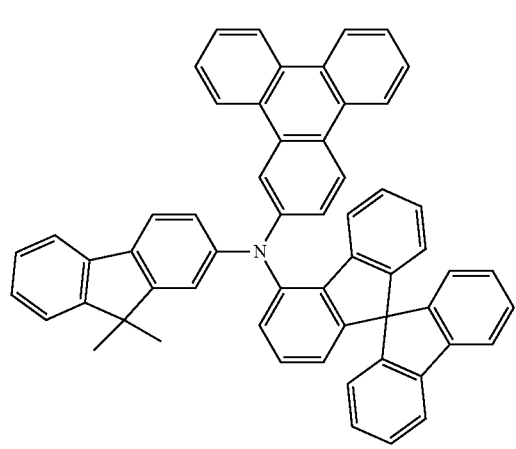
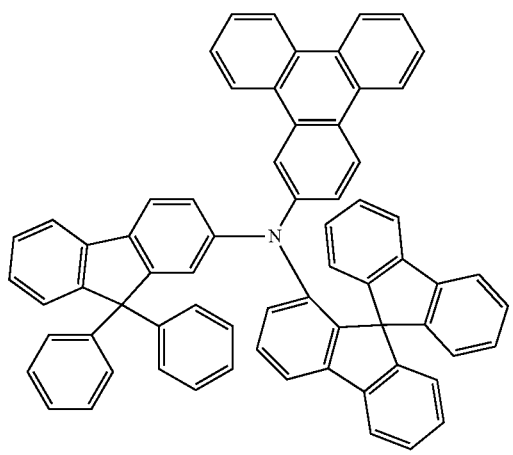

65
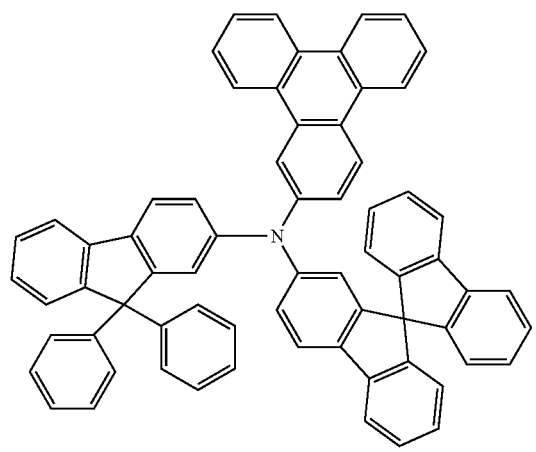
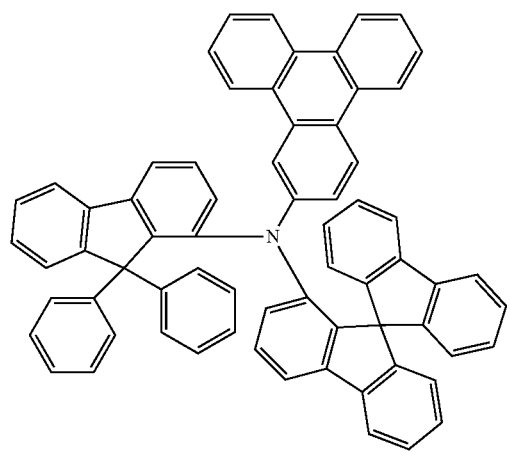
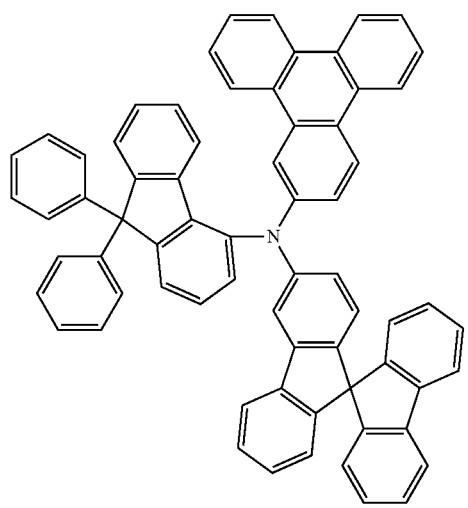
66
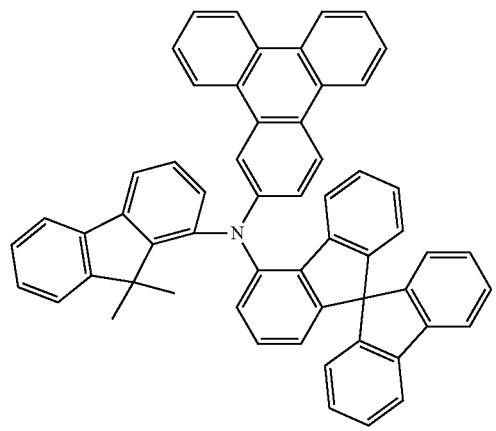
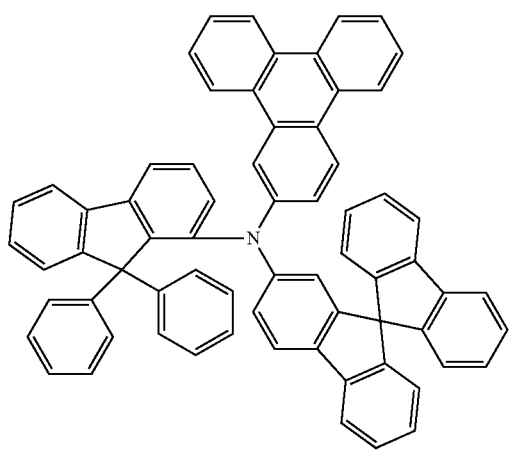
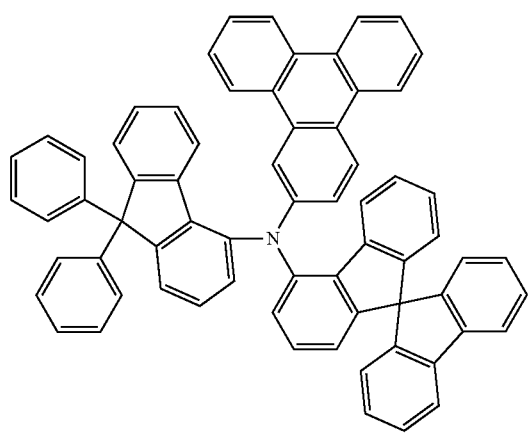

-continued
67
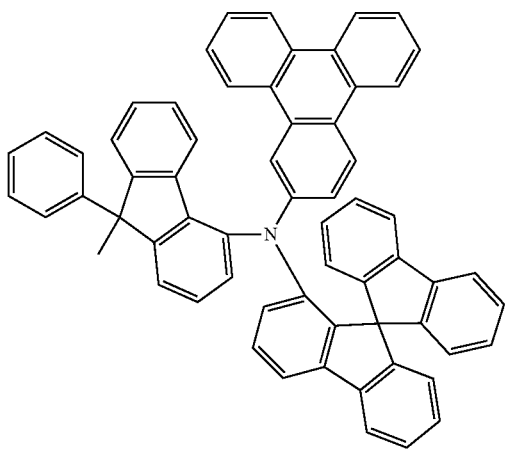
68
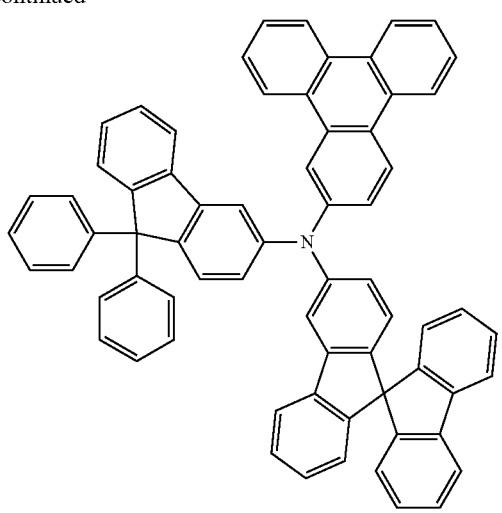
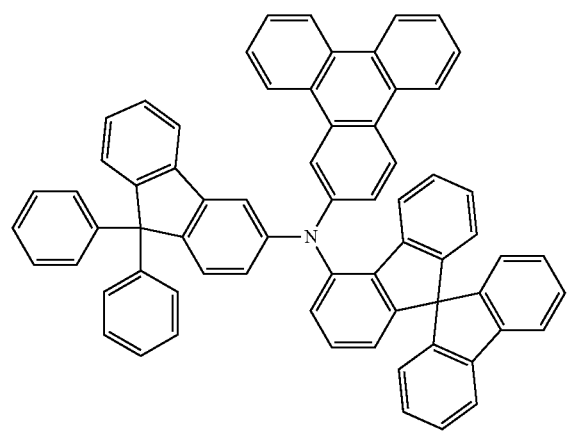
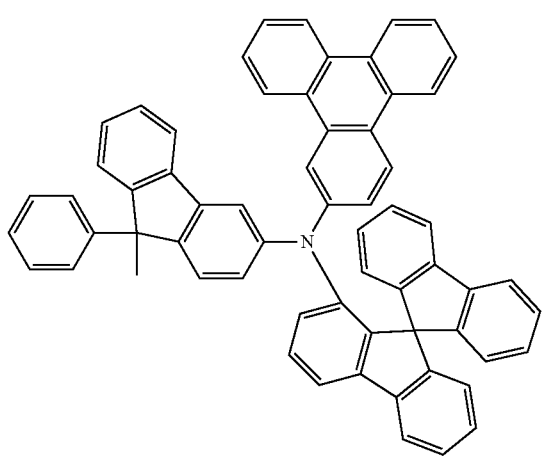
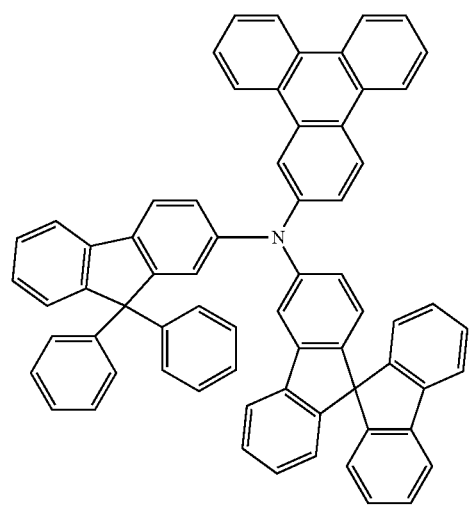
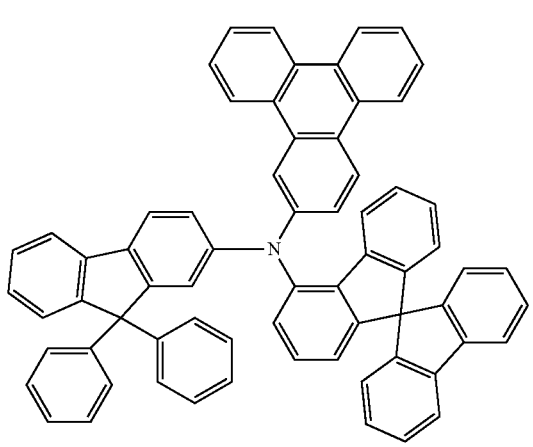

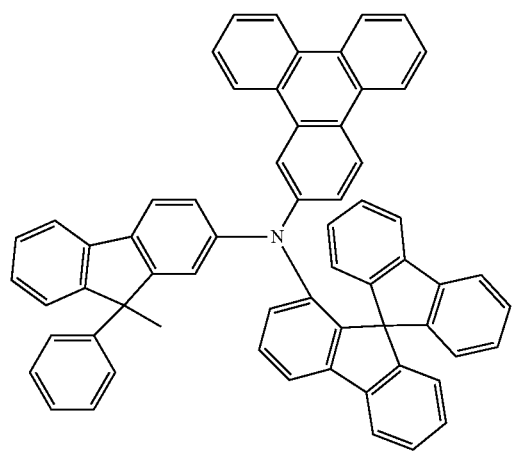
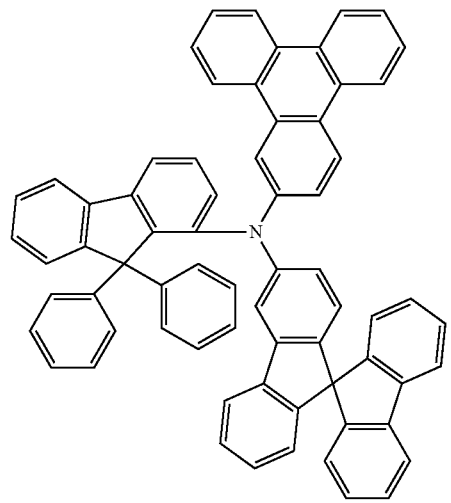
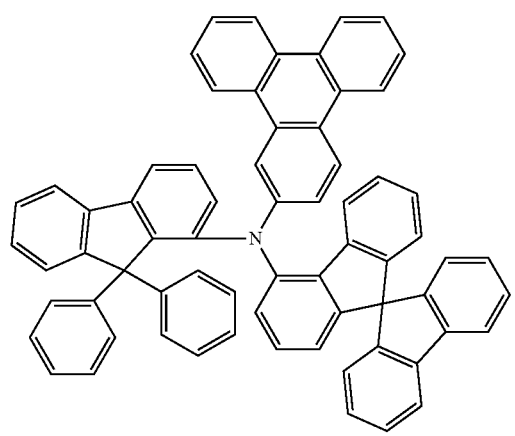
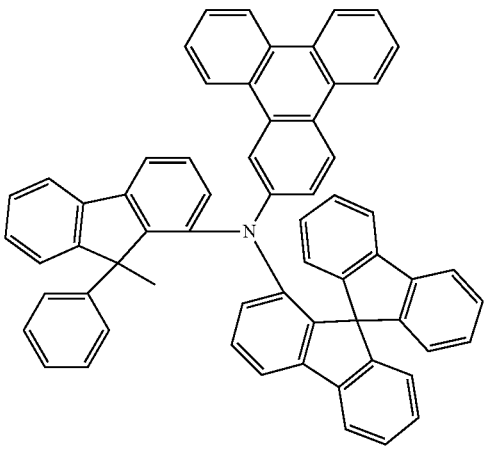
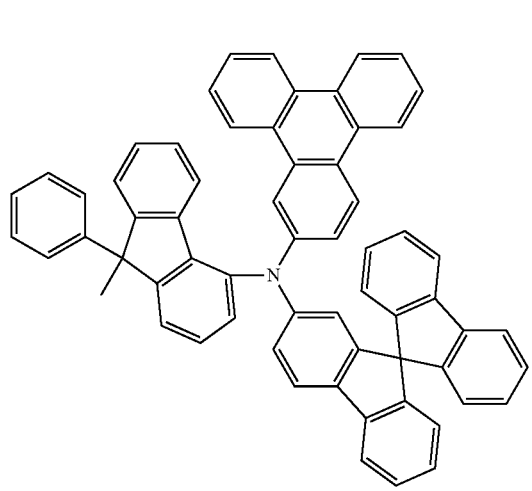
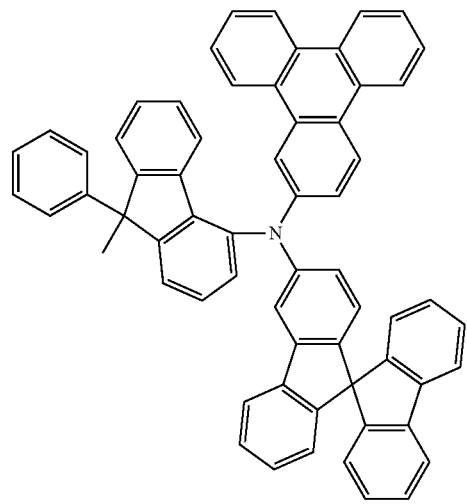

-continued
| 71 | 72 |
|---|---|
| 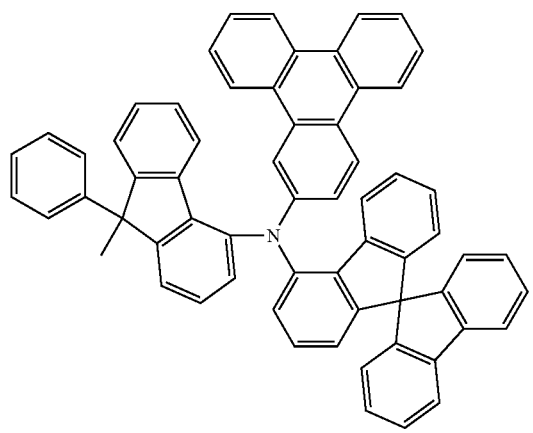 | 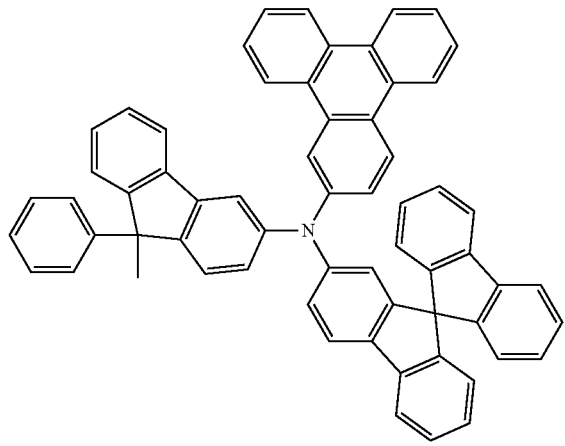 |
| 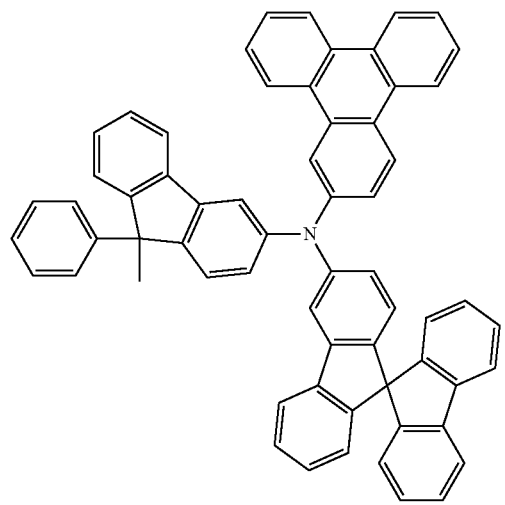 | 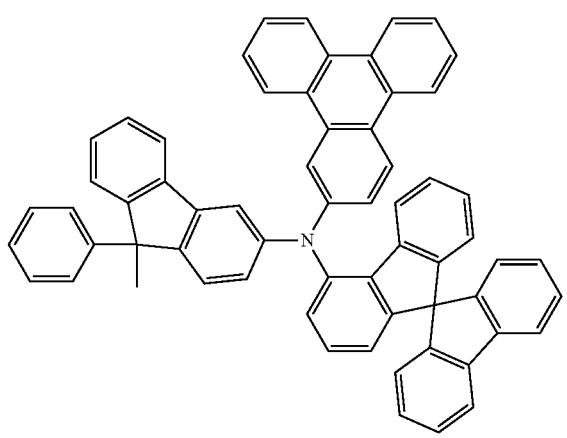 |
| 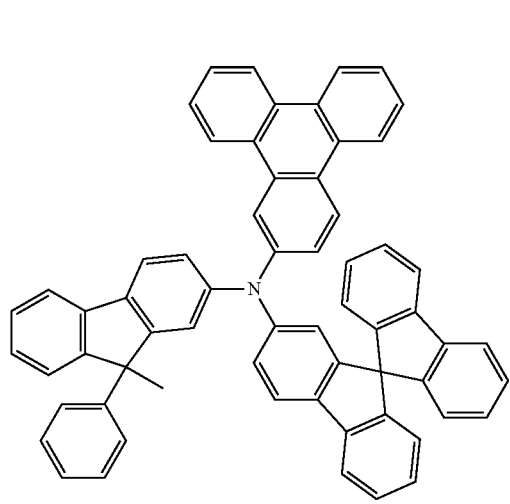 | 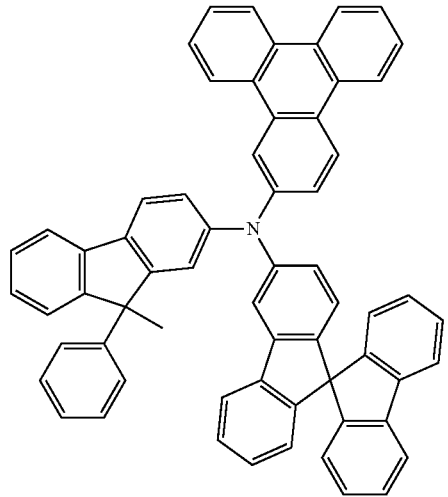 |

-continued
73
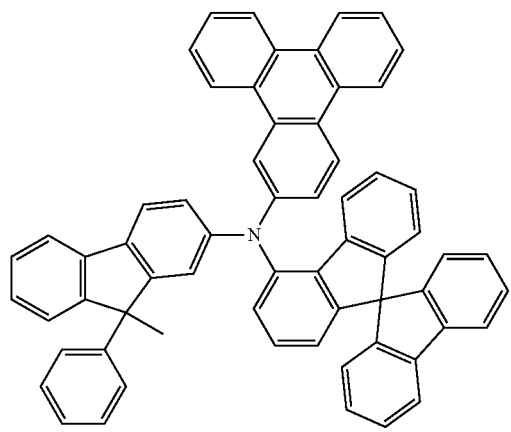
74
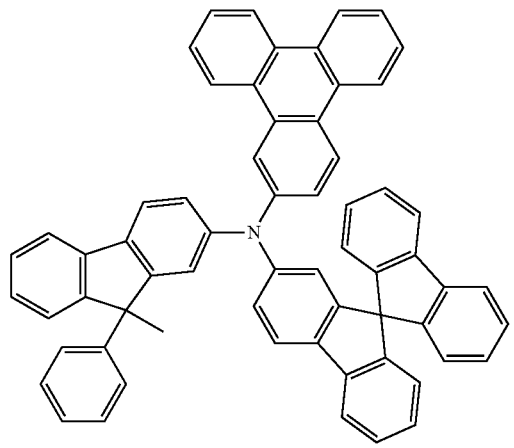
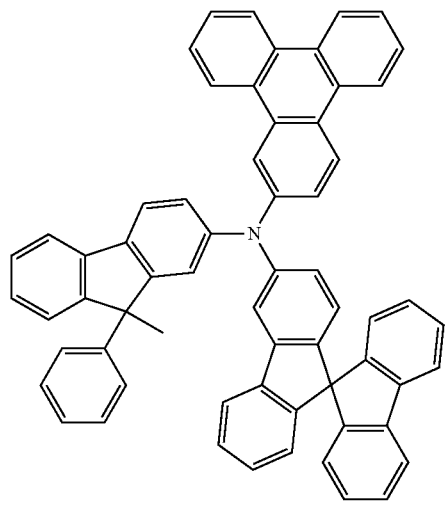
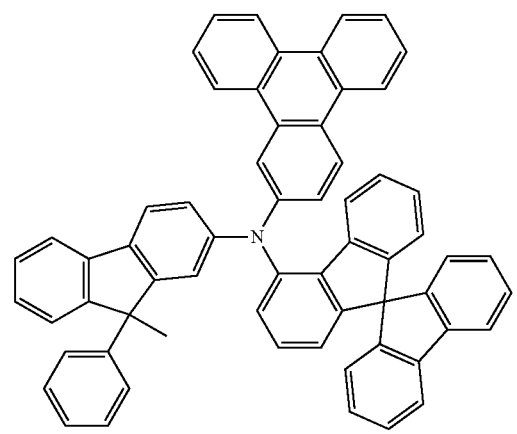
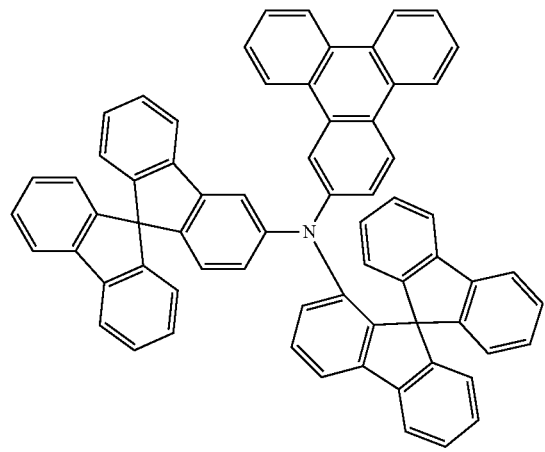
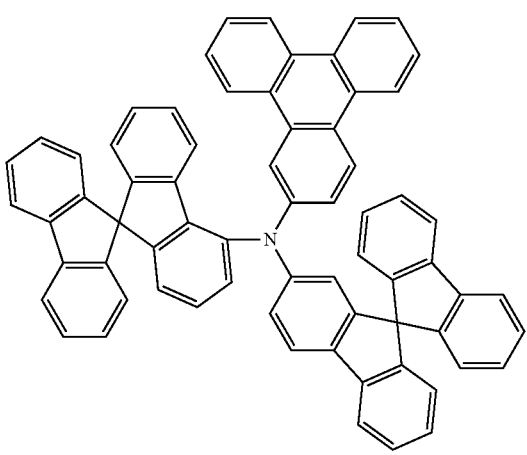

75
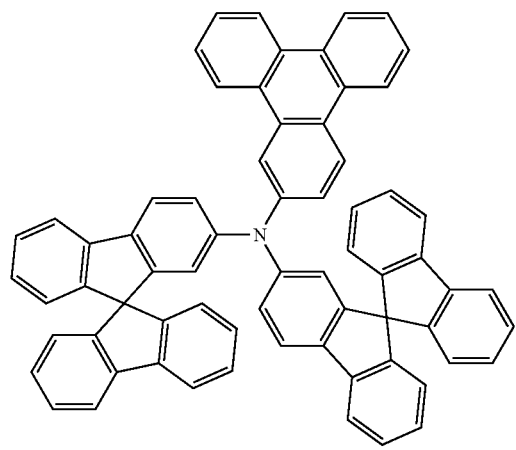
76
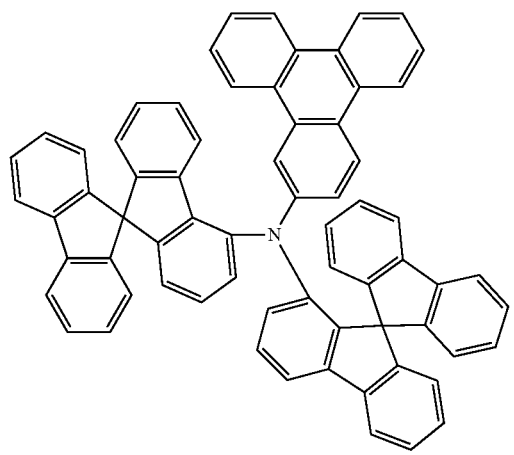
-continued
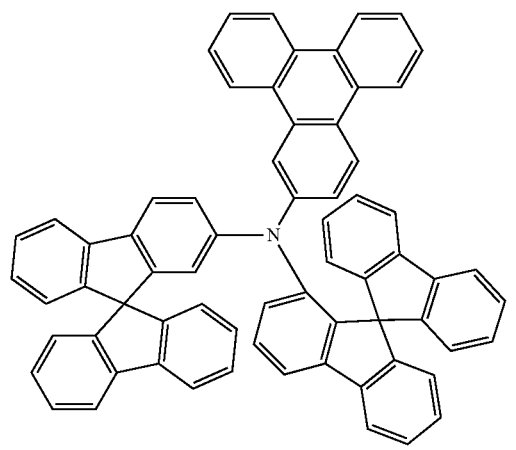
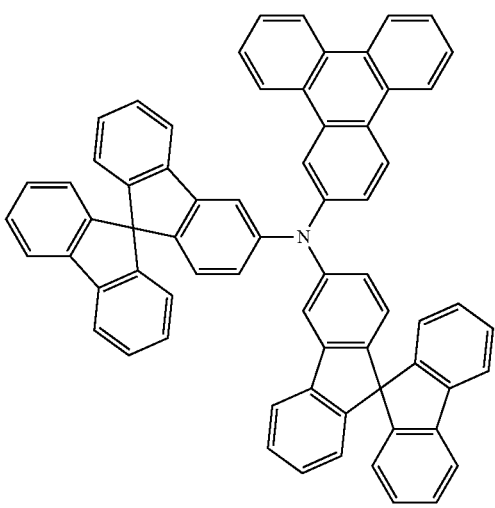
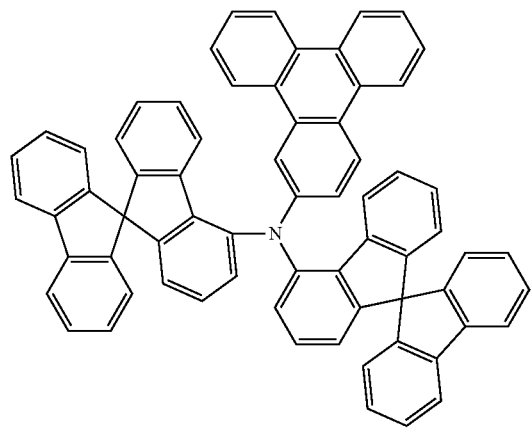
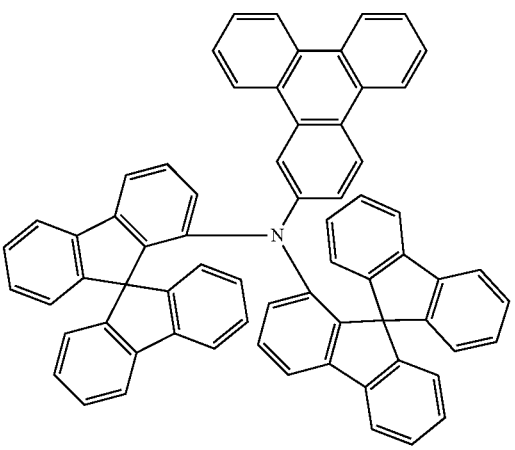

-continued
77
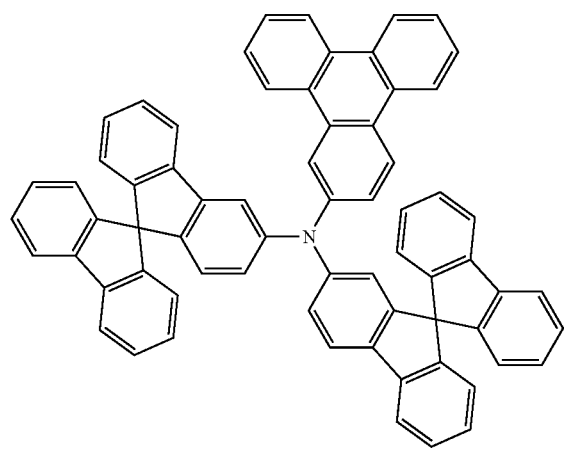
78
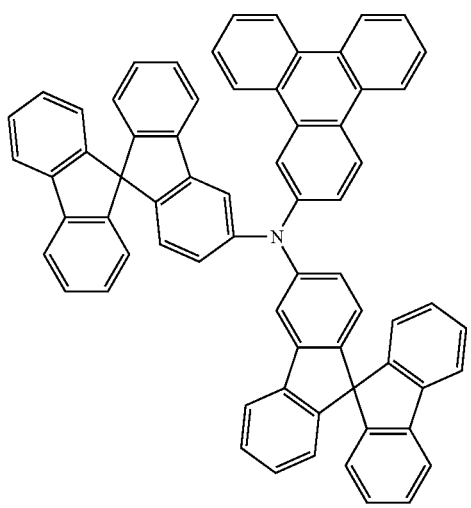
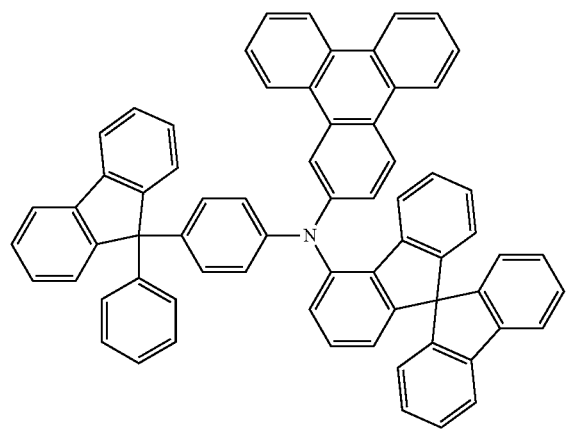
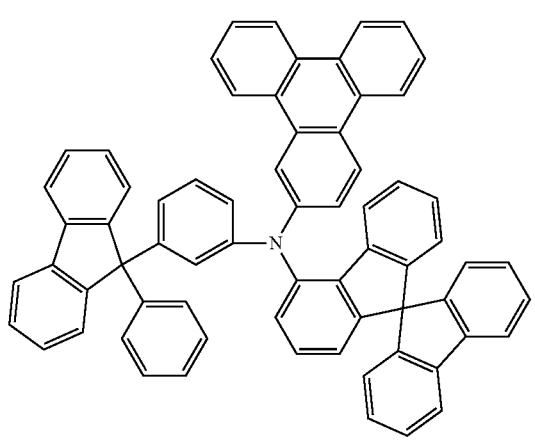
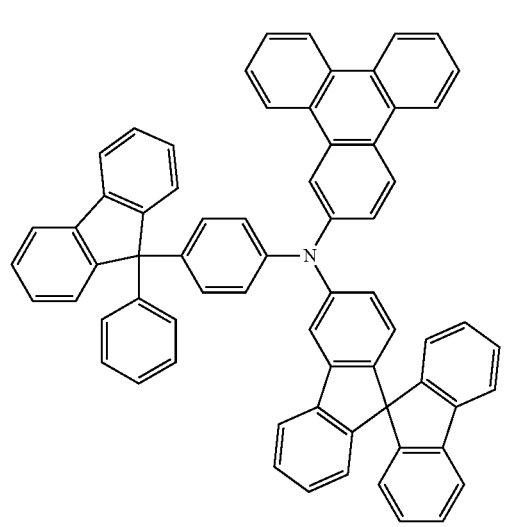
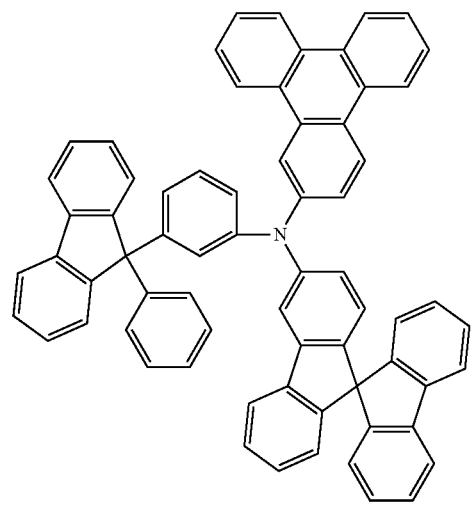

-continued
| 79 | 80 |
|---|---|
| 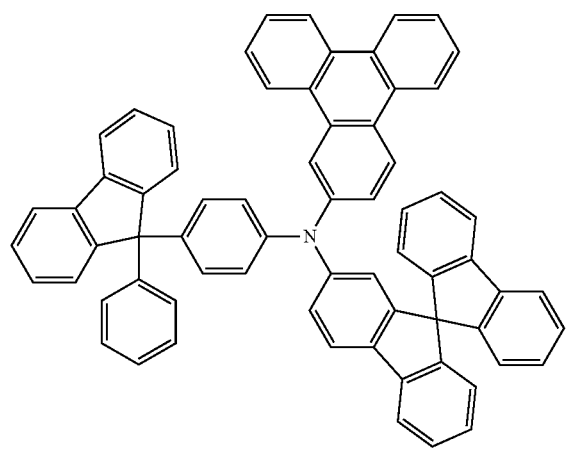 | 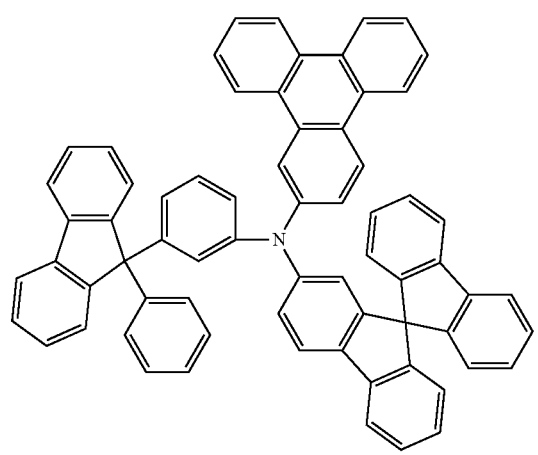 |
| 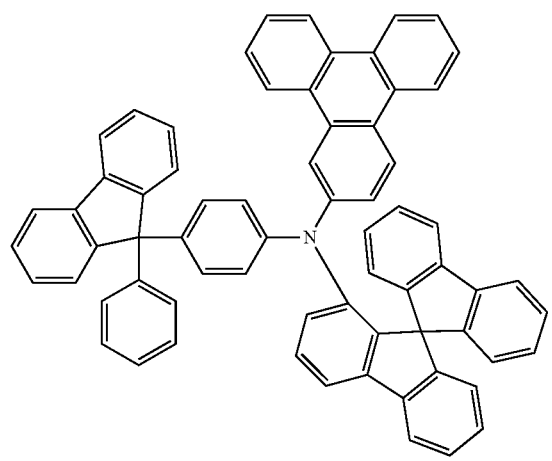 | 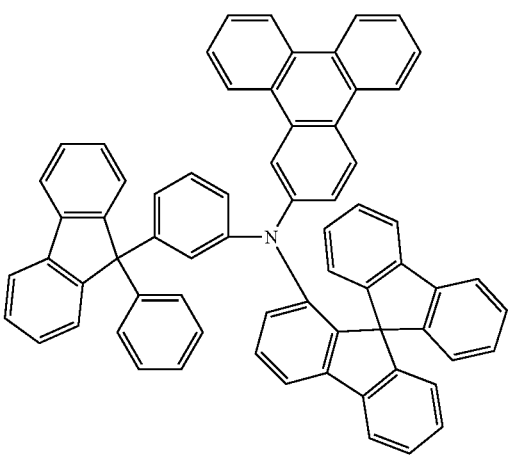 |
| 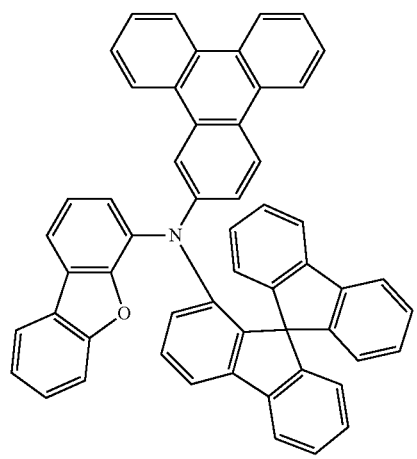 | 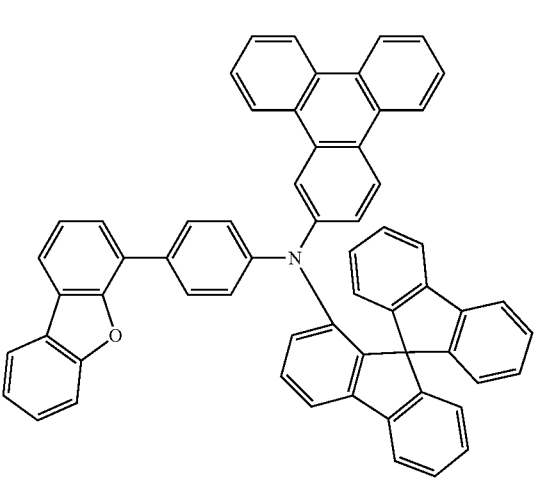 |

81
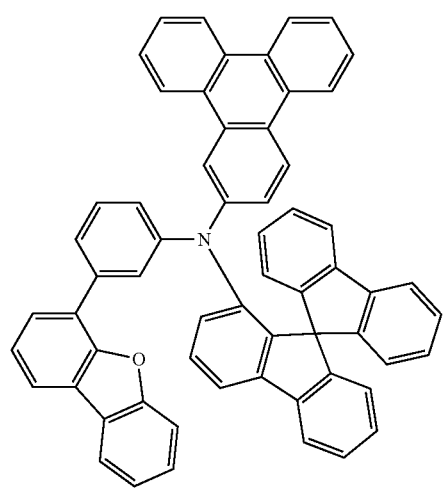
82
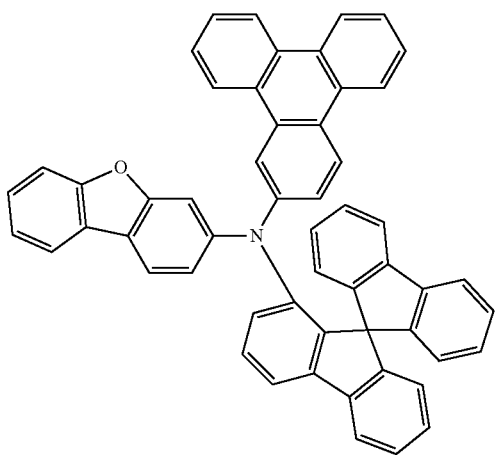
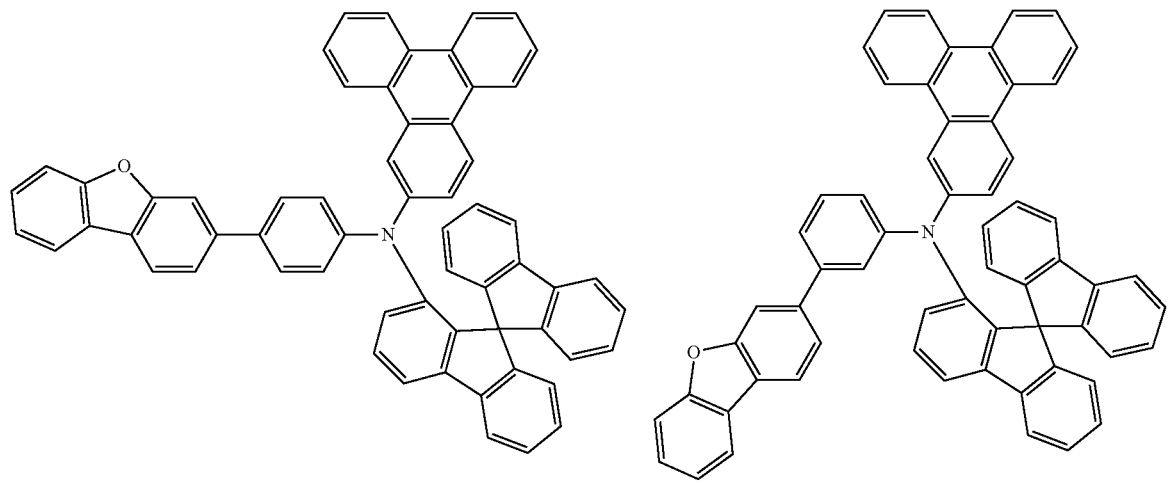
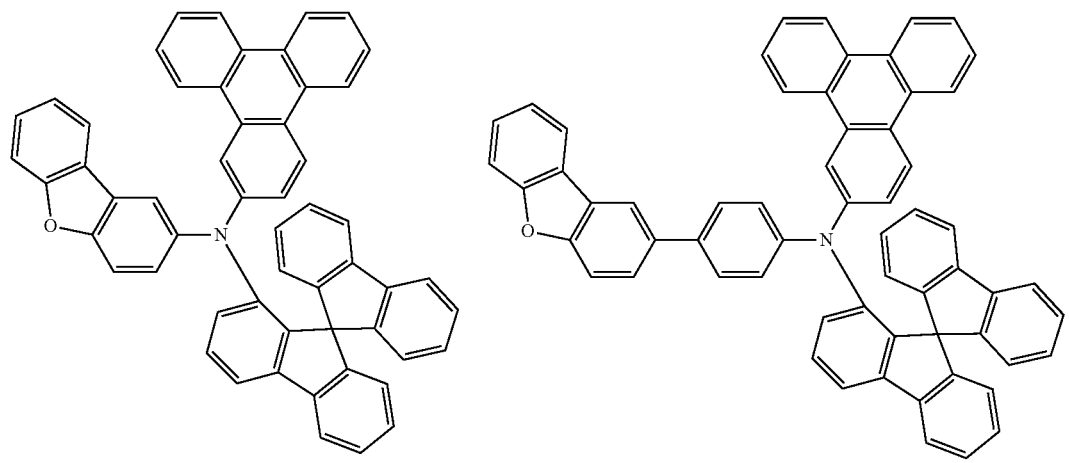

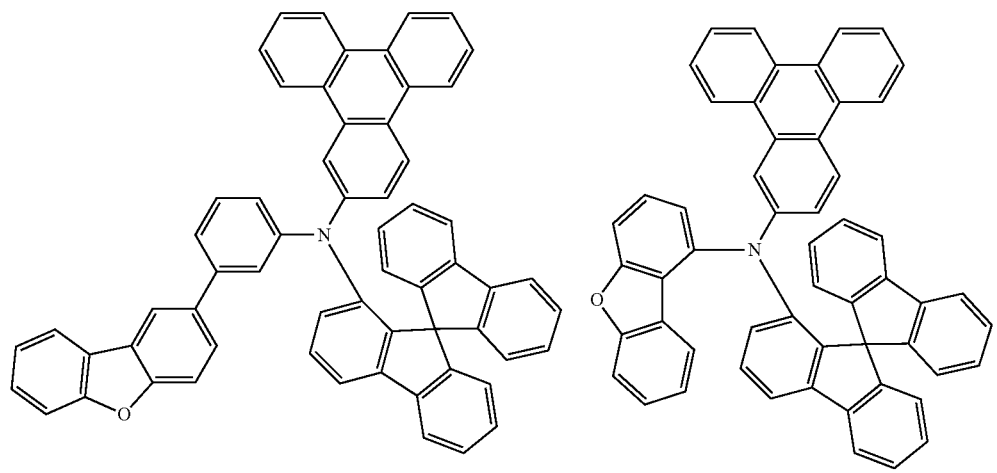
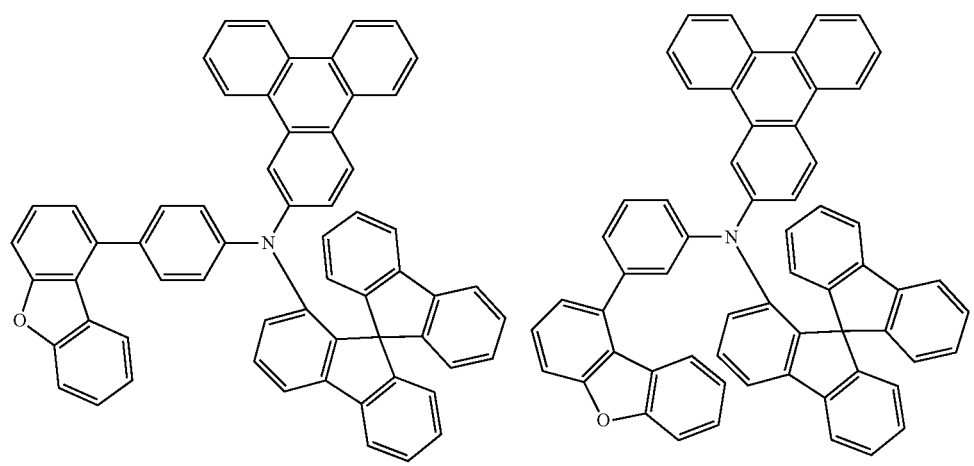
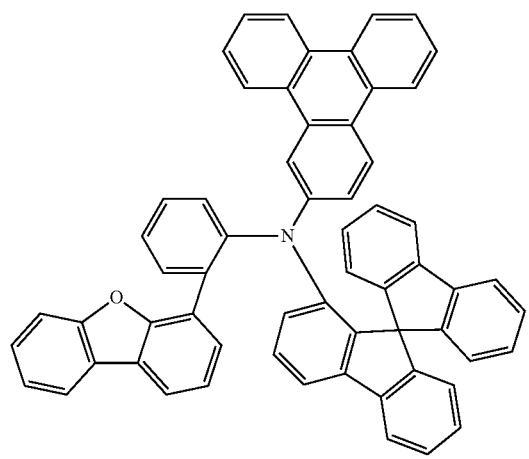

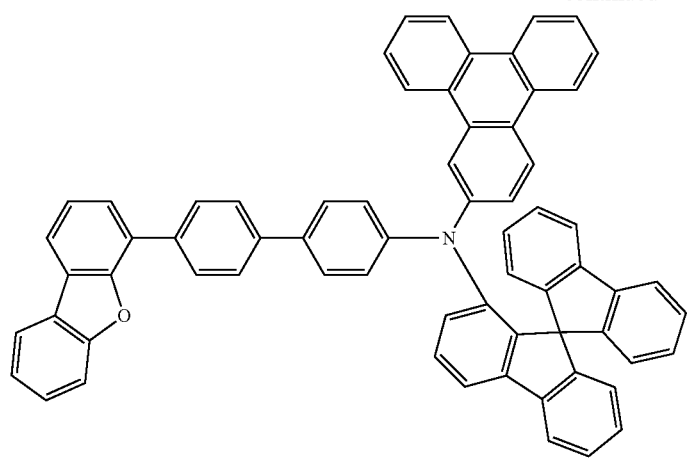
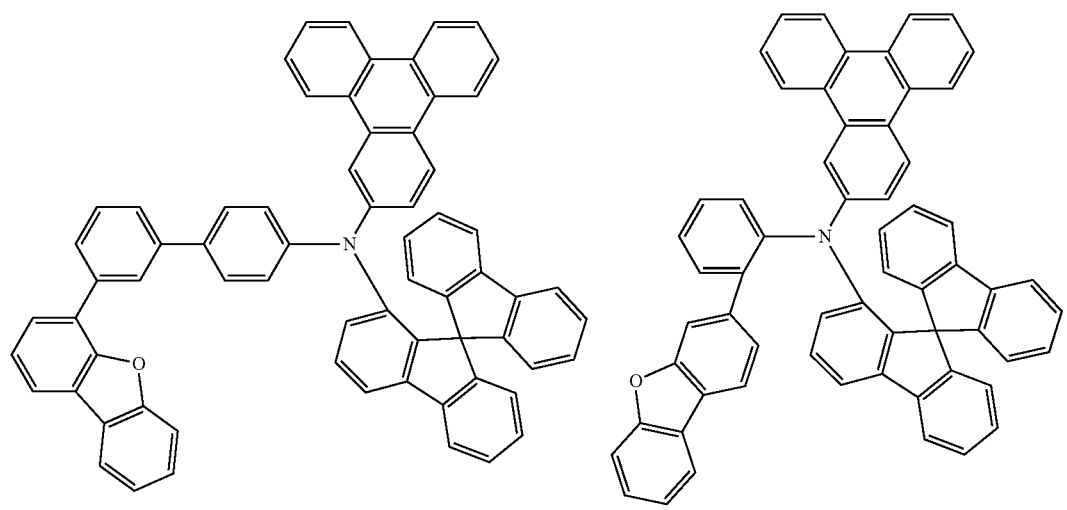
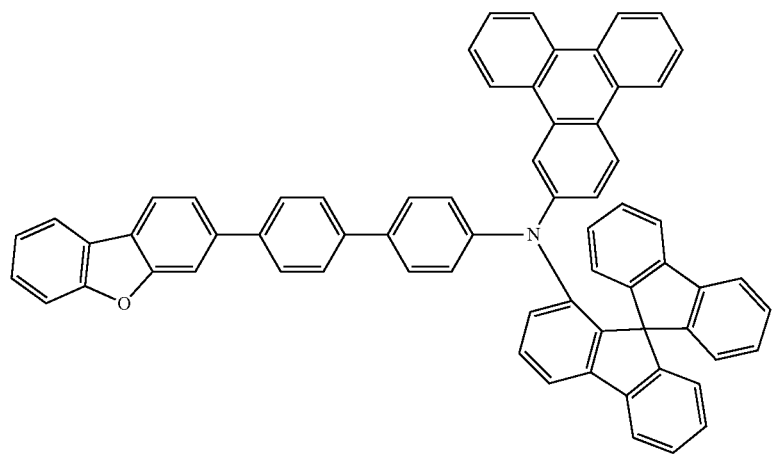

87 88
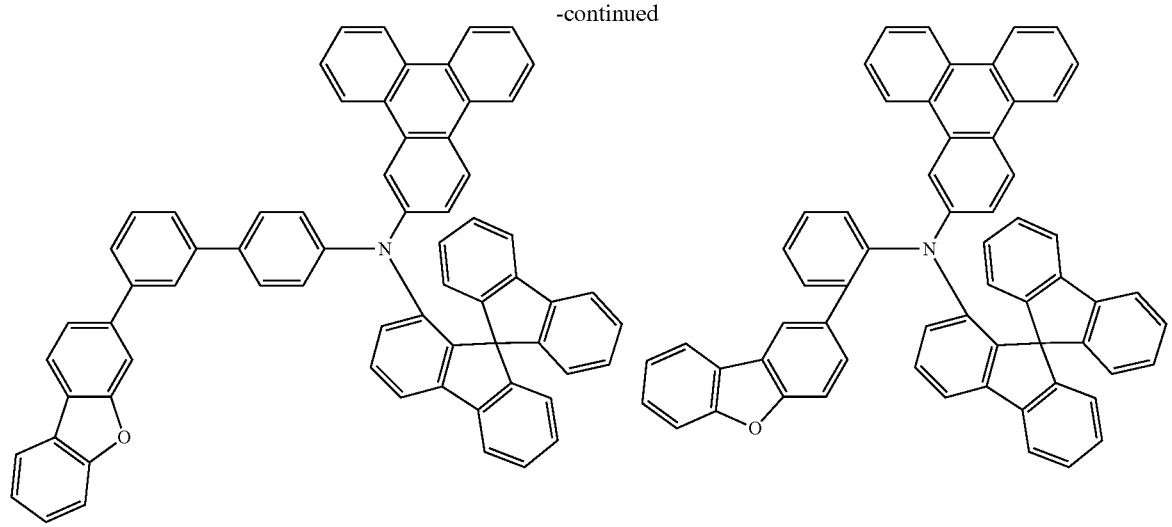
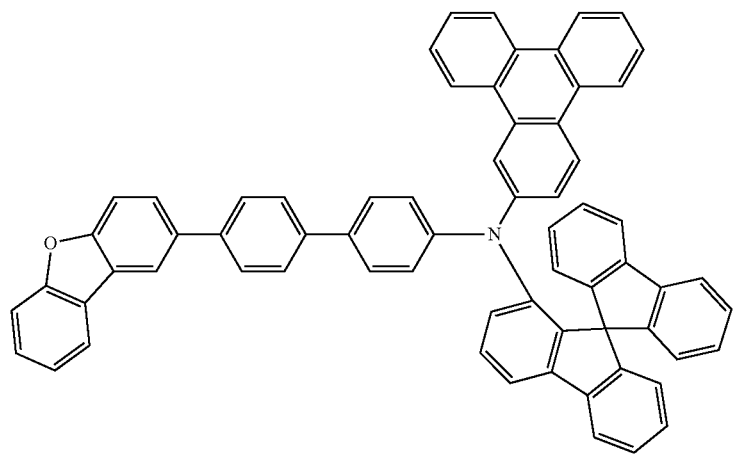
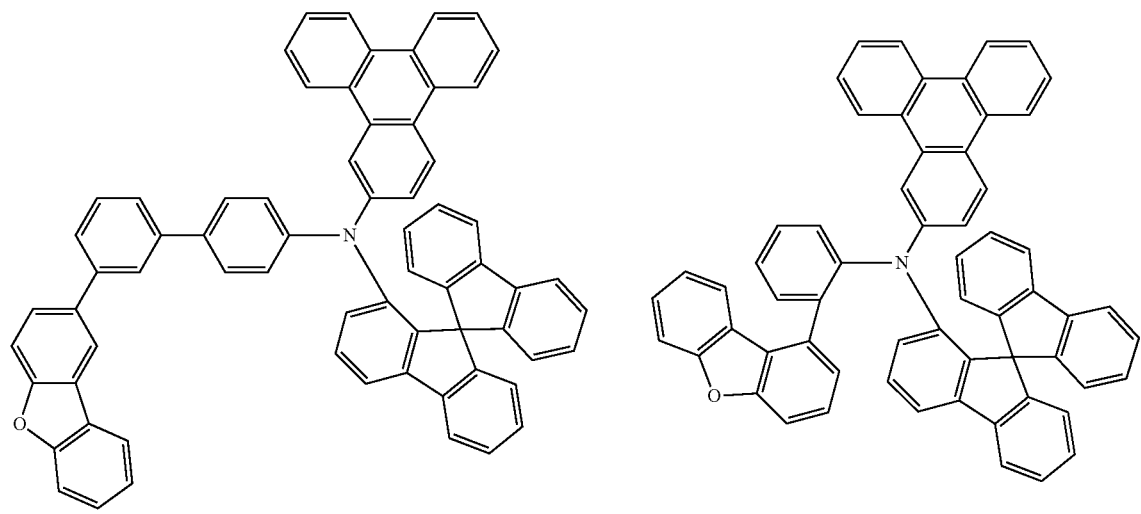

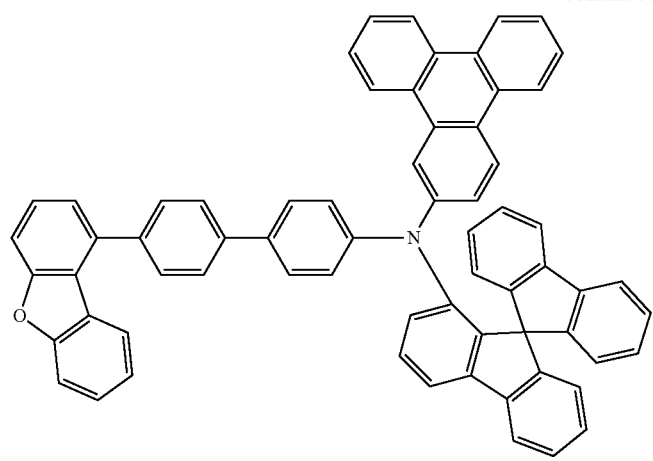
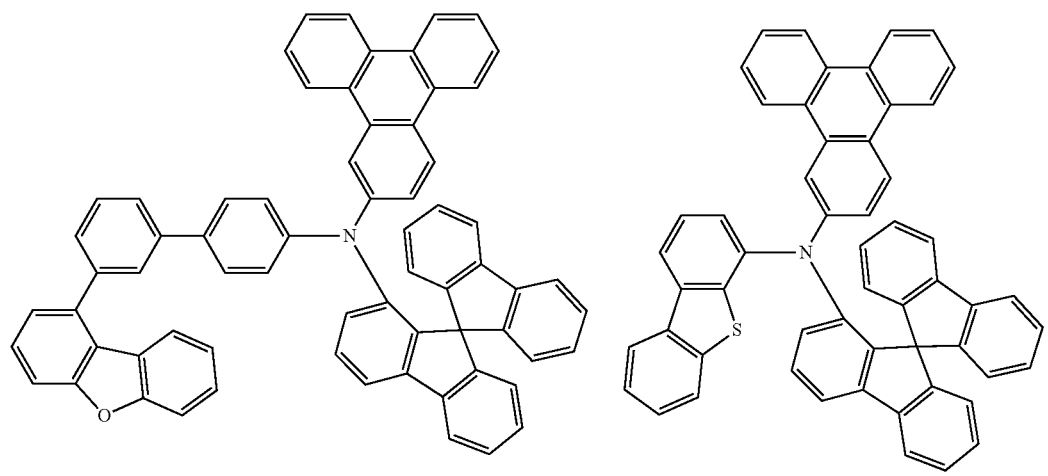
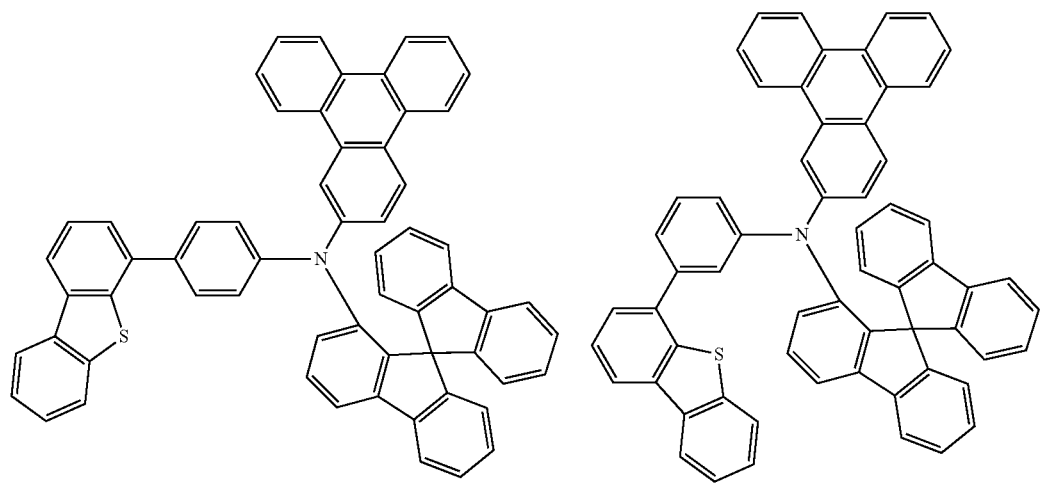

-continued
91
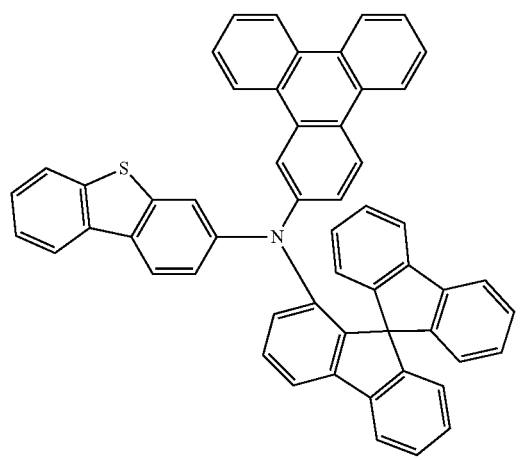
92
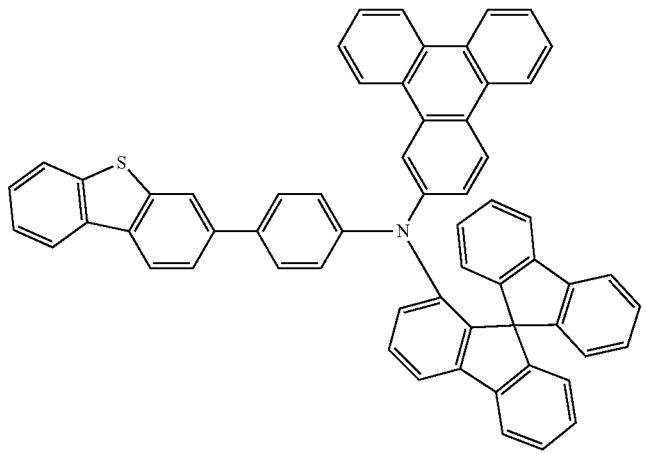
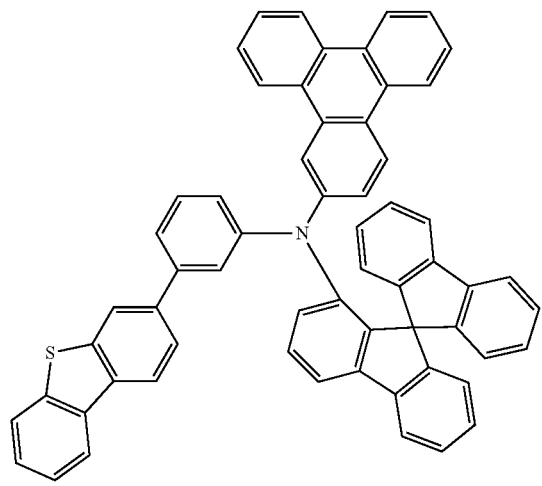
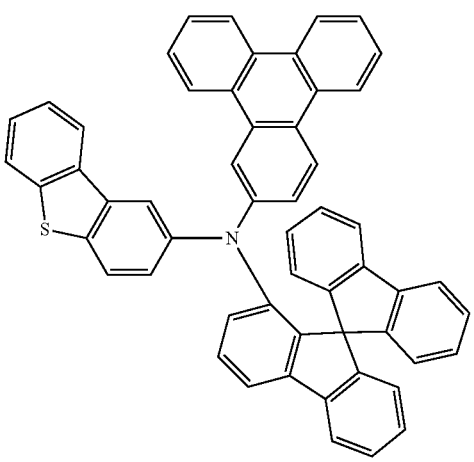
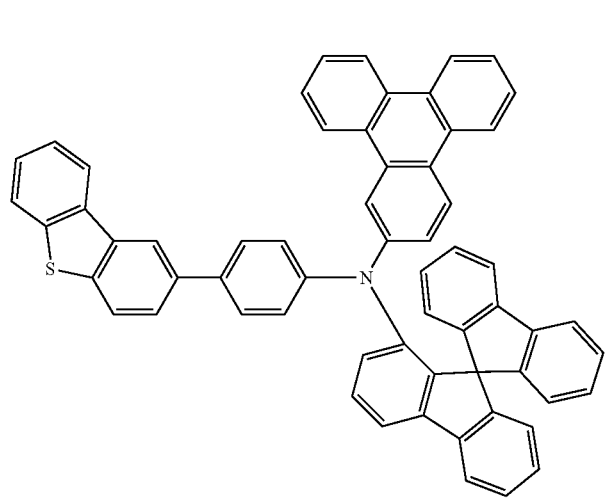
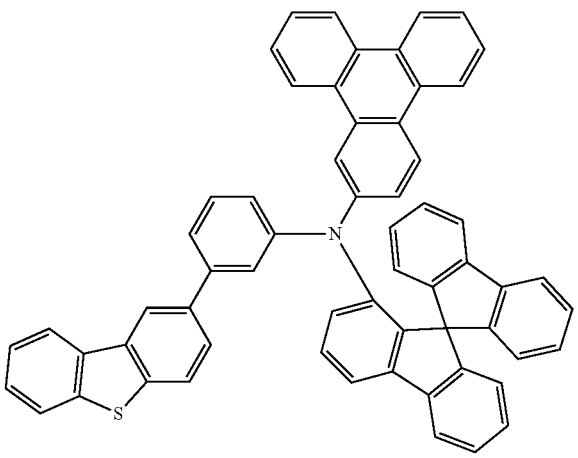

-continued
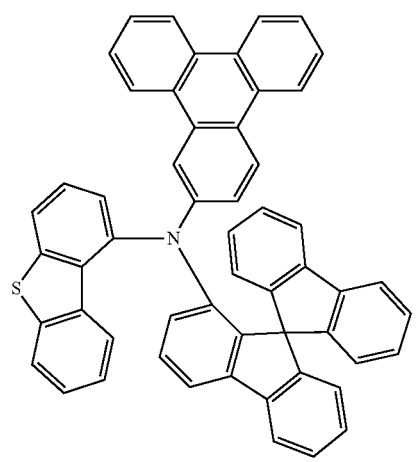
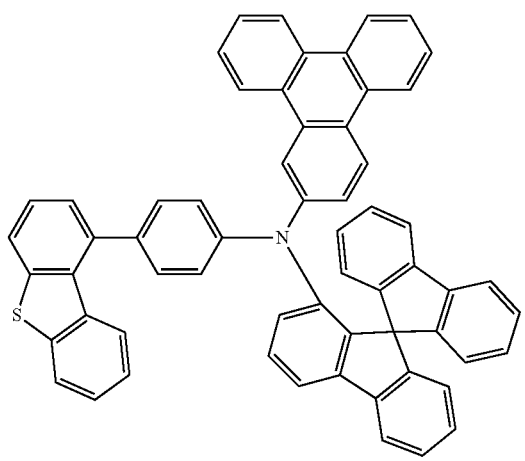
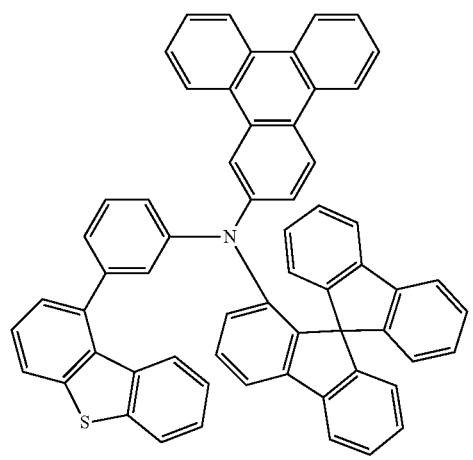
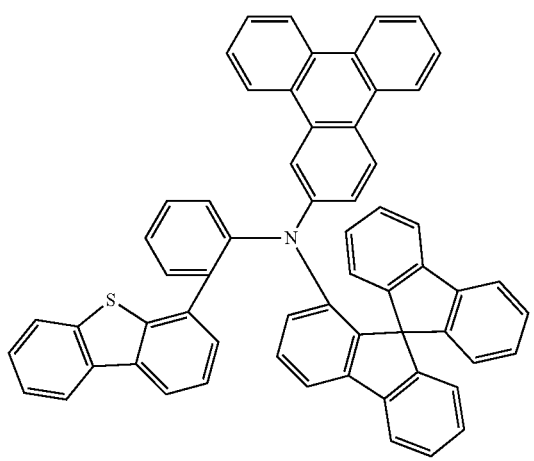
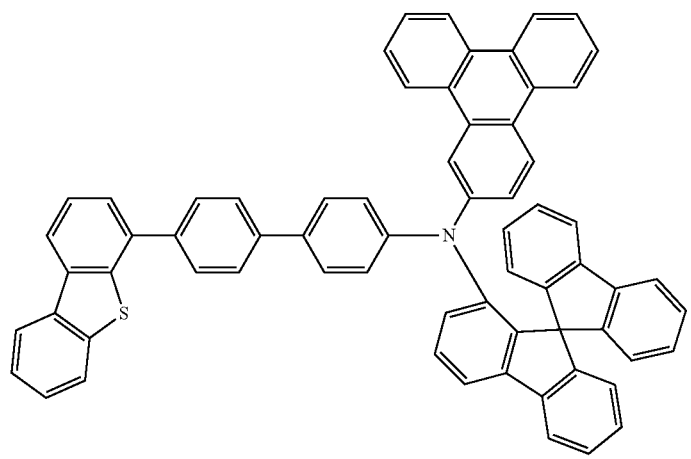

95 96
-continued
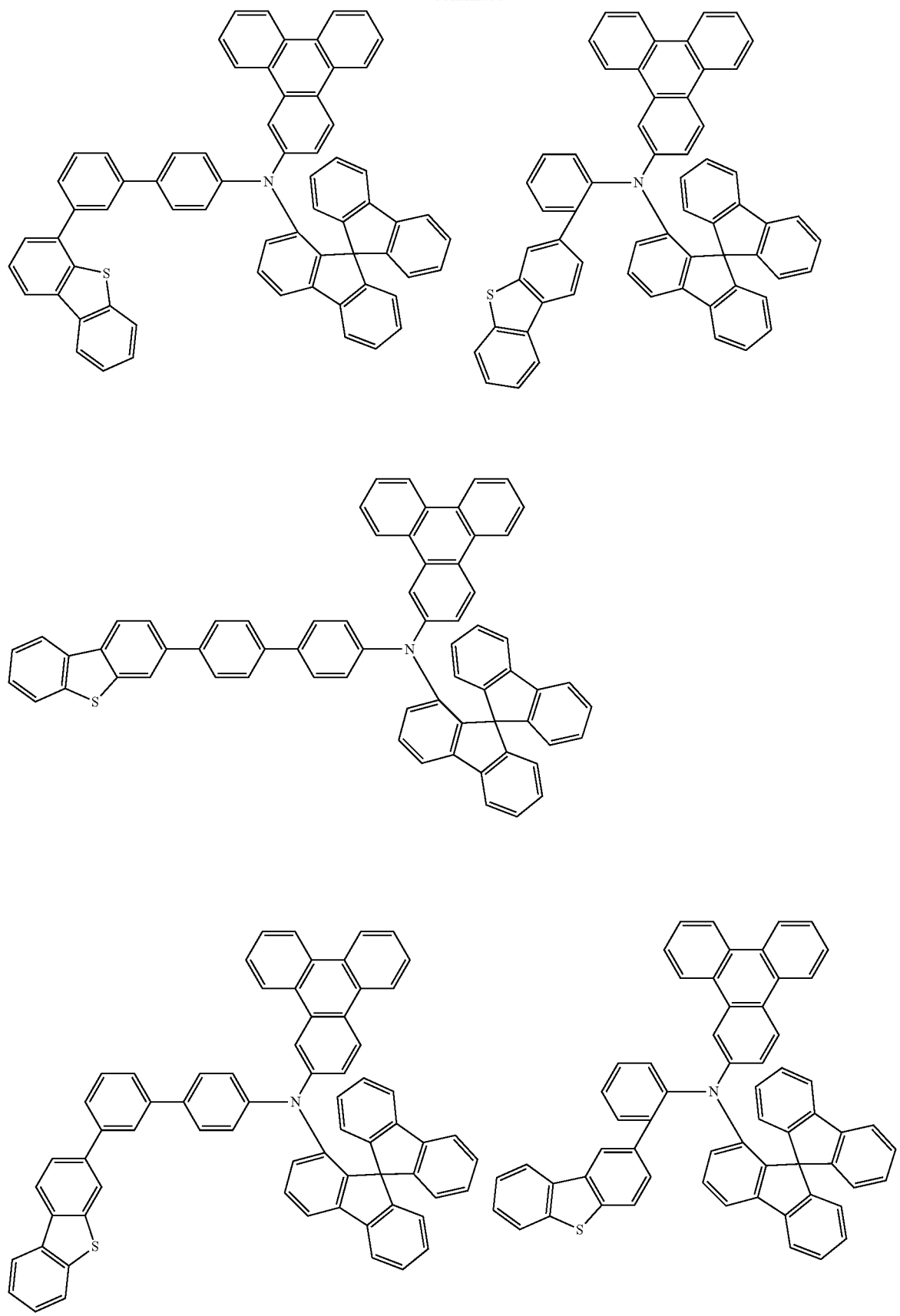

-continued
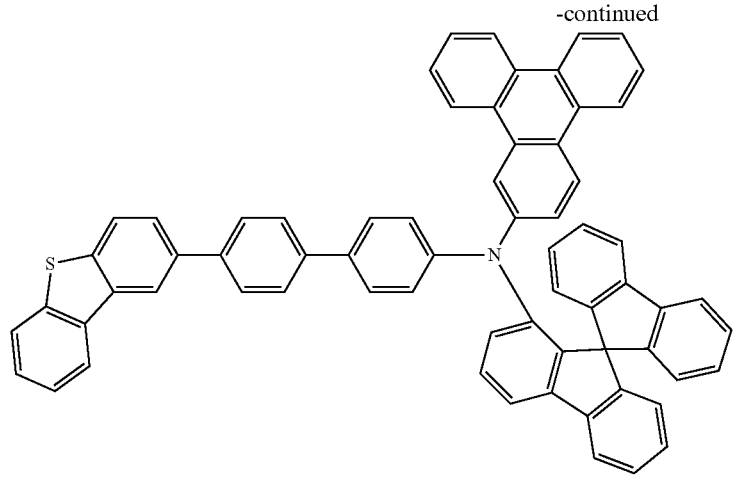
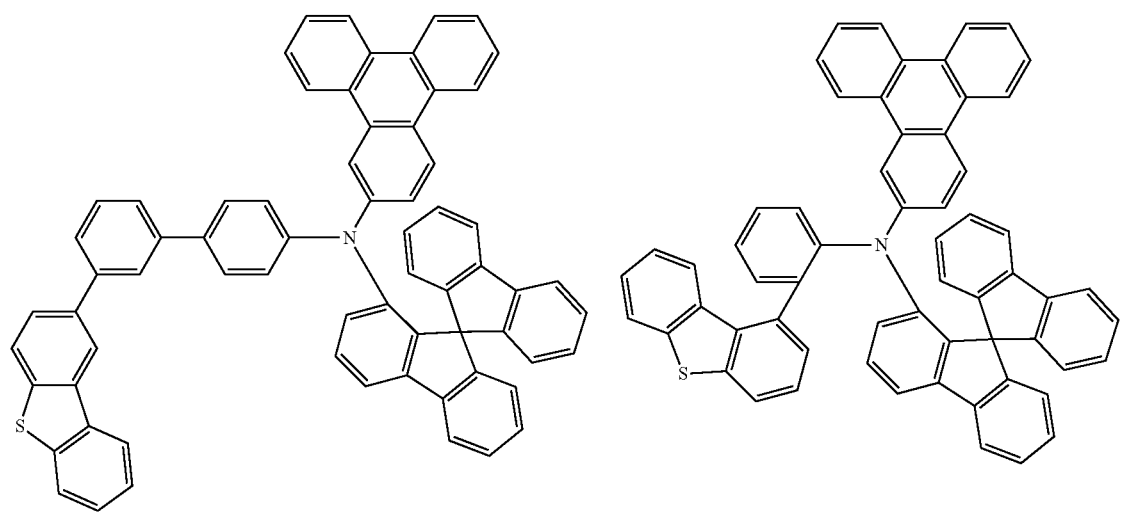
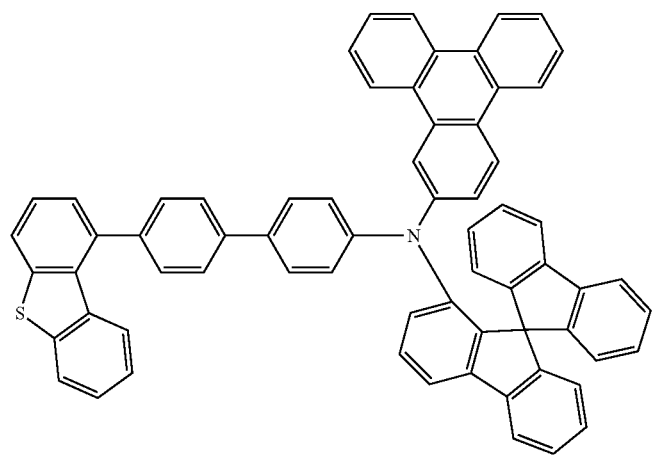

99 100
-continued
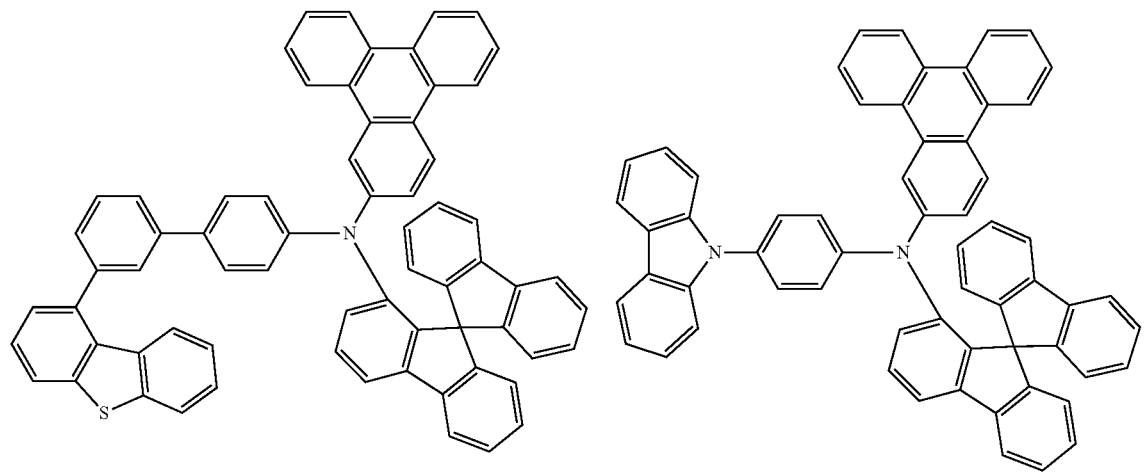
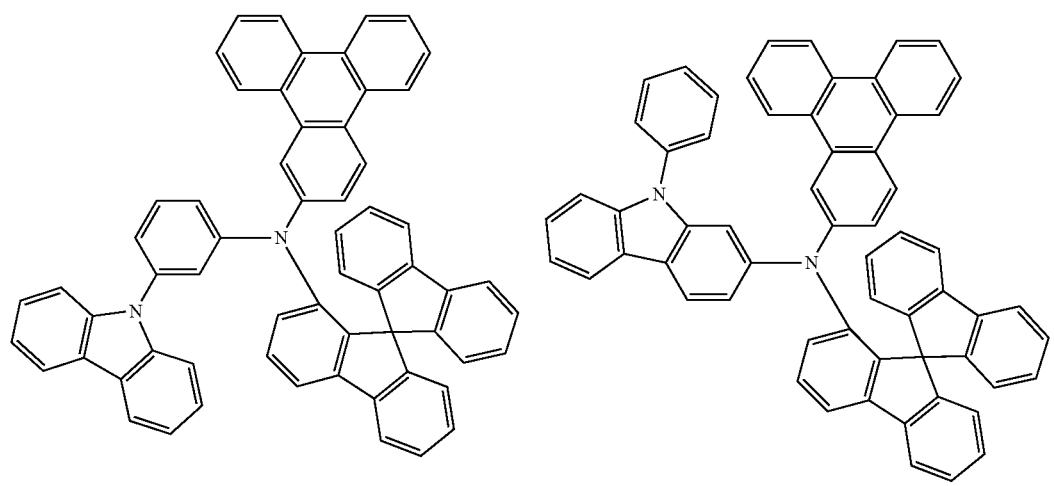
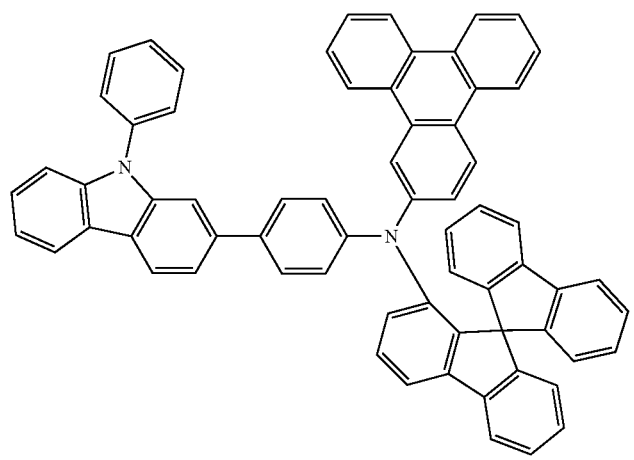

-continued
101 102
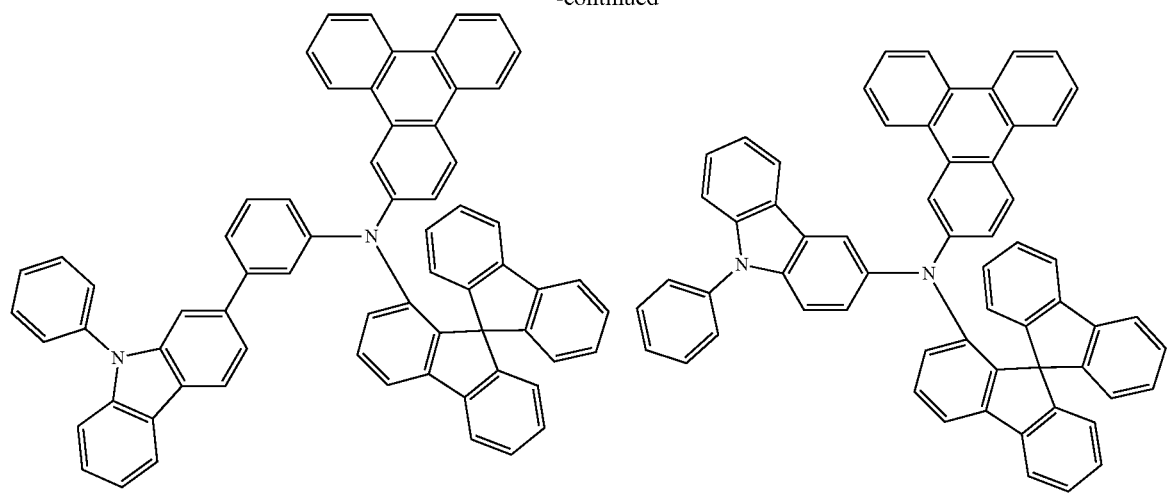
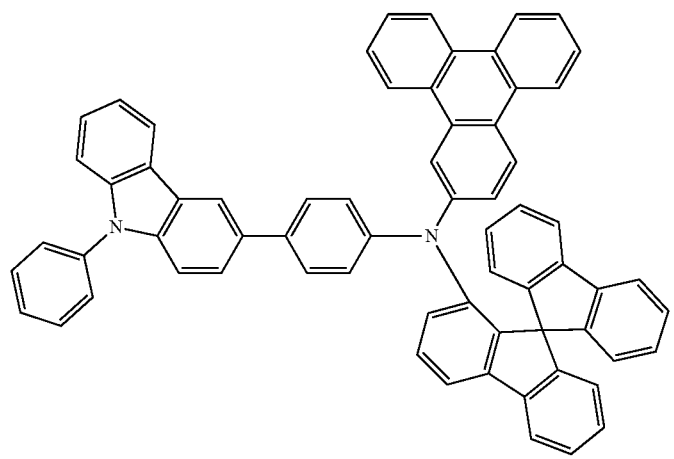
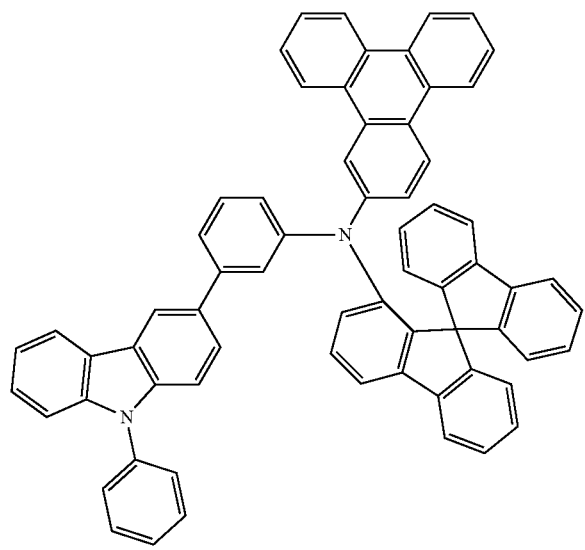

-continued
103                                                104
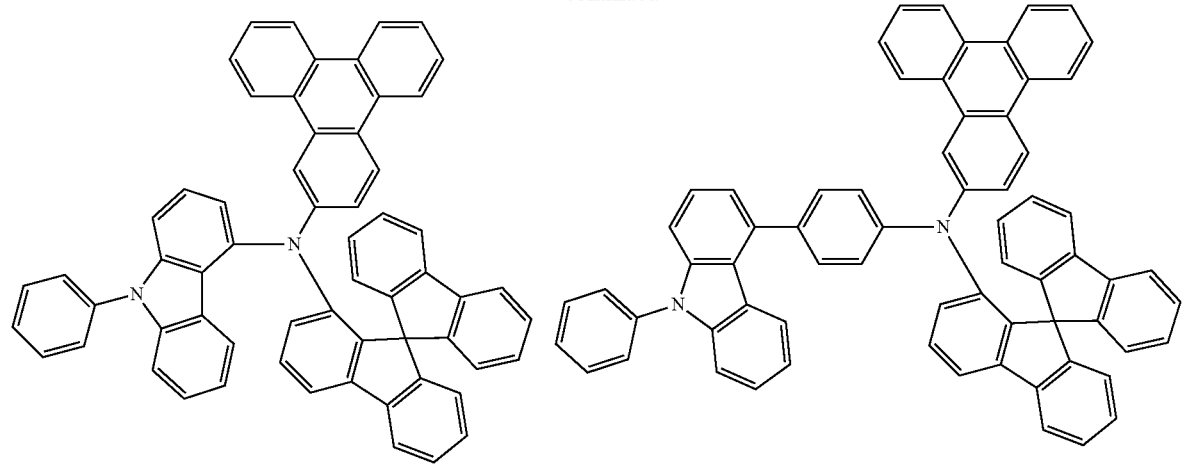
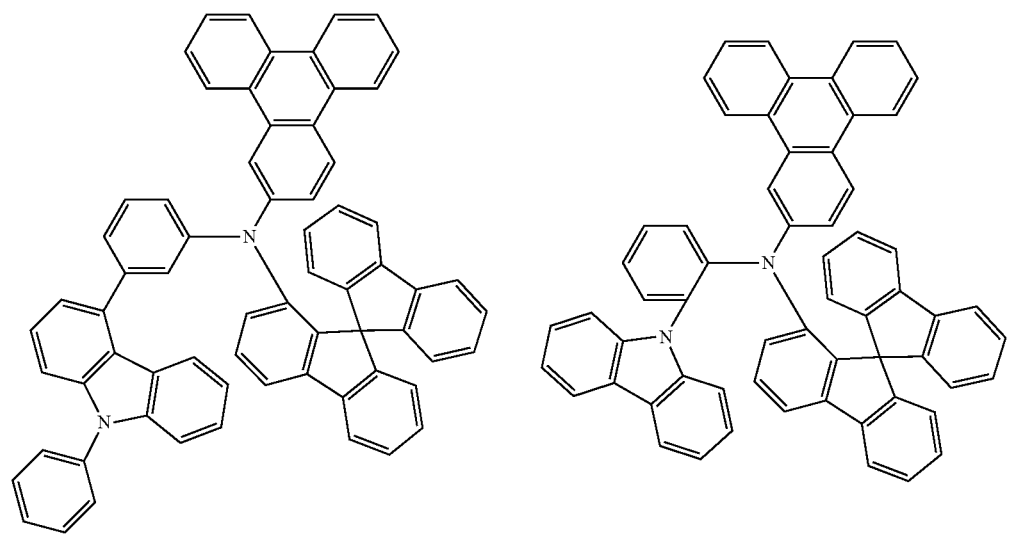
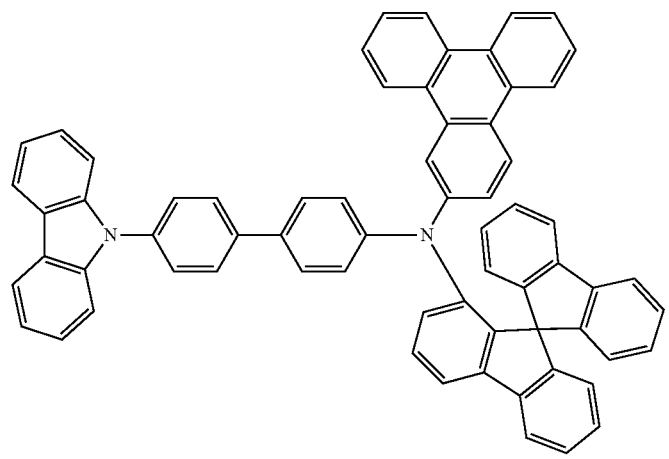

105 106
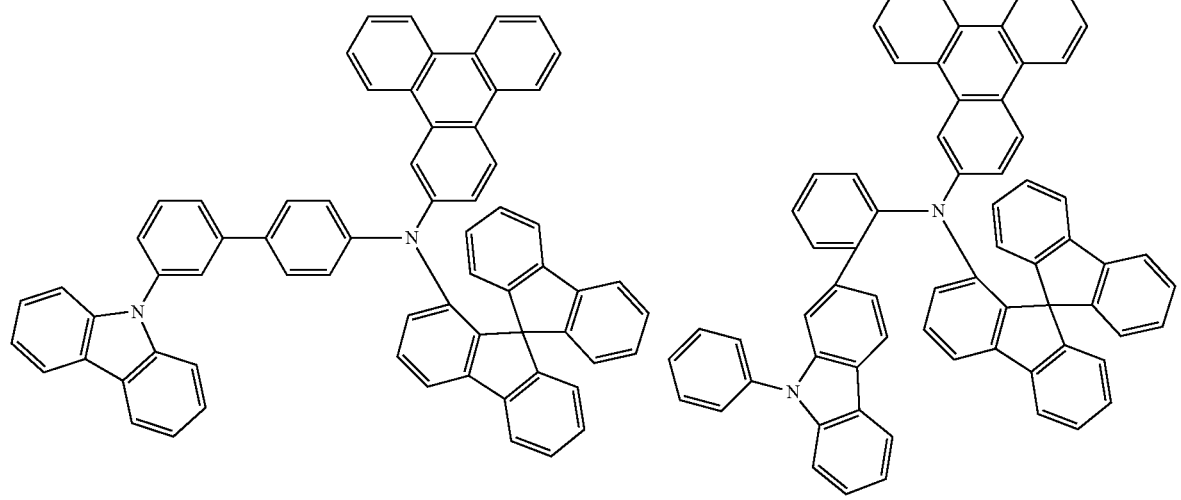
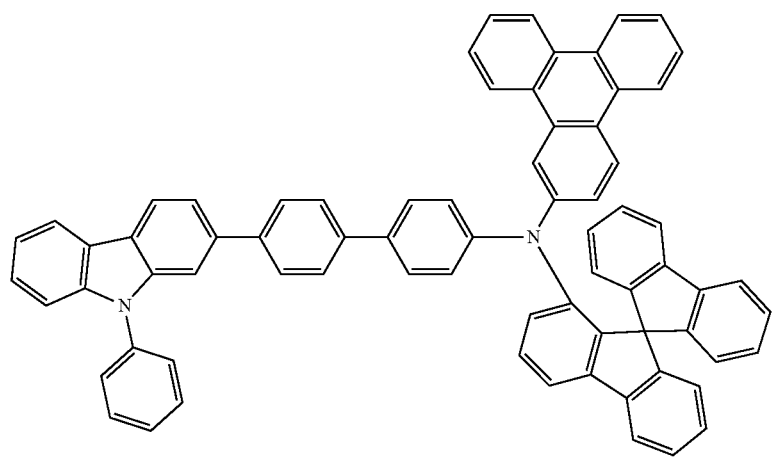
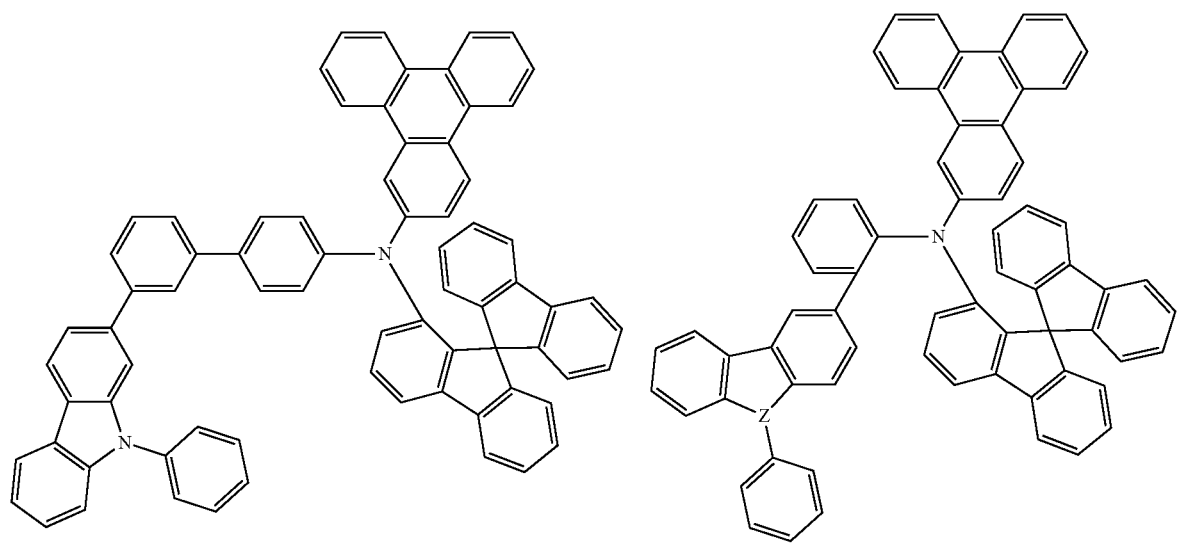

-continued
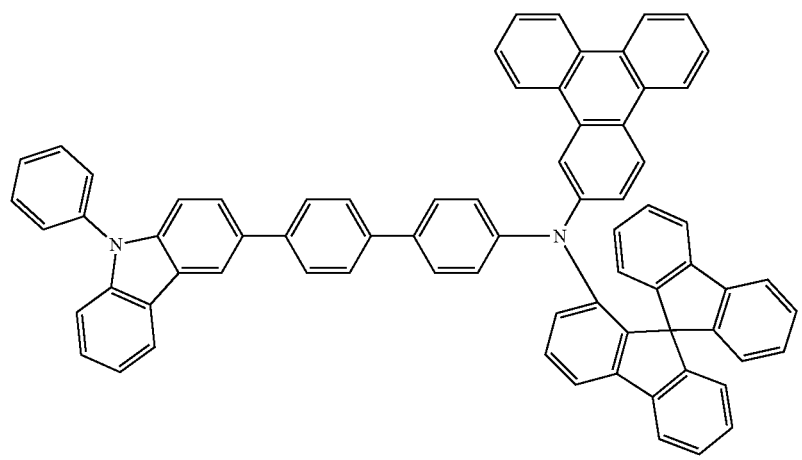
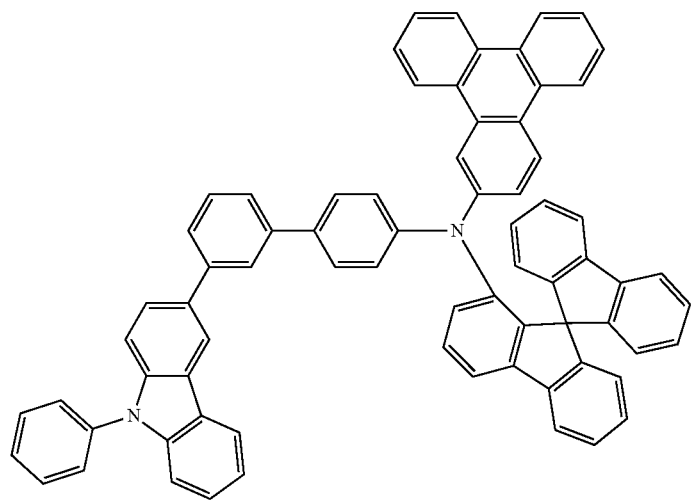
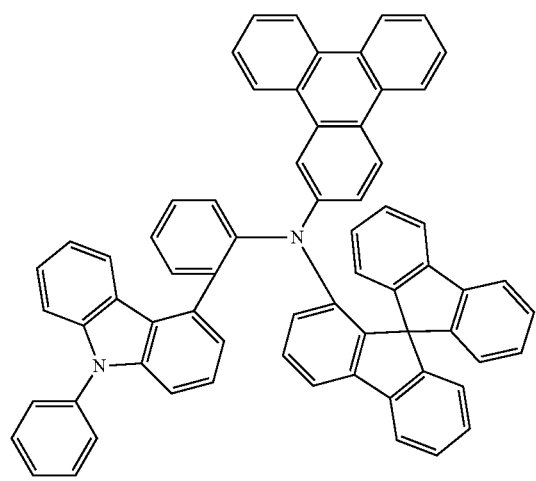

-continued
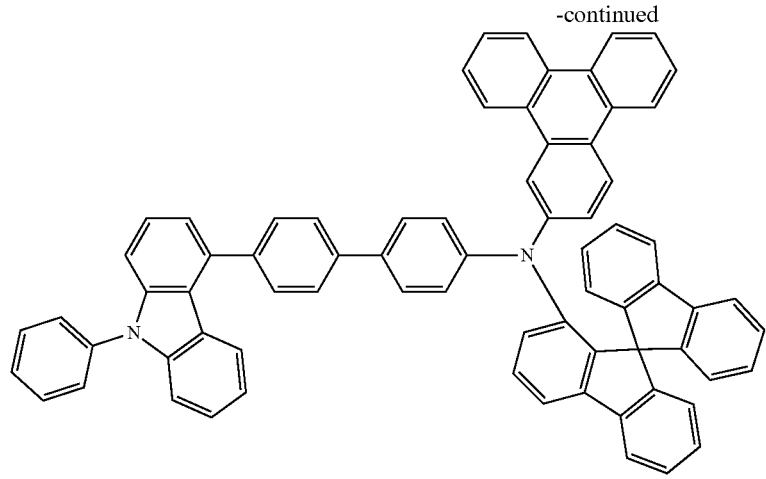
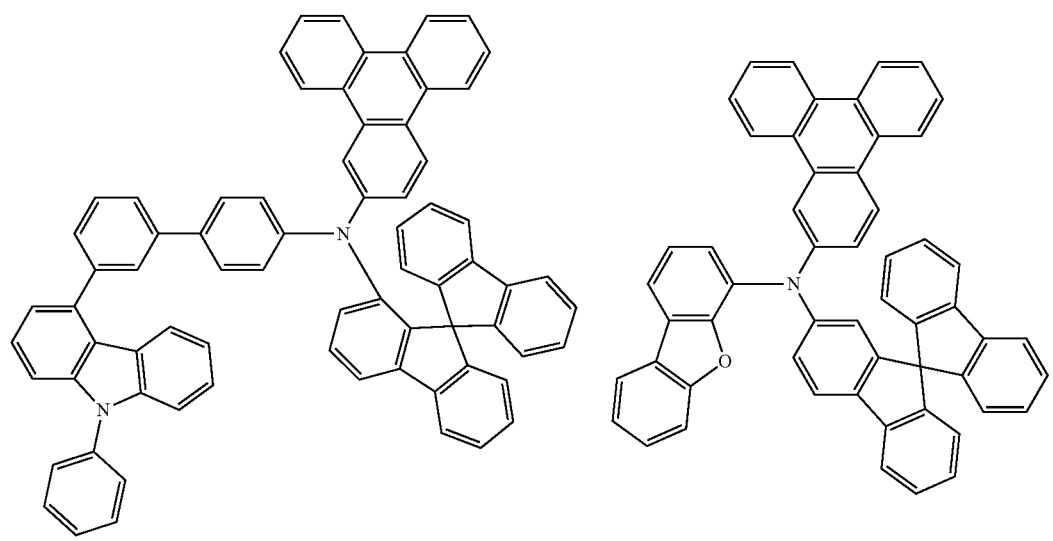
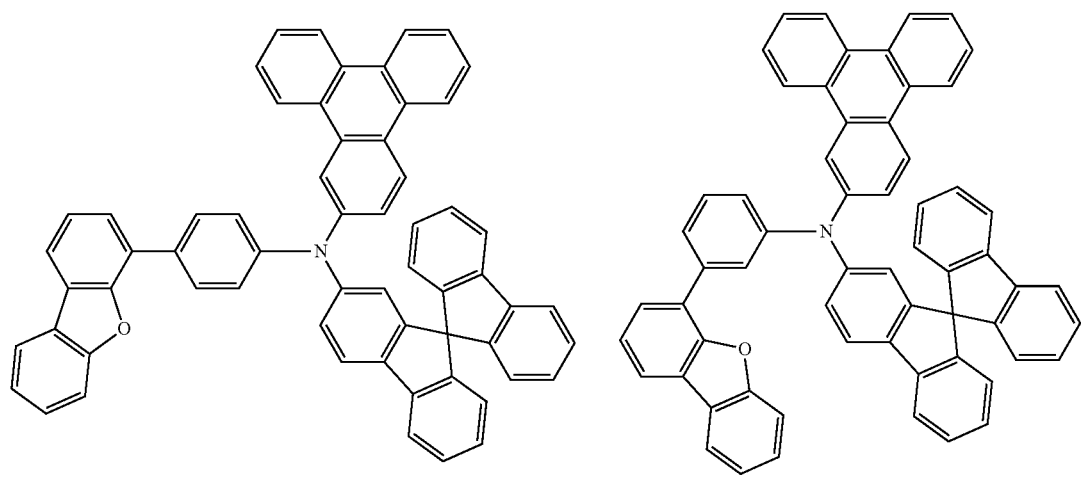

-continued
111
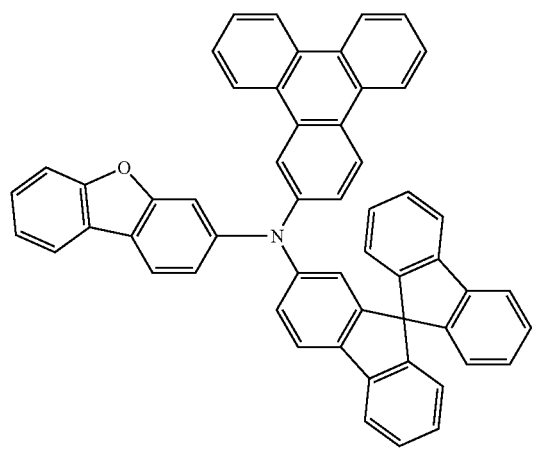
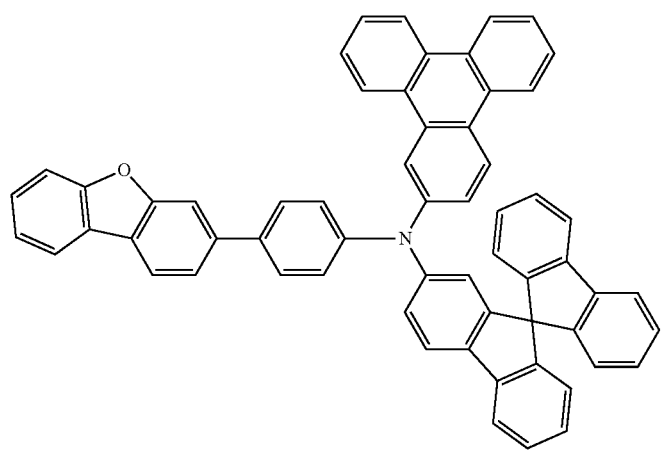
112
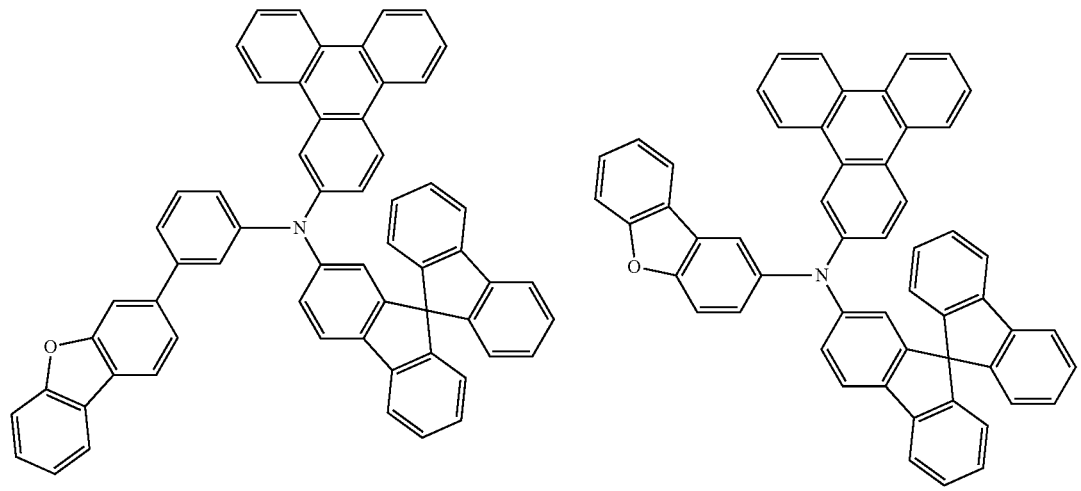

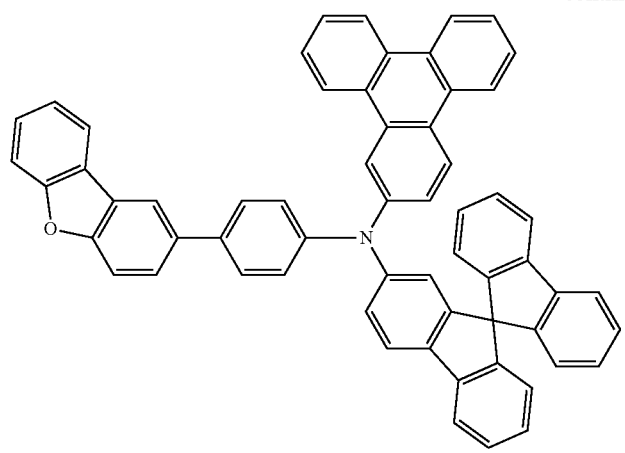
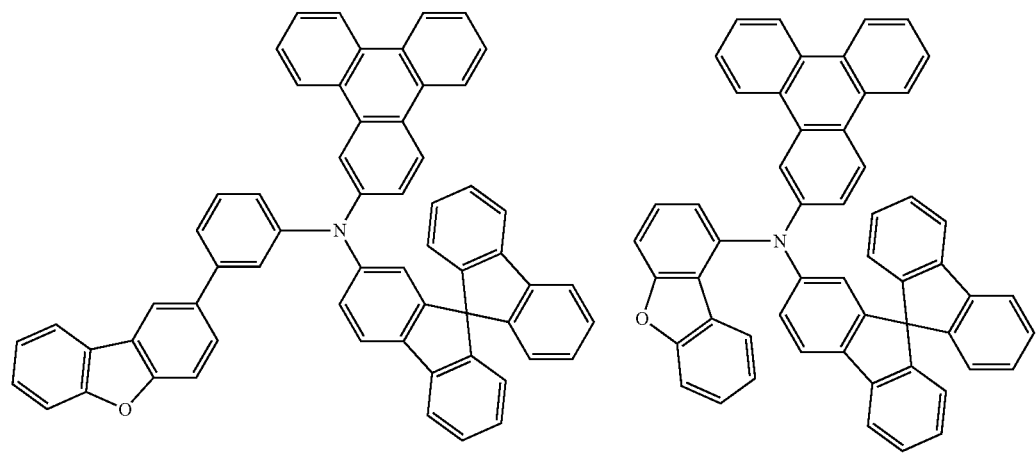
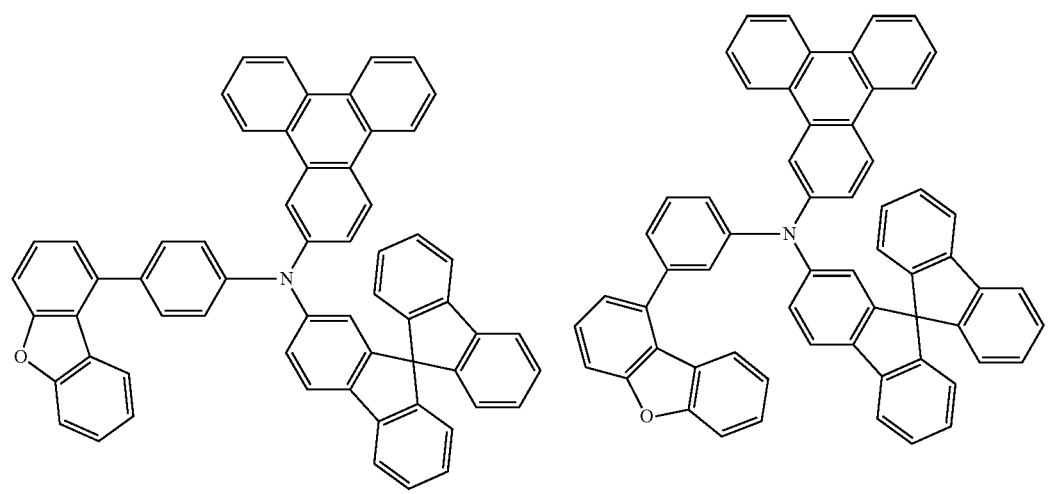

115
116
-continued
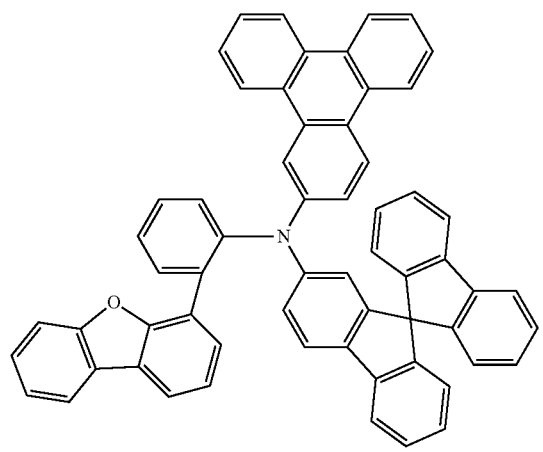
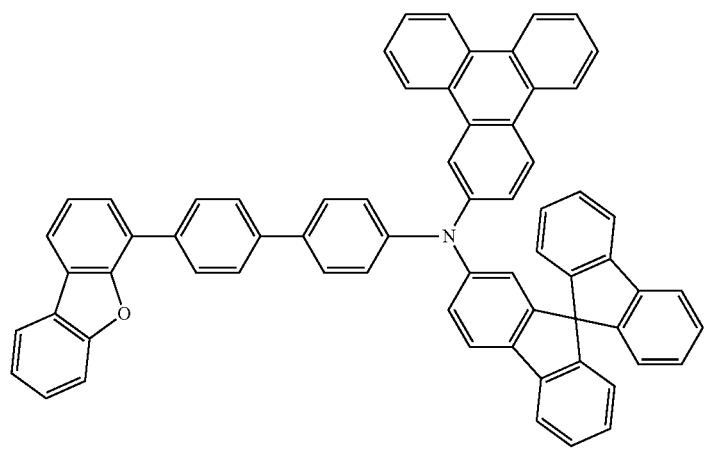
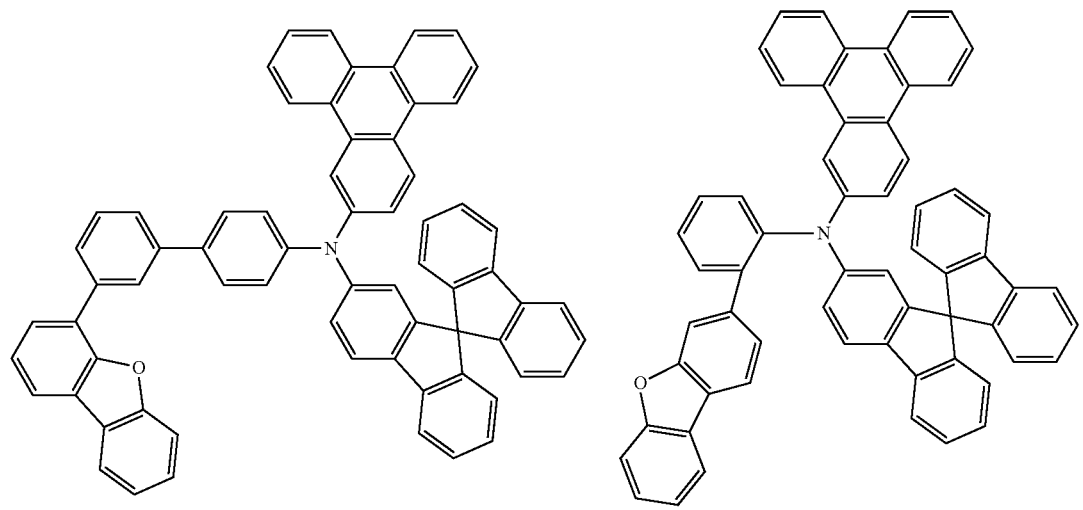

-continued
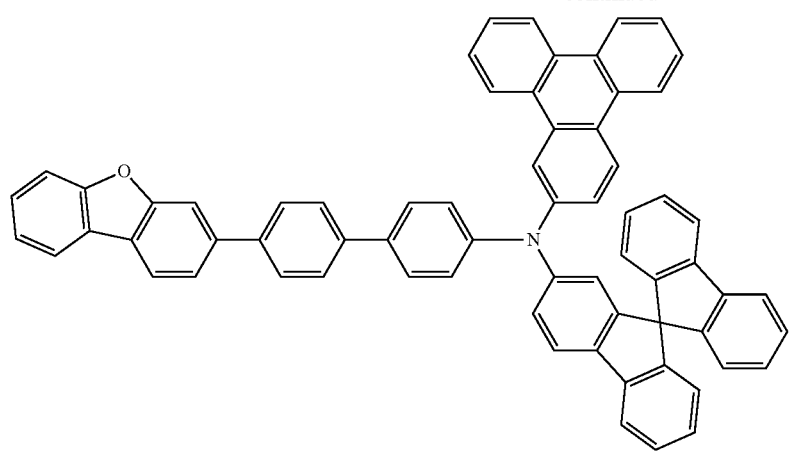
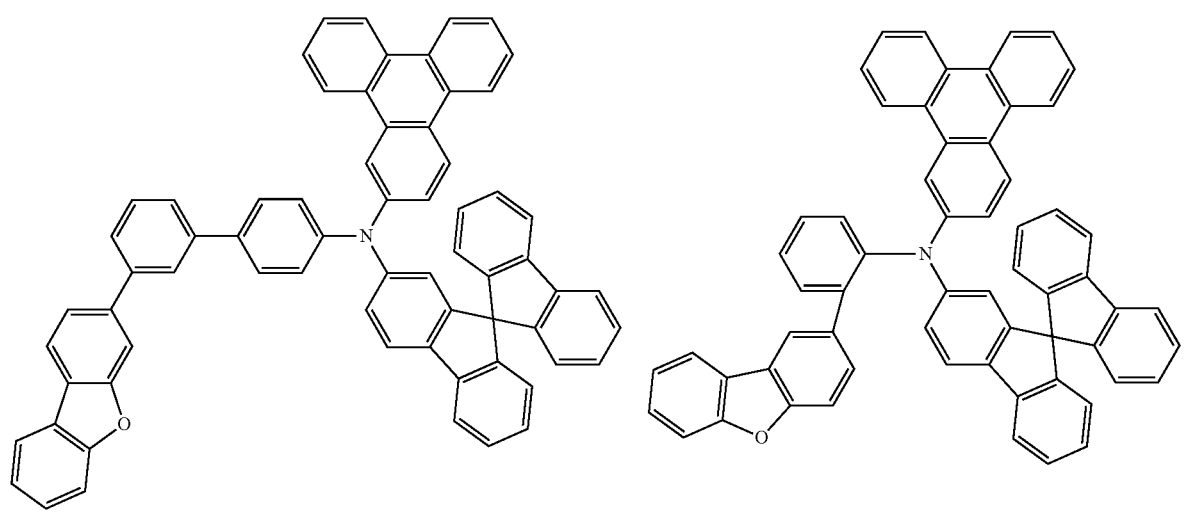
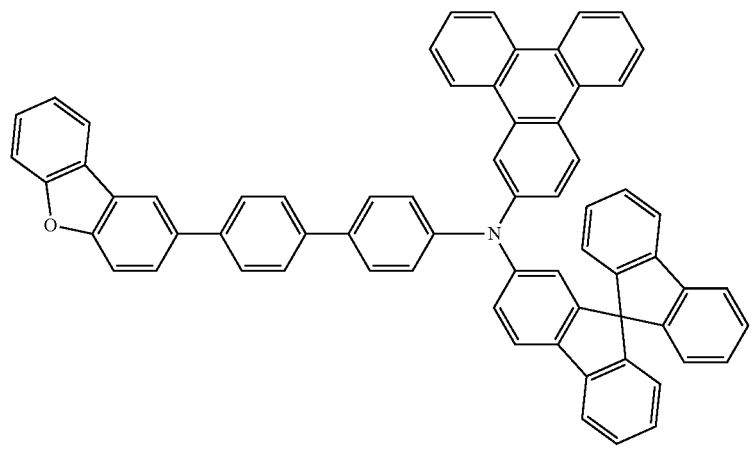

-continued
119
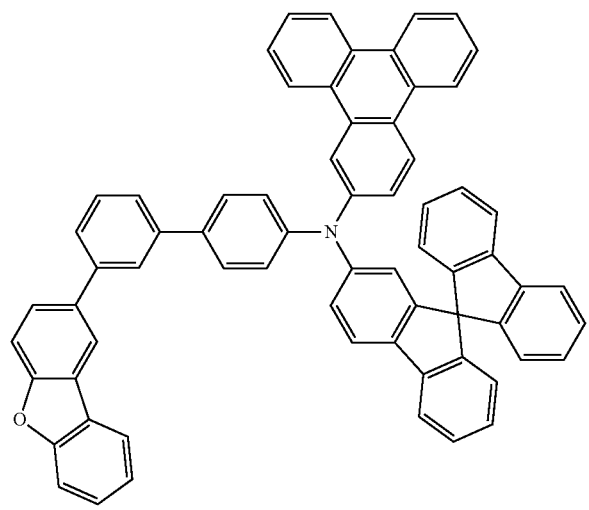
120
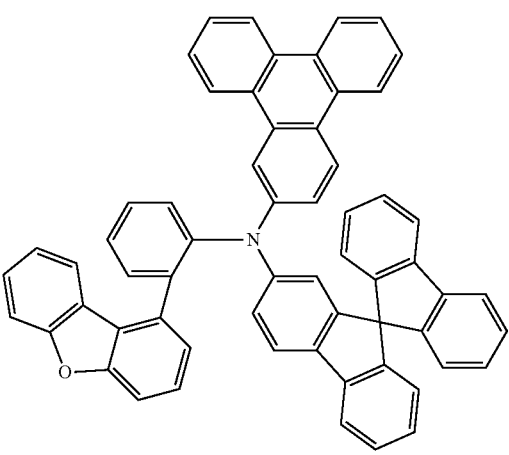
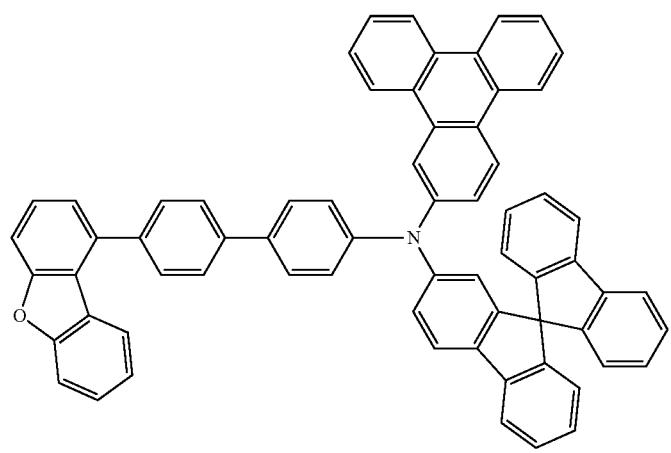
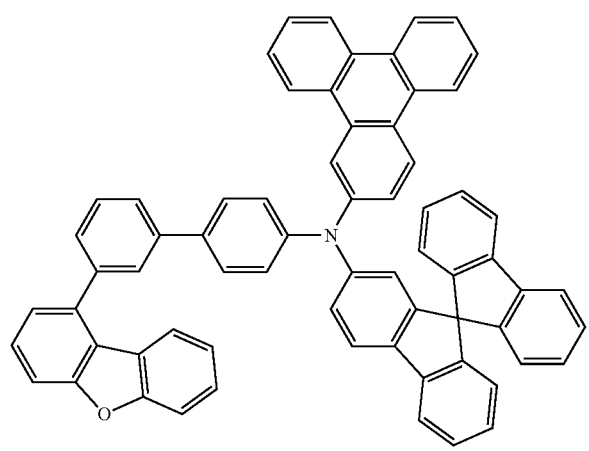

121
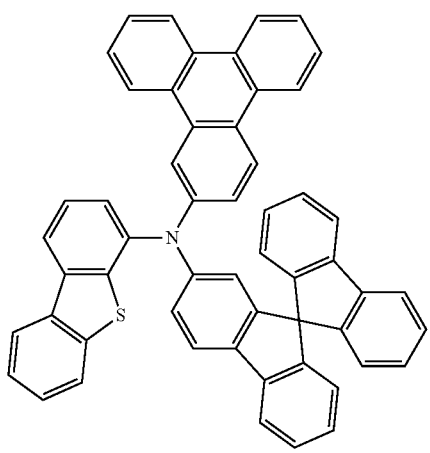
122
-continued
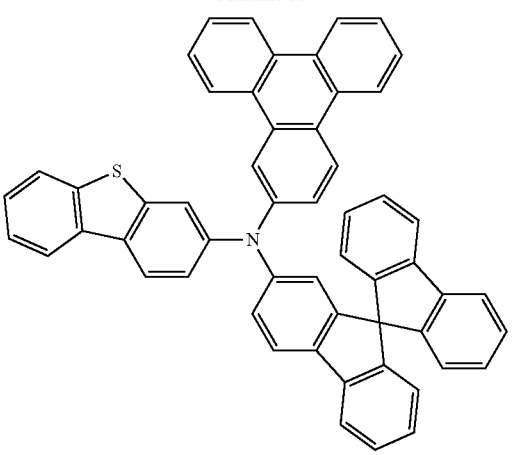
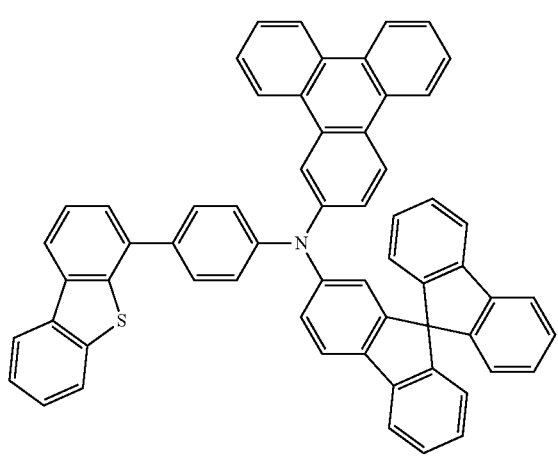
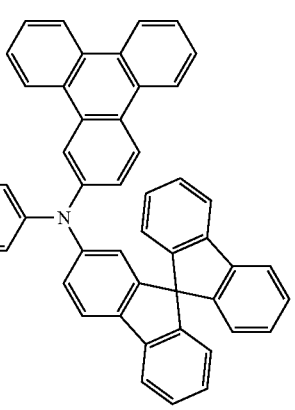
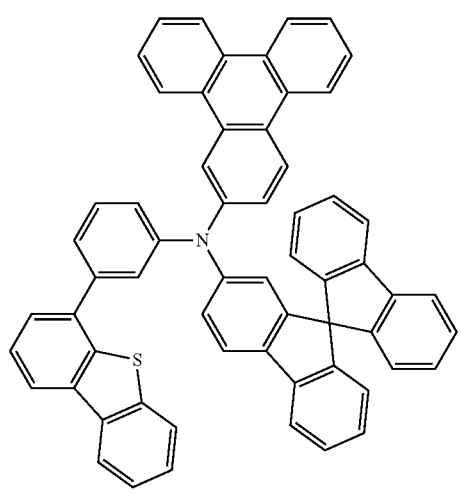
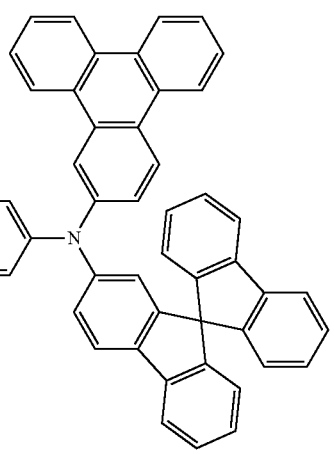

123
-continued
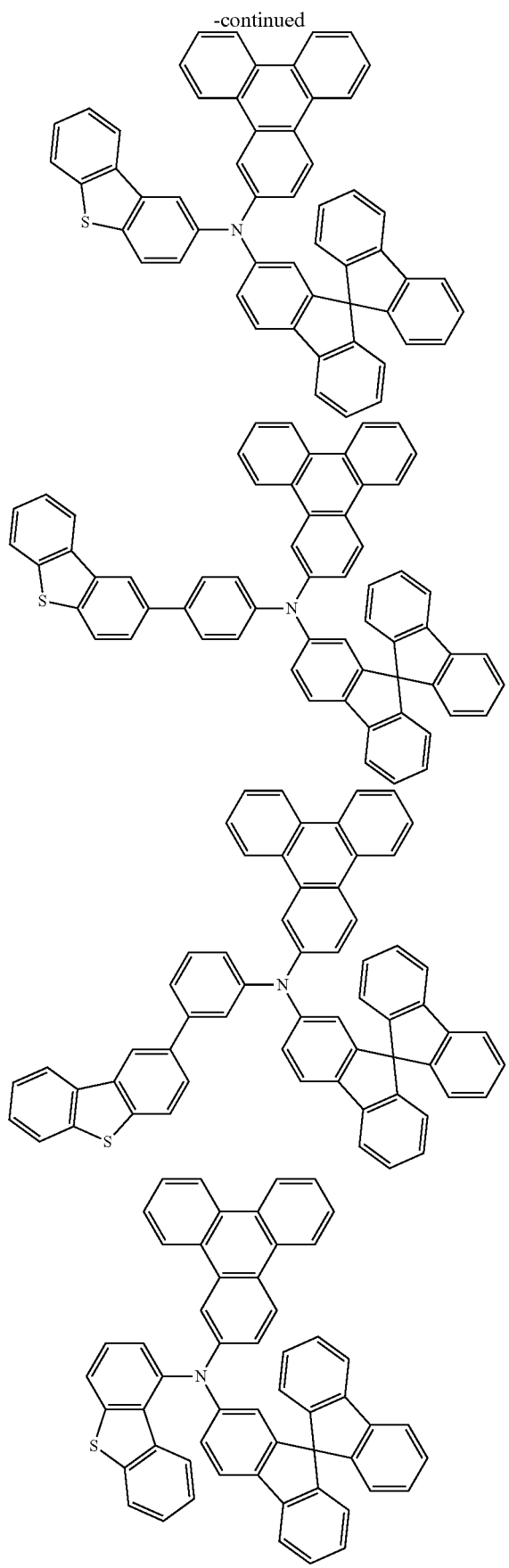
124
-continued
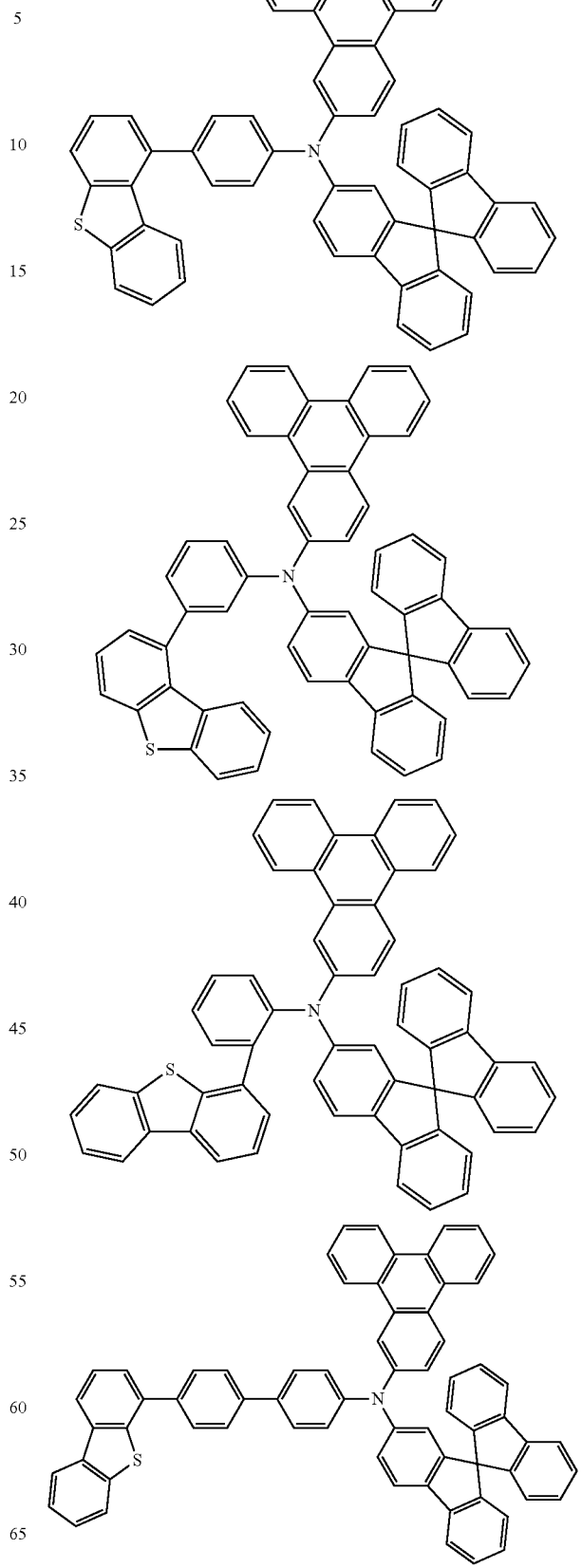

125
-continued
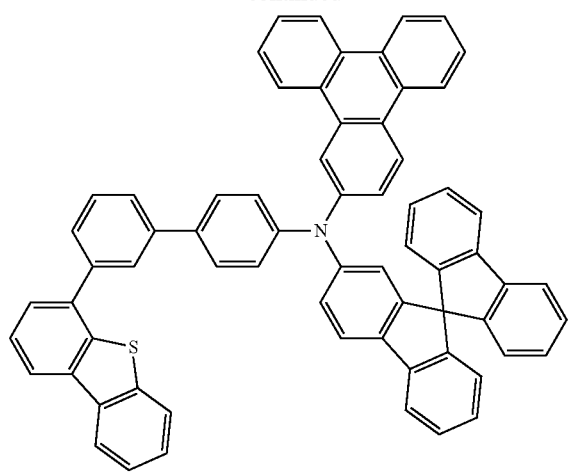
126
-continued
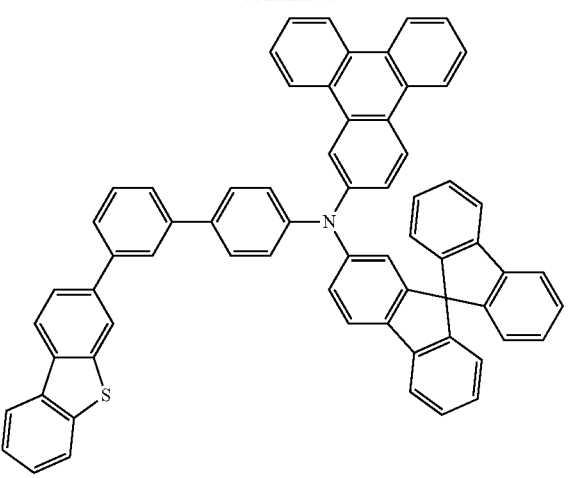
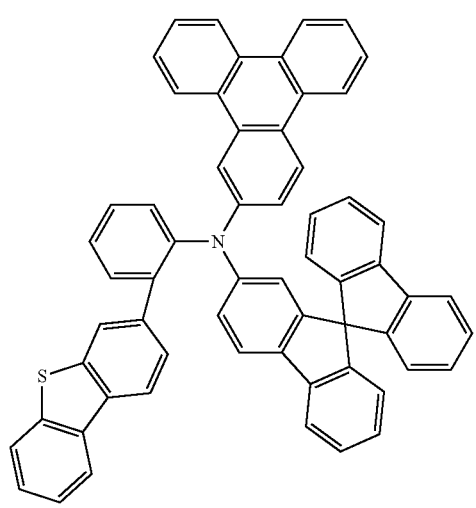
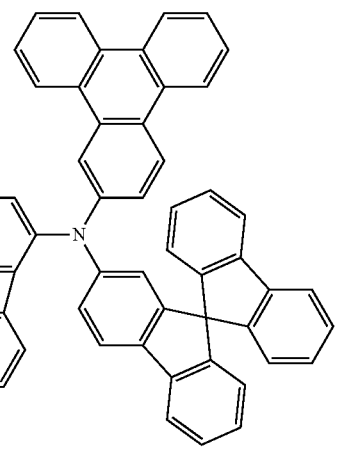
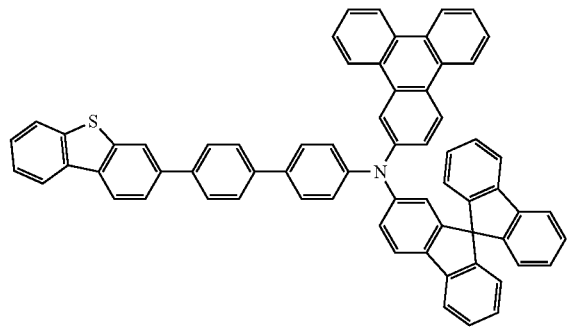 [SMILES: c1ccc2c(c1)-c1ccccc1C21c2ccccc2-c2ccc(N(c3ccc(-c4ccc(-c5ccc6c(c5)sc5ccccc56)cc4)cc3)c3ccc4c5ccccc5c5ccccc5c4c3)cc21]
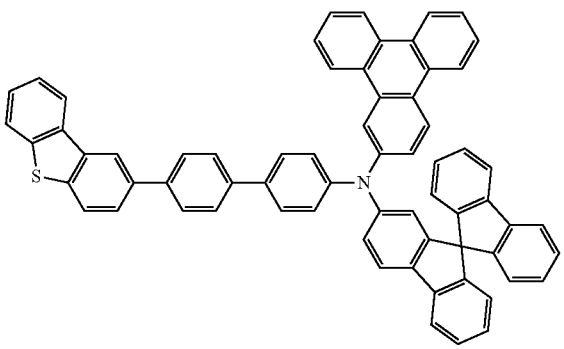

127
-continued
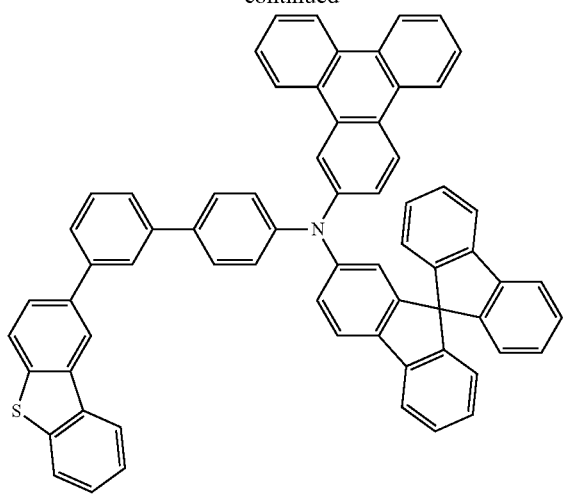
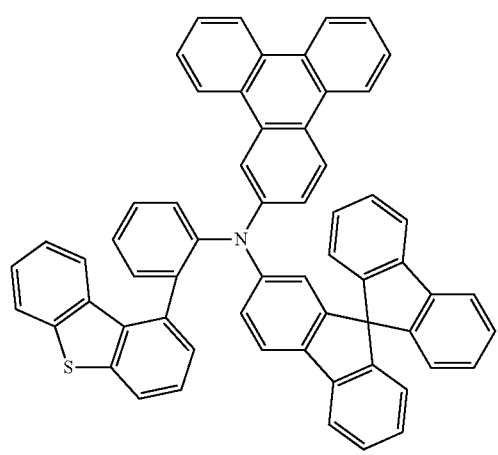
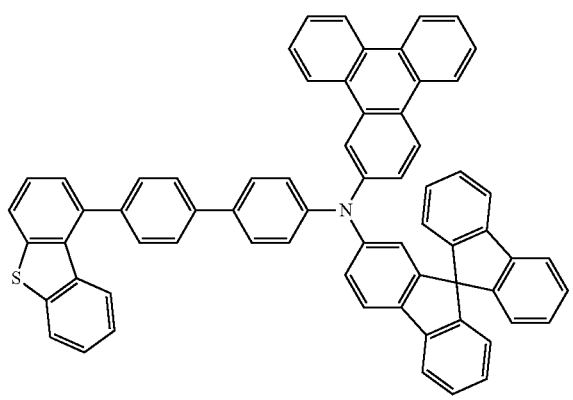
128
-continued
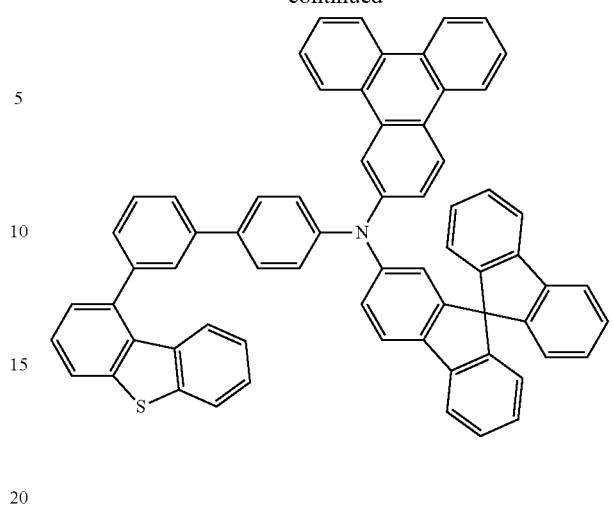
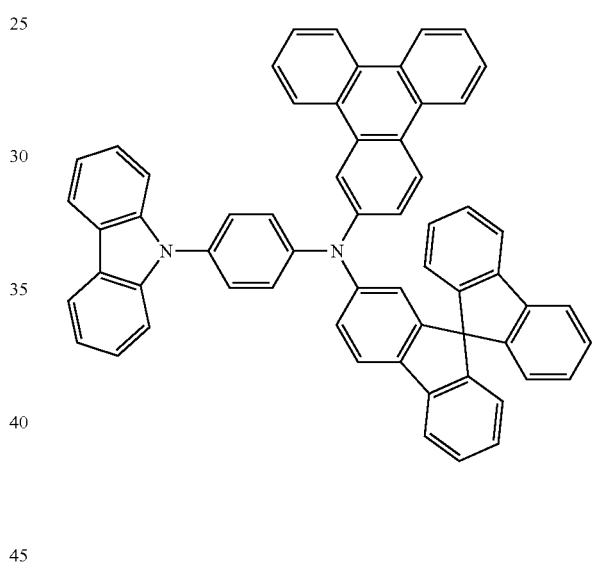
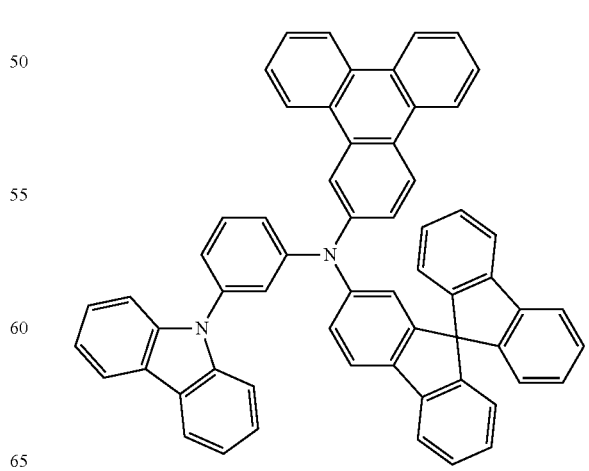

129
-continued
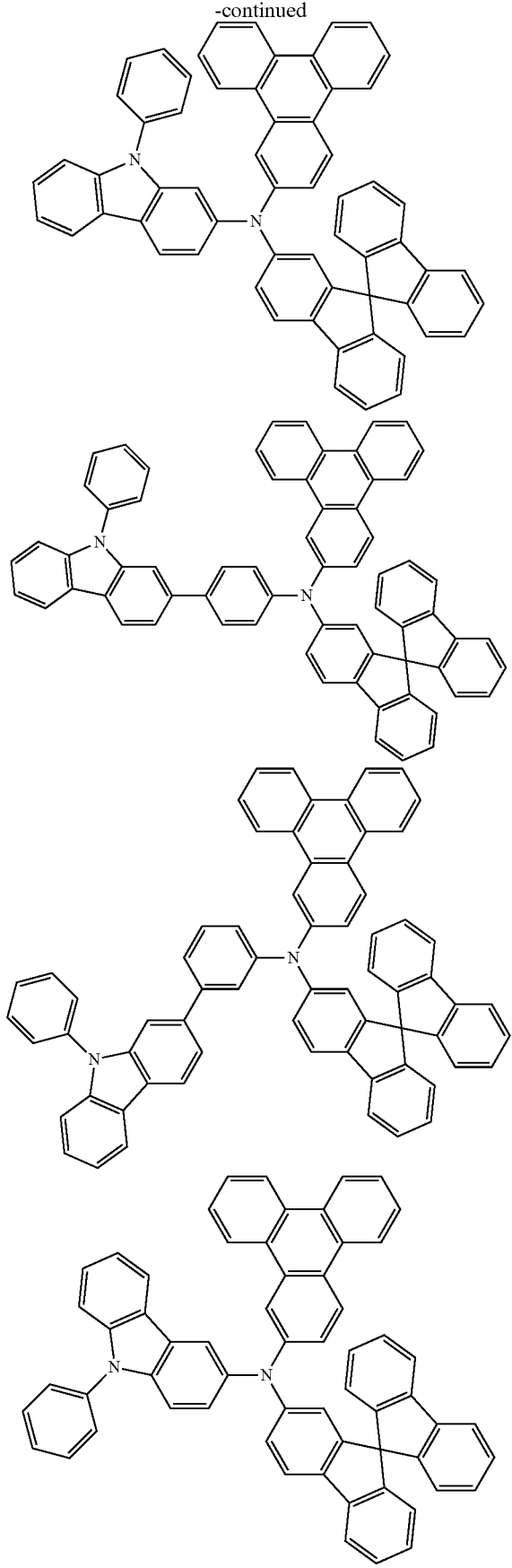
130
-continued
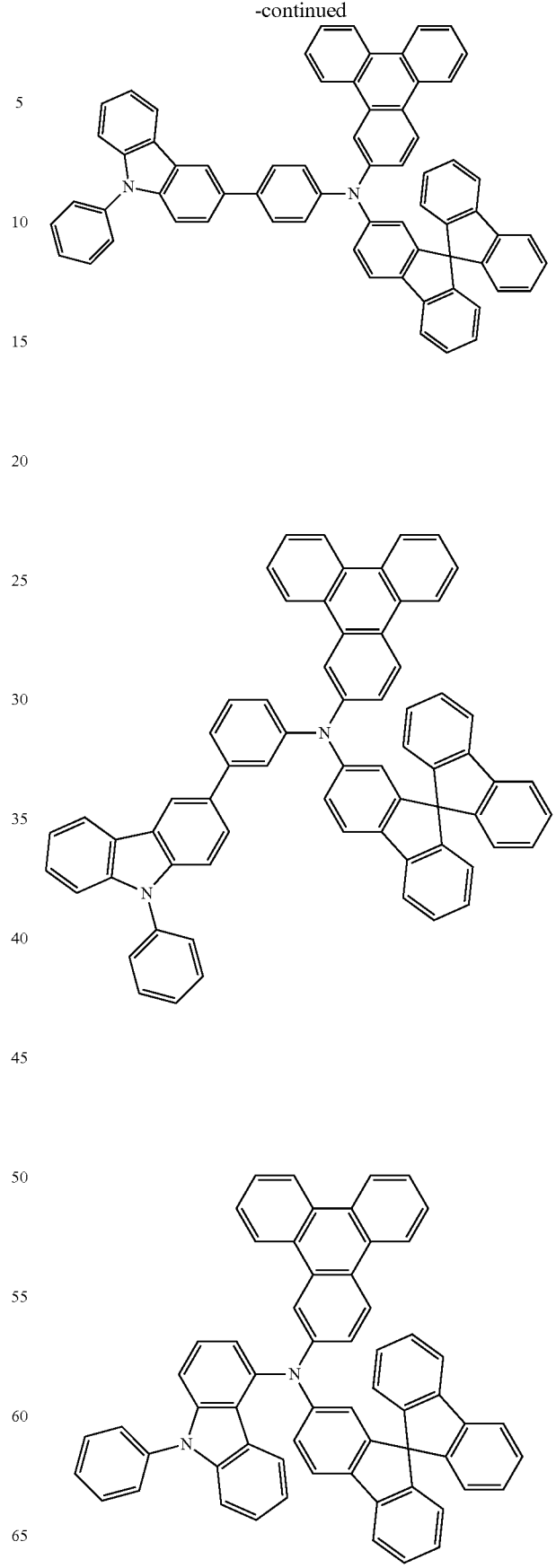

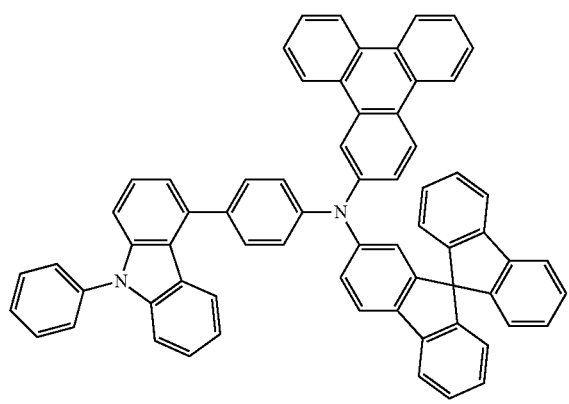
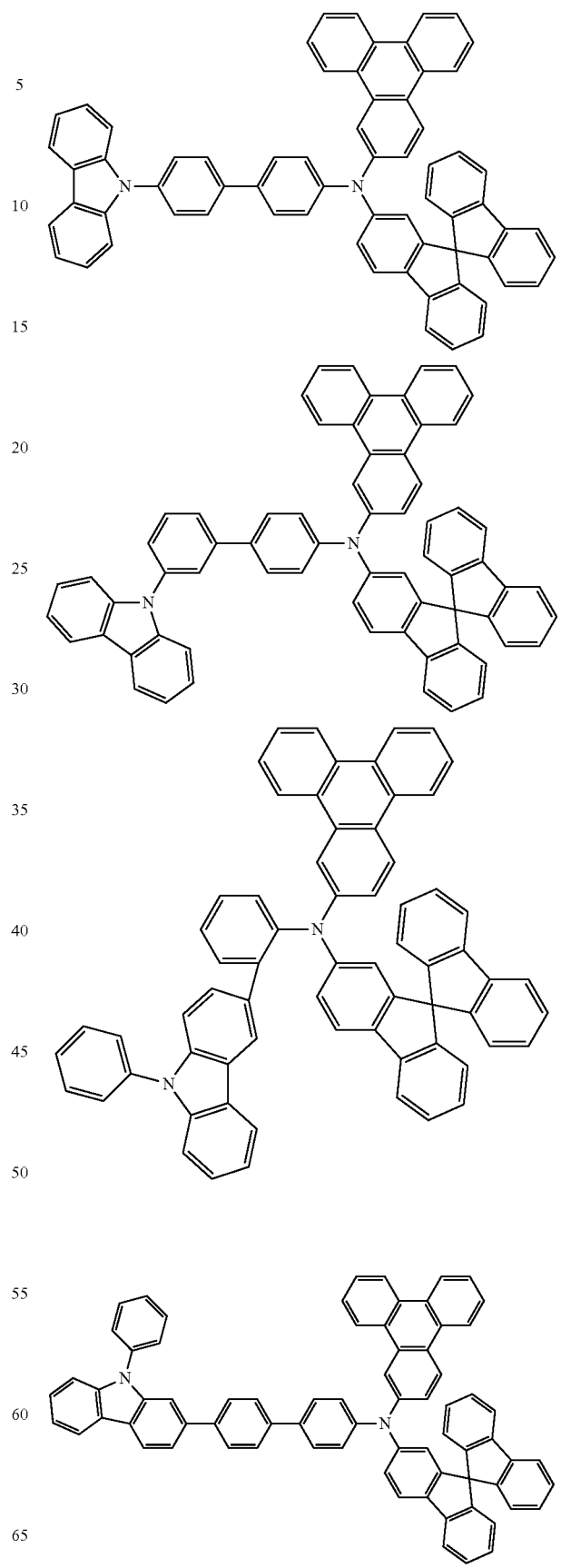

133
-continued
134
-continued
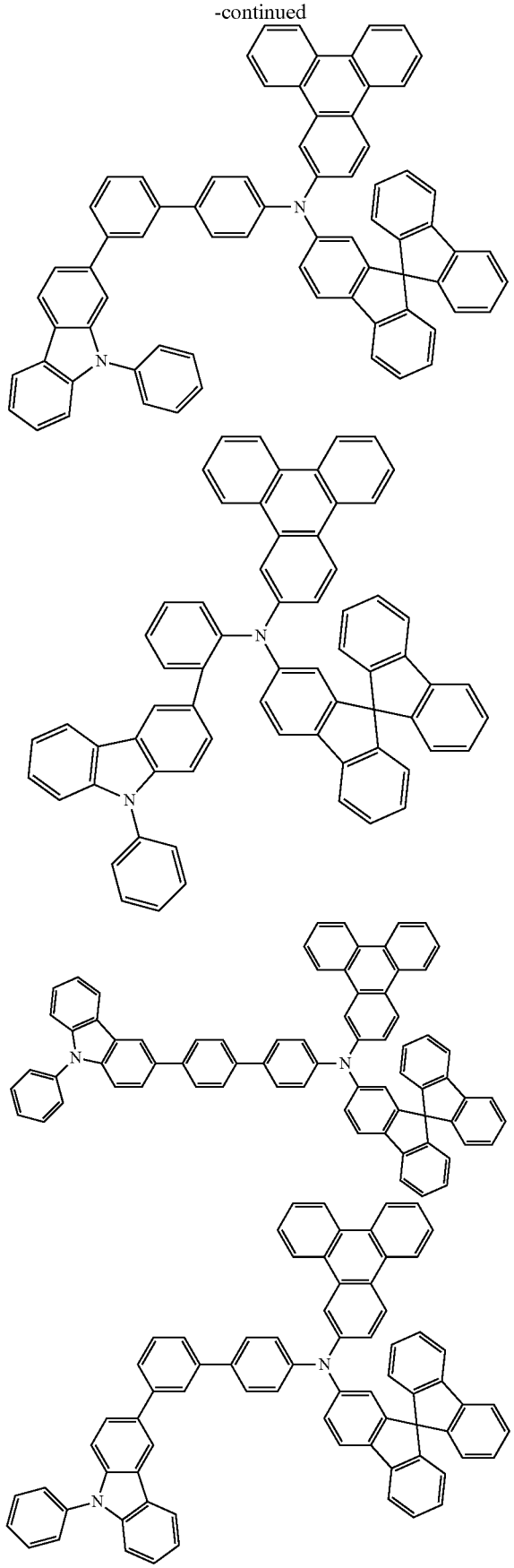
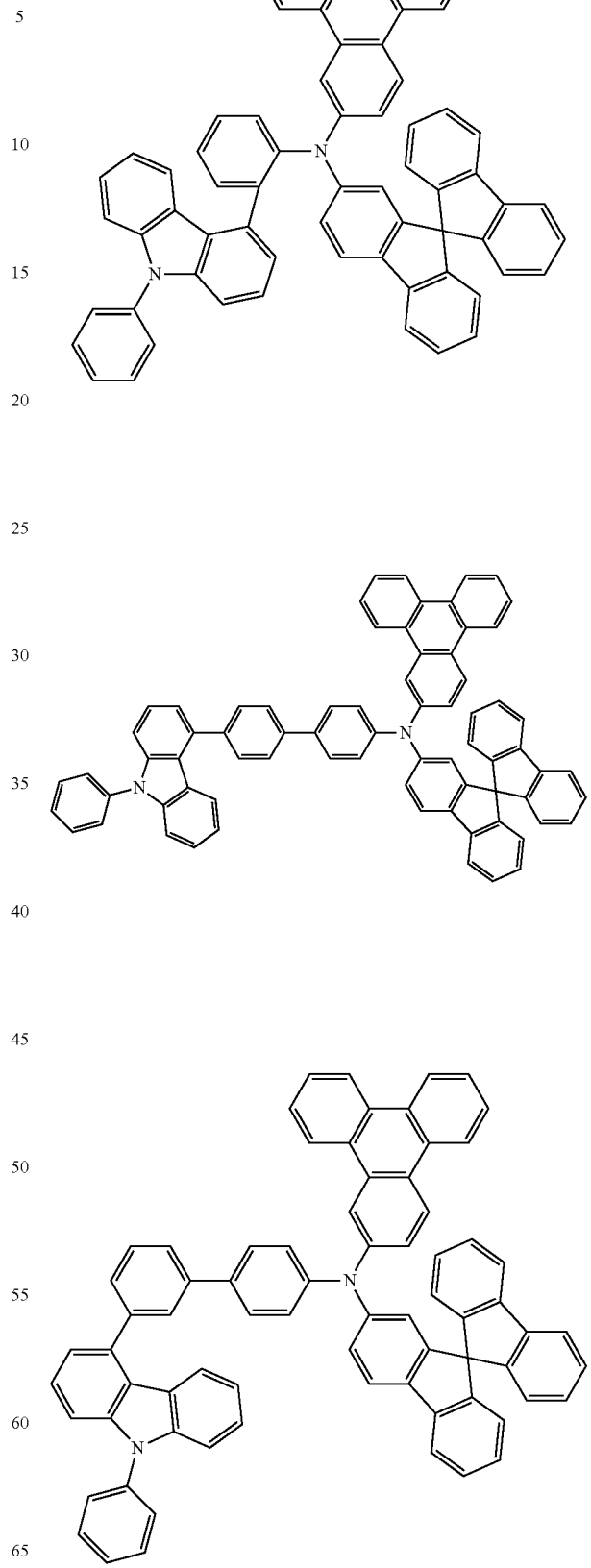

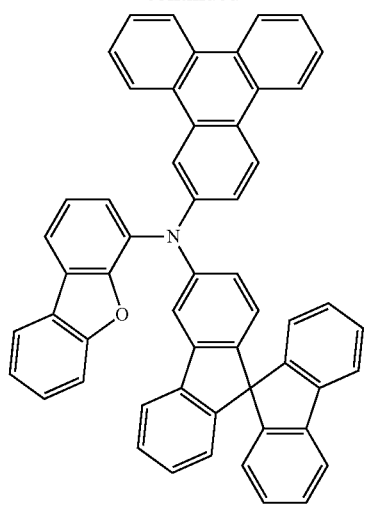
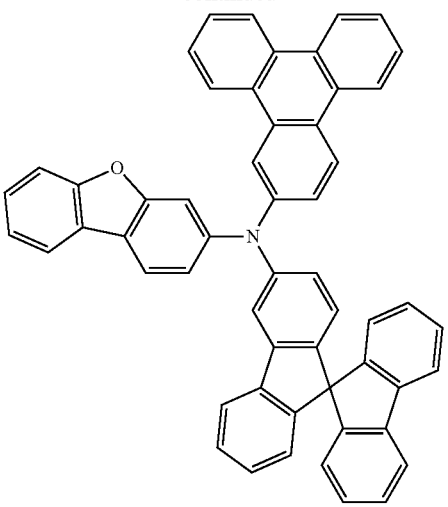
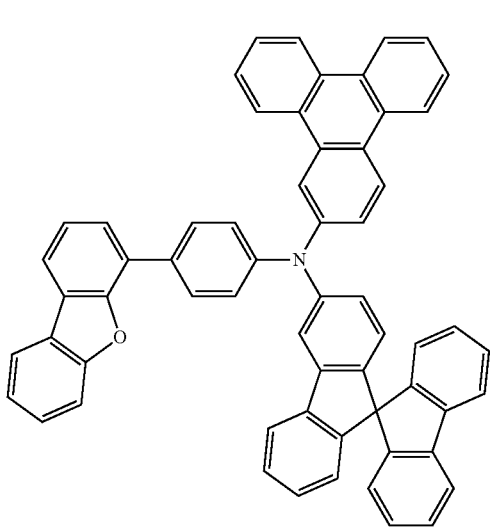
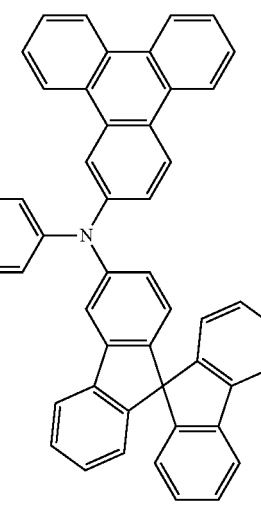
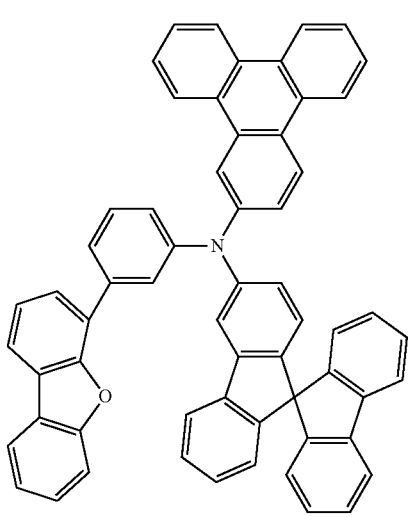
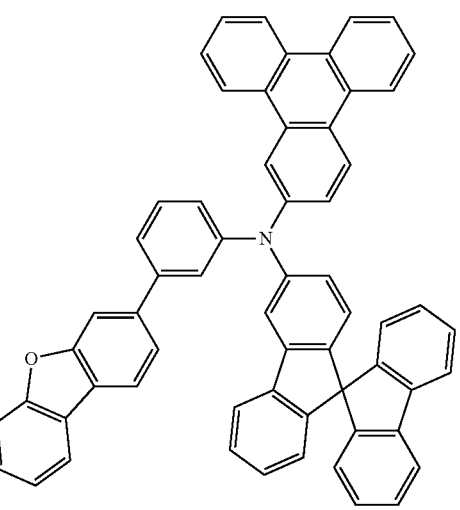

137
-continued
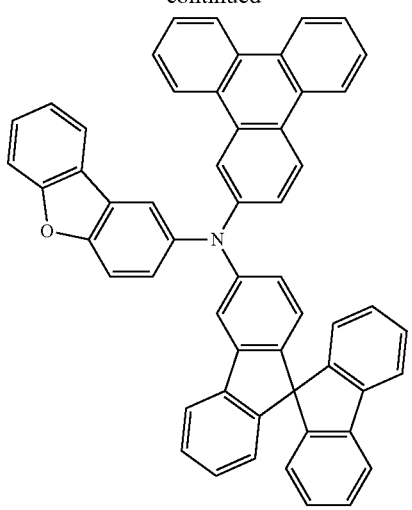
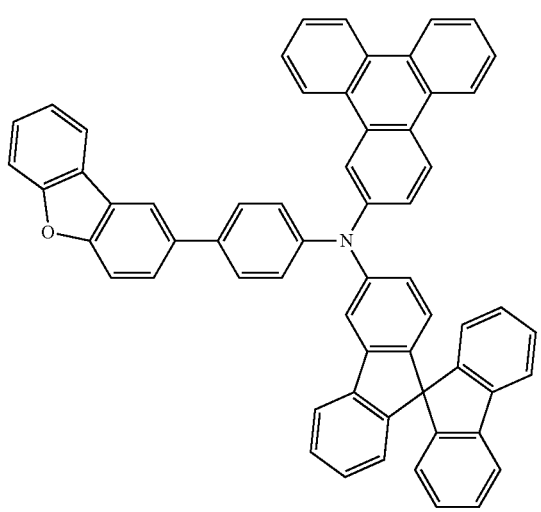
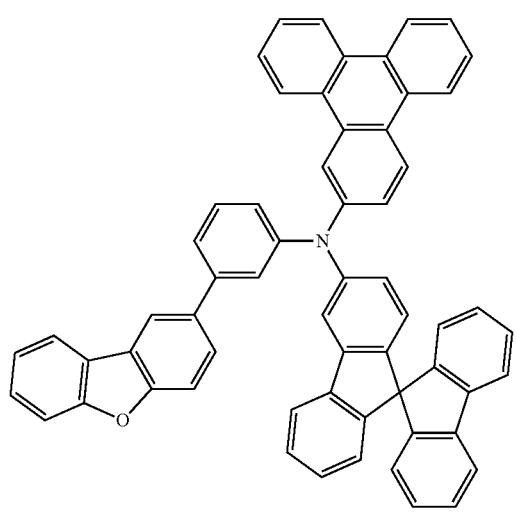
138
-continued
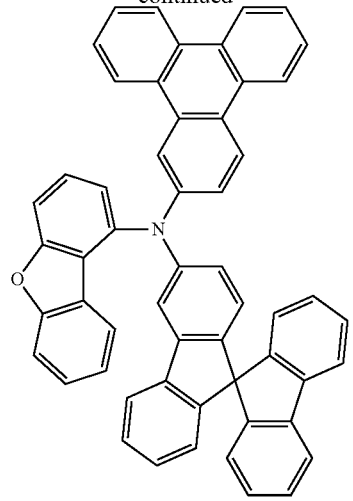
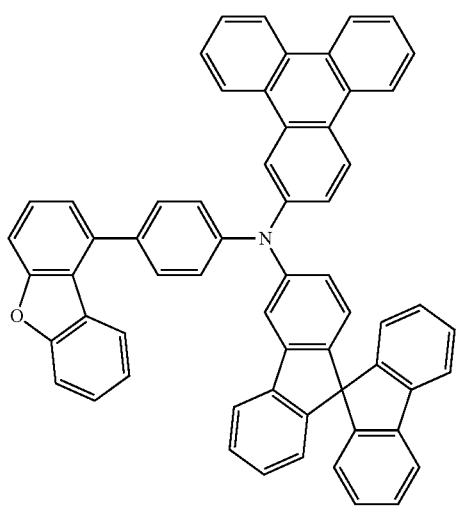
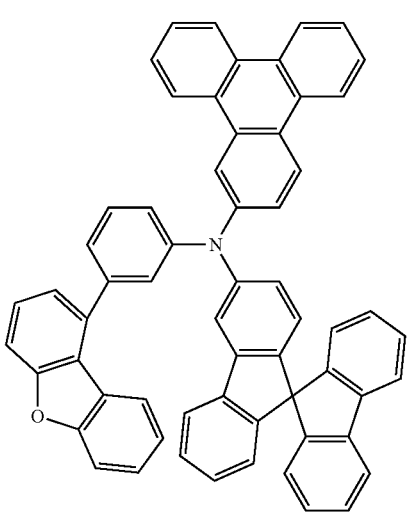

-continued
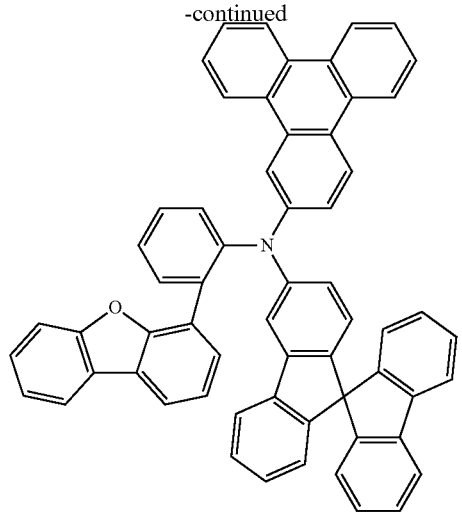
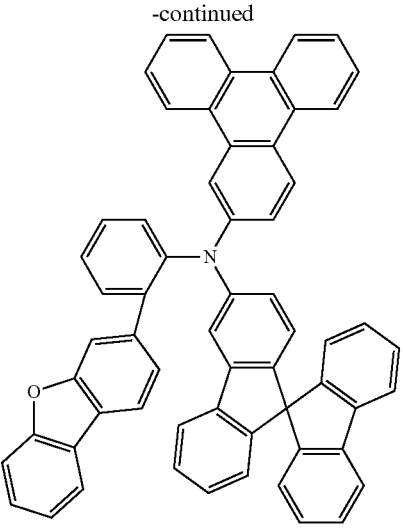
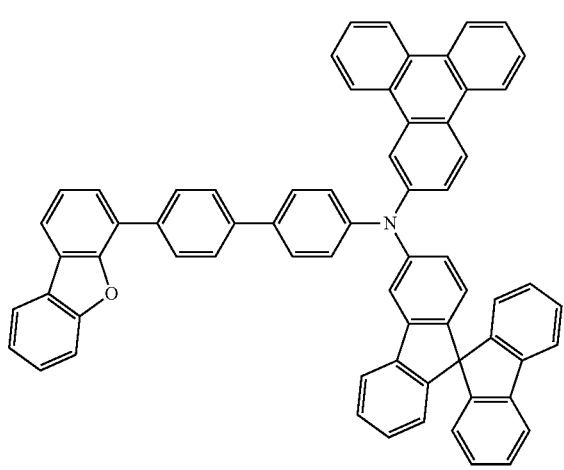
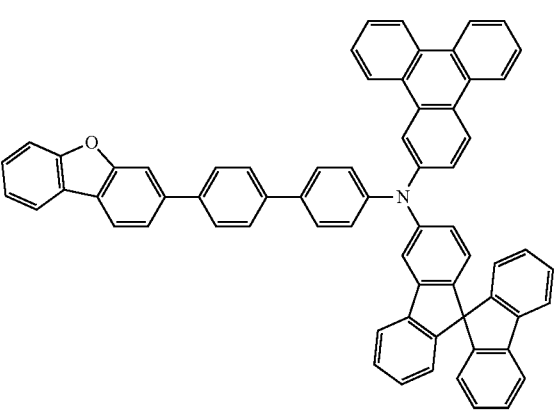
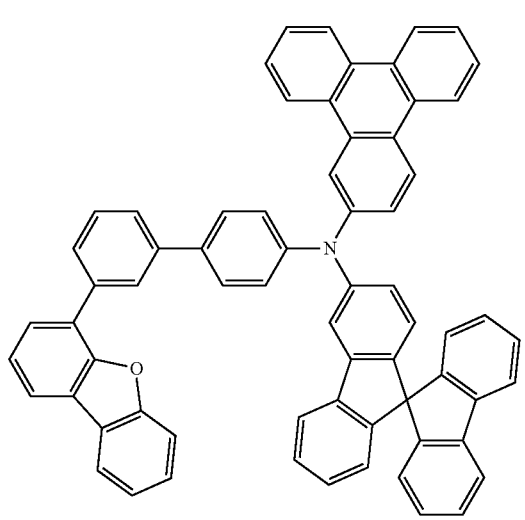
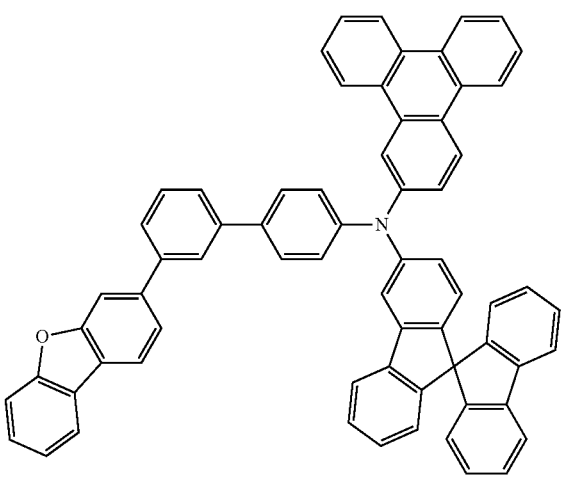

141
-continued
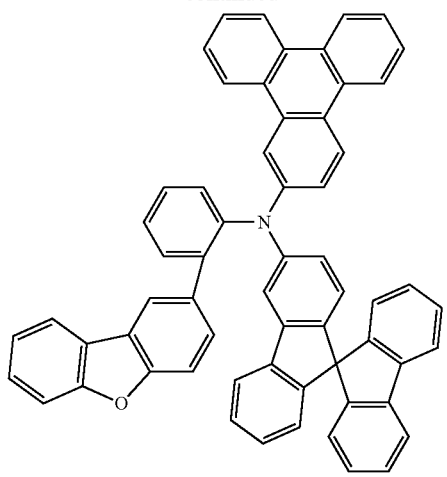
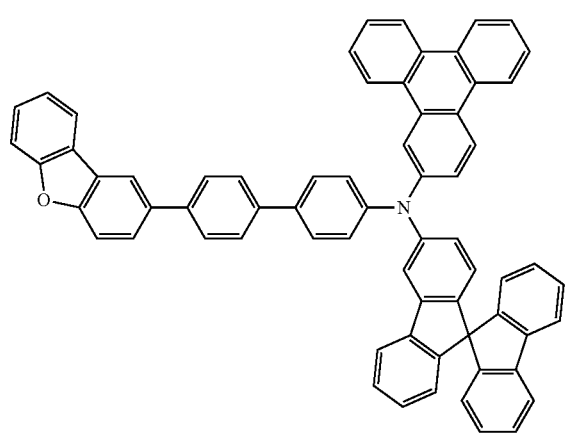
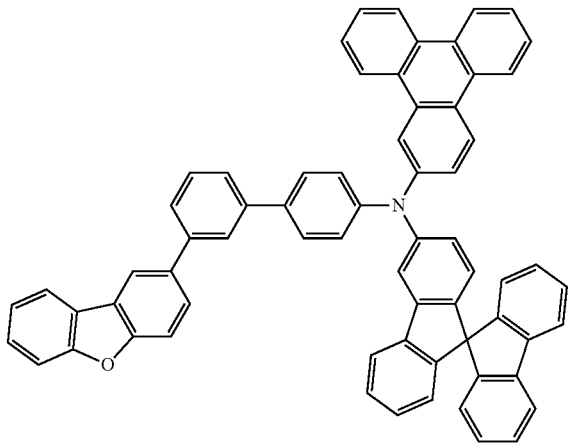
142
-continued
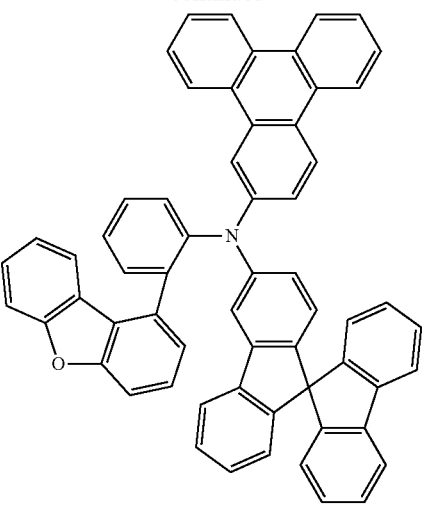
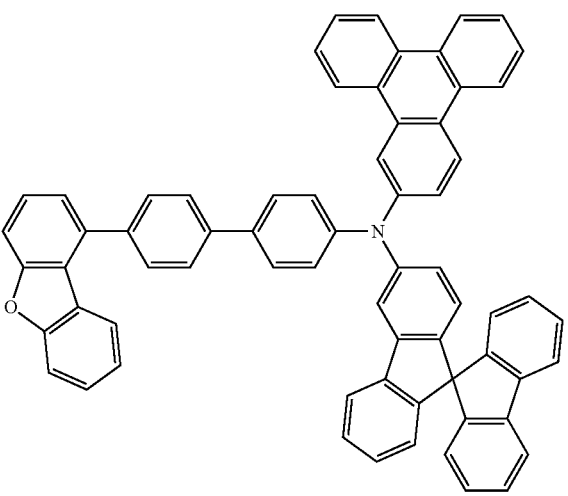
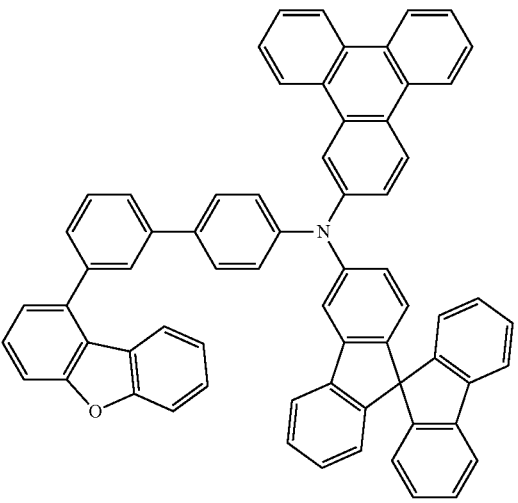

143
-continued
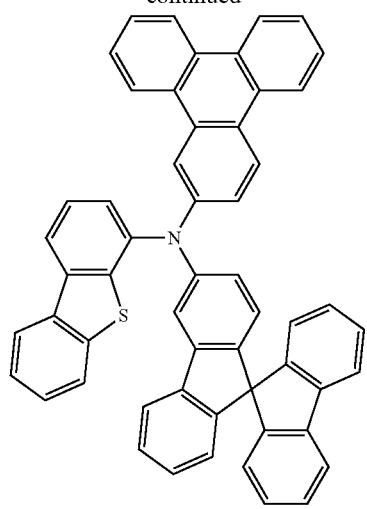
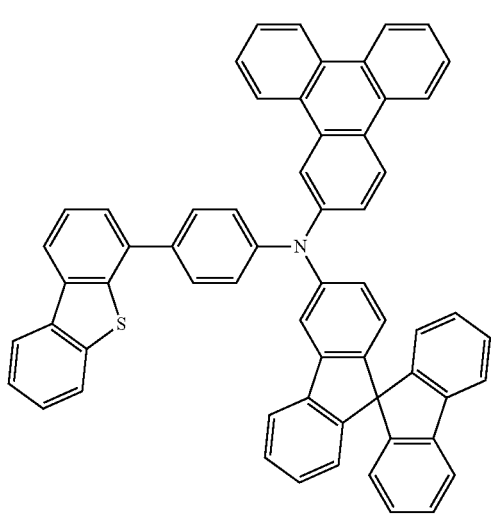
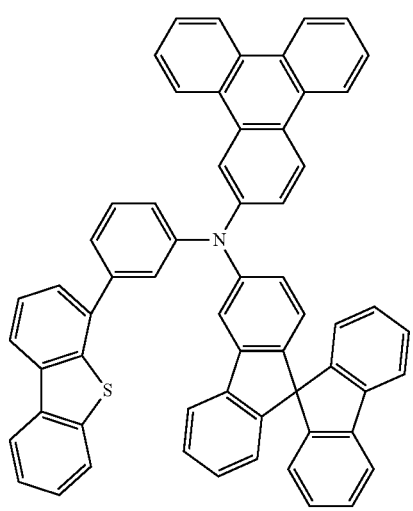
144
-continued
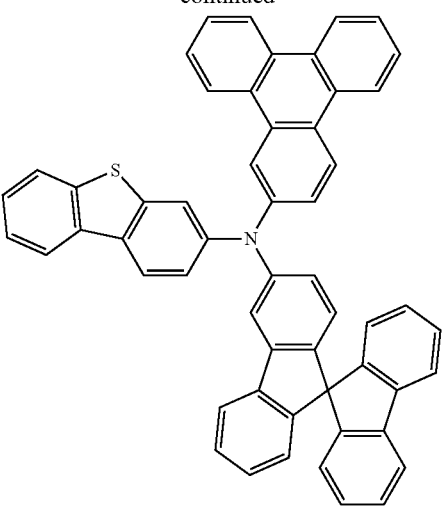
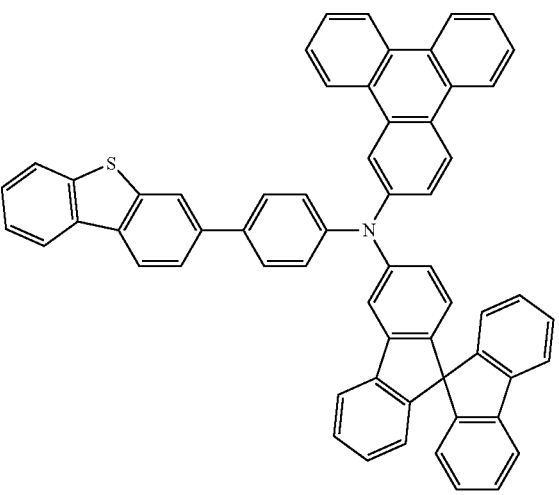
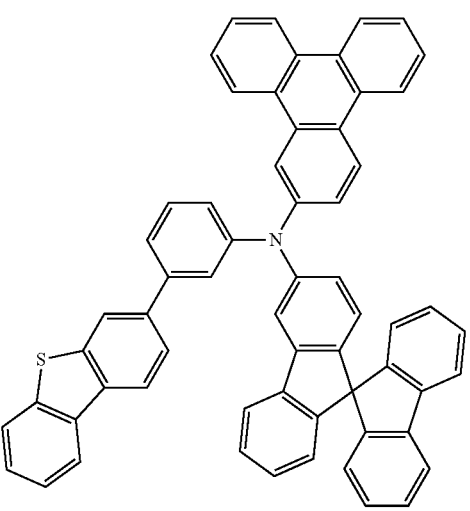

-continued
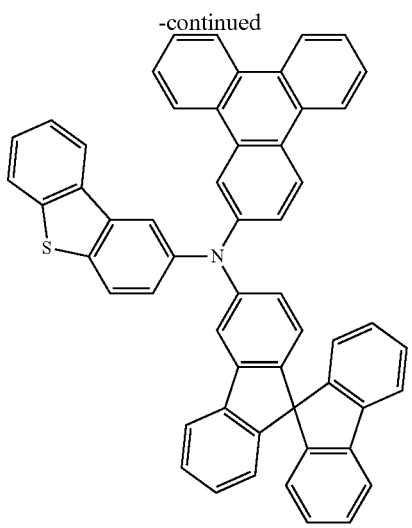
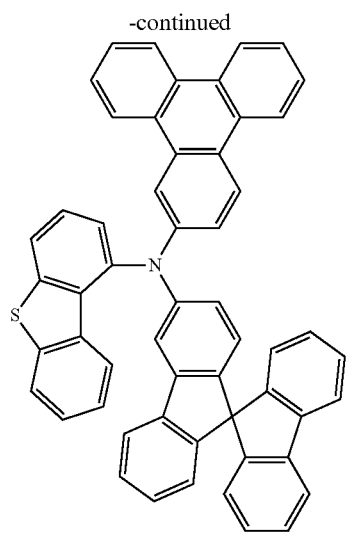
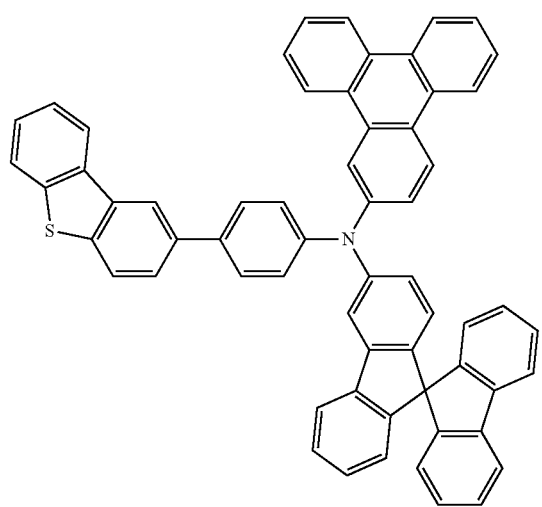
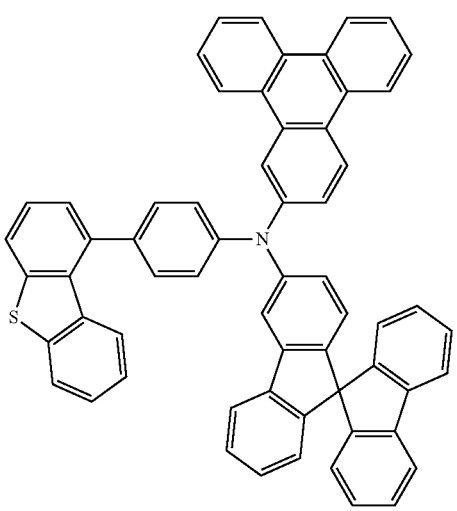
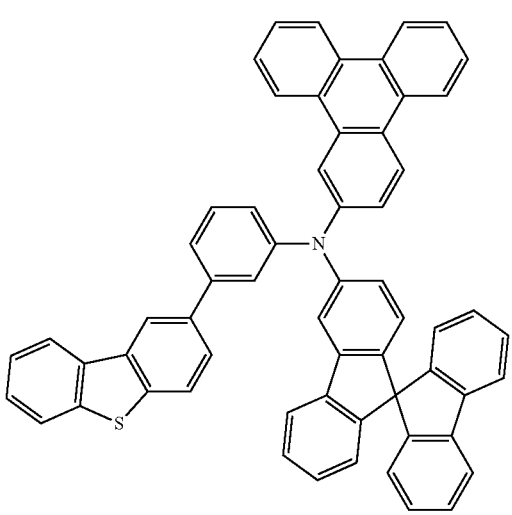
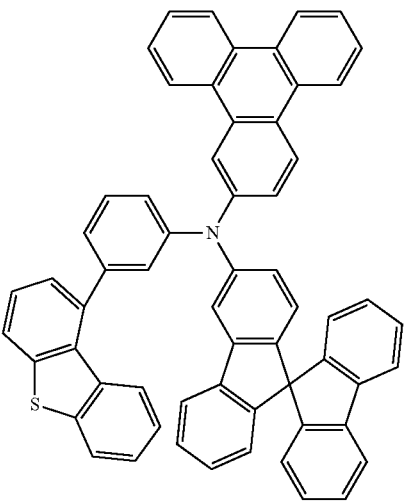

147
-continued
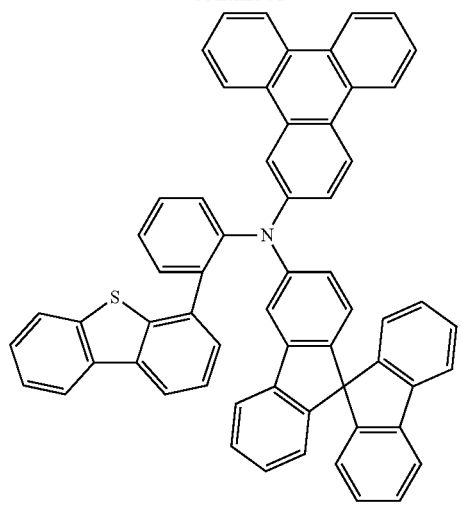
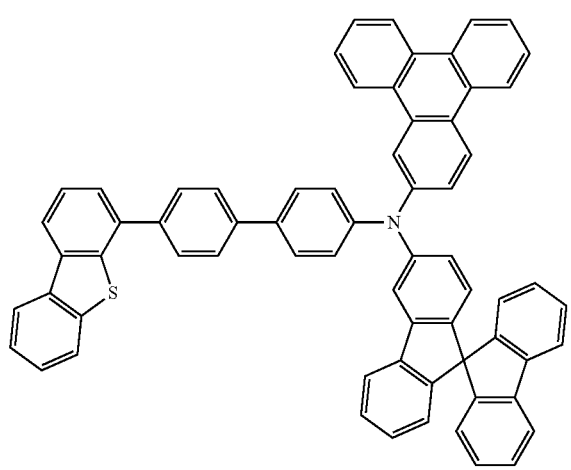
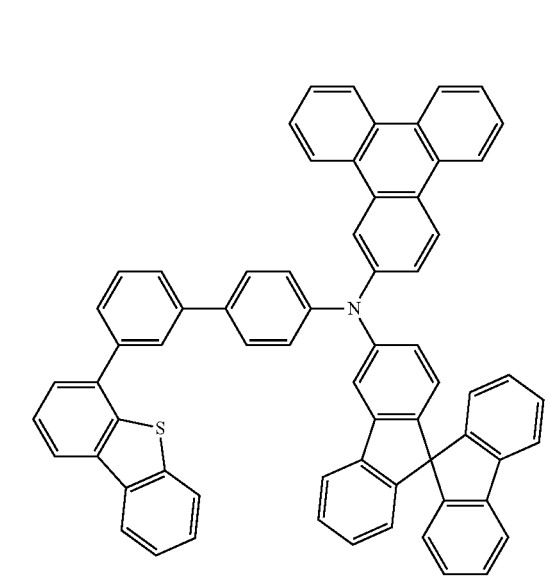
148
-continued
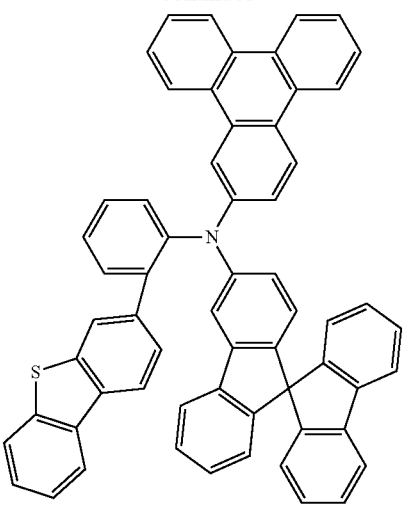
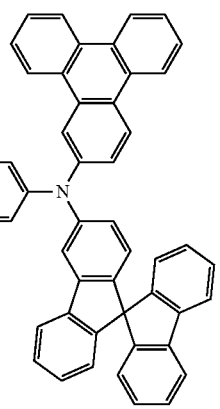
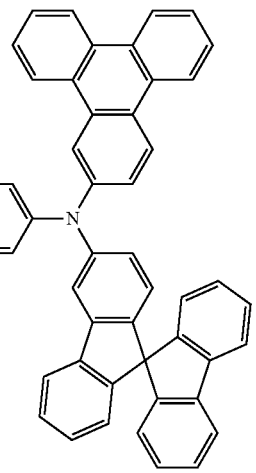

149
-continued
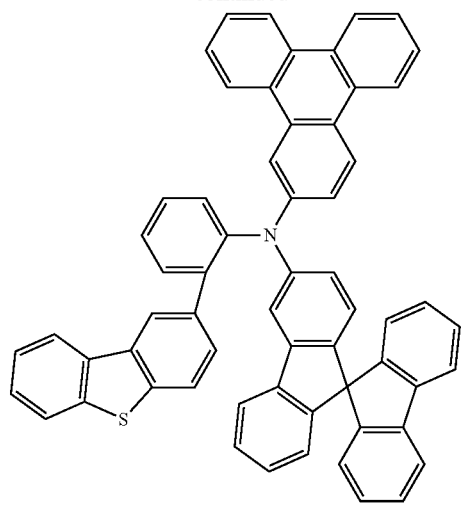
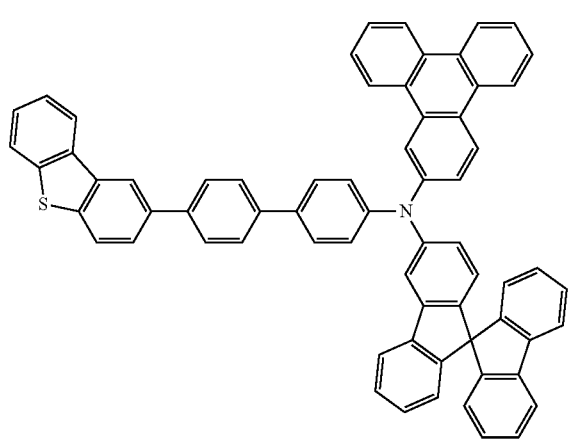
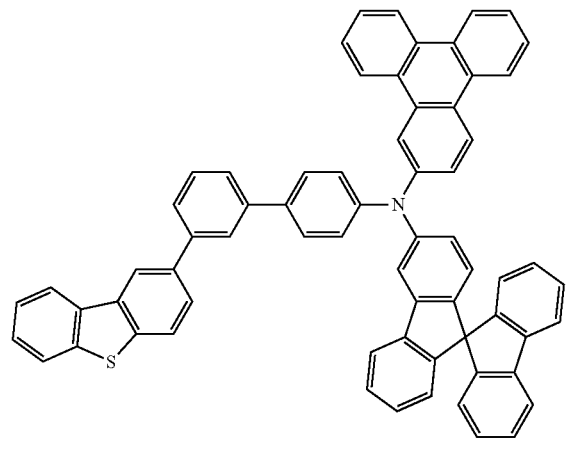
150
-continued
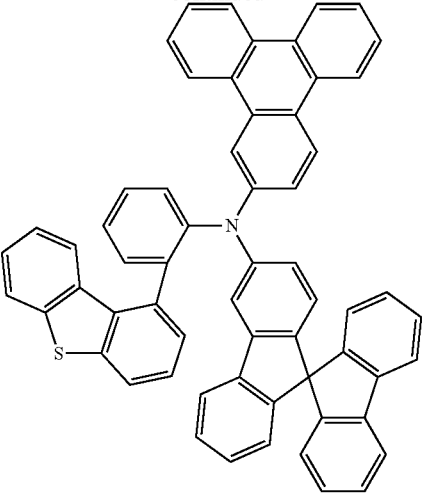
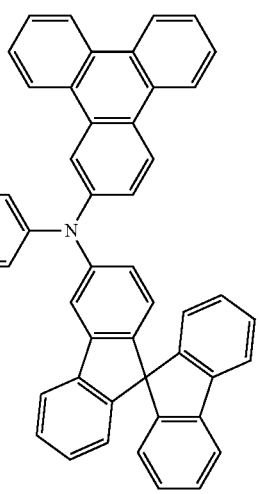
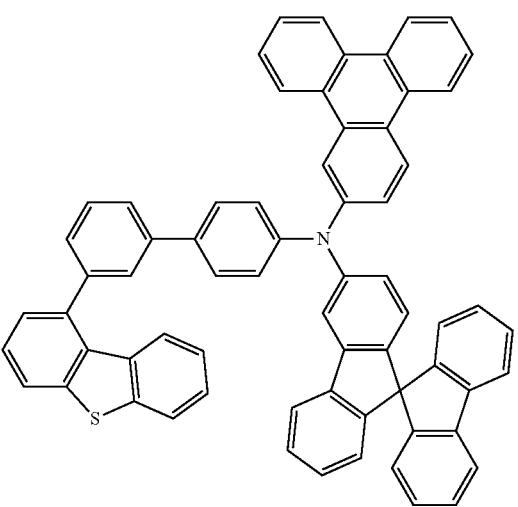

151
-continued
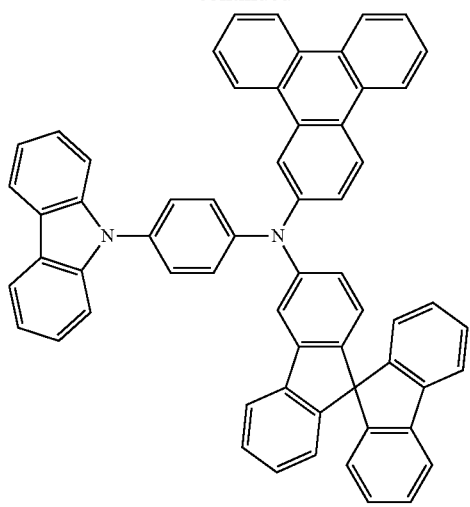
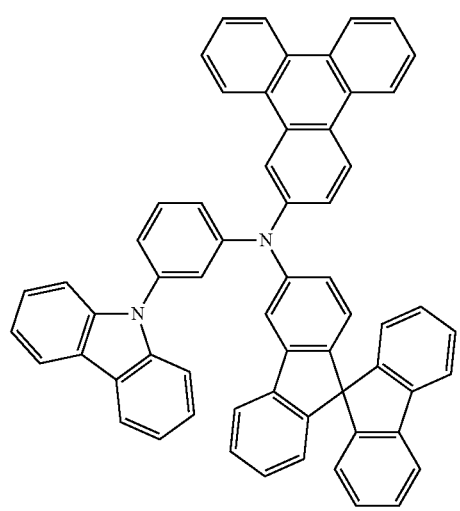
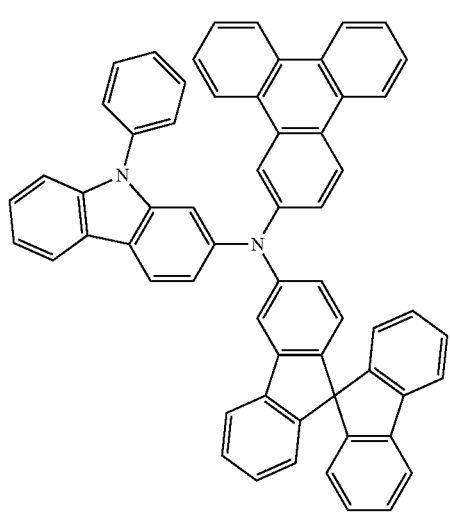
152
-continued
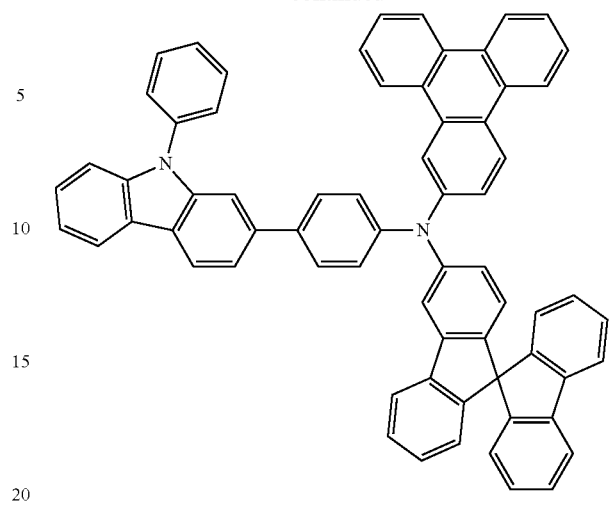
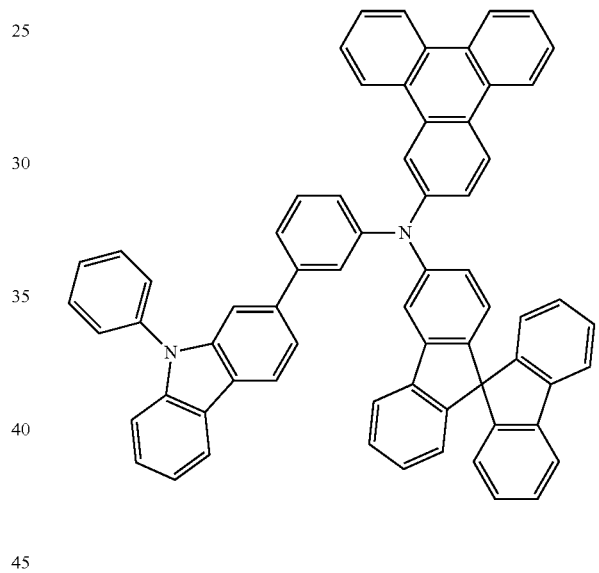
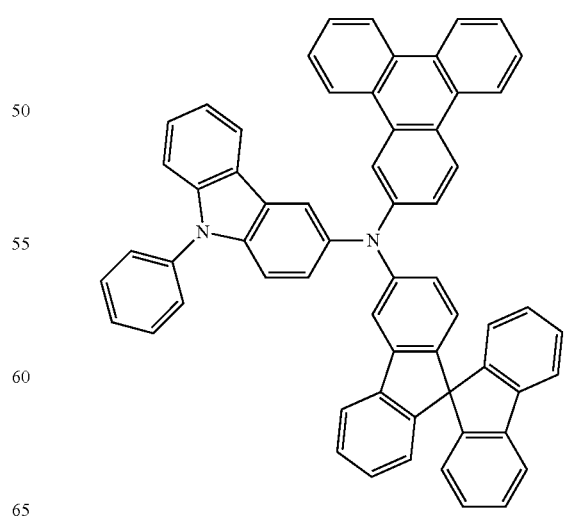

-continued
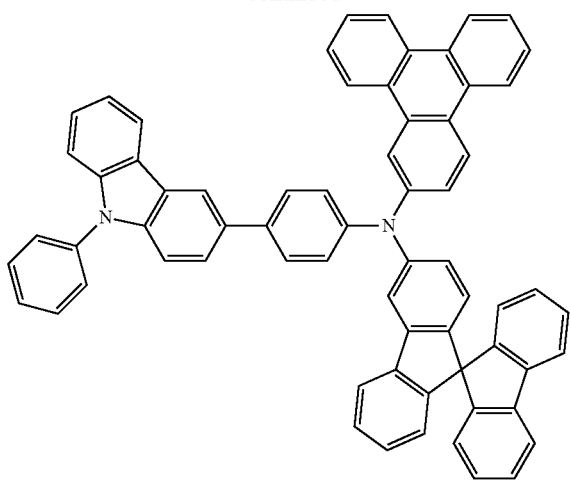
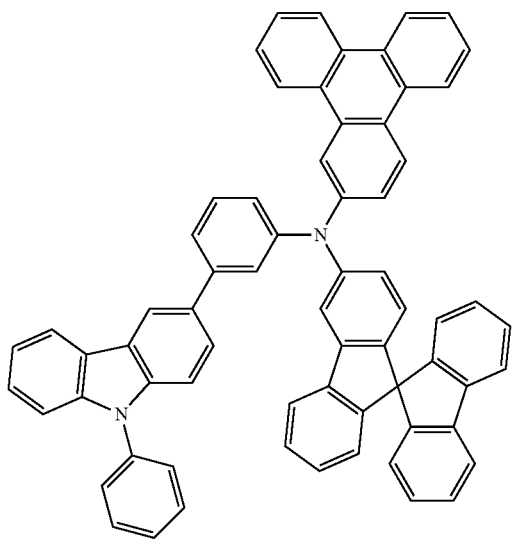
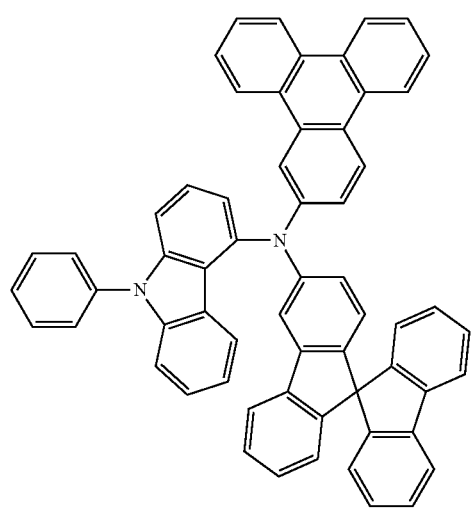
-continued
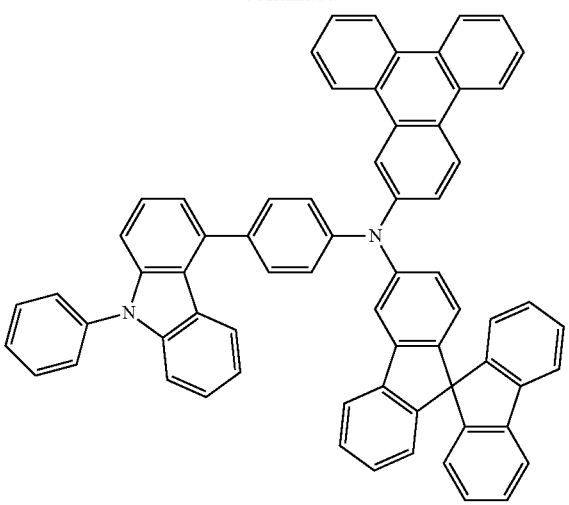
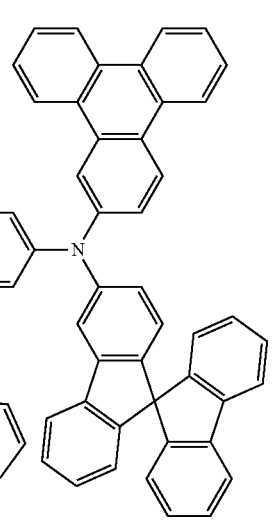
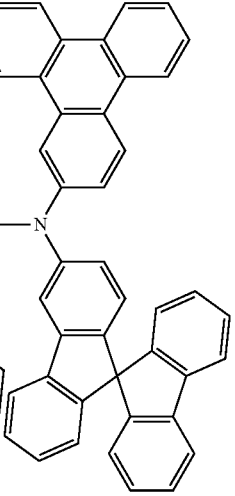

155
-continued
156
-continued
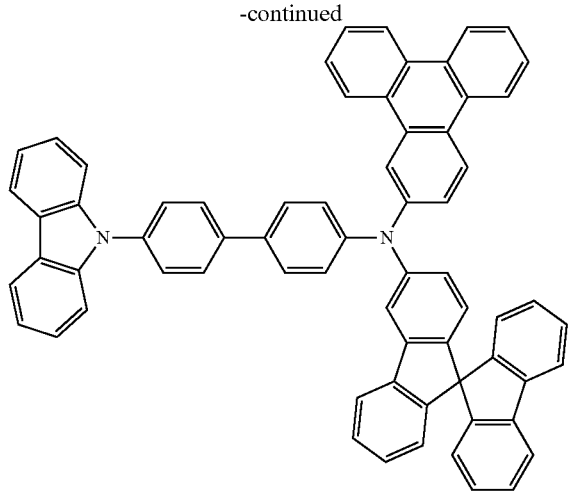
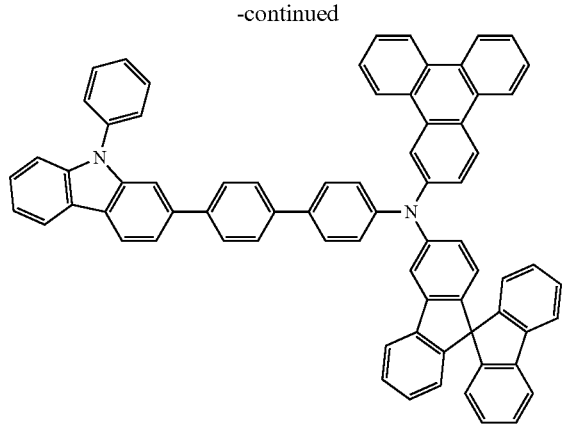
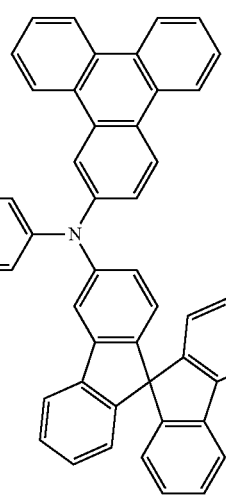
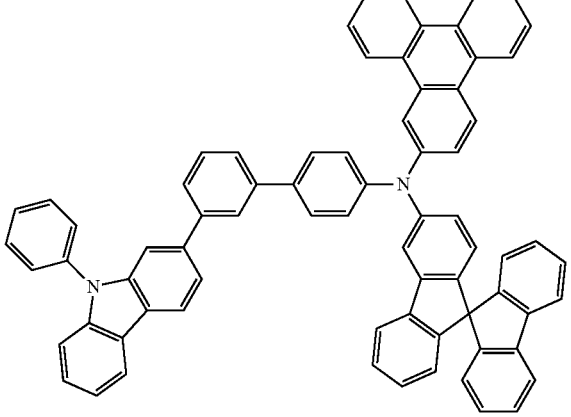
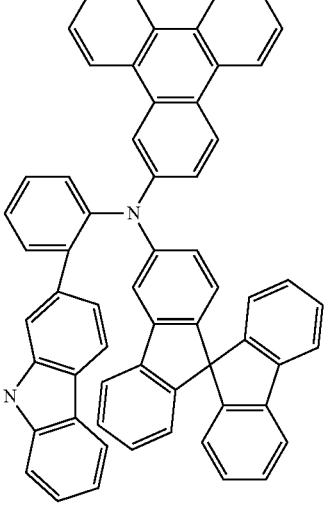
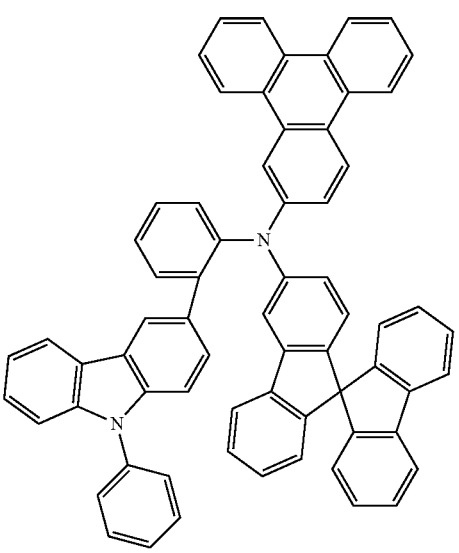

157
-continued
158
-continued
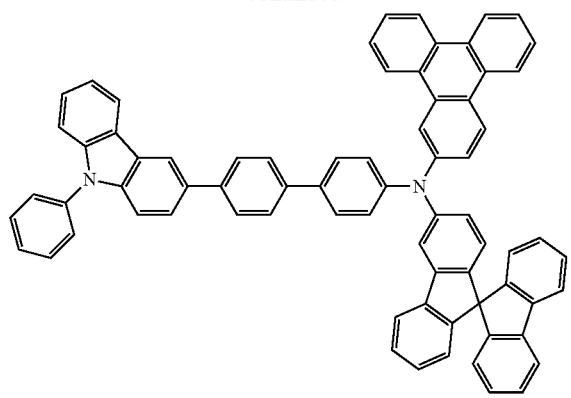
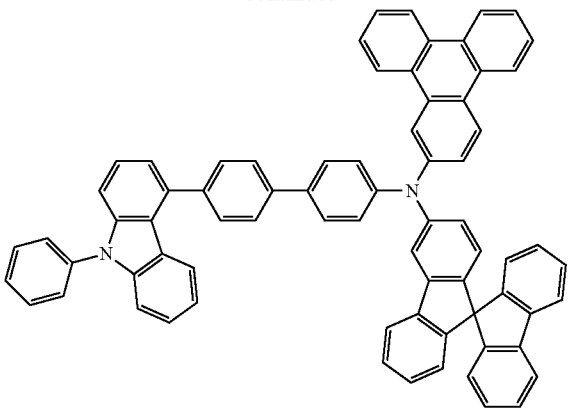

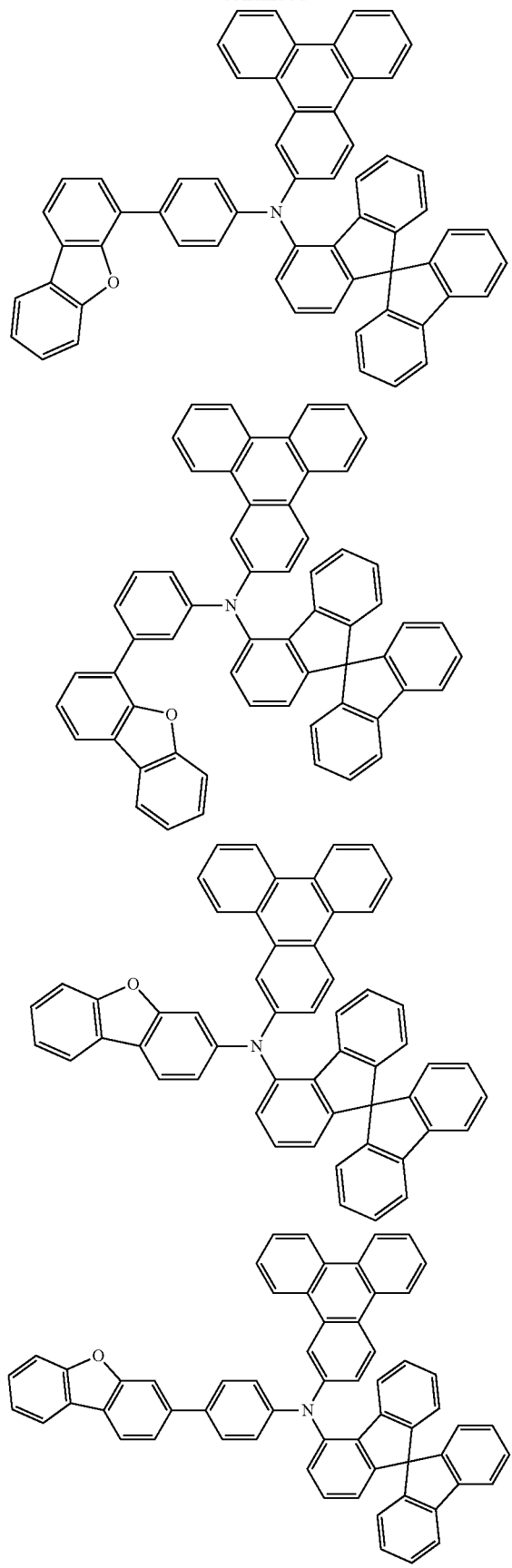

161
-continued
162
-continued
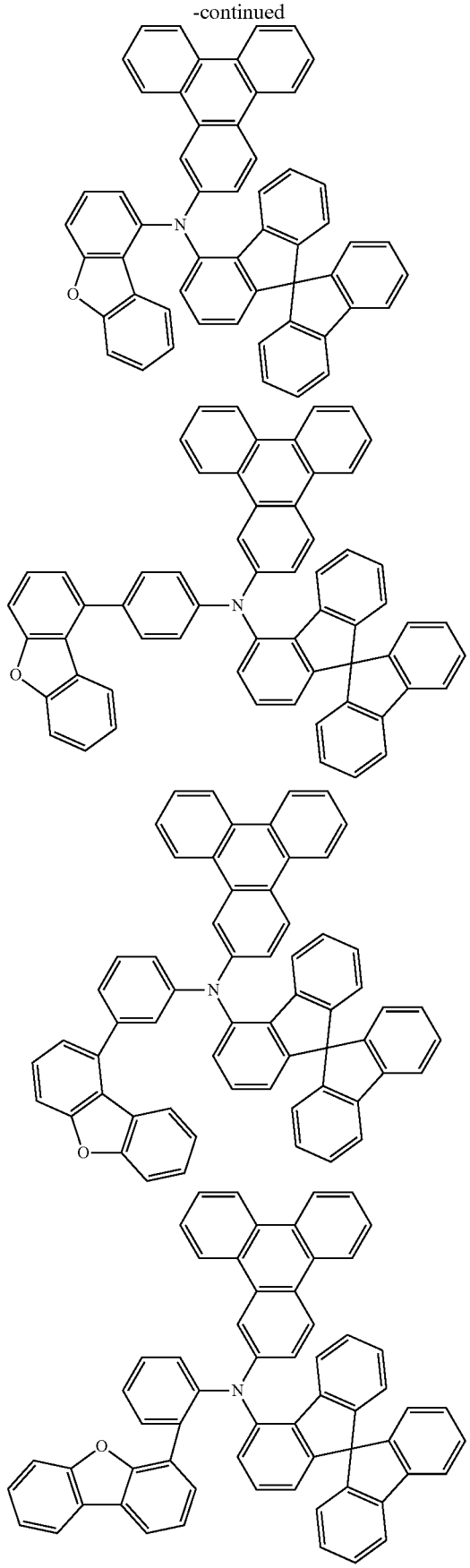
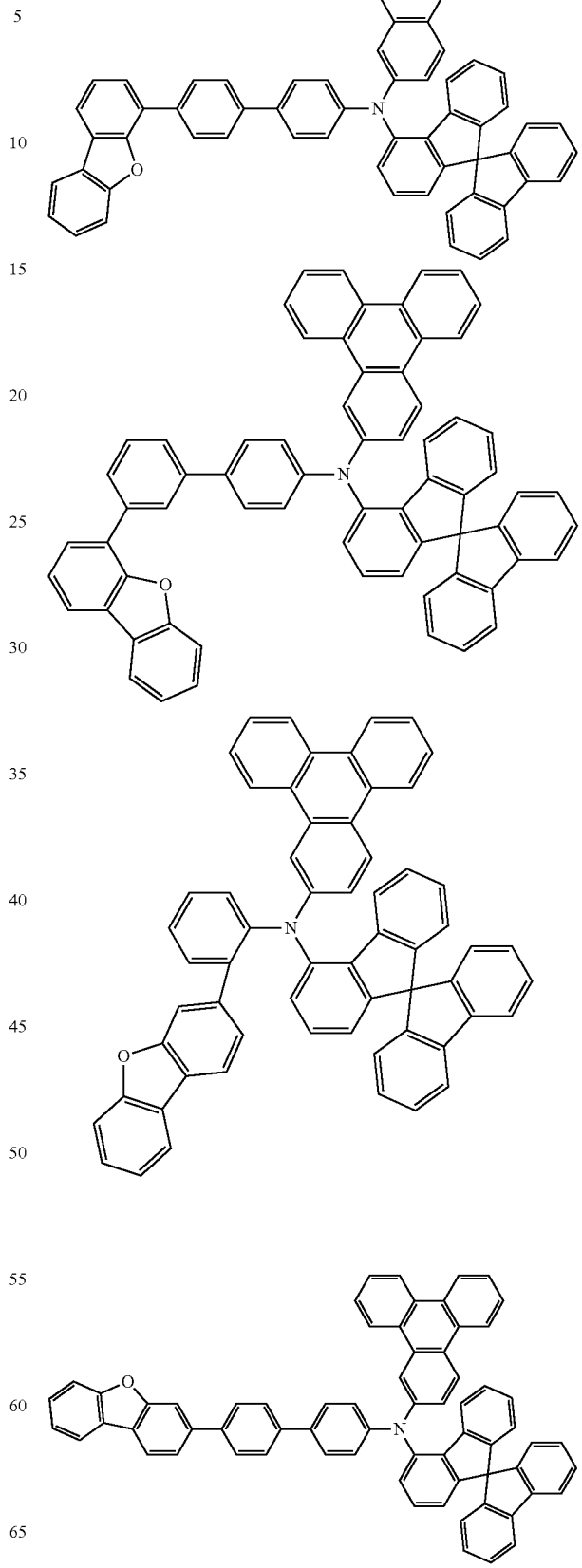

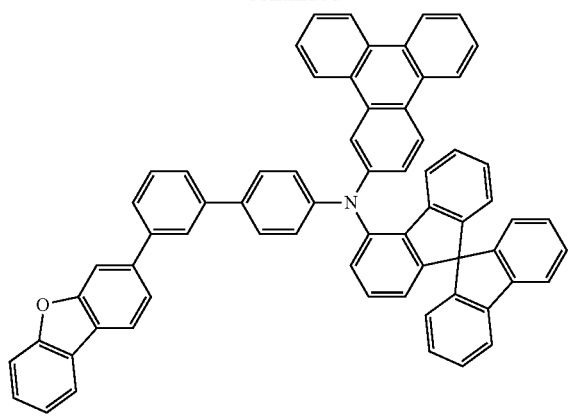
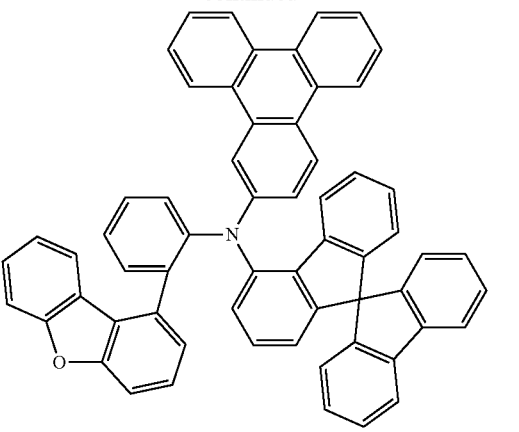

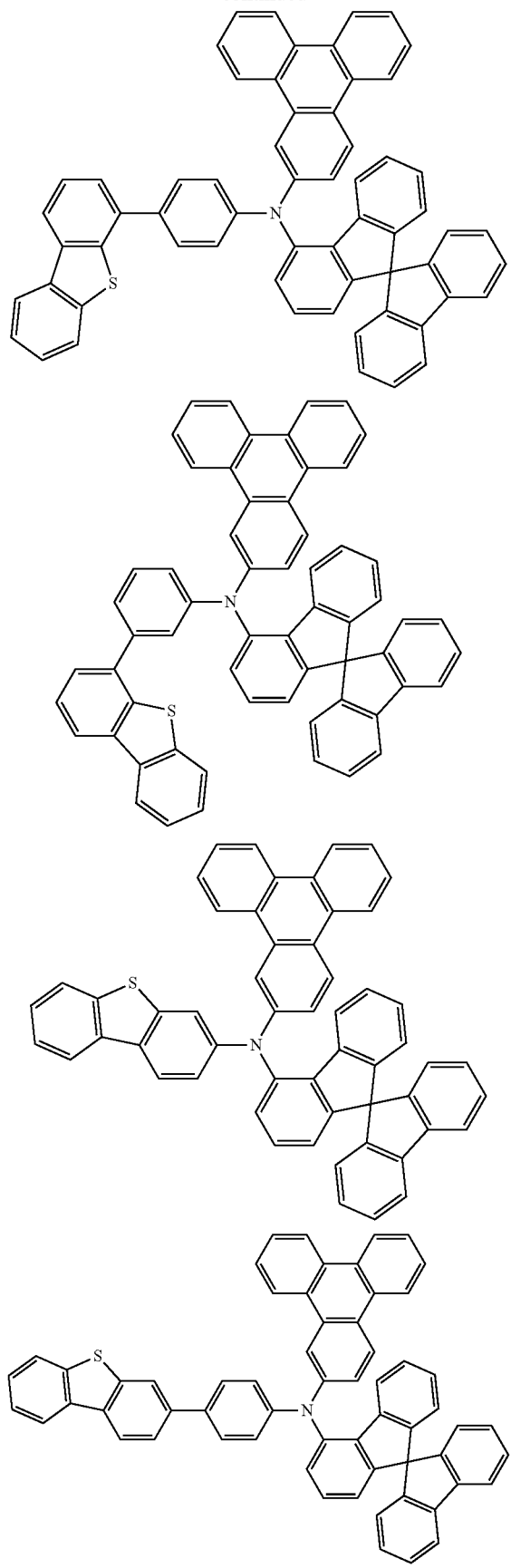
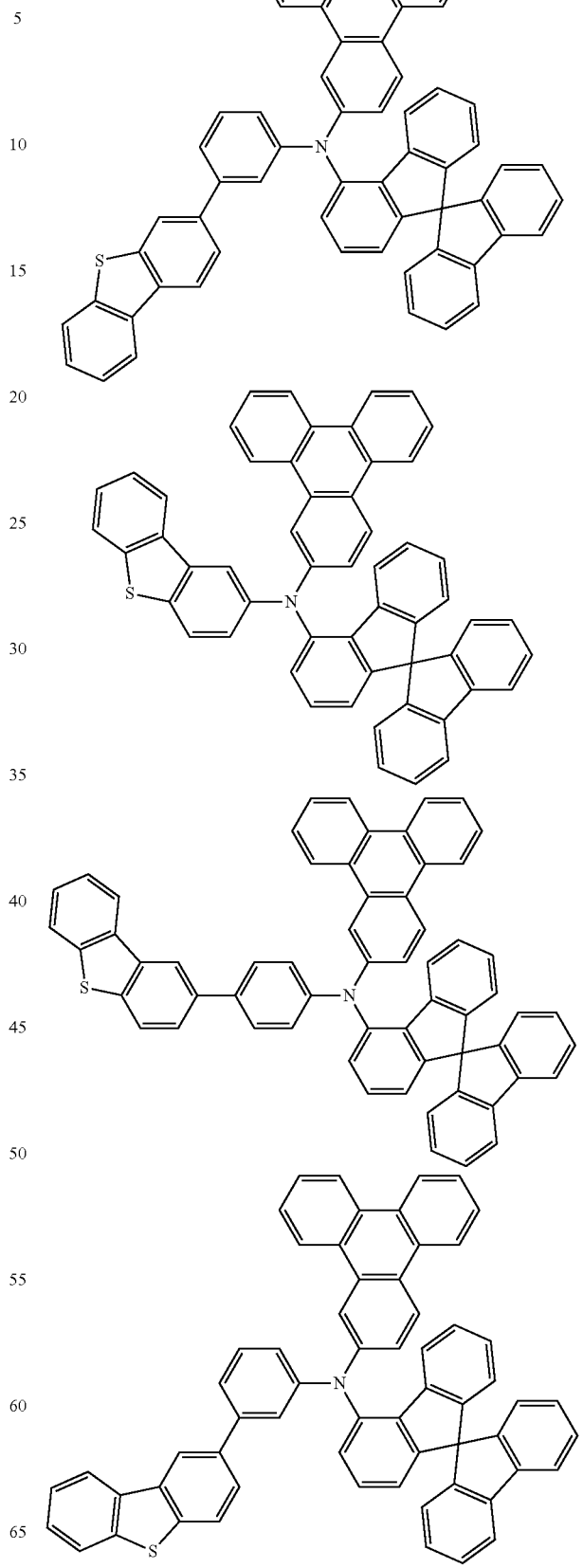

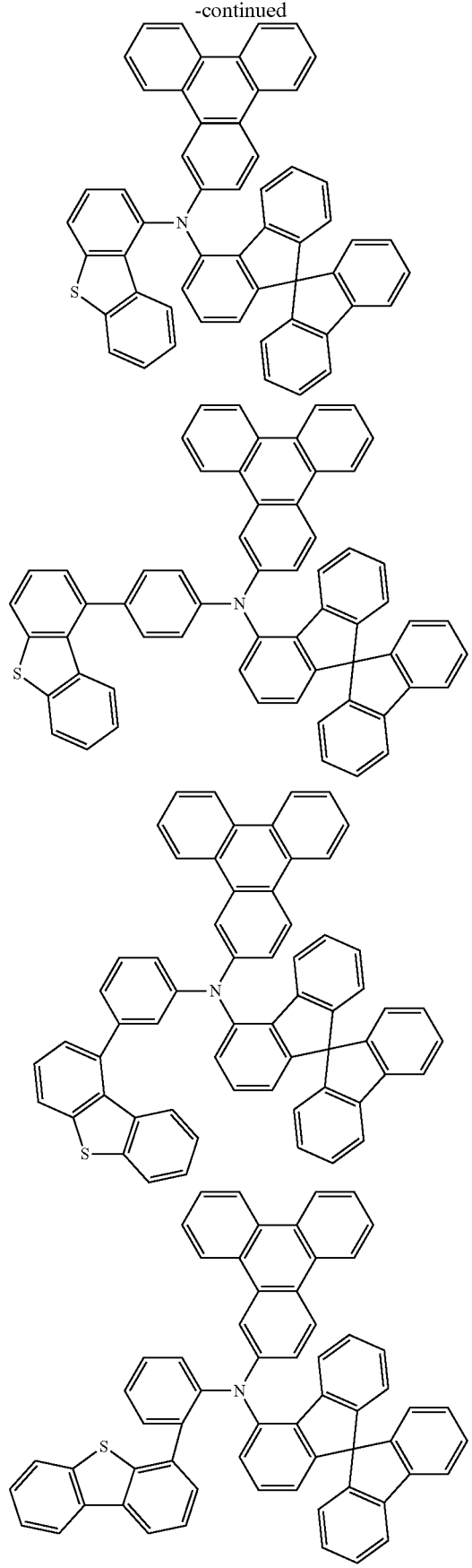
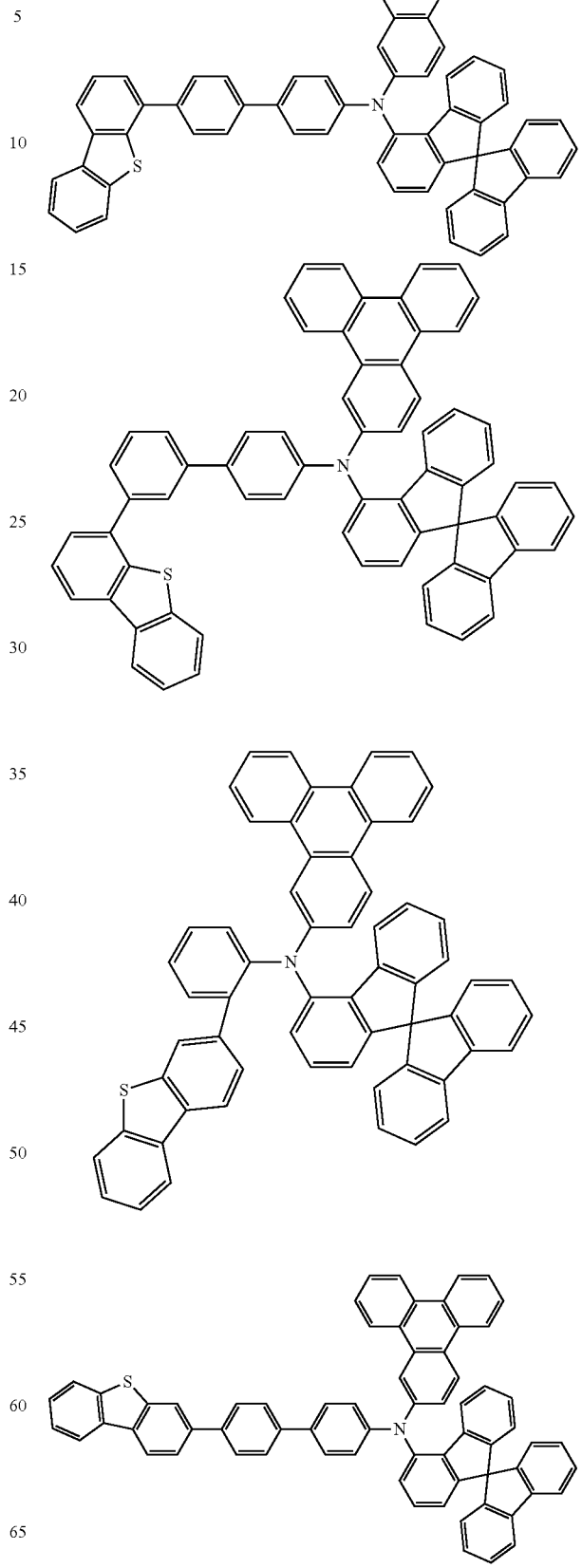

169
-continued
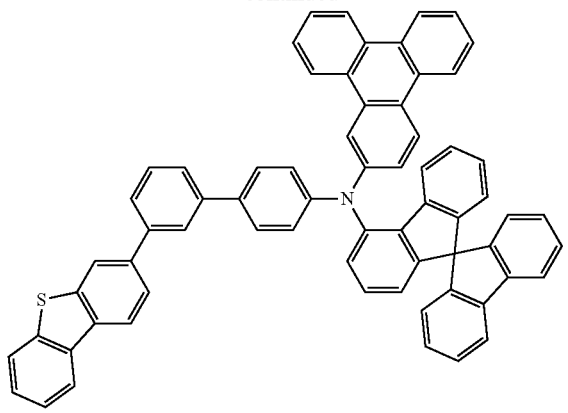
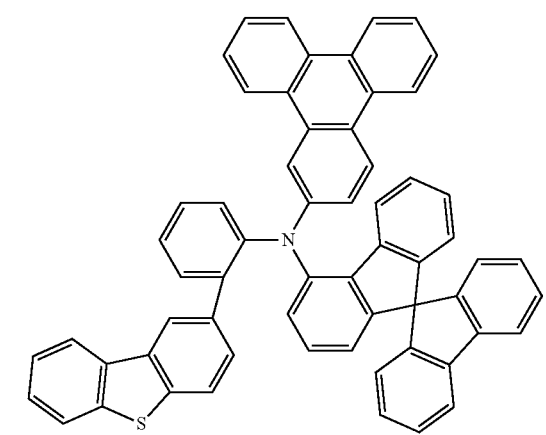
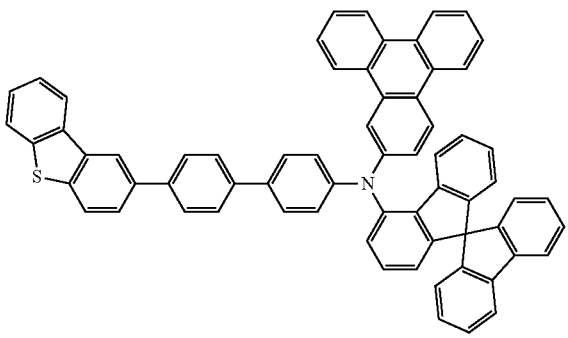
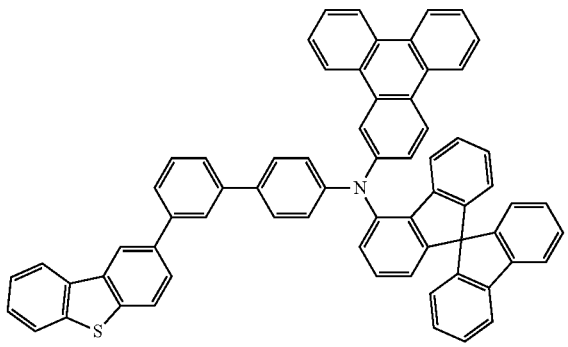
170
-continued
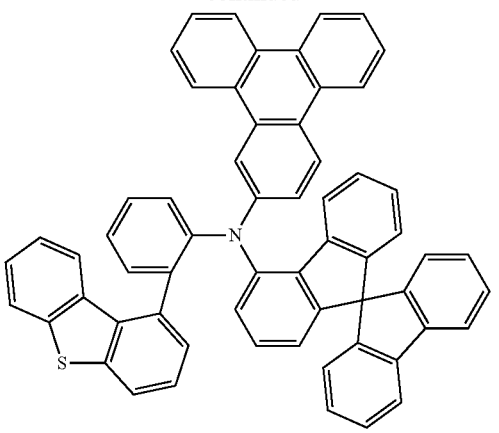
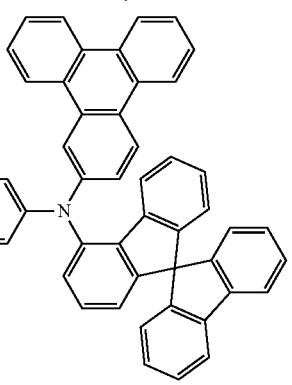
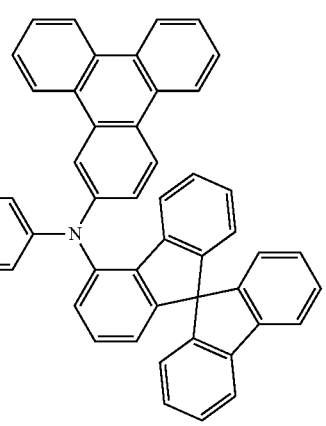
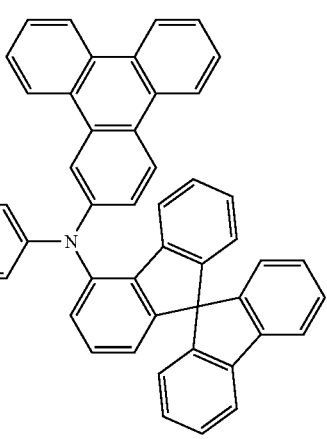

171
-continued
172
-continued
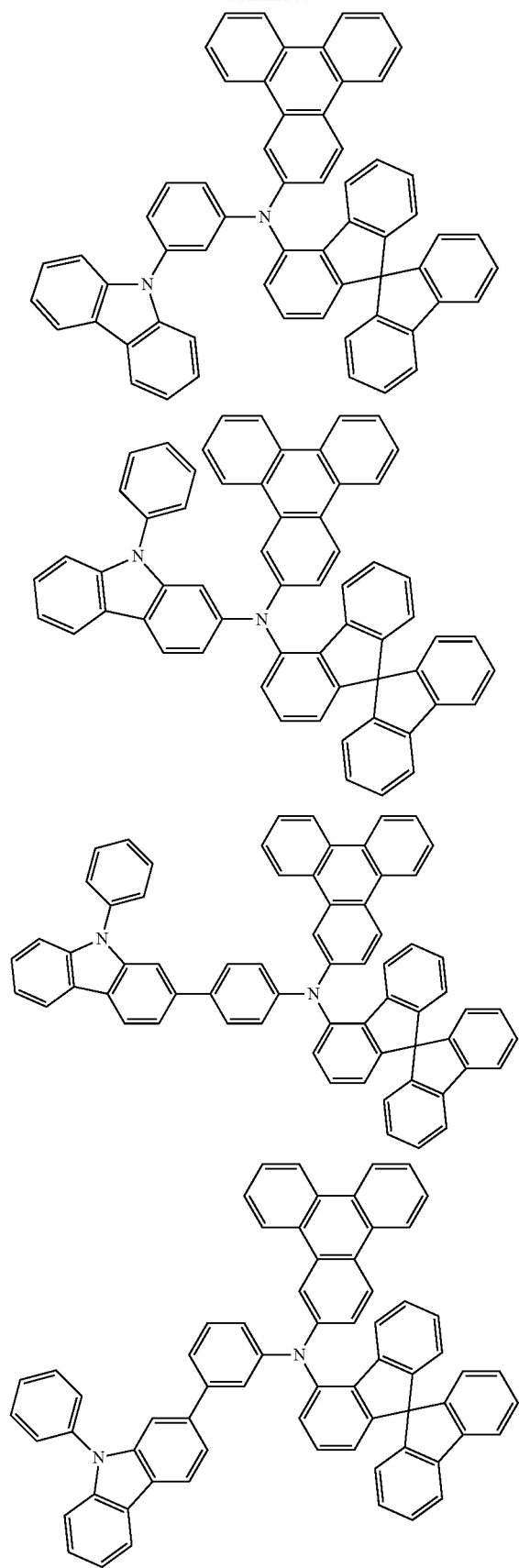
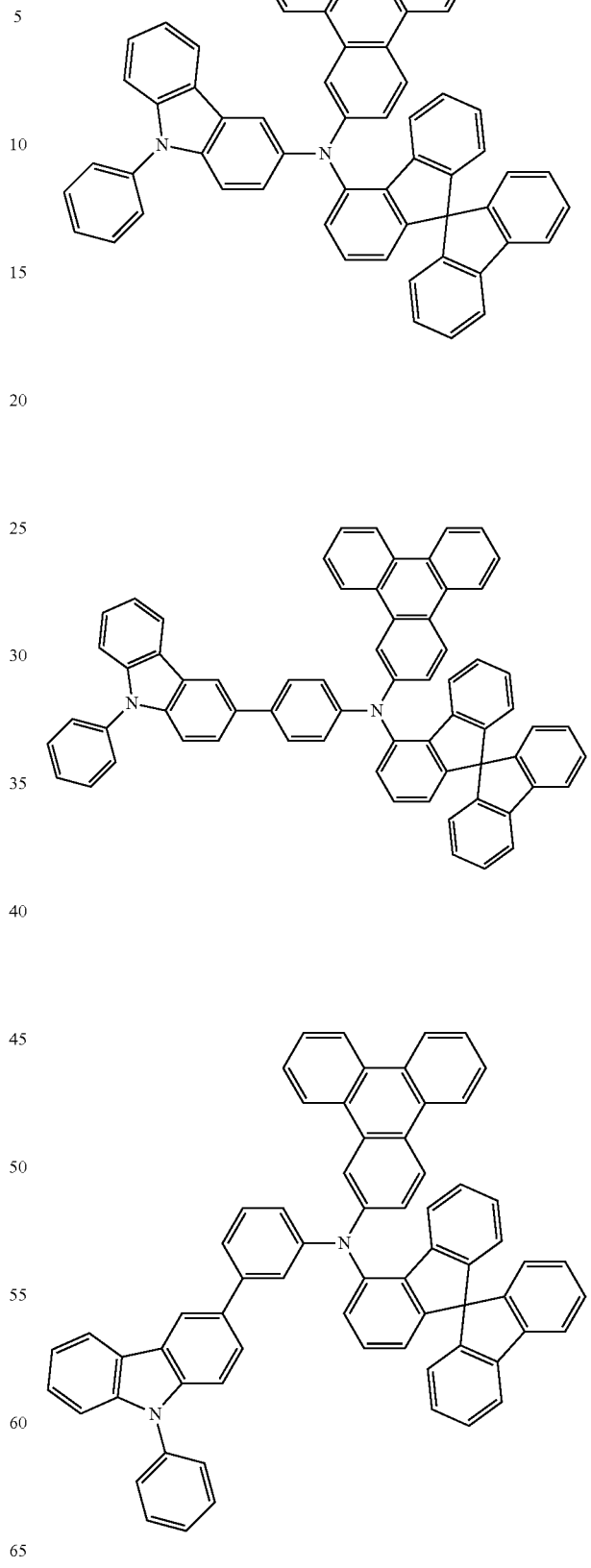

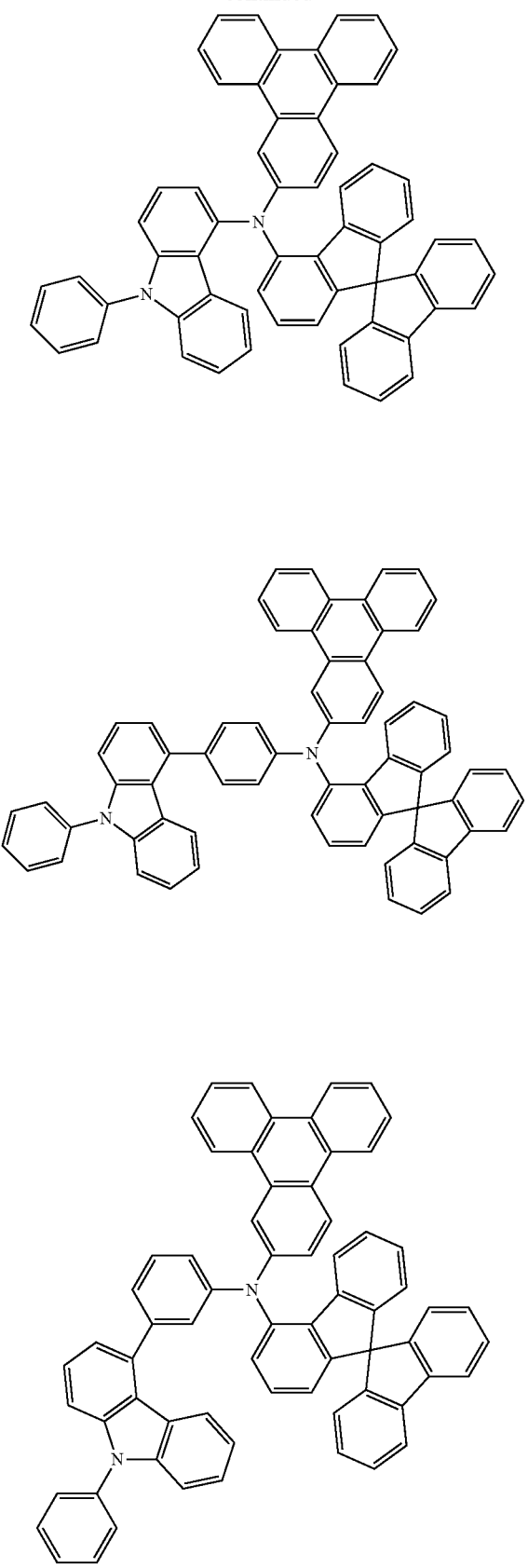
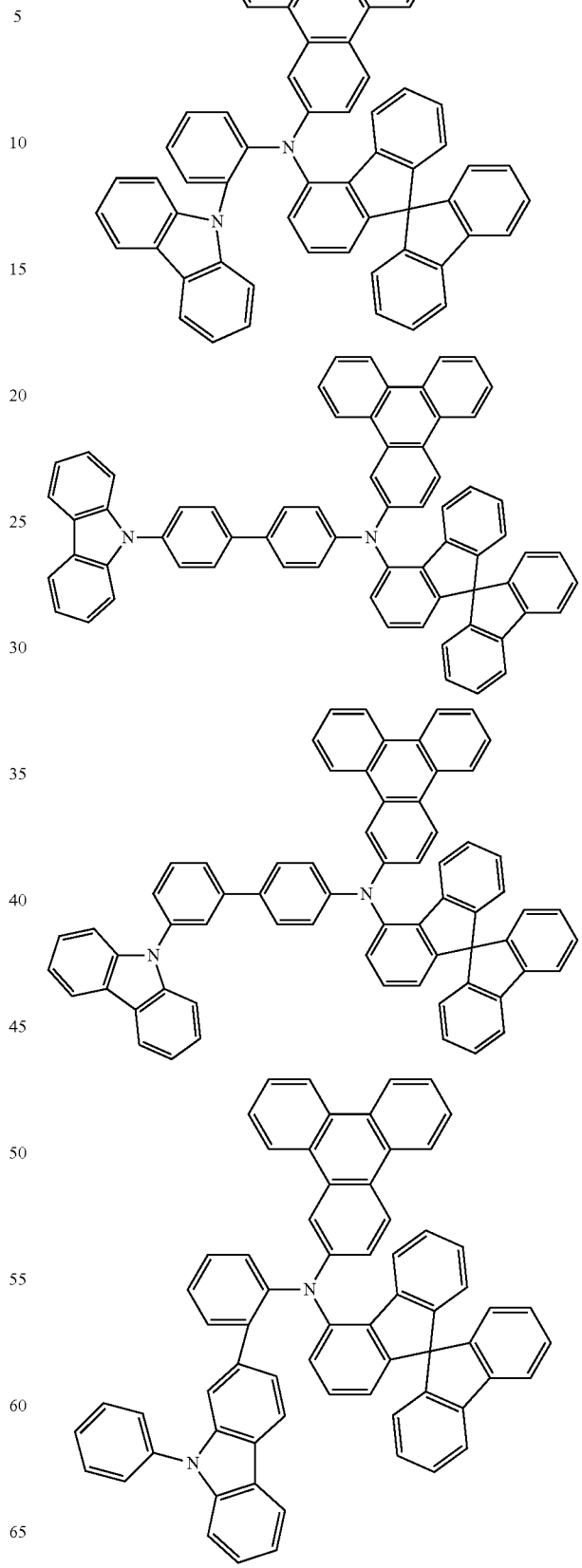

175
-continued
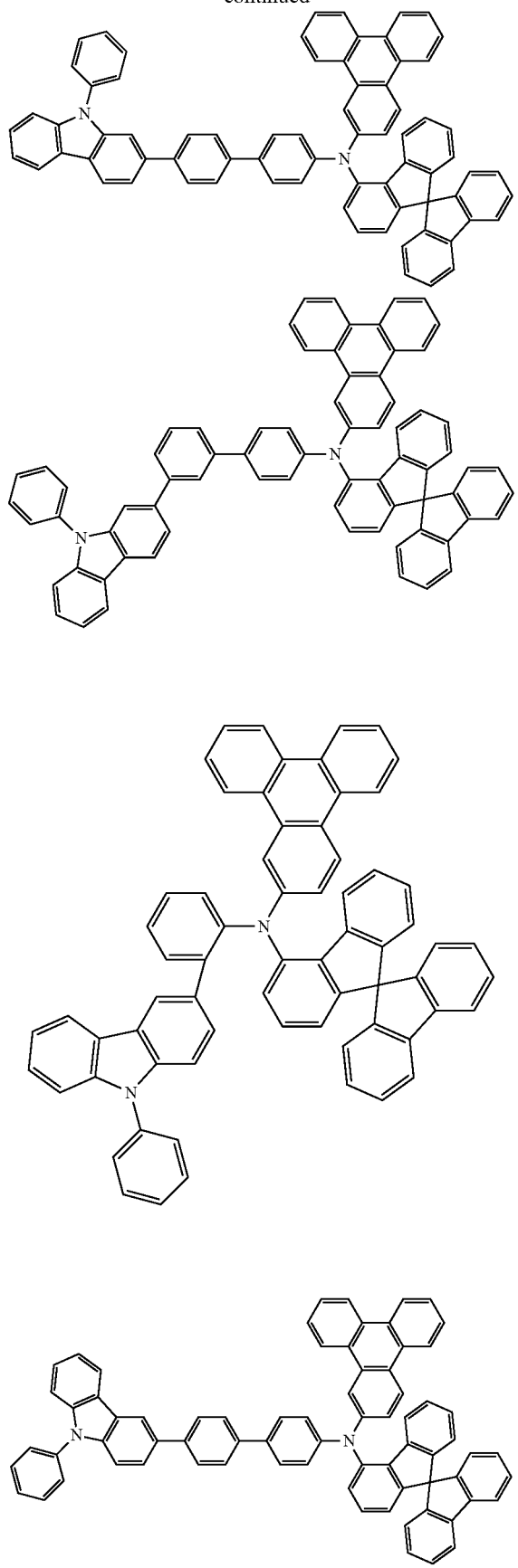
176
-continued
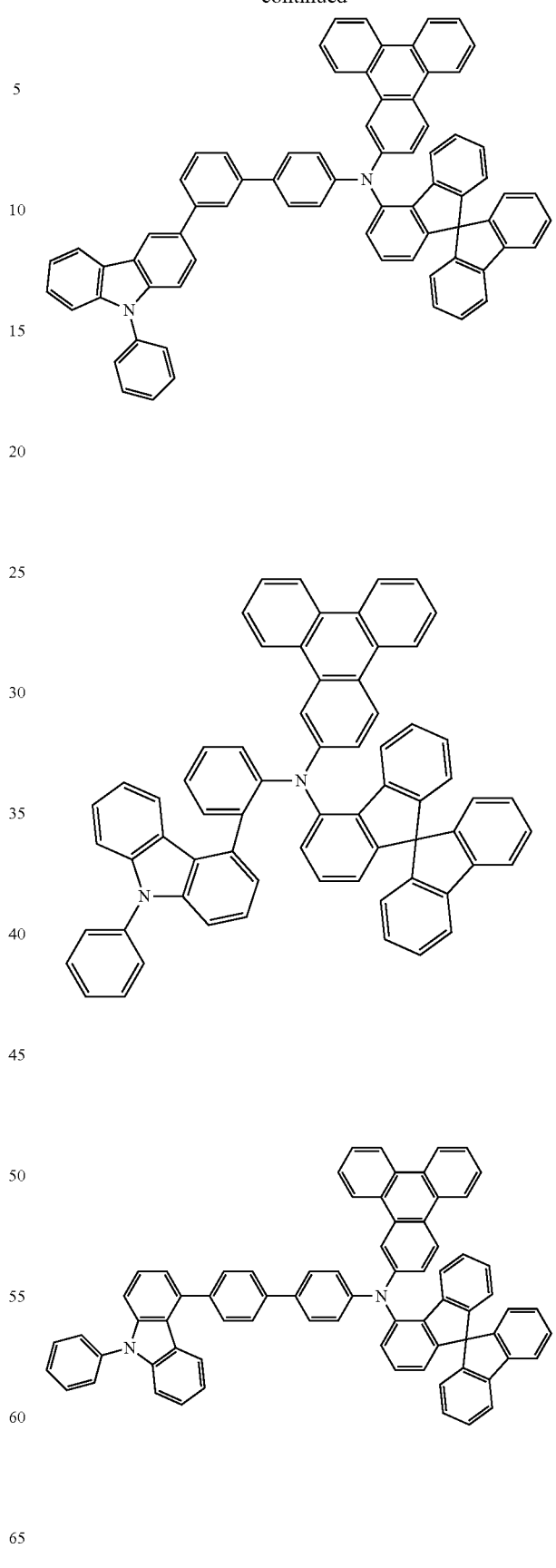

177
-continued
178
-continued
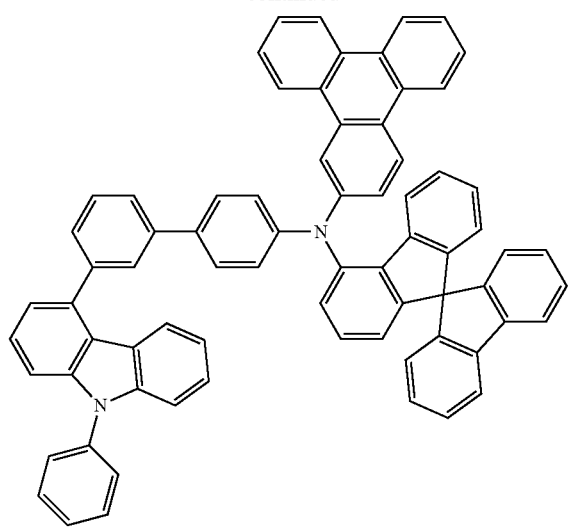 [SMILES: c1ccc(-n2c3ccccc3c3c(-c4cccc(-c5ccc(N(c6ccc7c8ccccc8c8ccccc8c7c6)c6cccc7c6-c6ccccc6C76c7ccccc7-c7ccccc76)cc5)c4)cccc32)cc1]
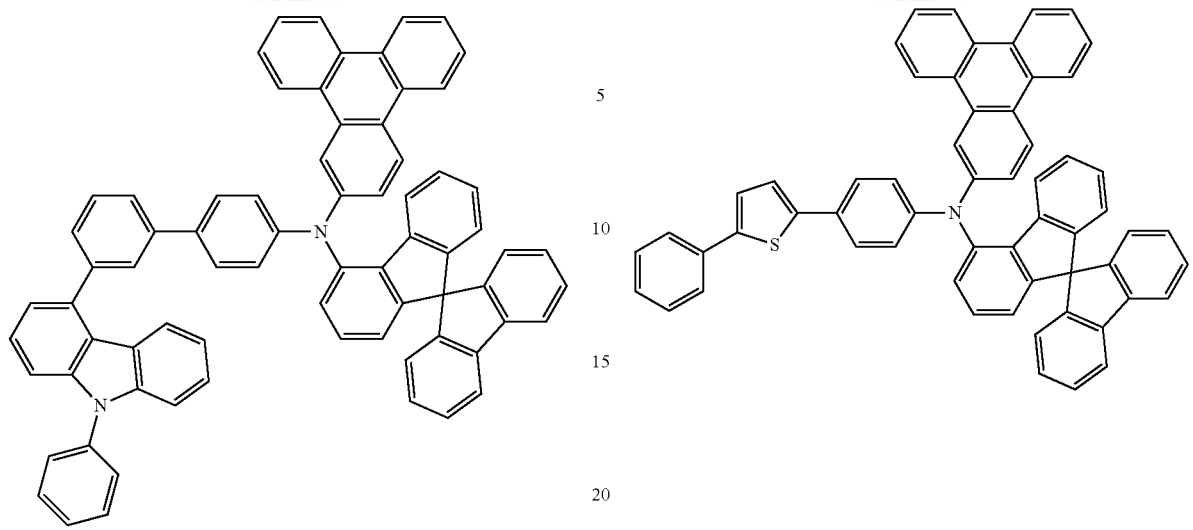
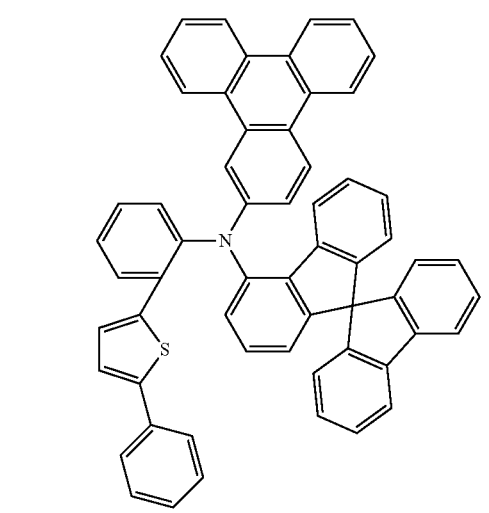
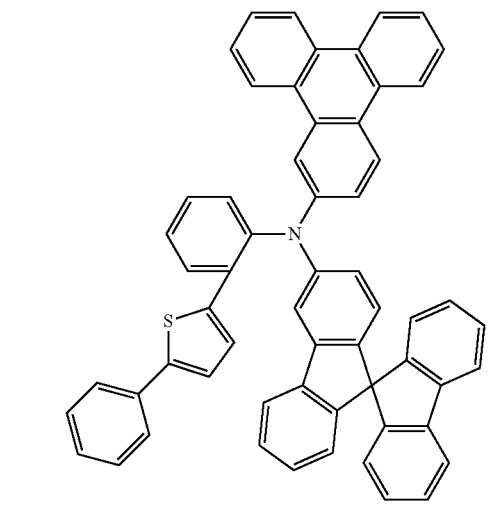
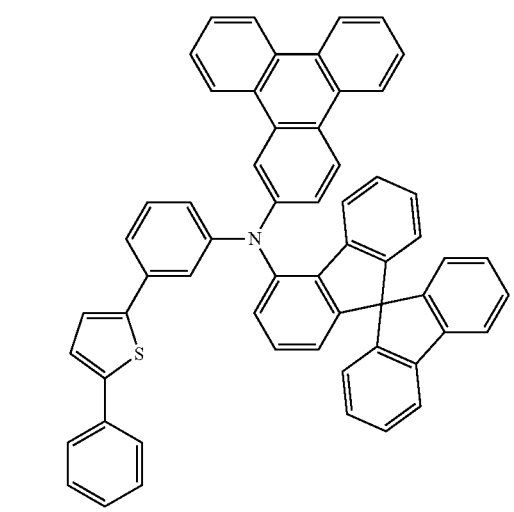
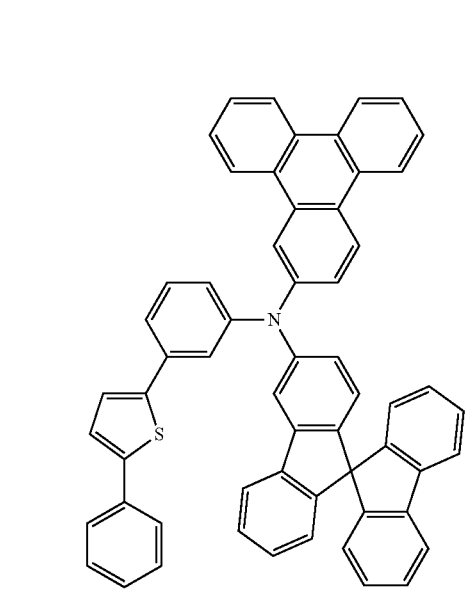

-continued
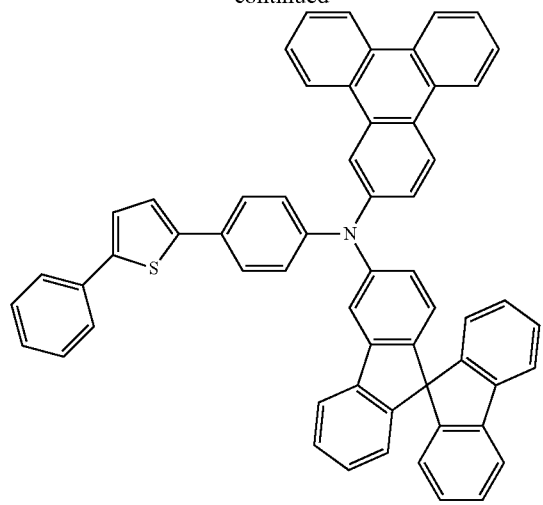
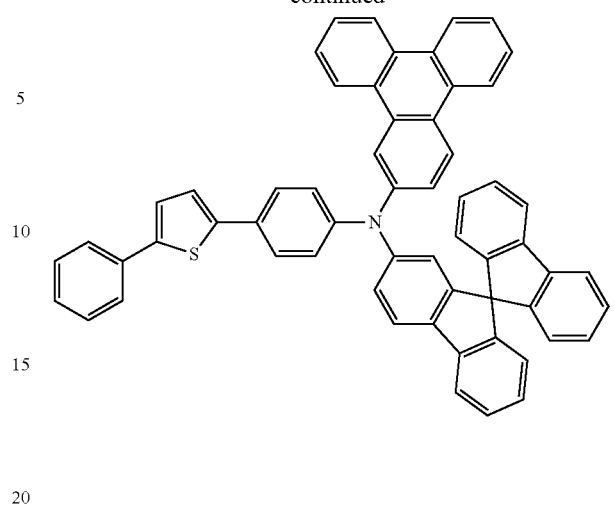
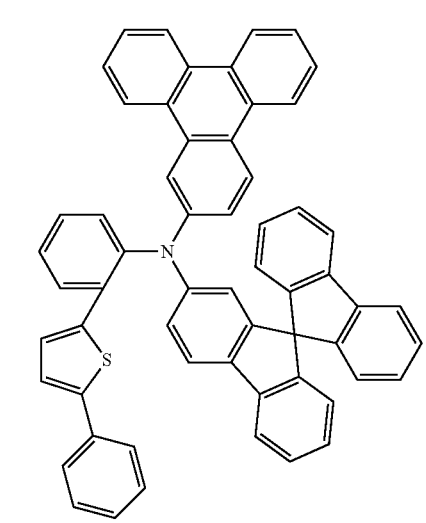
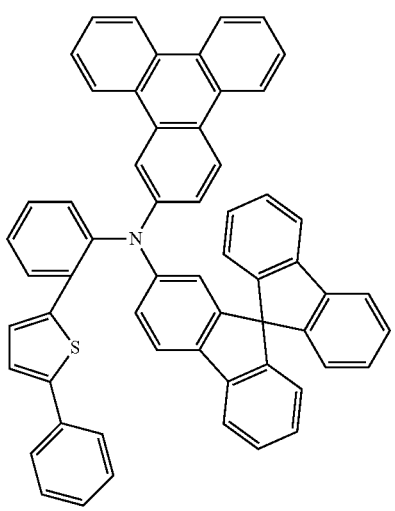
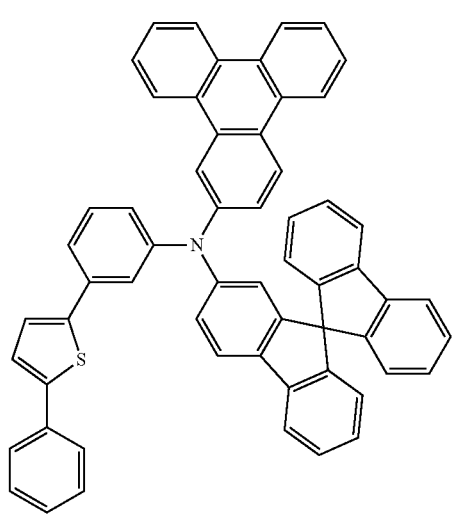
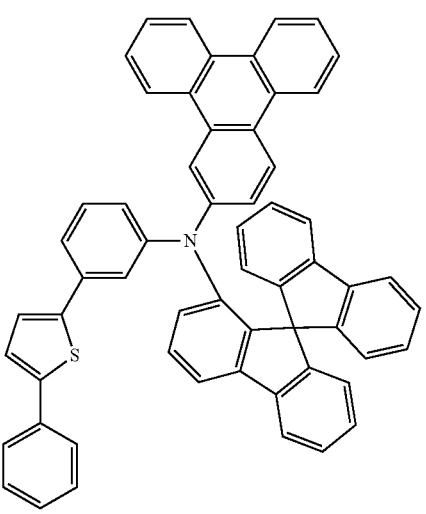

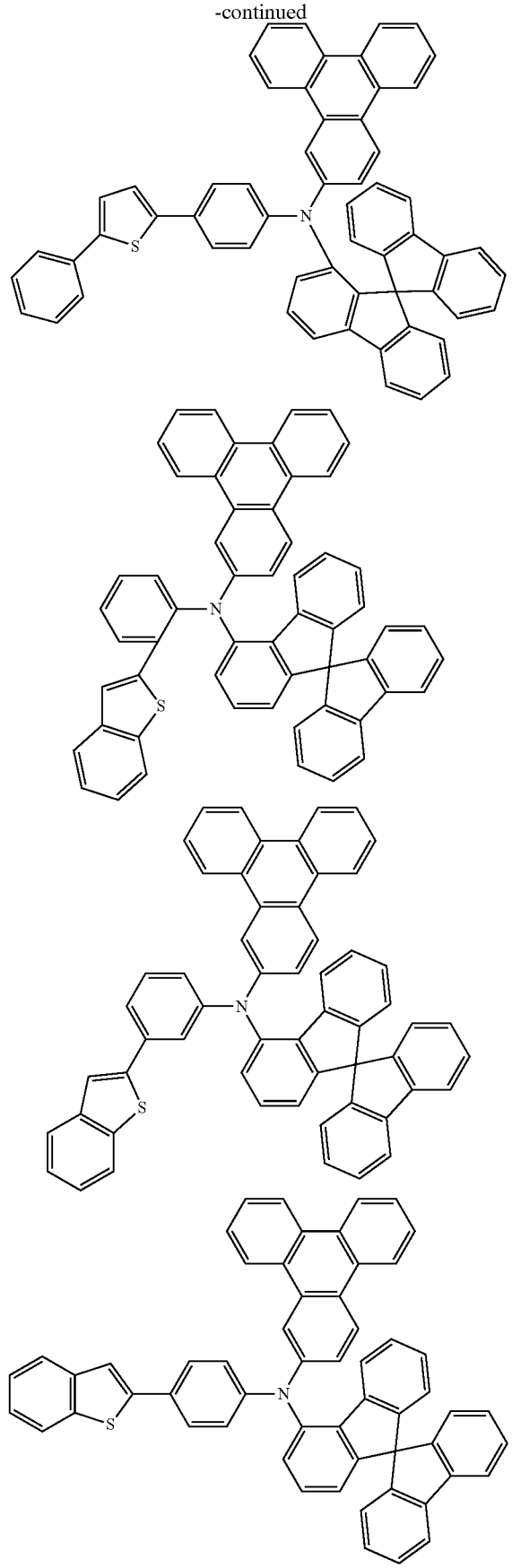
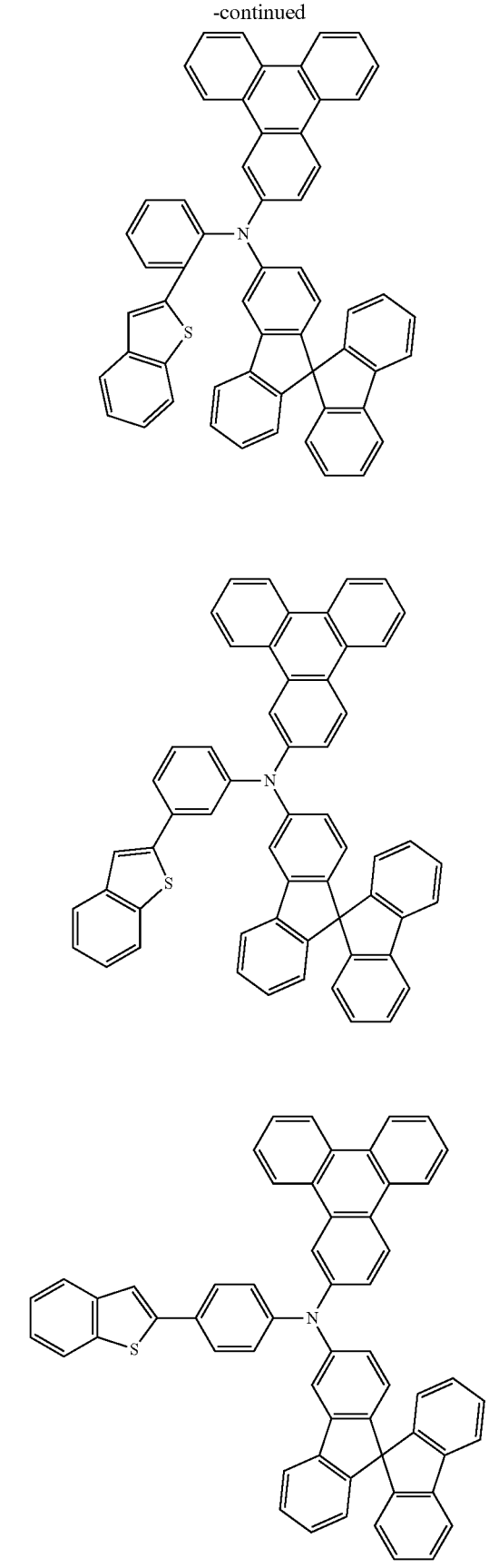

183
-continued
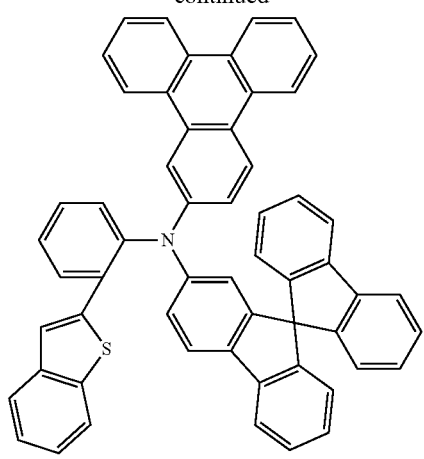
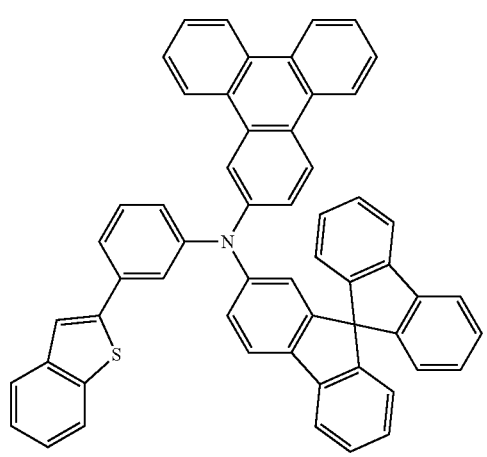
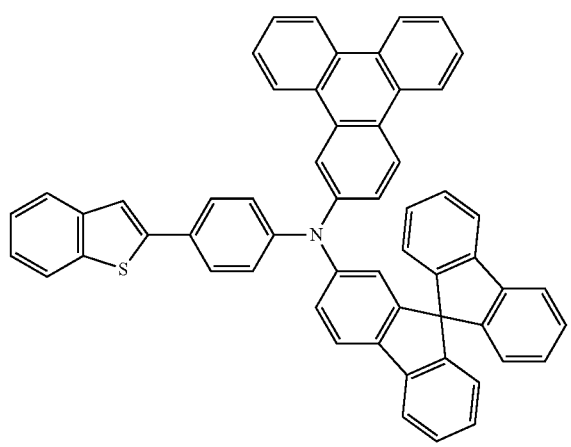
184
-continued
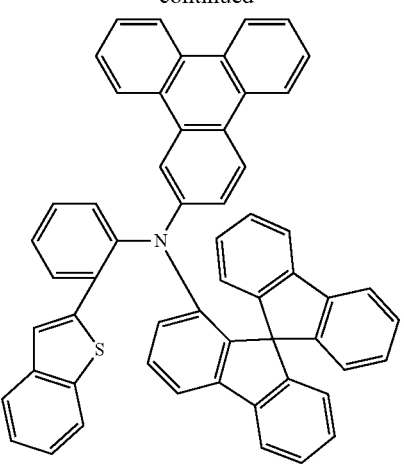
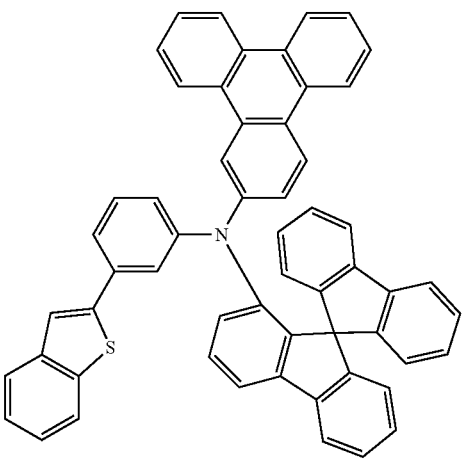
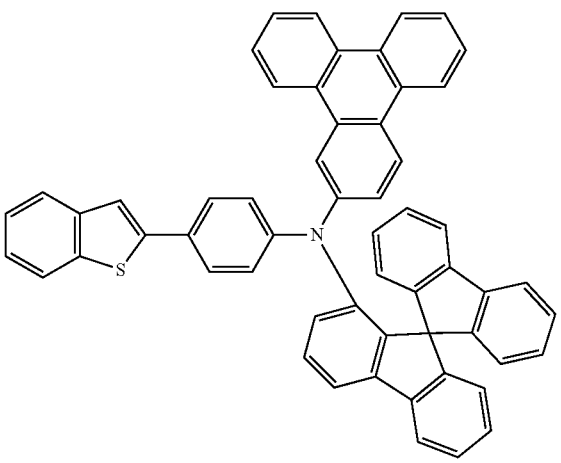

185
-continued
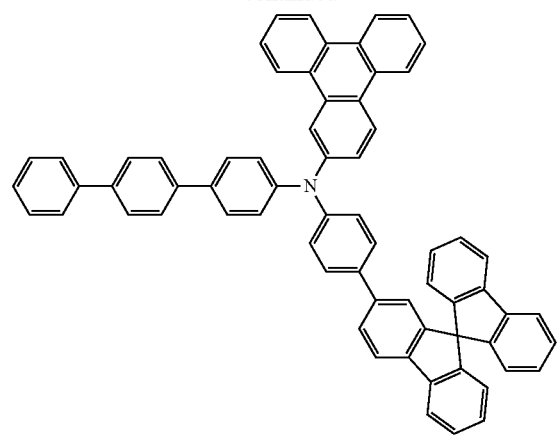
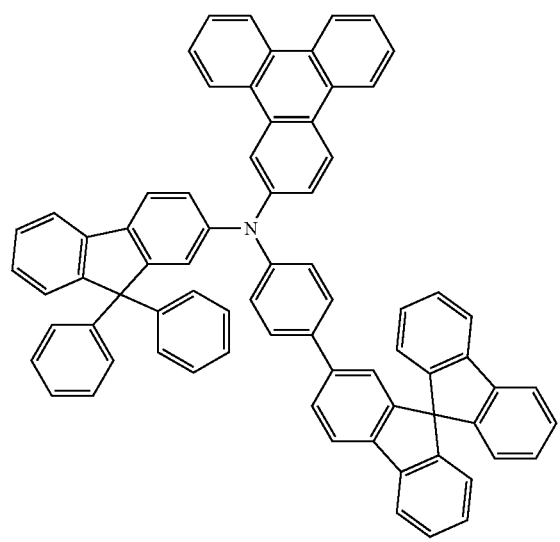
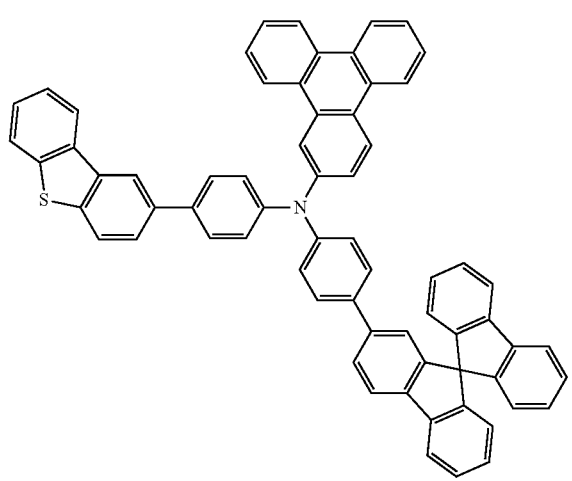
186
-continued
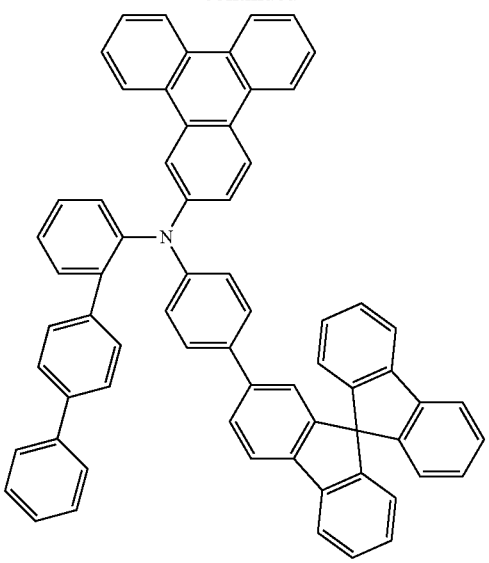
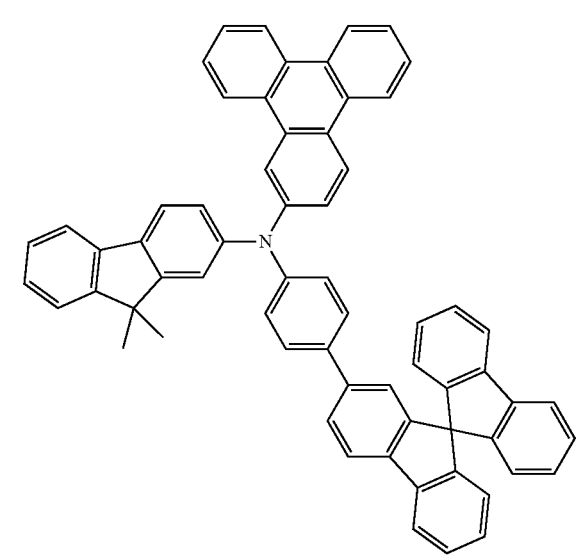
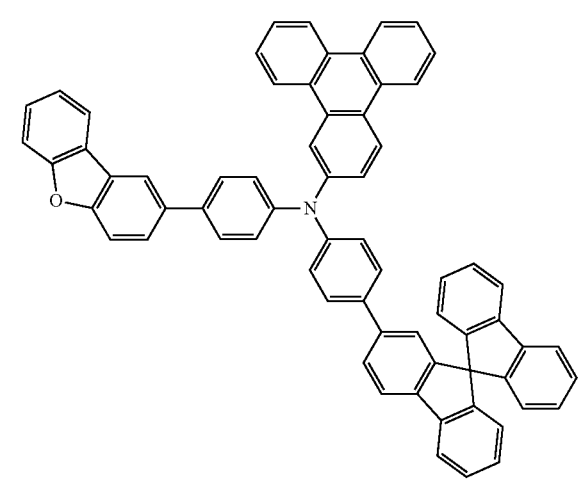

-continued
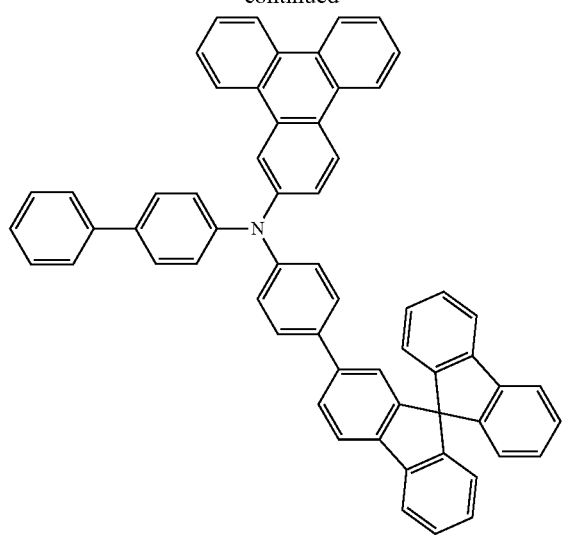
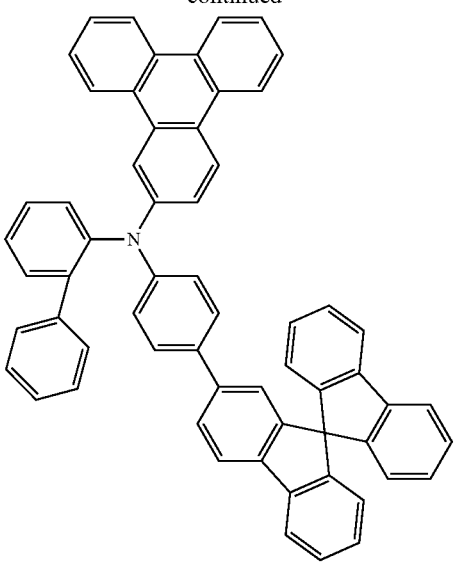
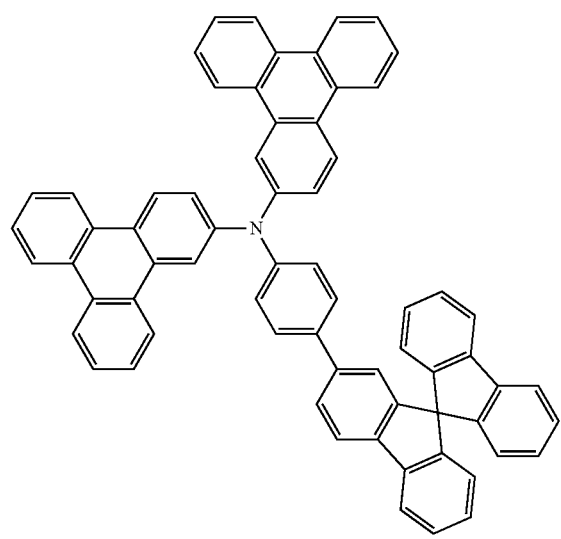
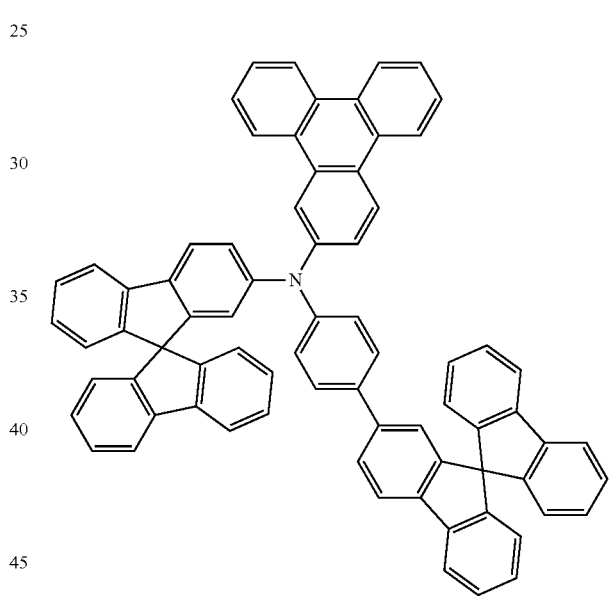
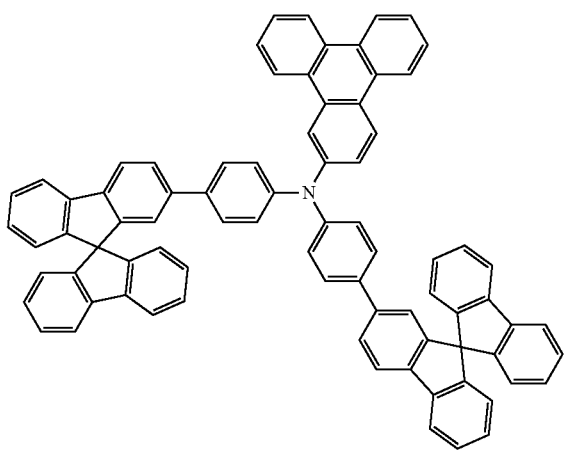
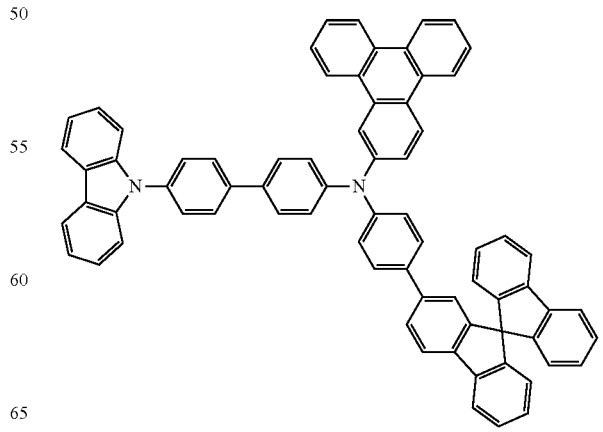

189
-continued
190
-continued
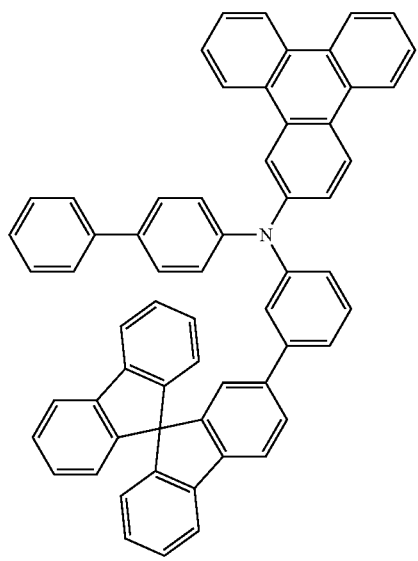
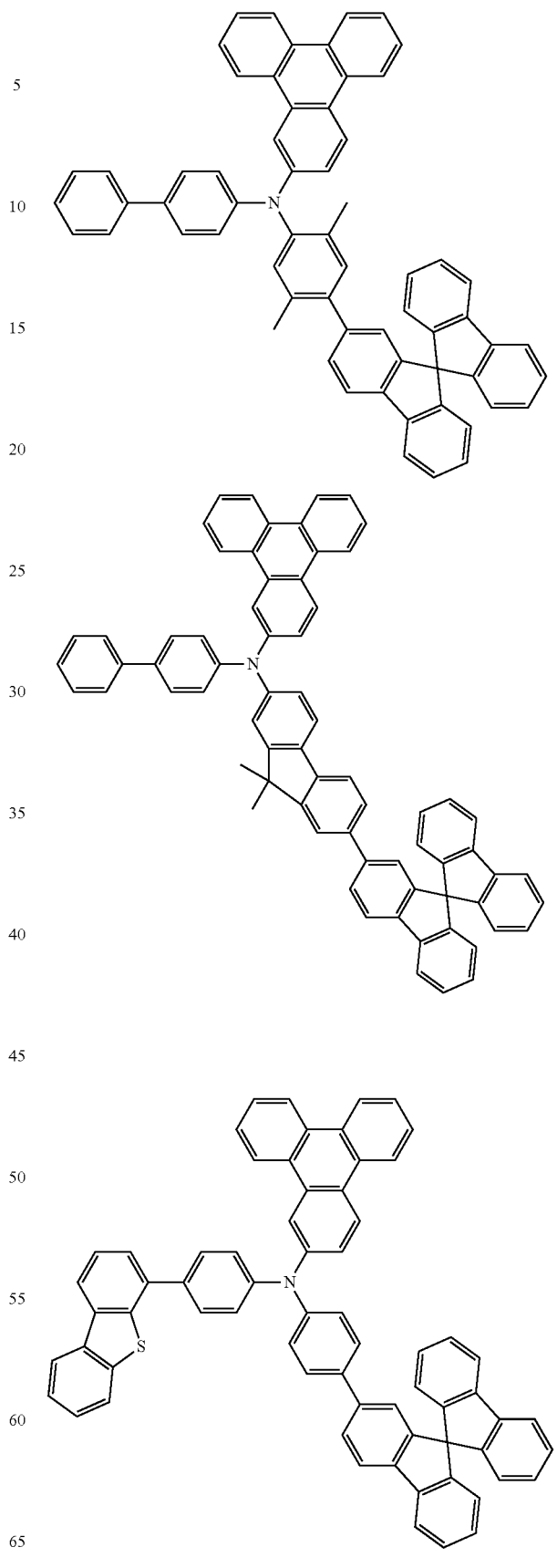

191
-continued
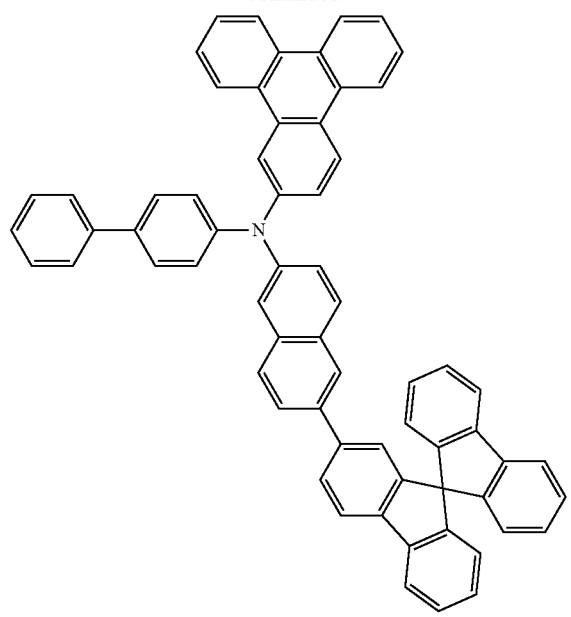
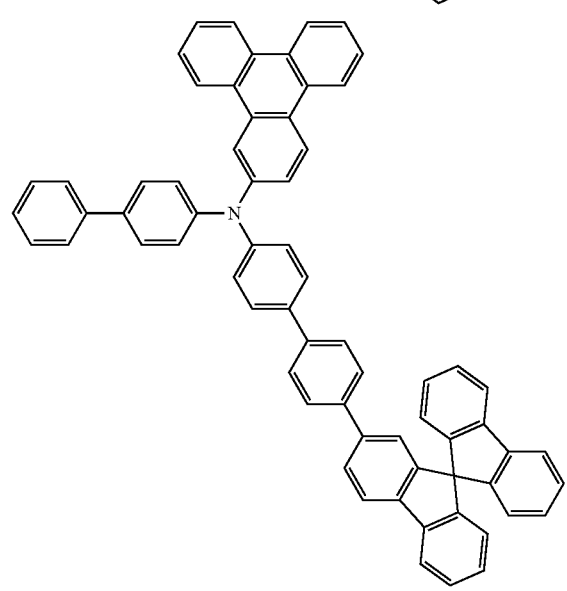
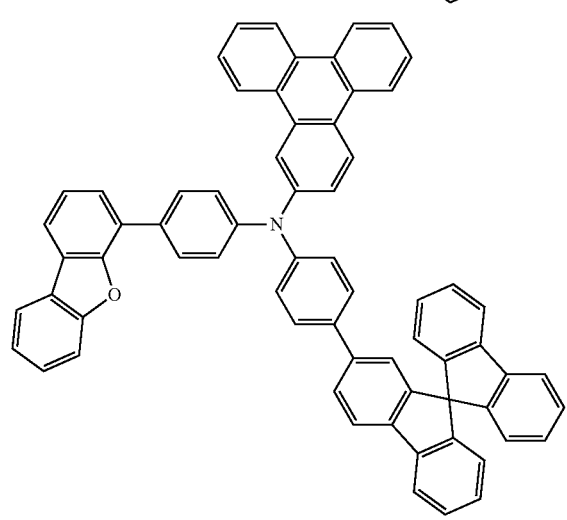
192
-continued
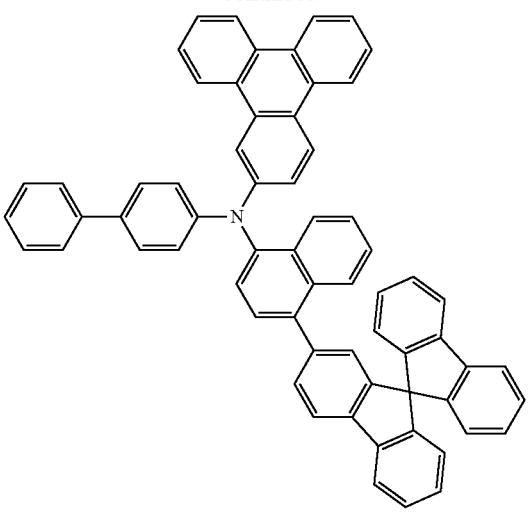
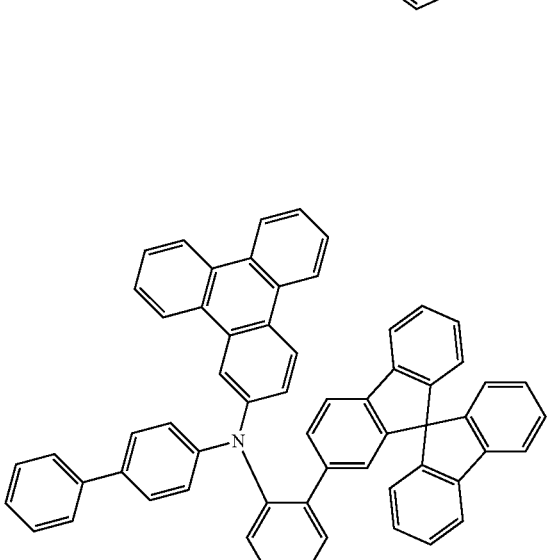

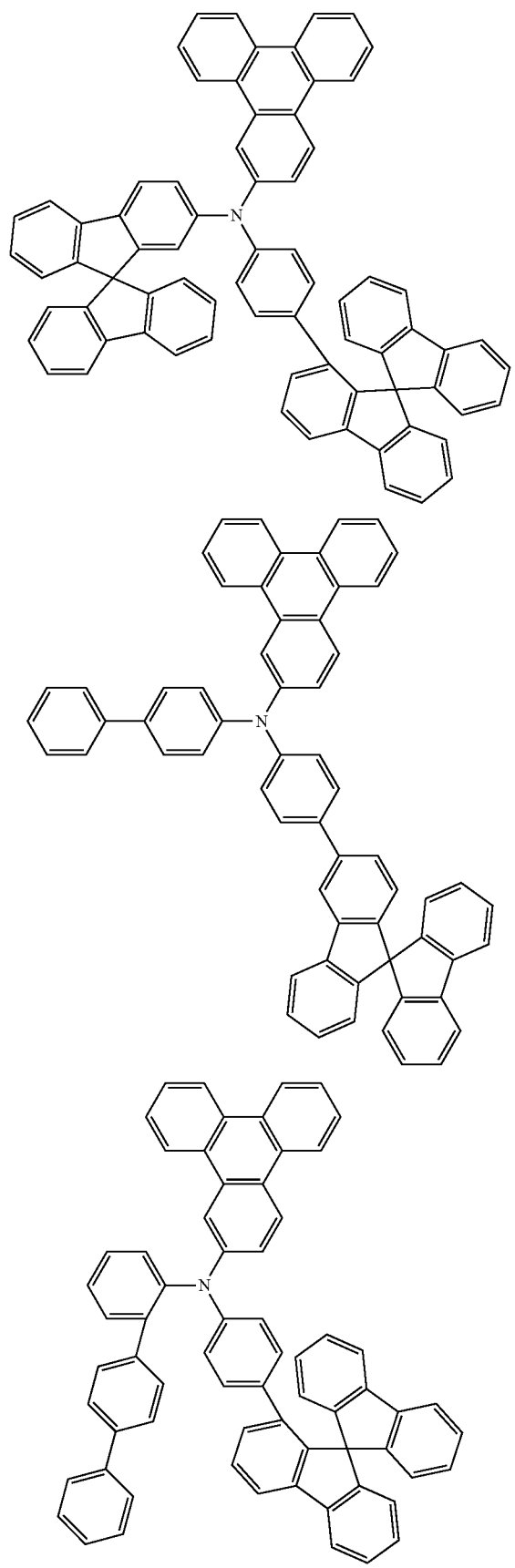
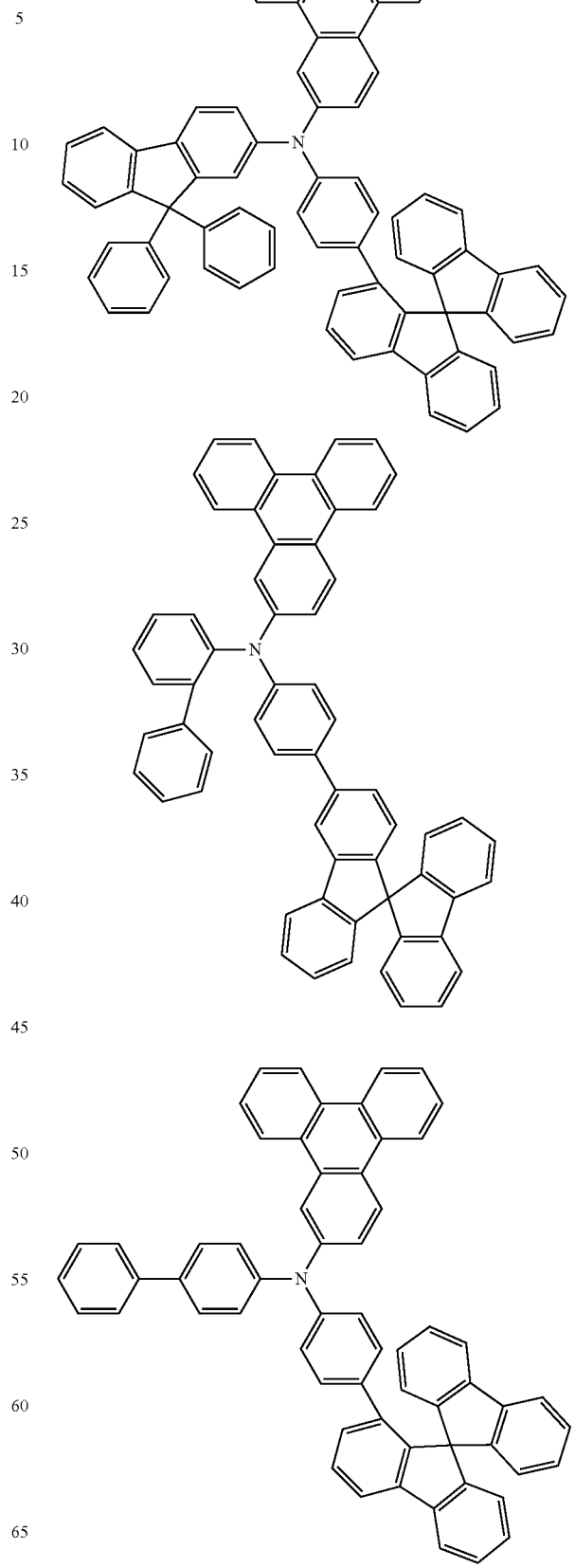

-continued
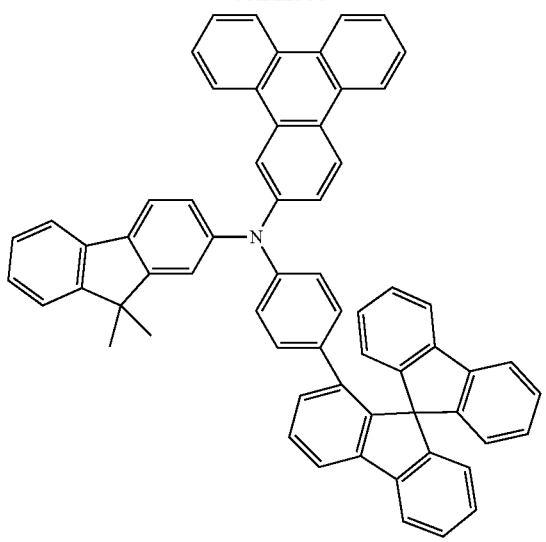
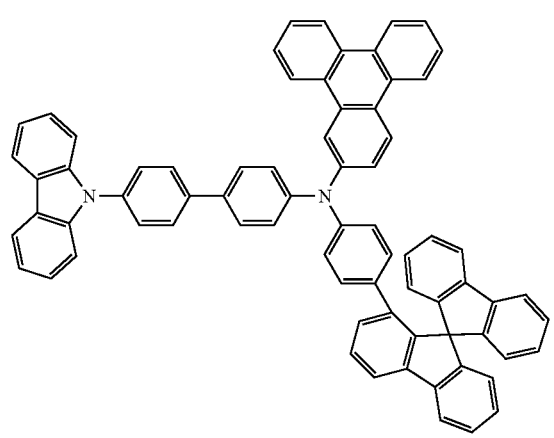
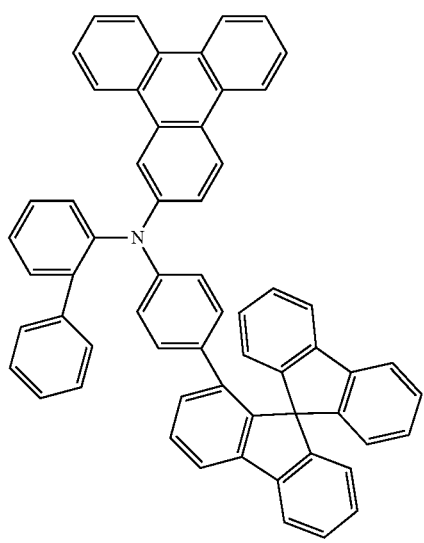
-continued
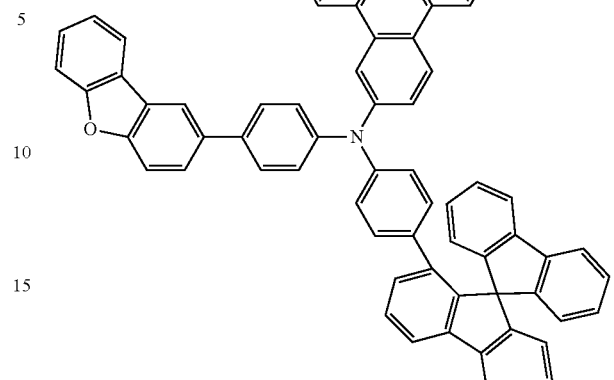
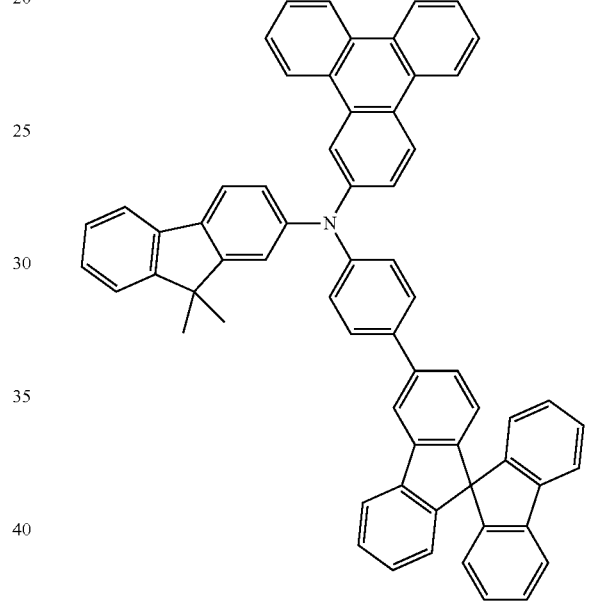
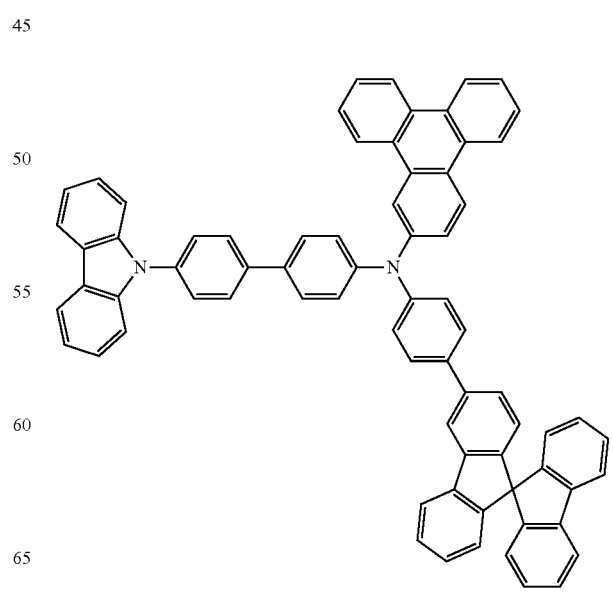

197
-continued
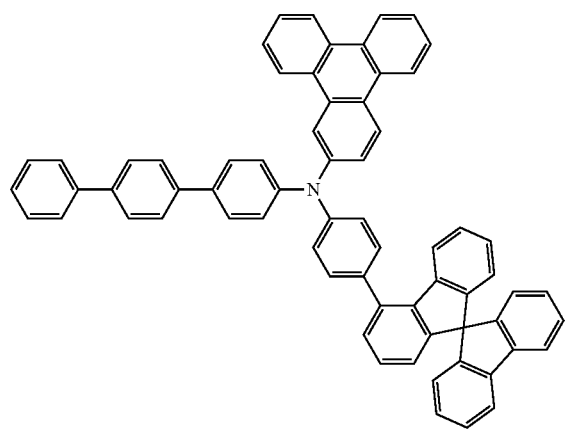
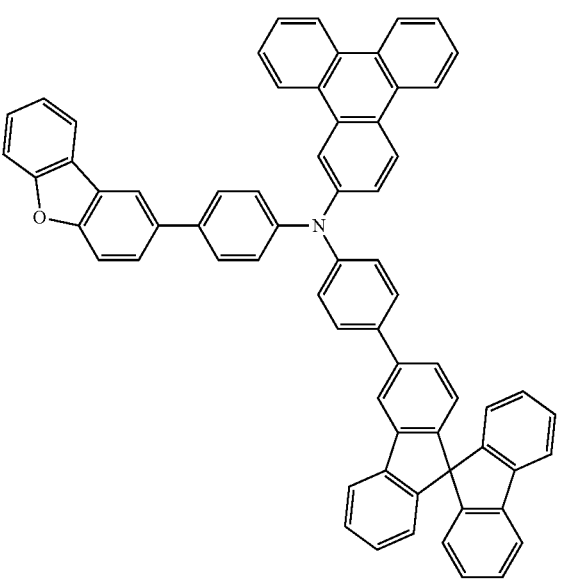
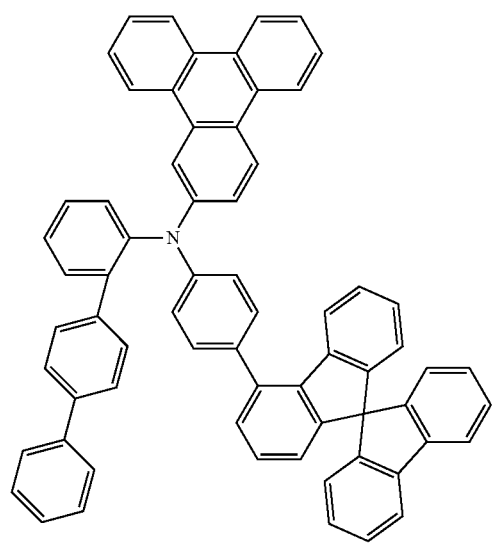
198
-continued
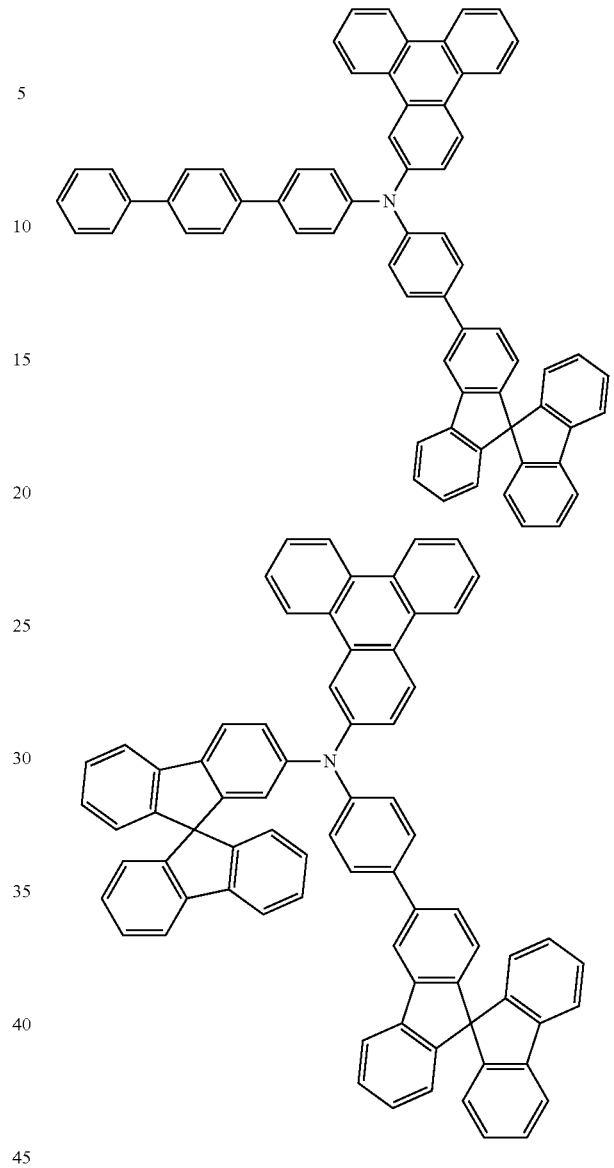
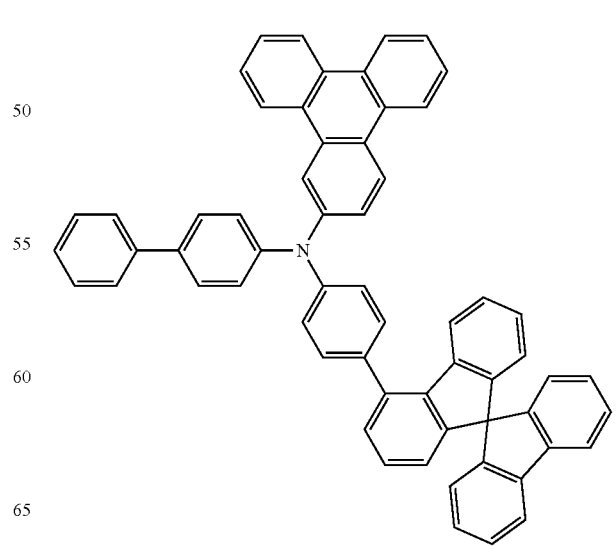

199
-continued
200
-continued
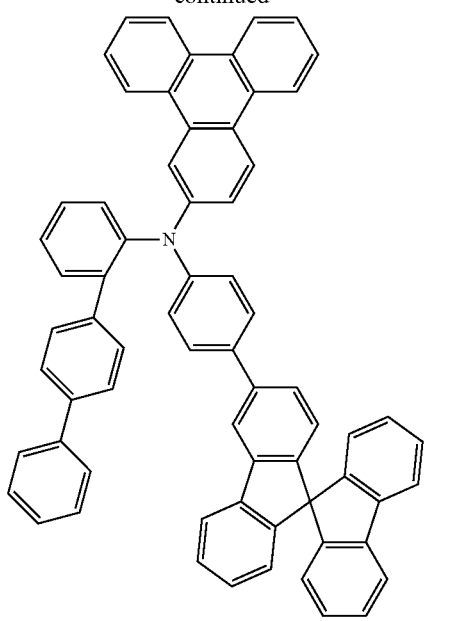
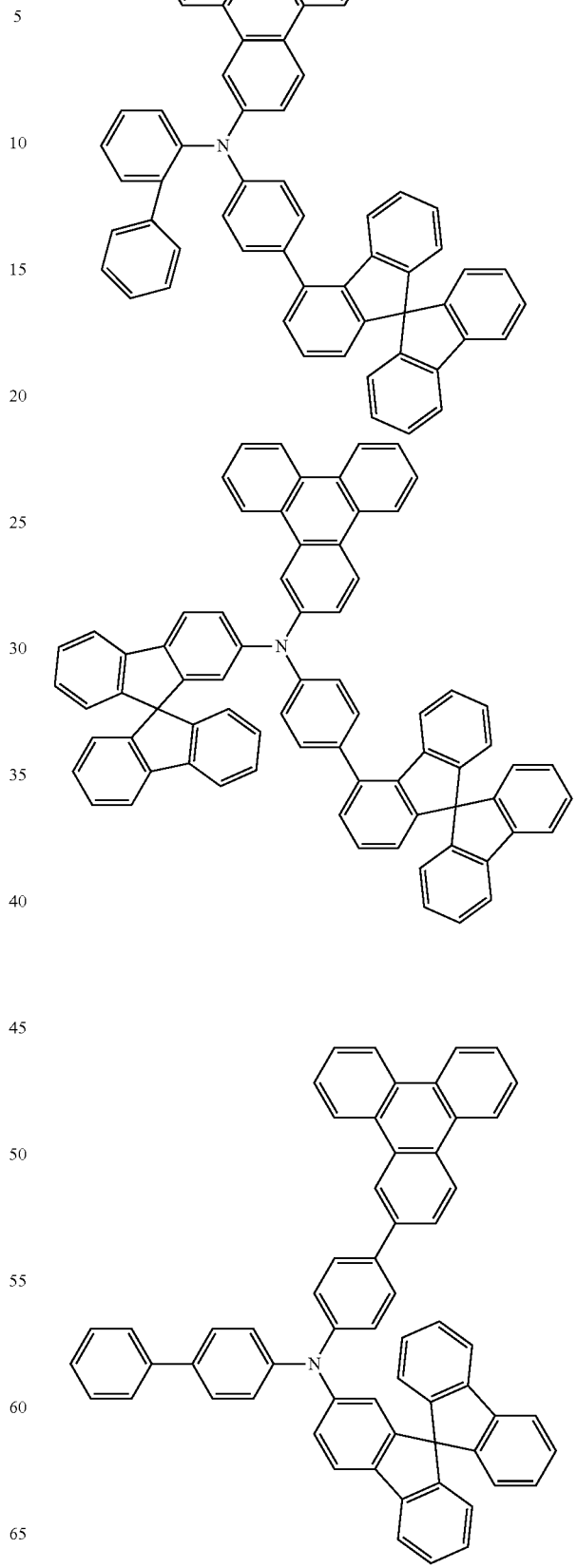

201
-continued
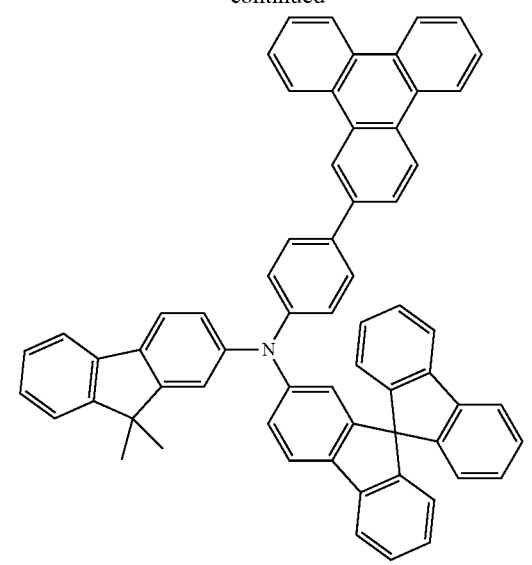
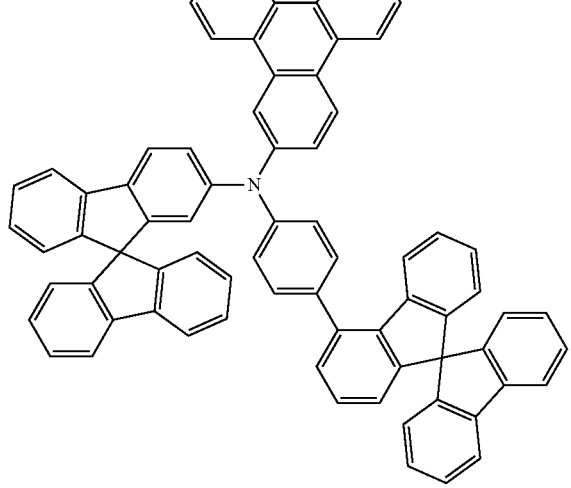
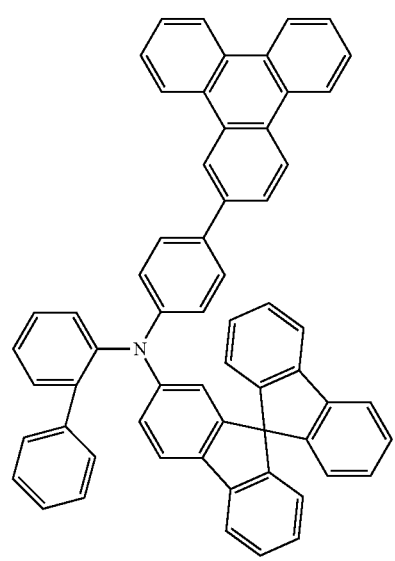
202
-continued
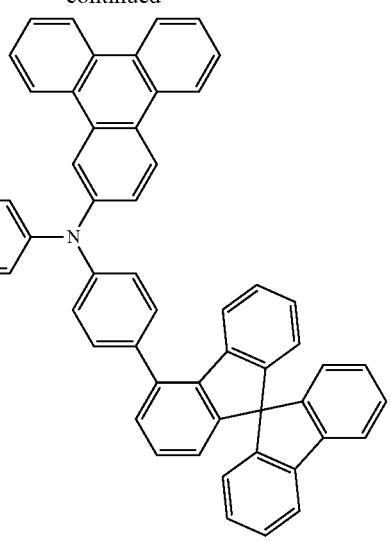
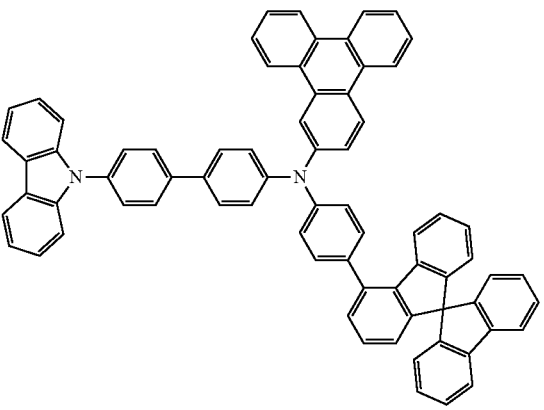
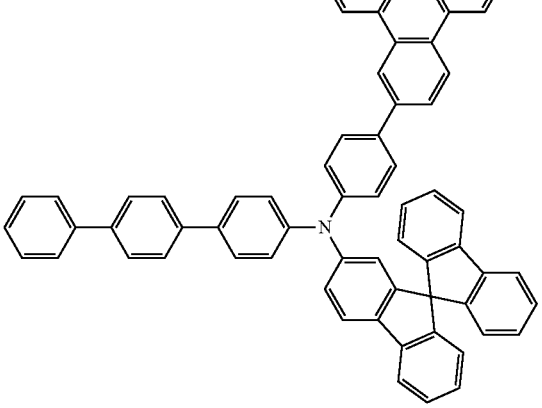

203
-continued
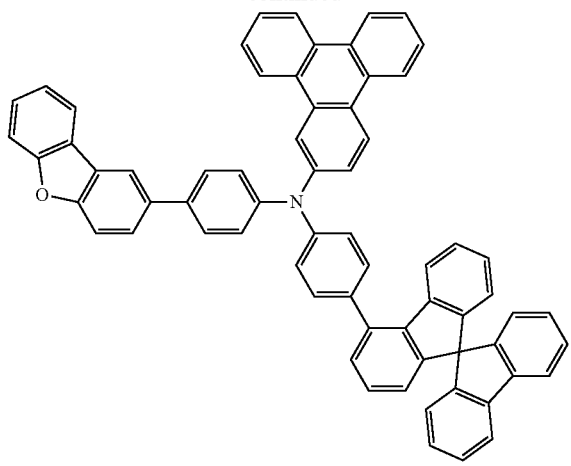
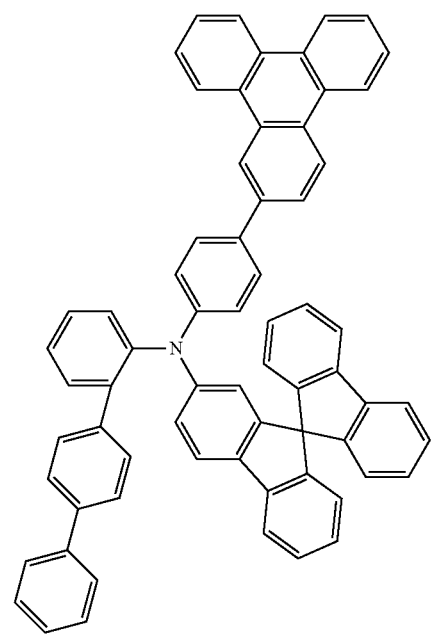
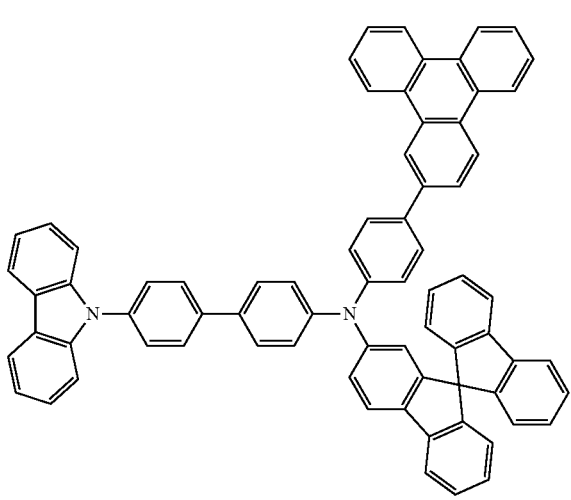
204
-continued
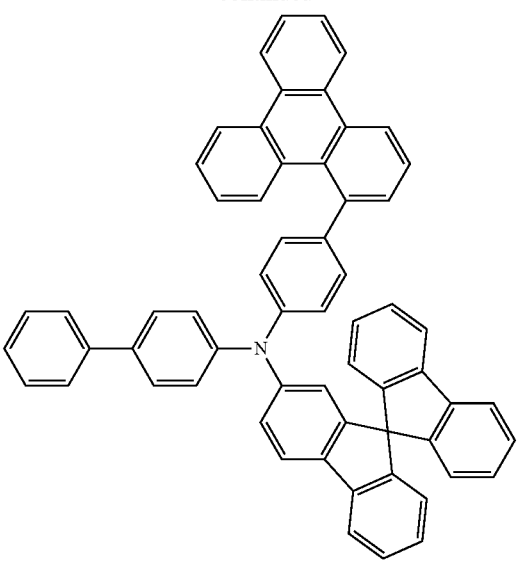
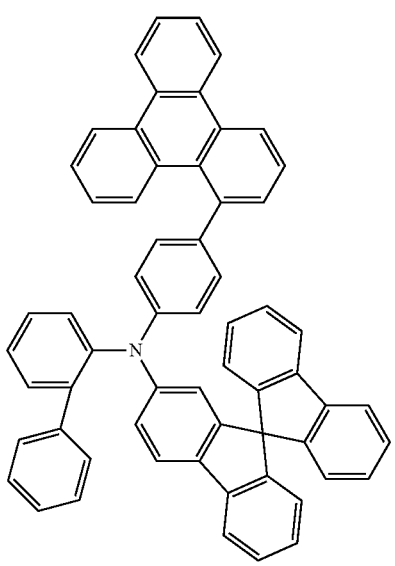

205
-continued
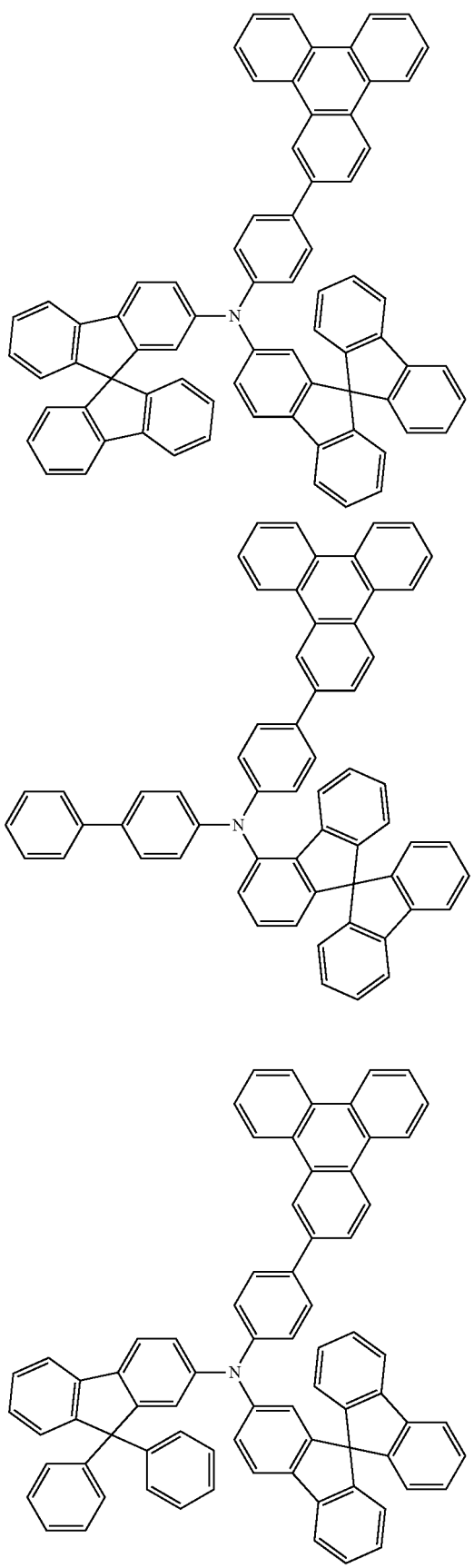
206
-continued
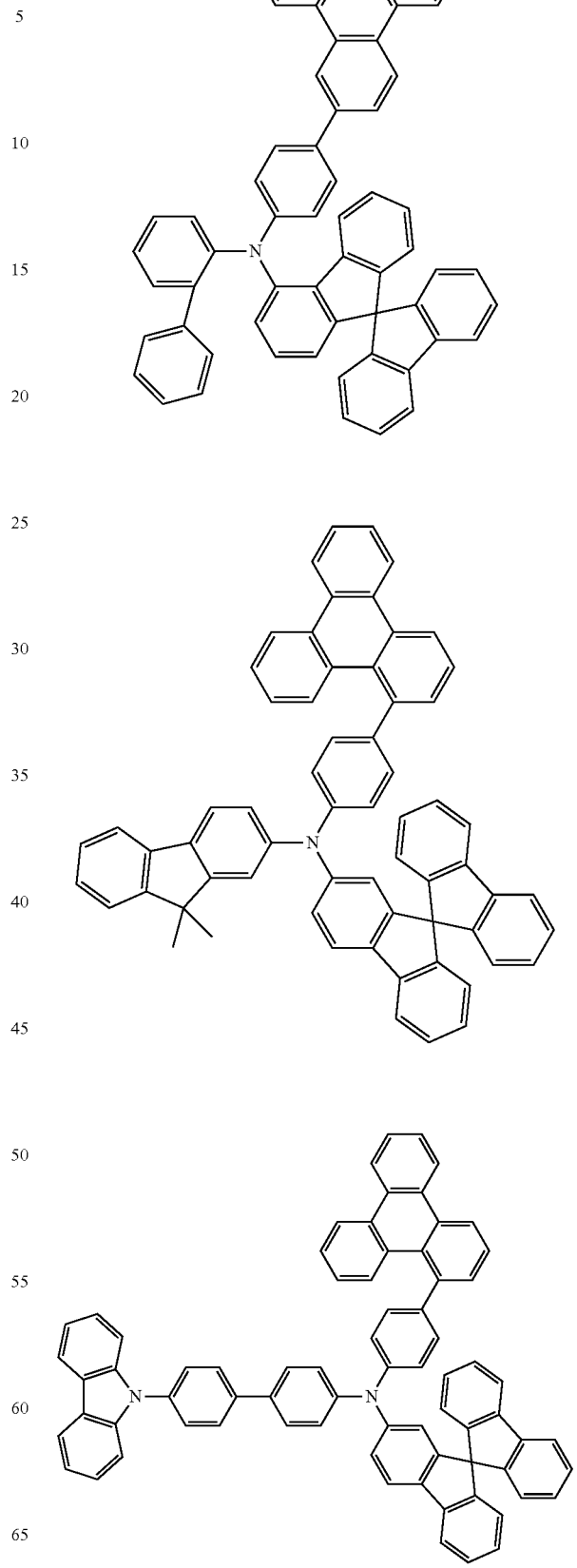

207
-continued
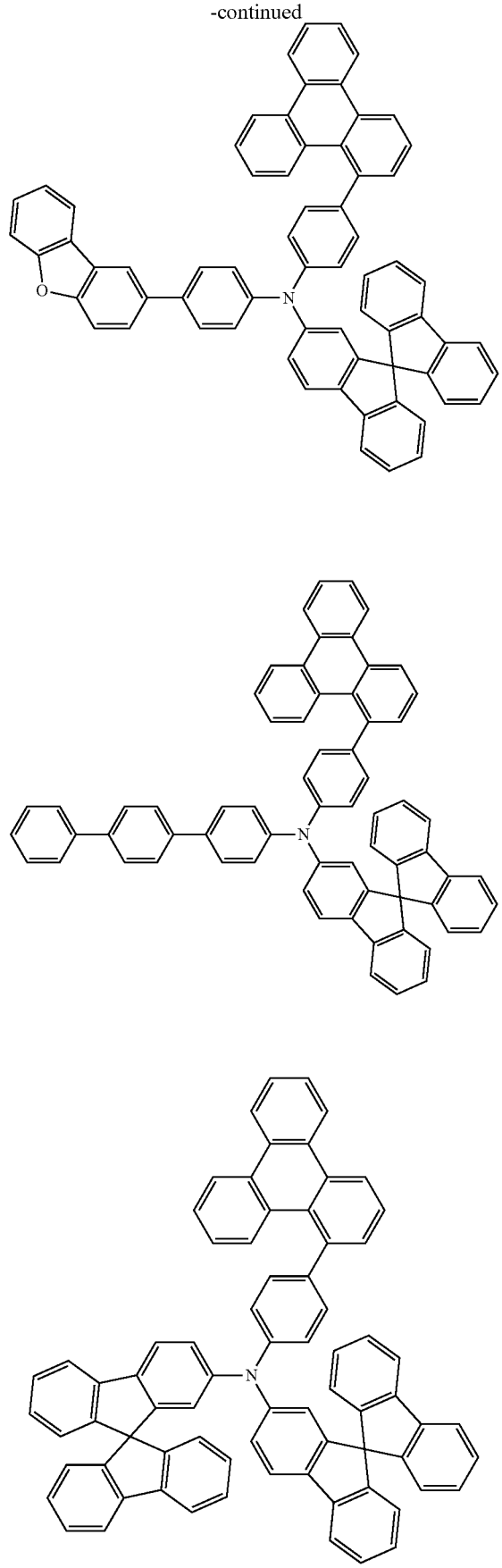
208
-continued
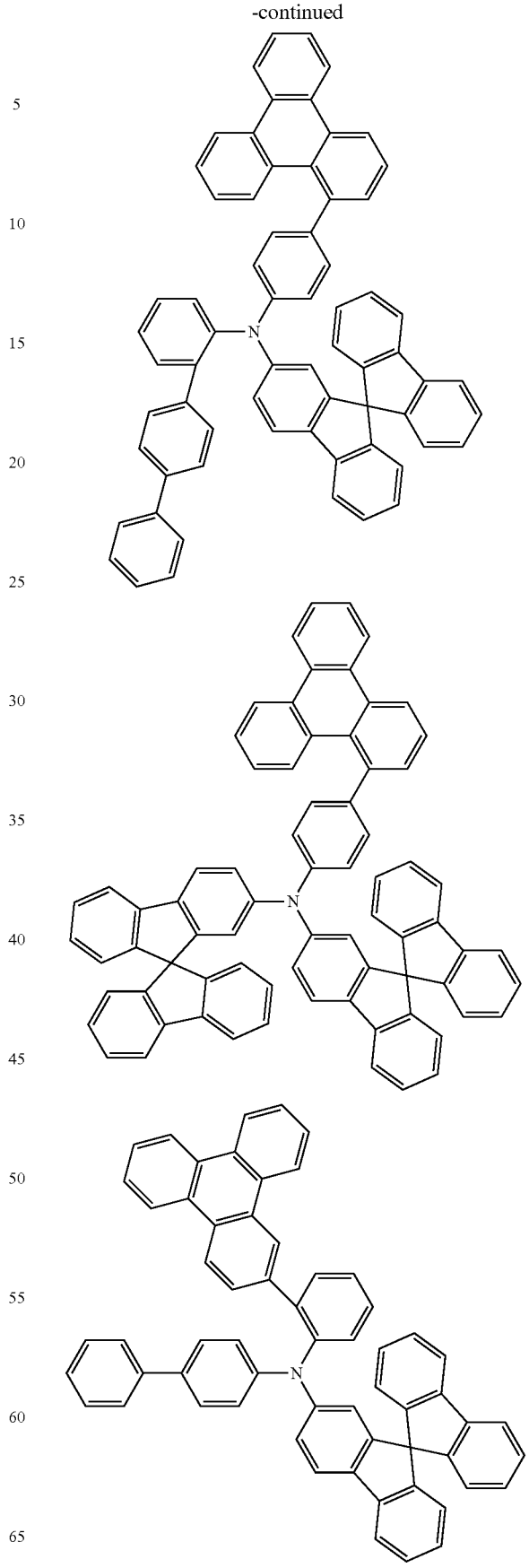

-continued
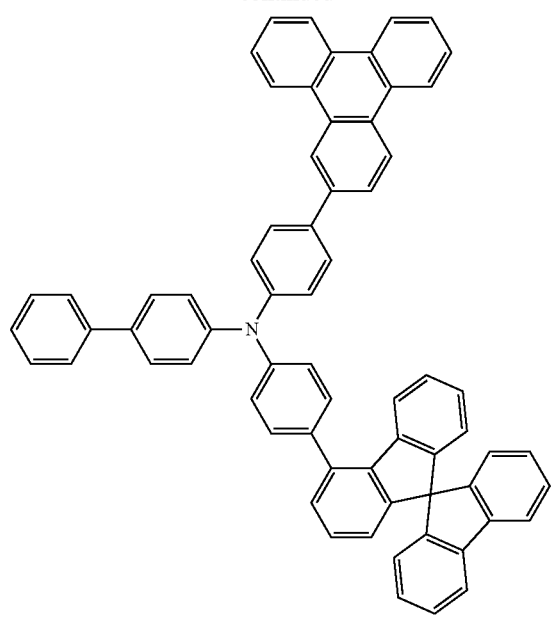
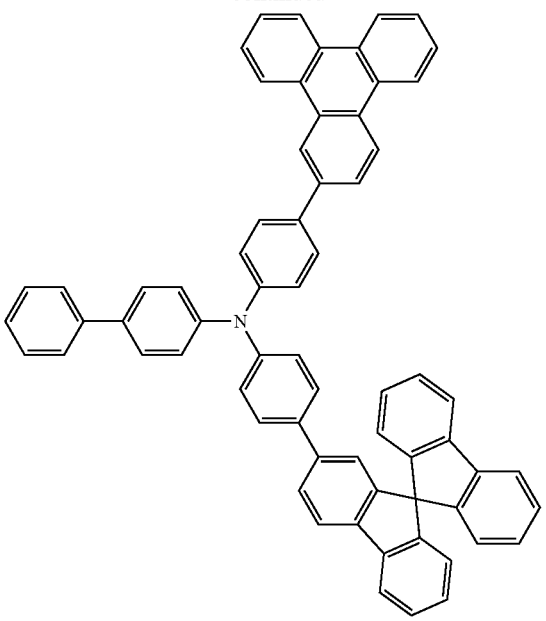
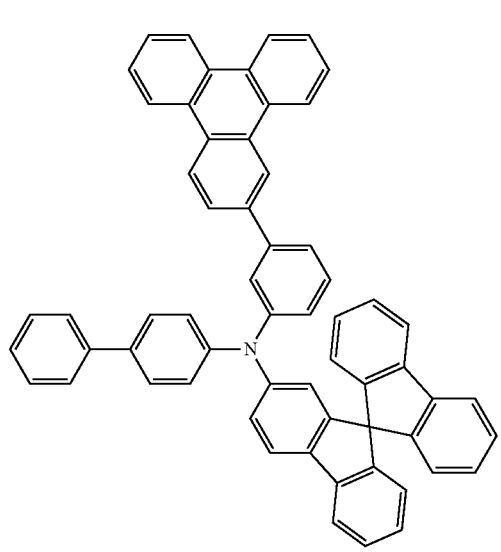
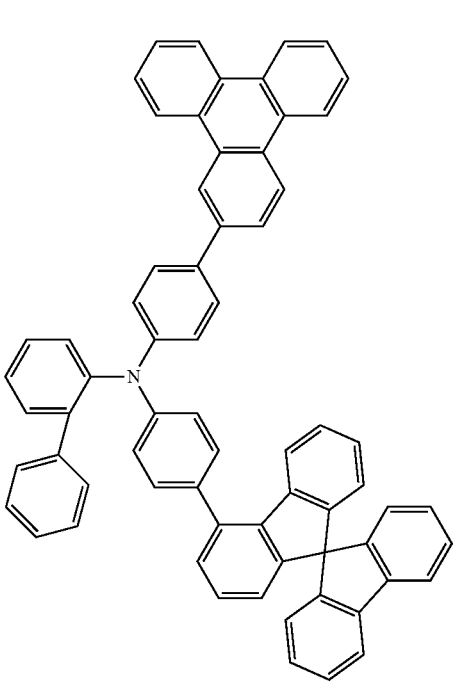

211
-continued
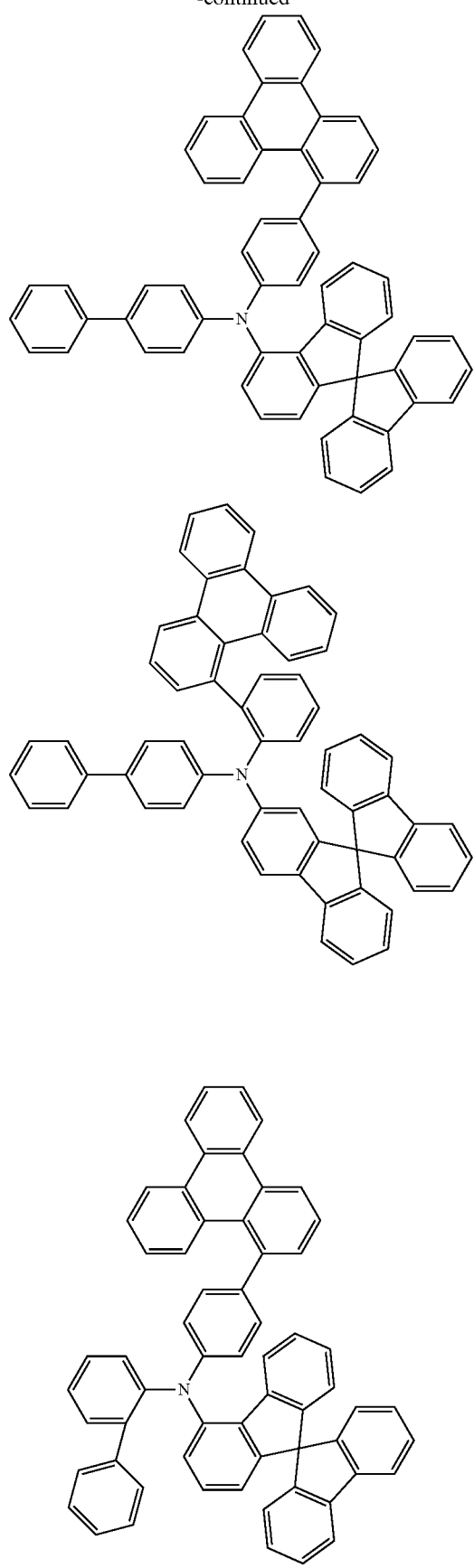
212
-continued
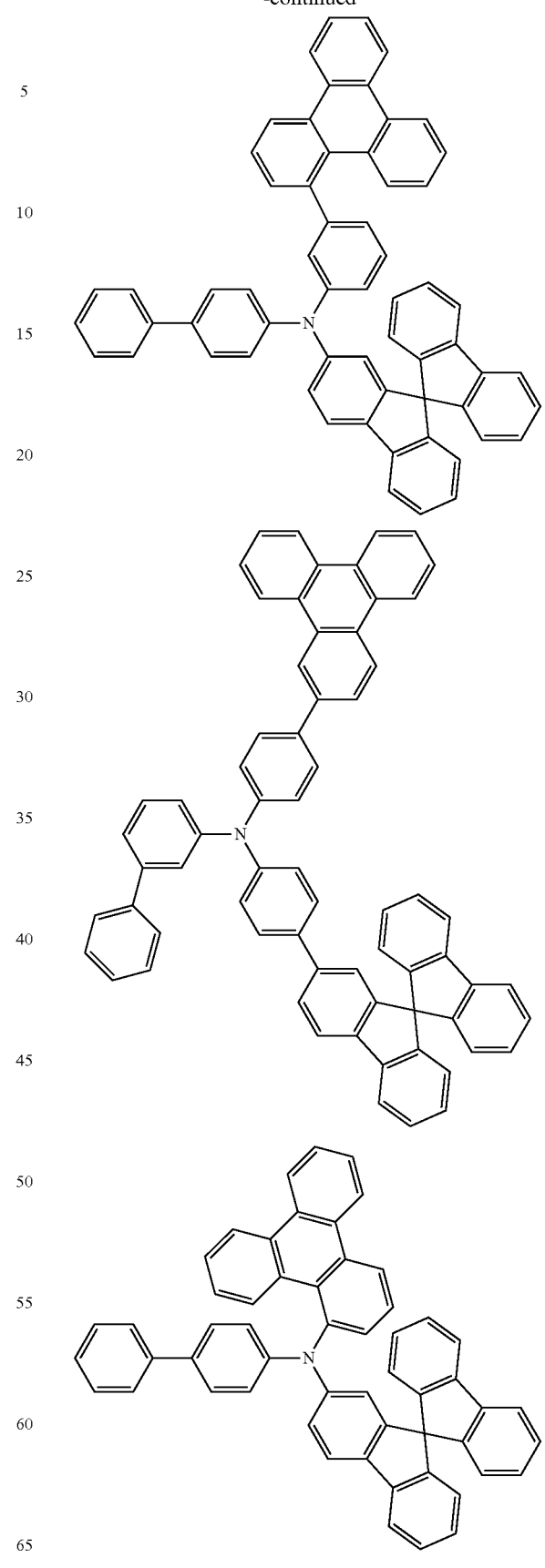

213
-continued
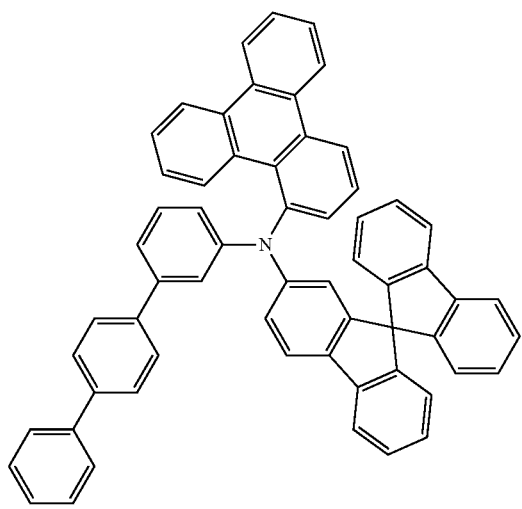
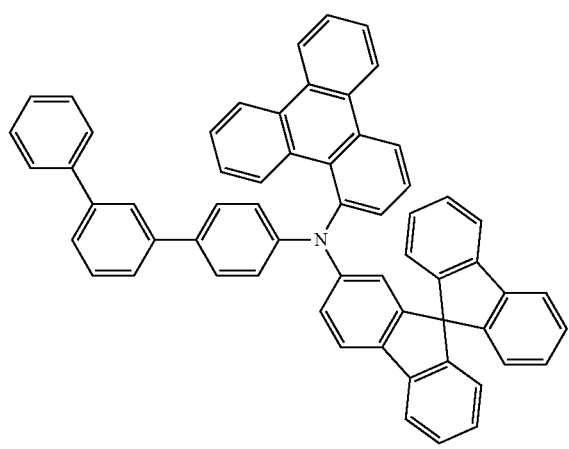
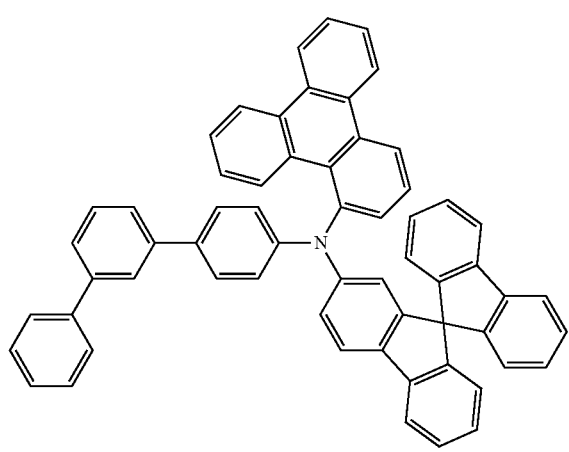
214
-continued
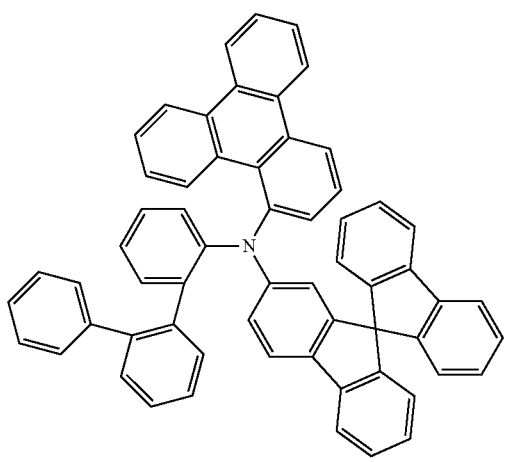
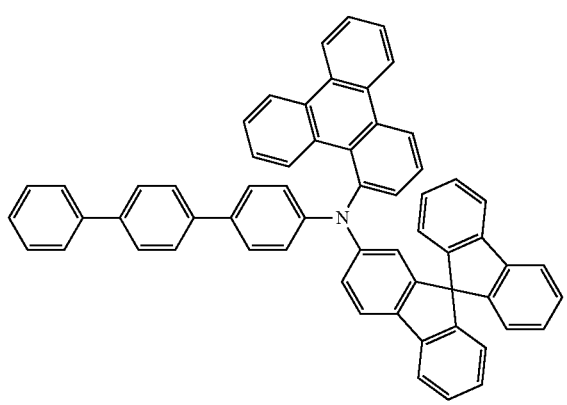
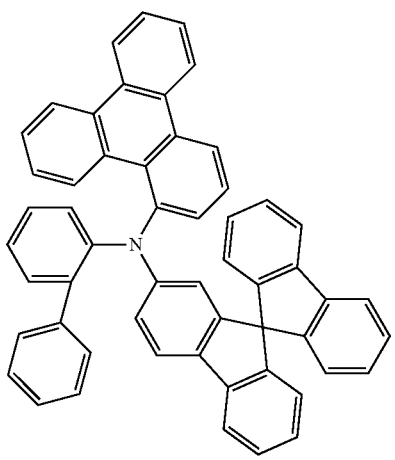

215
-continued
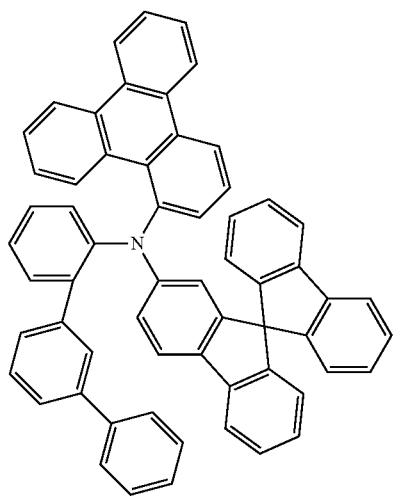
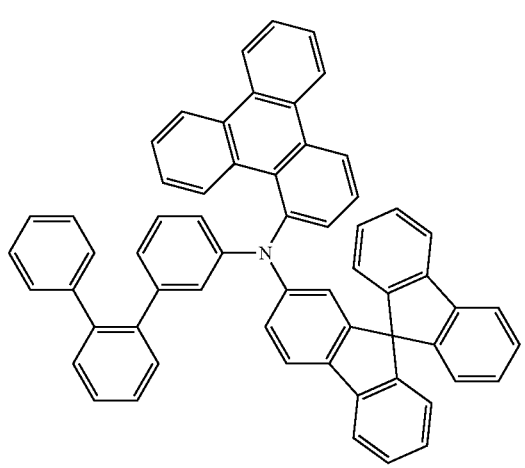
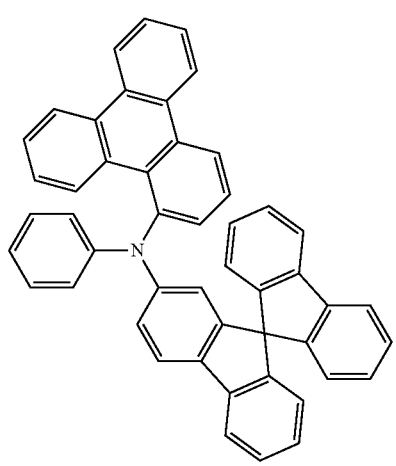
216
-continued
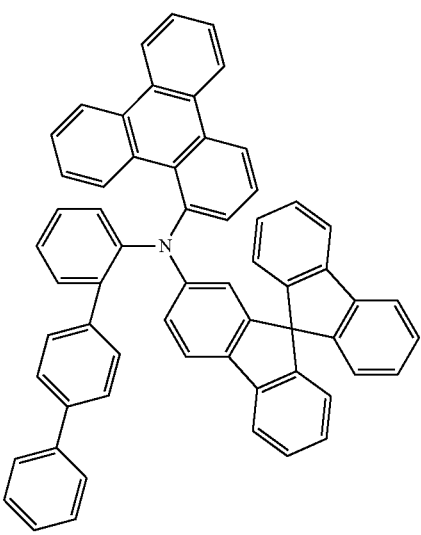
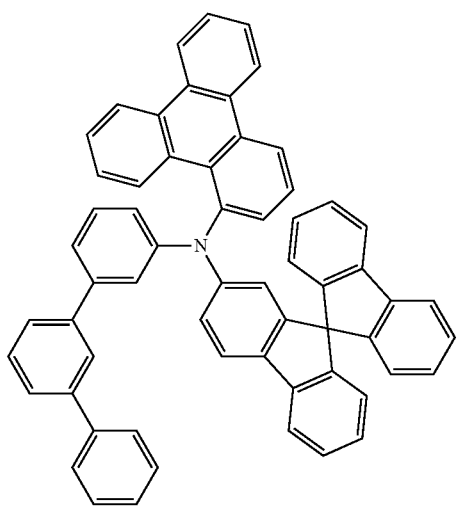
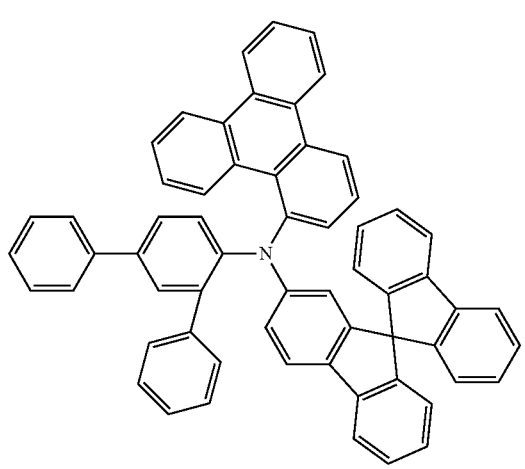

217
-continued
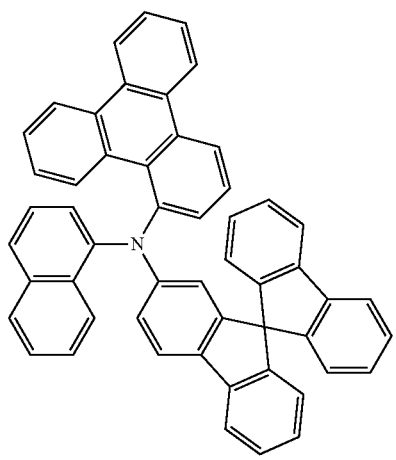
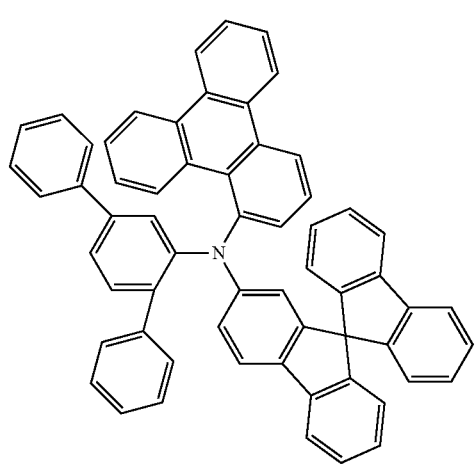
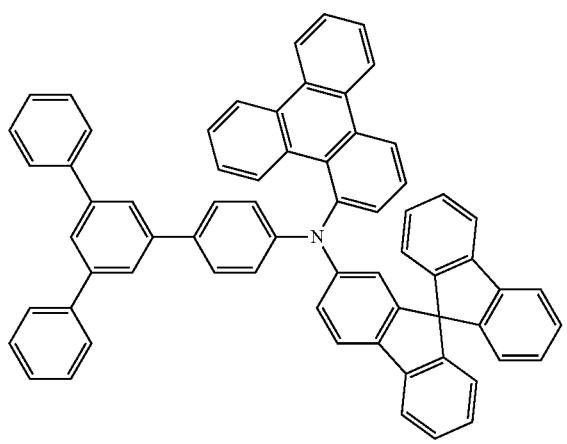
218
-continued
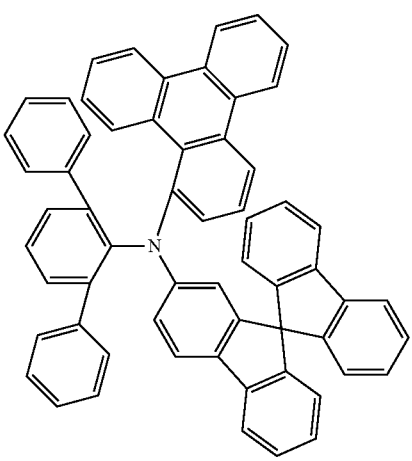
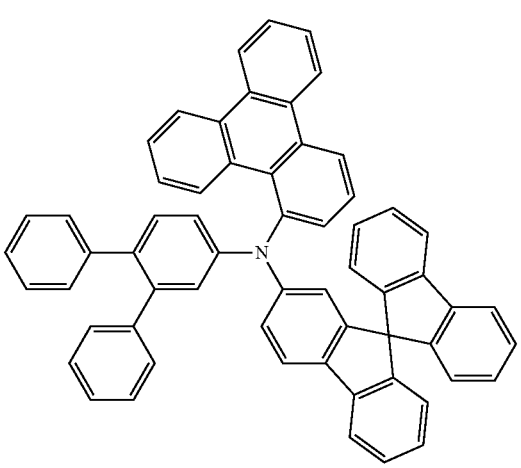
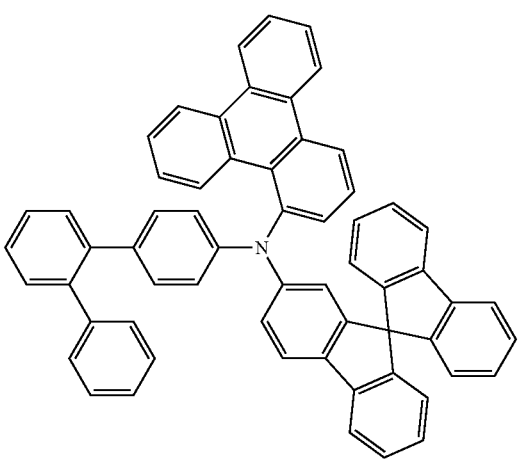

219
-continued
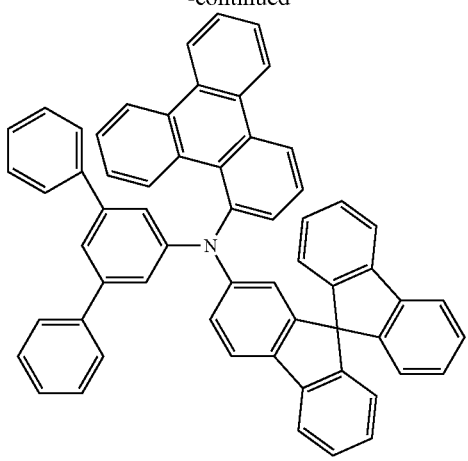
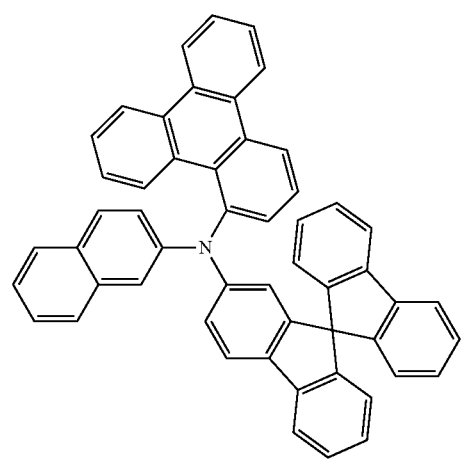
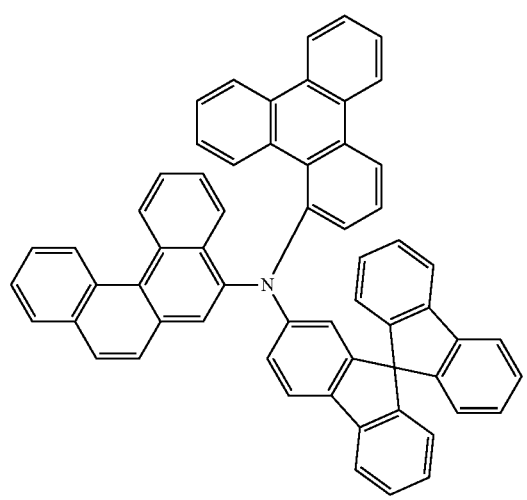
220
-continued
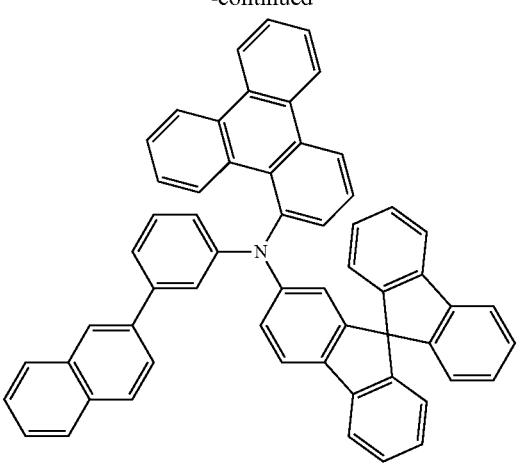
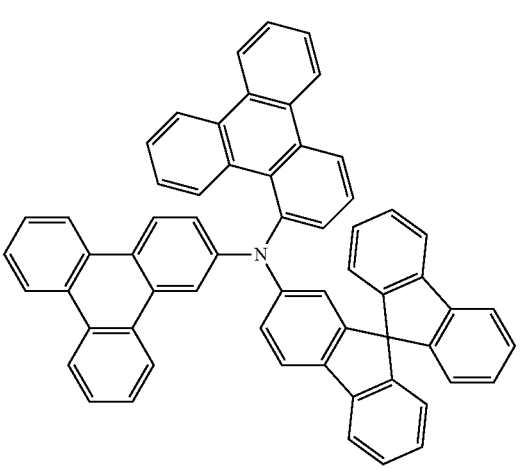
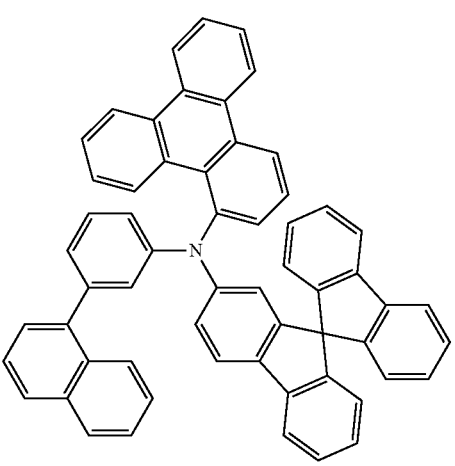

221
-continued
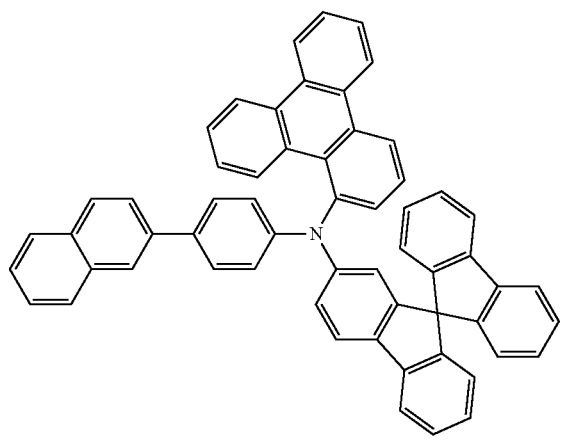
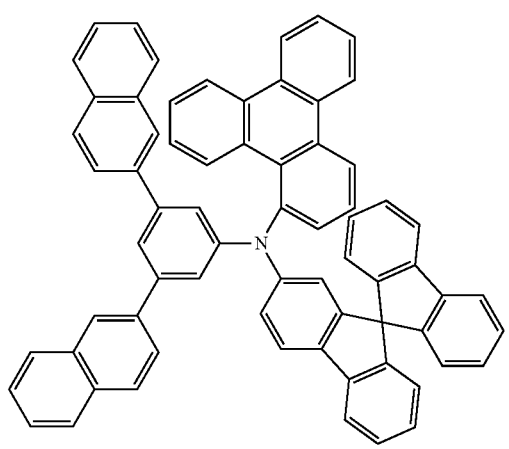
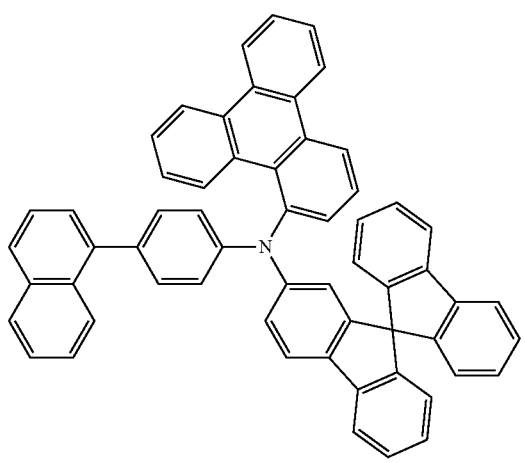
222
-continued
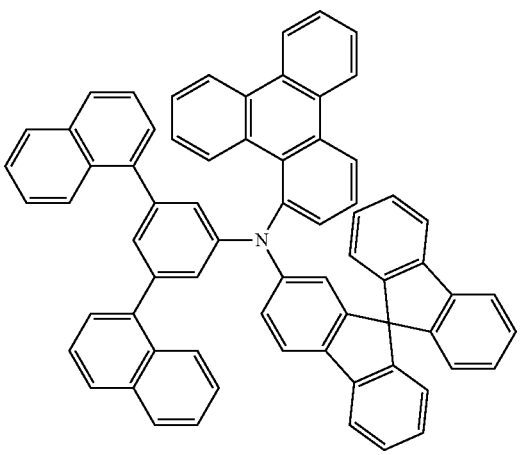
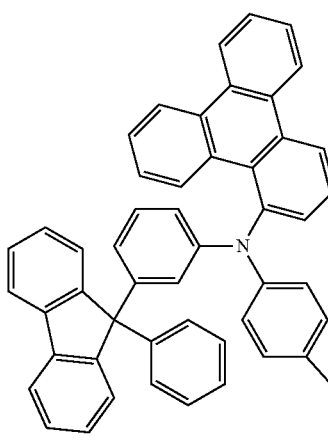
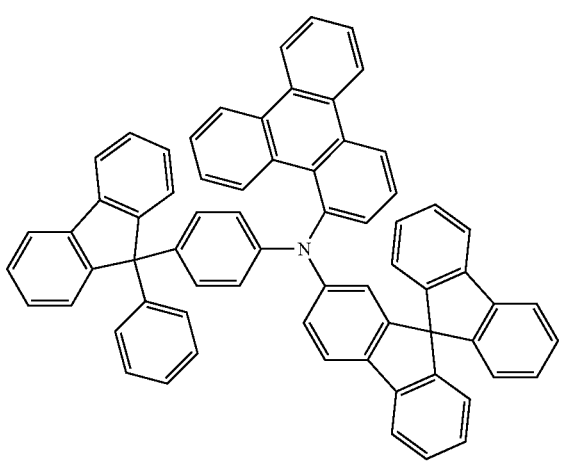

223
-continued
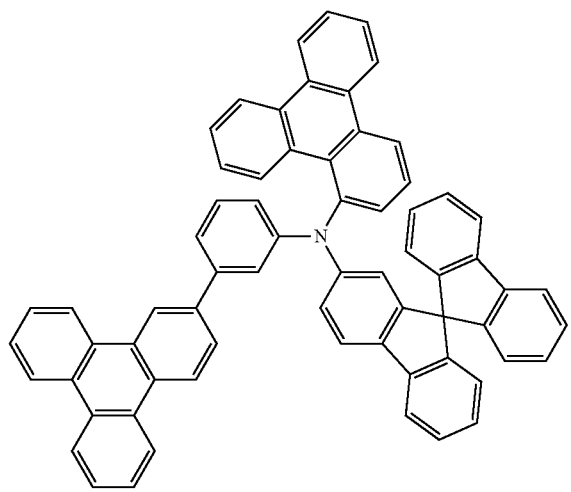
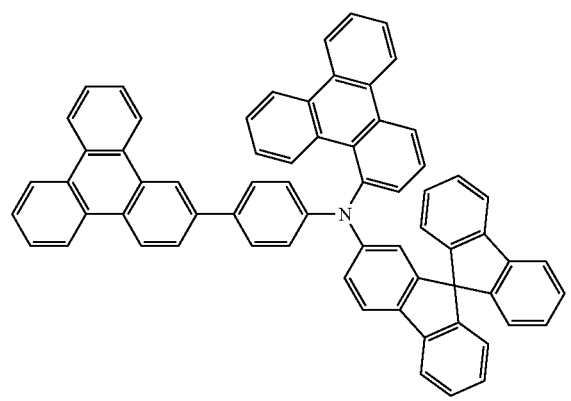
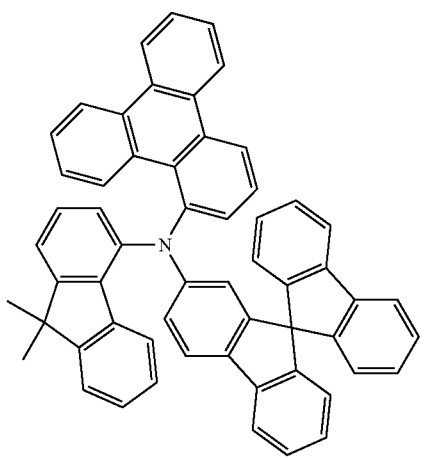
224
-continued
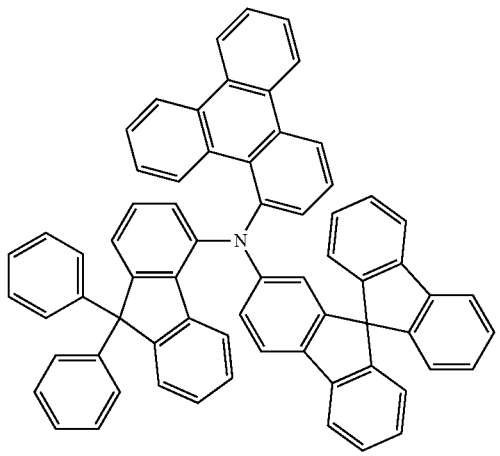
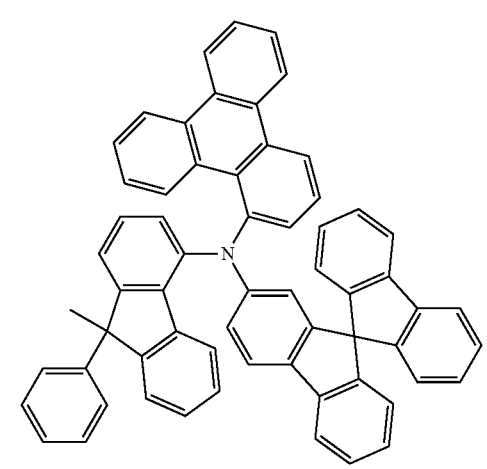
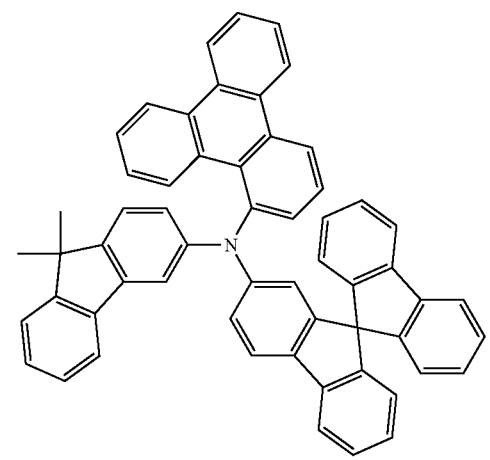

225
-continued
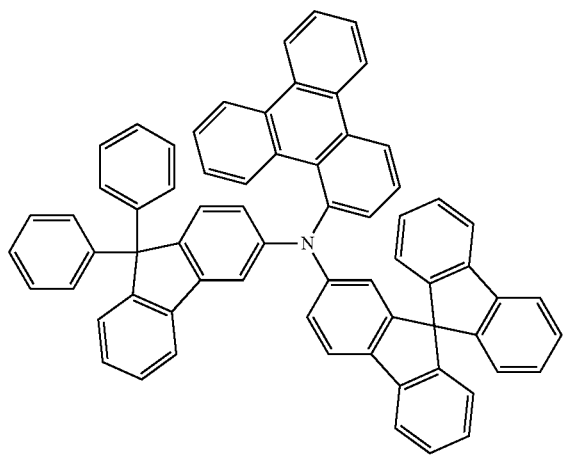
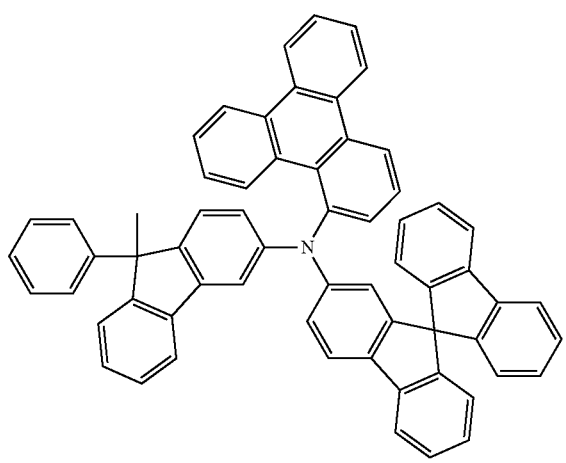
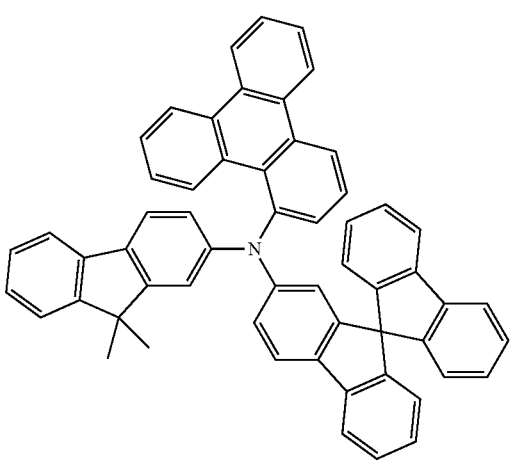
226
-continued
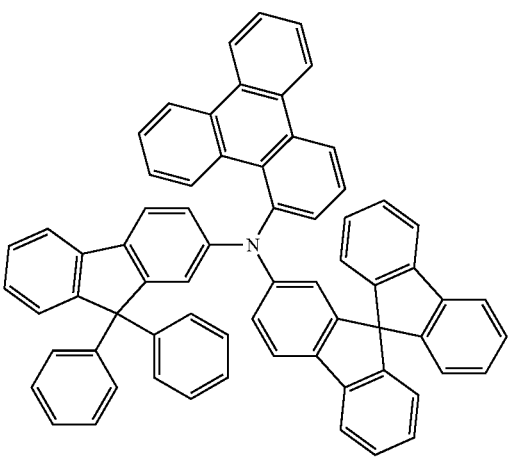
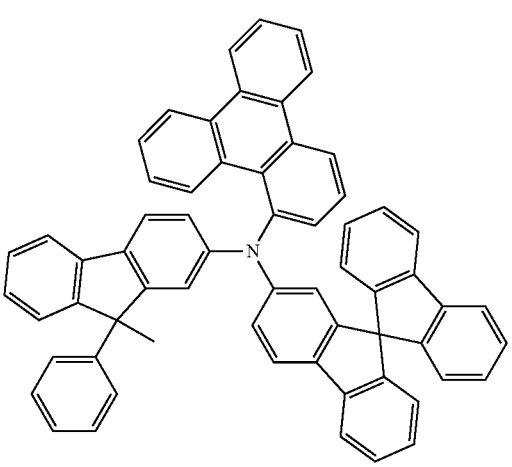
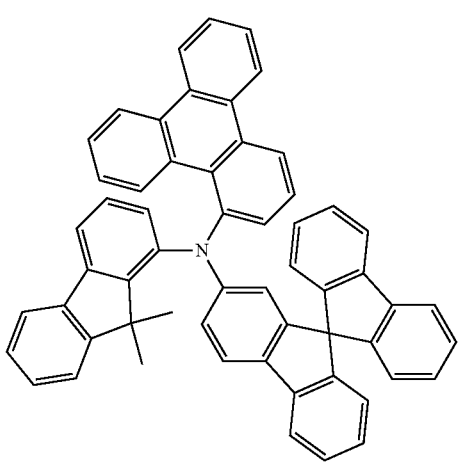

227
-continued
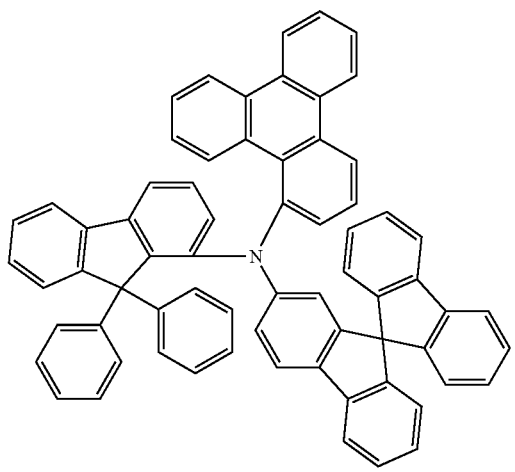
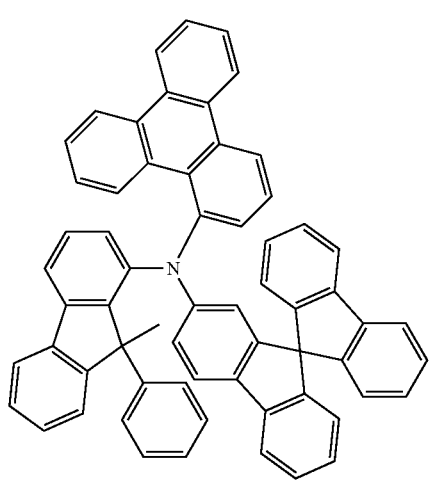
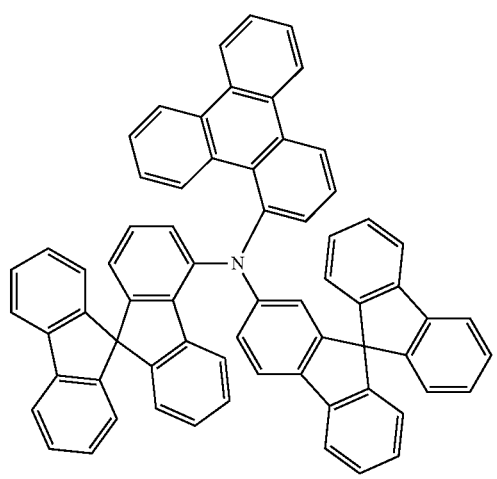
228
-continued
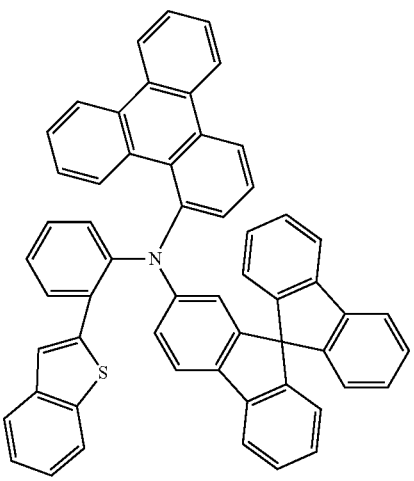
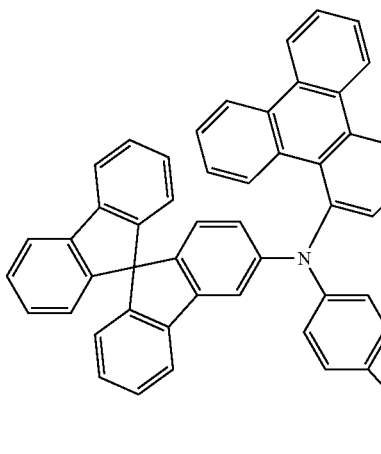
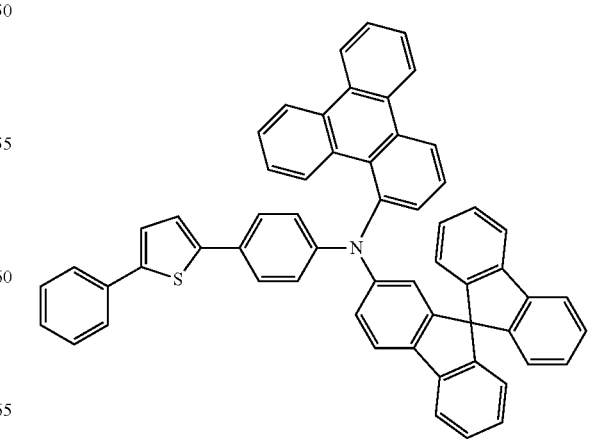

229
-continued
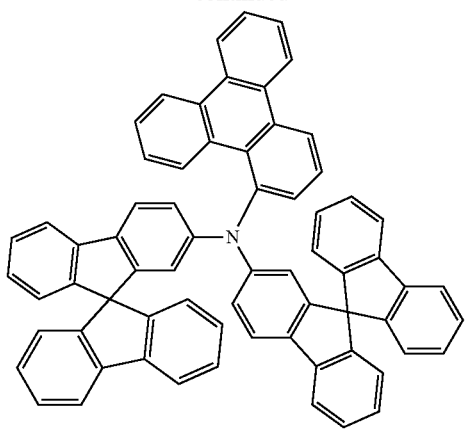
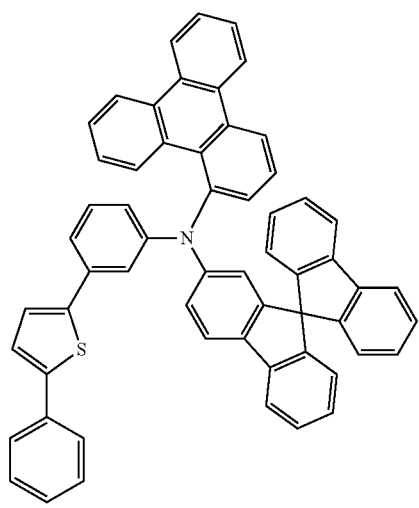
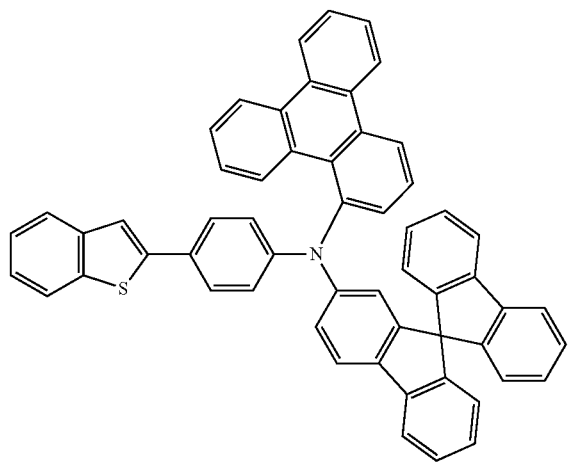
230
-continued
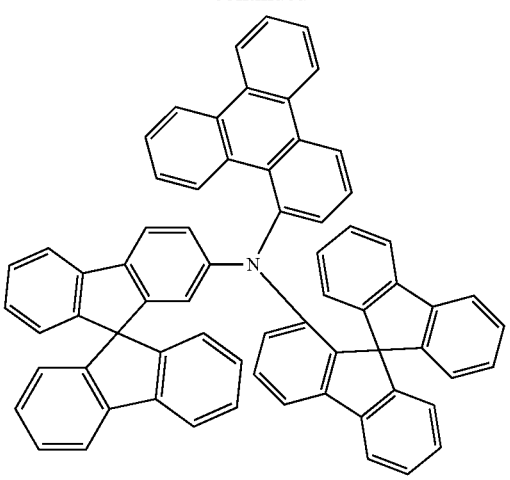
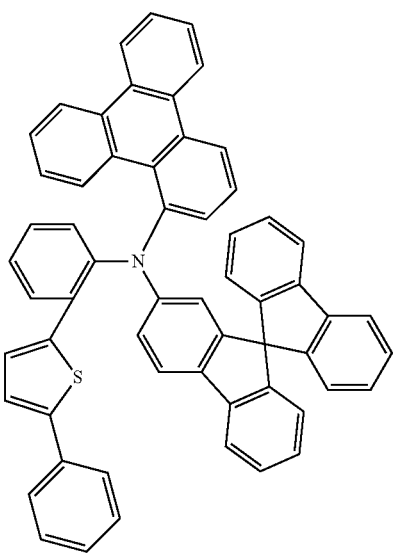
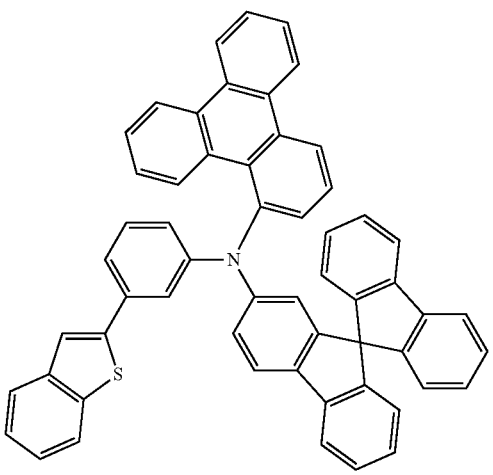 [SMILES: c1cc(-c2cc3ccccc3s2)cc(N(c2ccc3c(c2)C2(c4ccccc4-c4ccccc42)c2ccccc2-3)c2cccc3c4ccccc4c4ccccc4c23)c1]

231    232
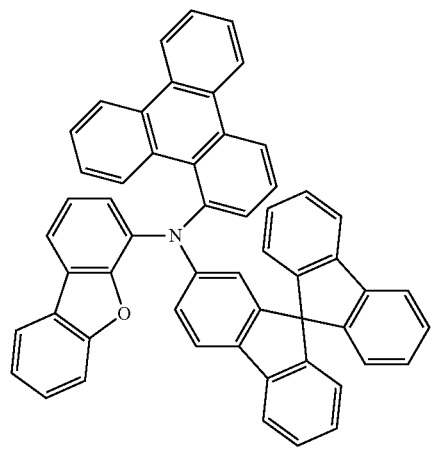
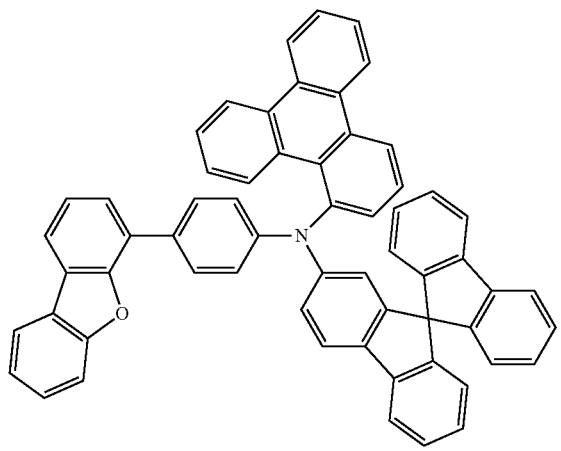
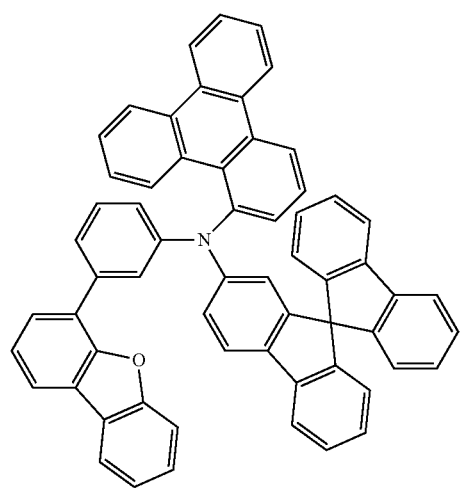
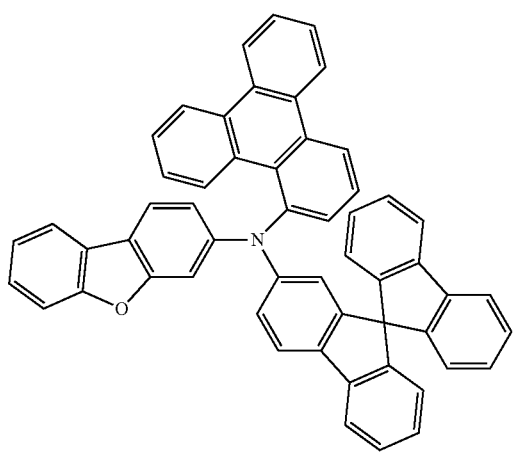
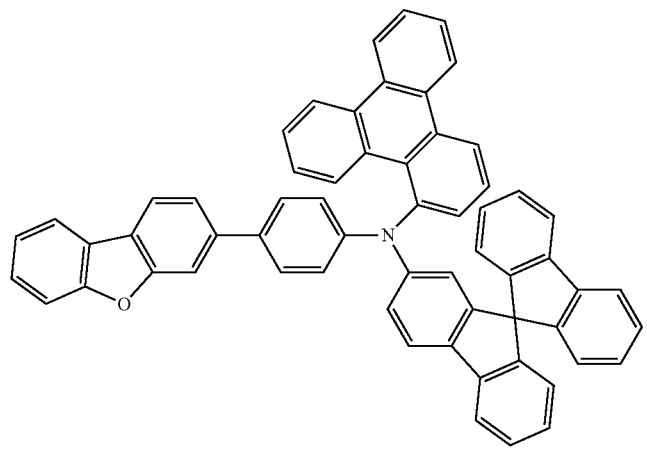

233 234
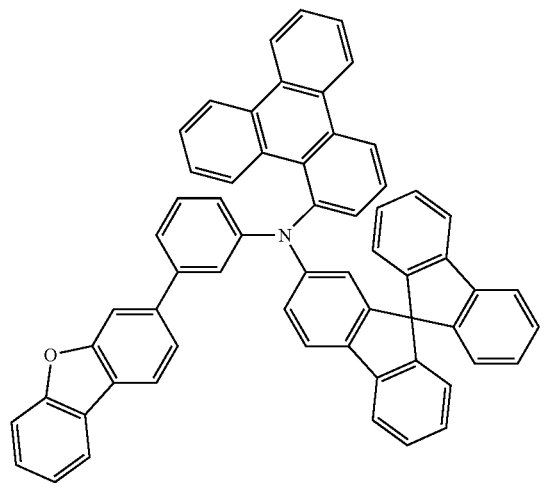
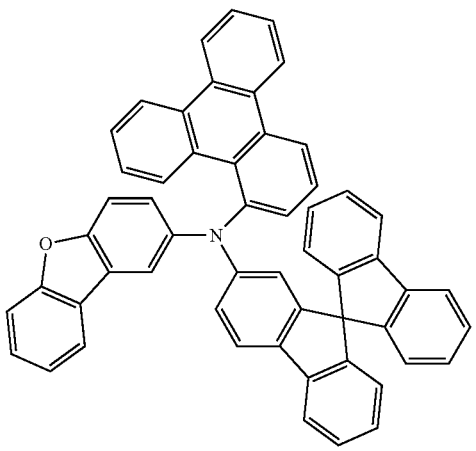
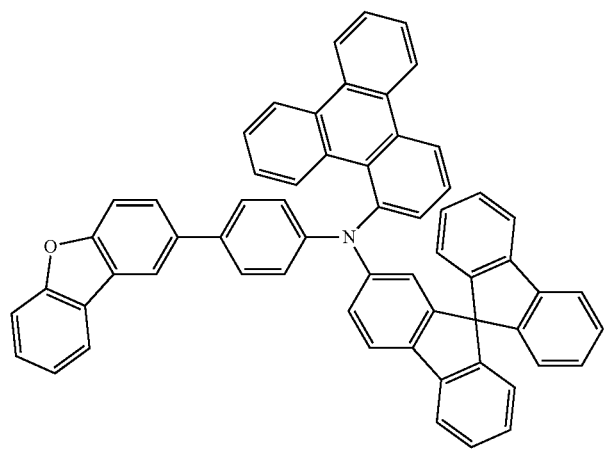
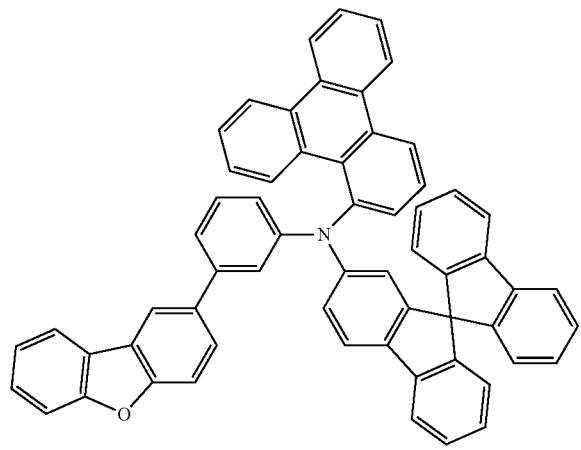
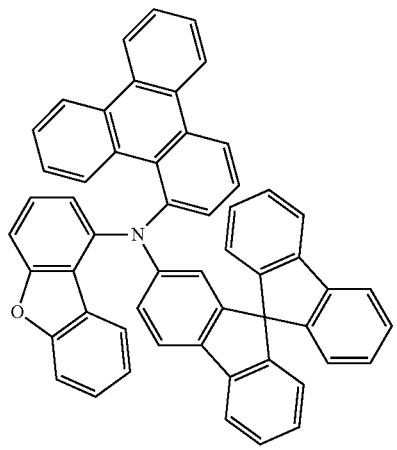

-continued
235
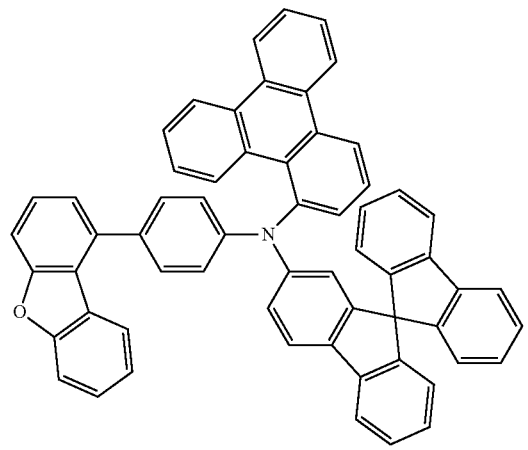
236
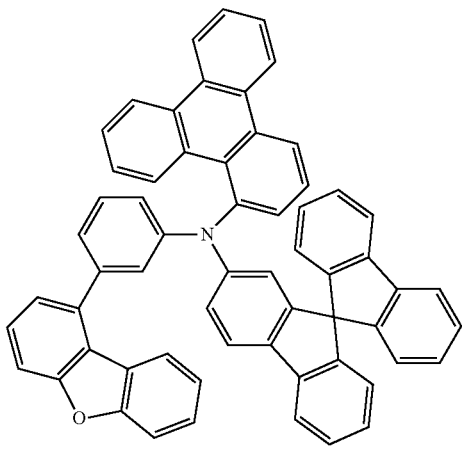
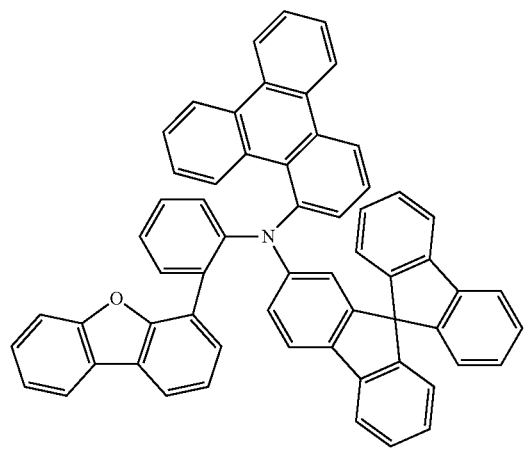
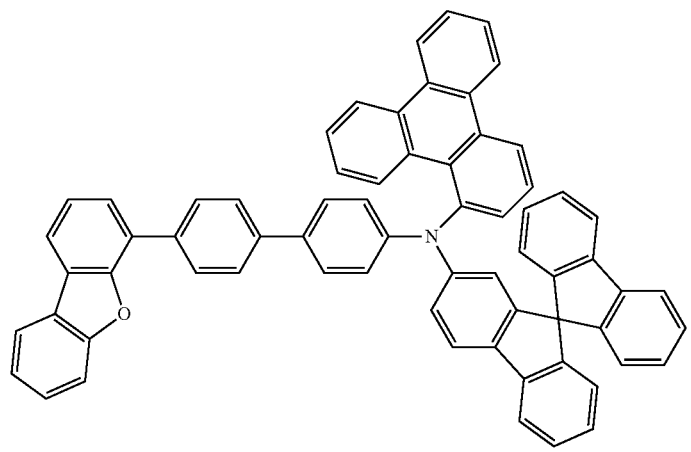

237 238
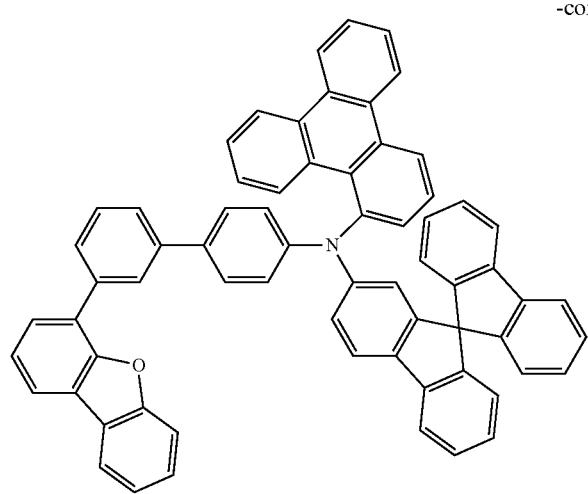
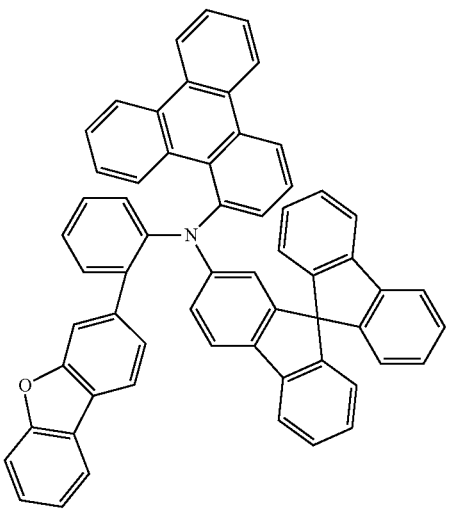
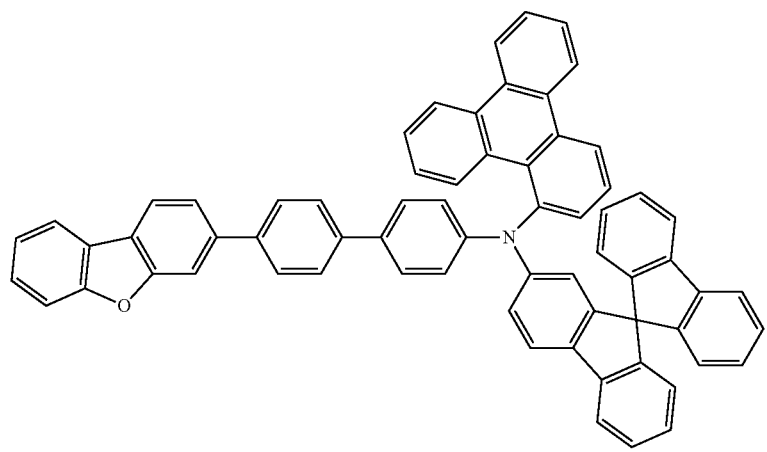
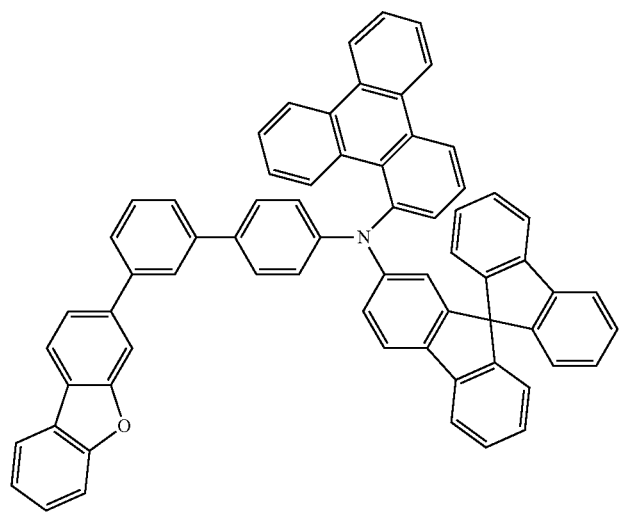
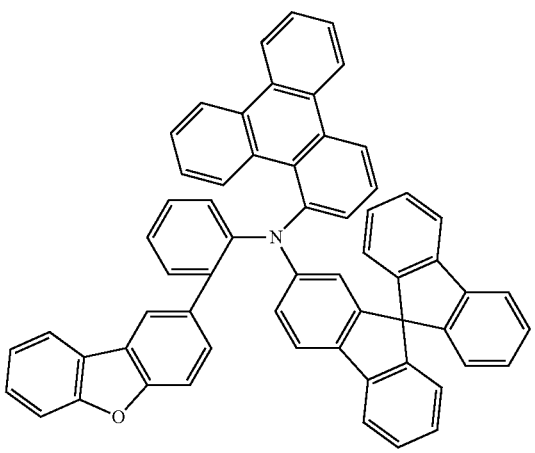

-continued
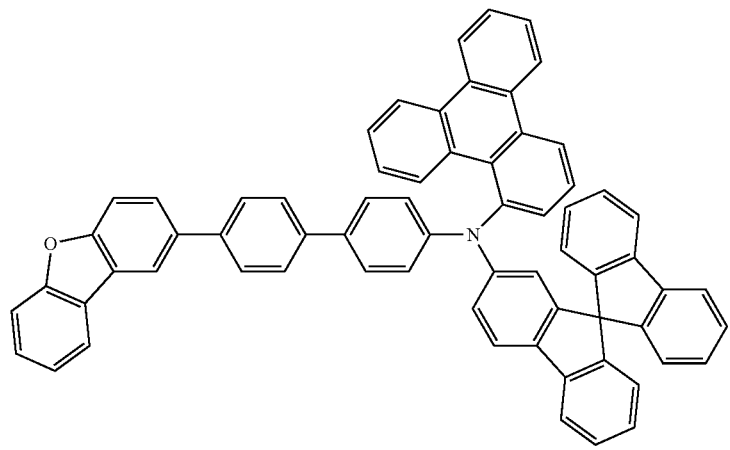
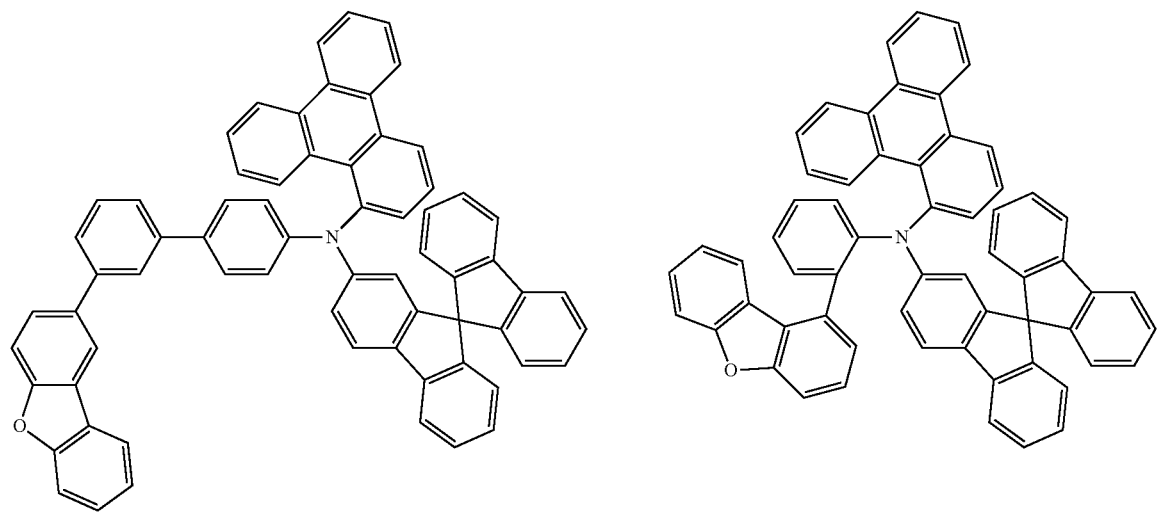
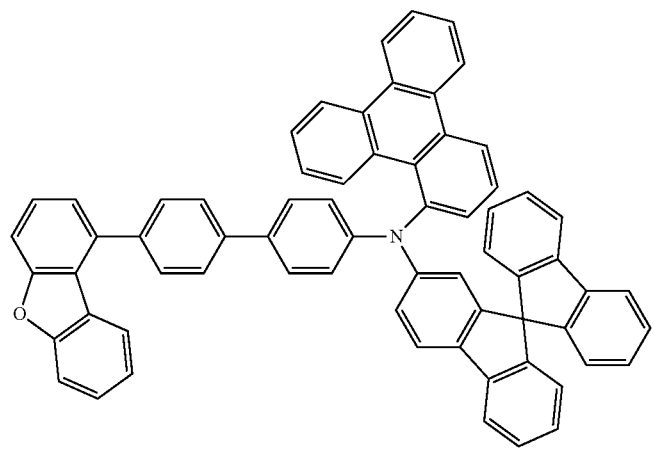

241
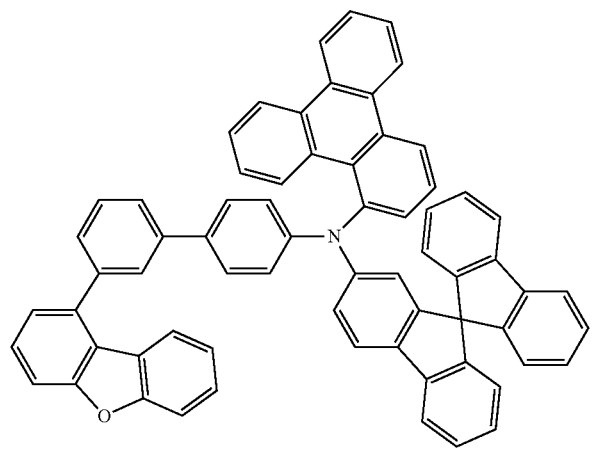
242
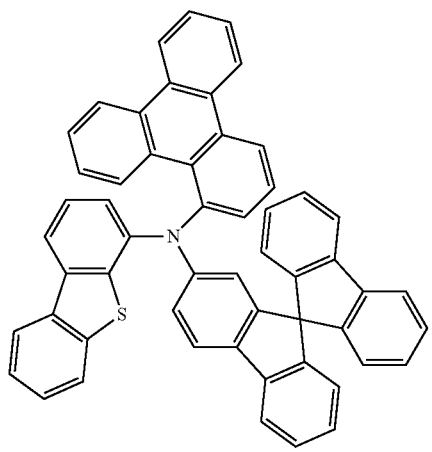
-continued
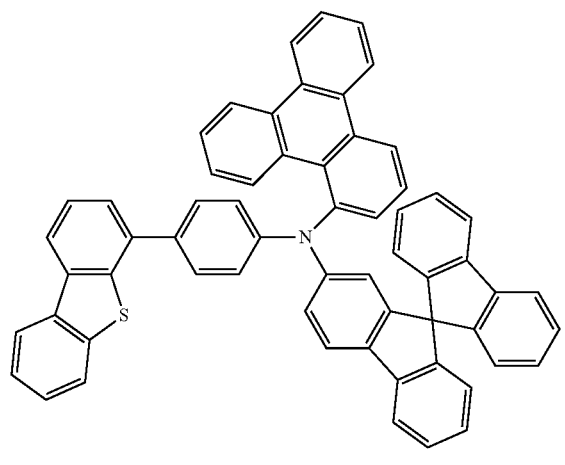
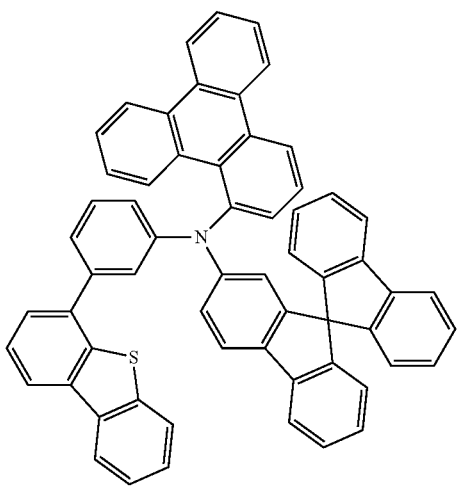
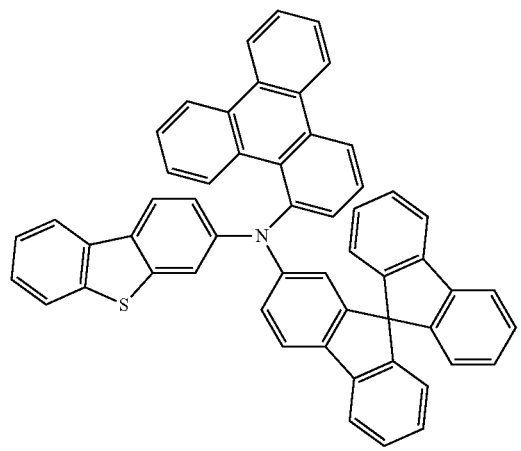

-continued
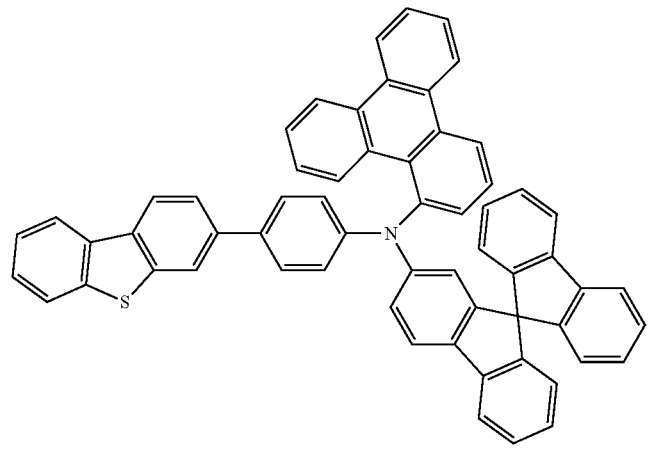
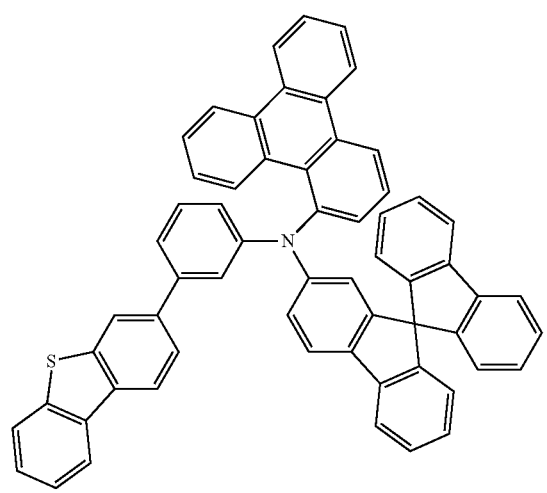
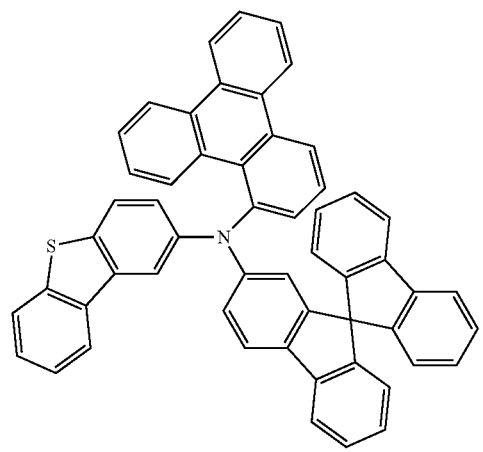
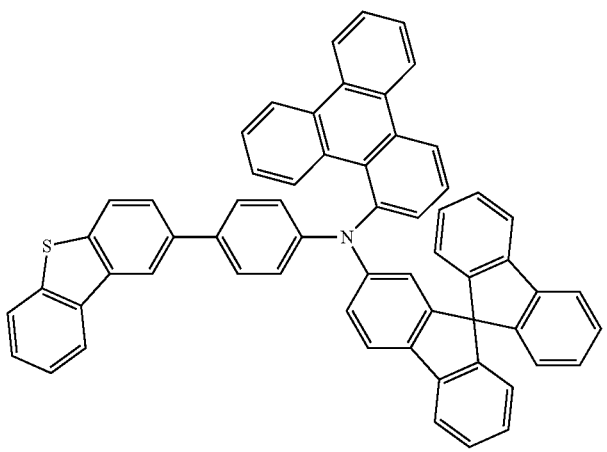

245
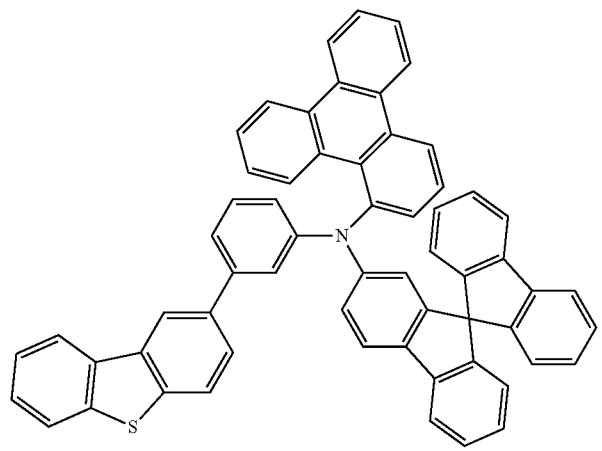
246
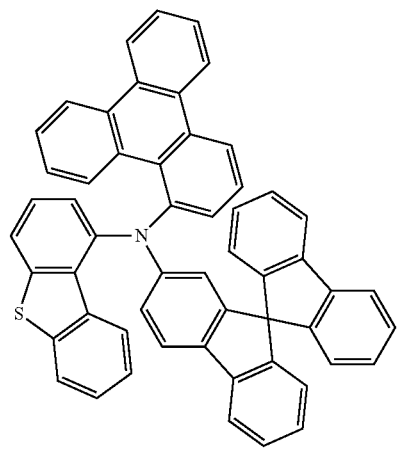
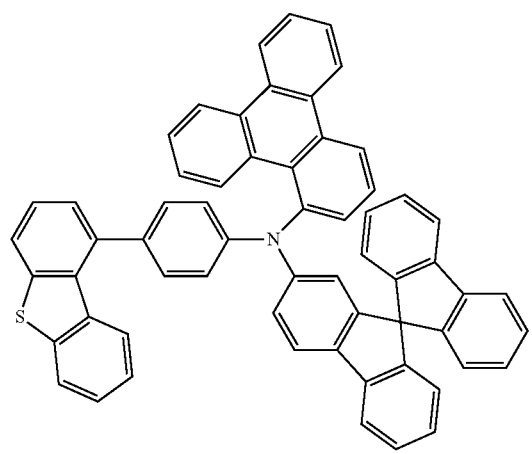
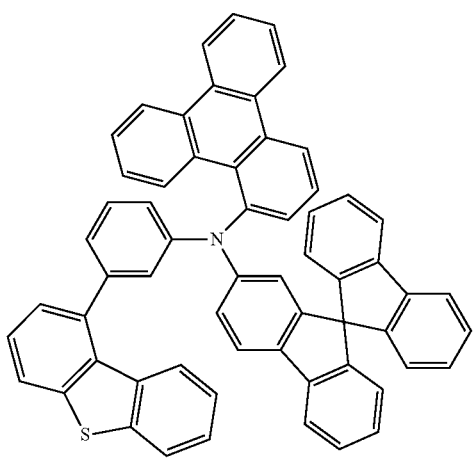
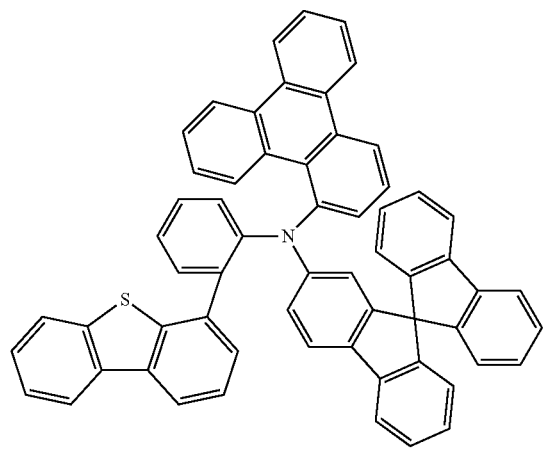

-continued
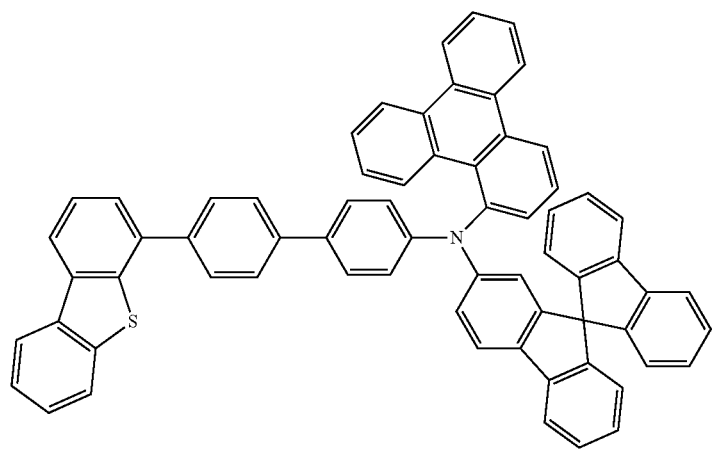
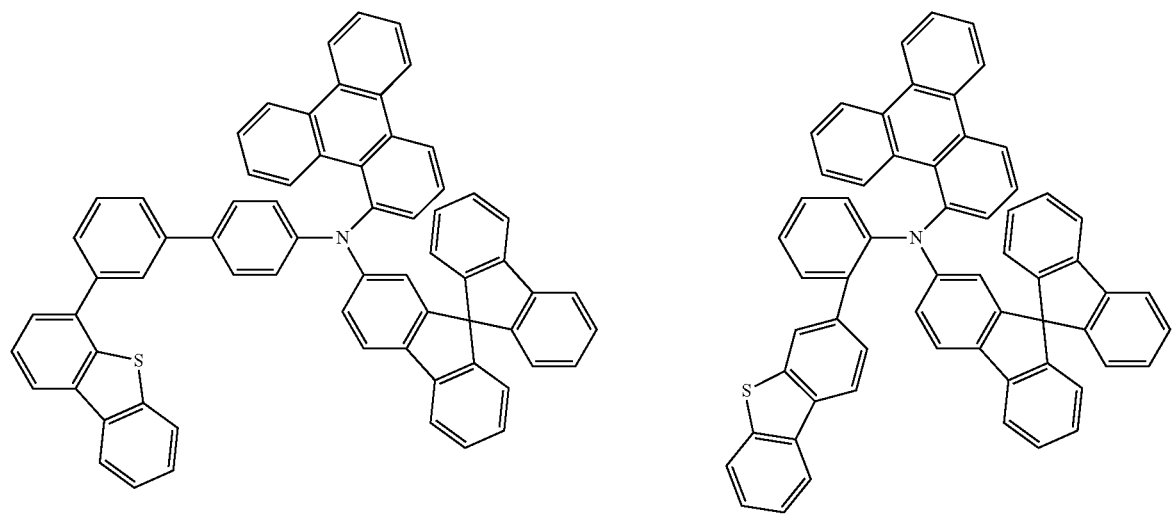
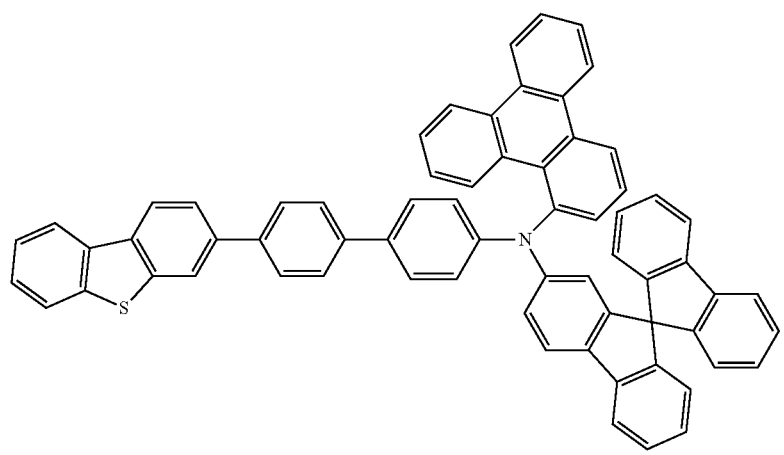

-continued
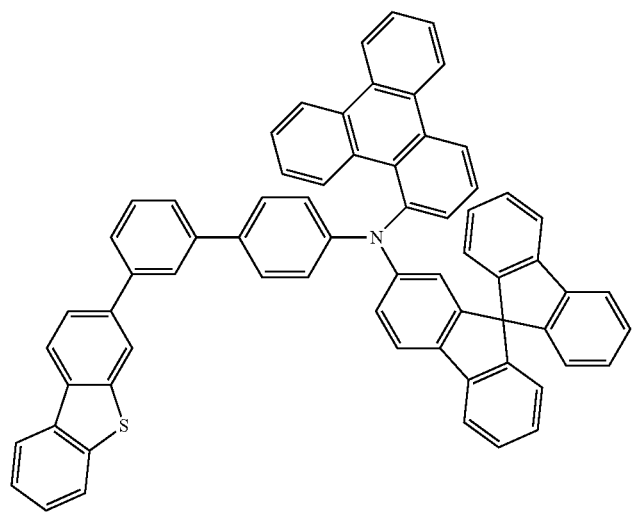
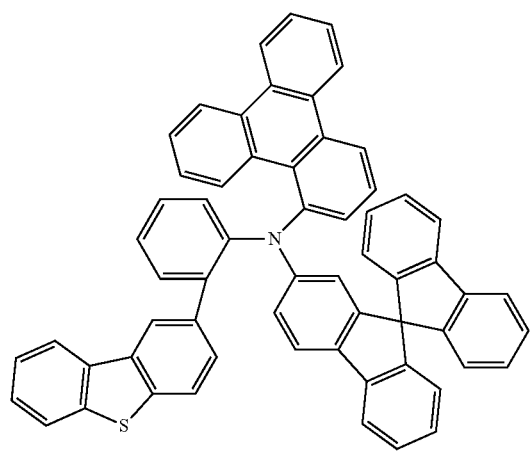
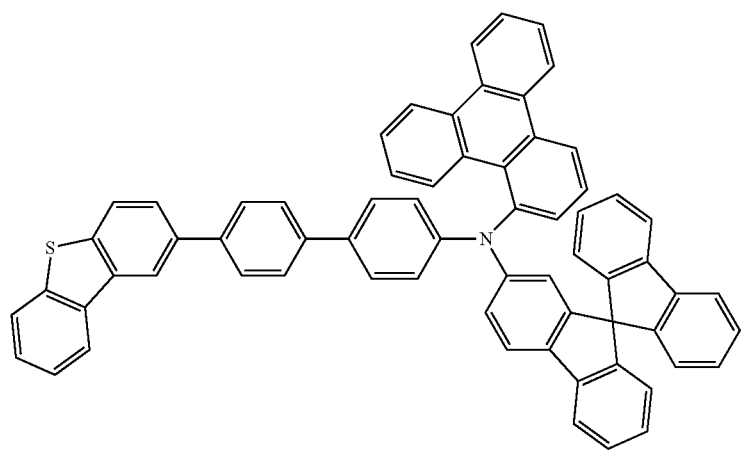

-continued
251 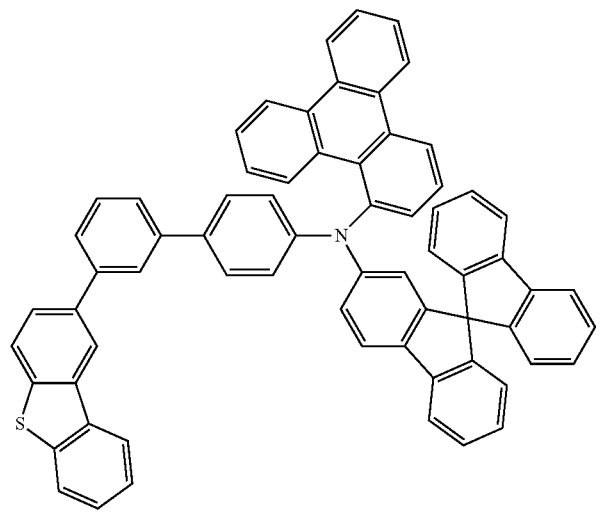
252 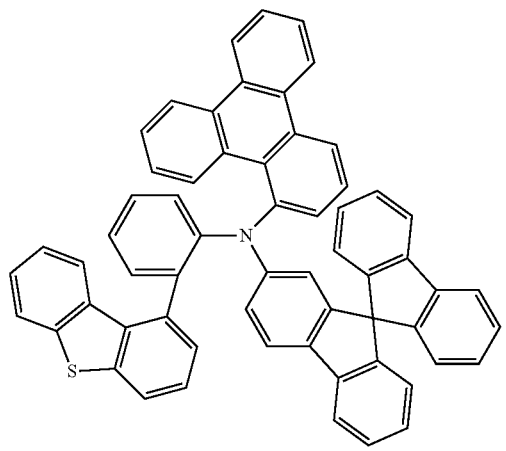
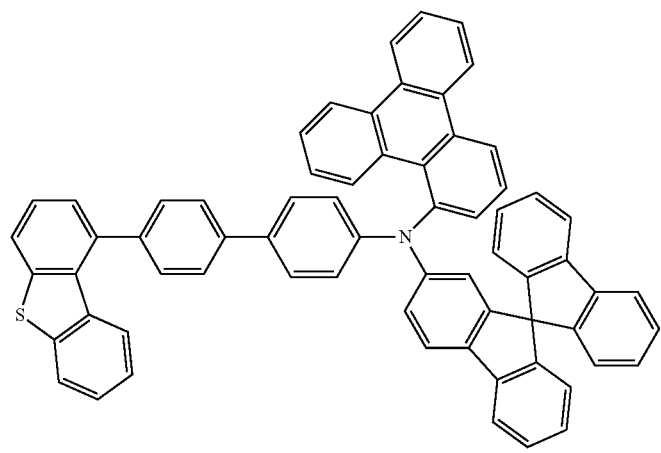
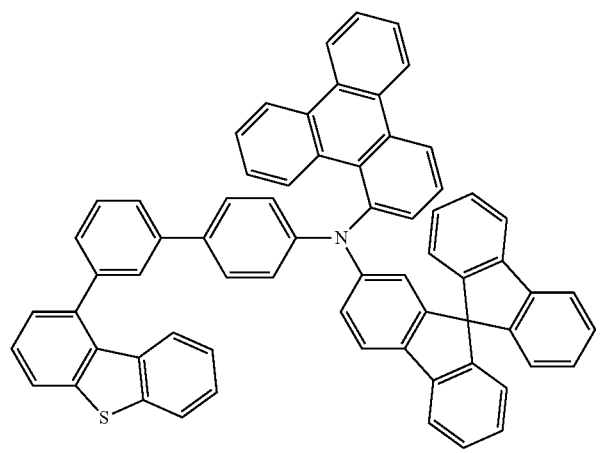
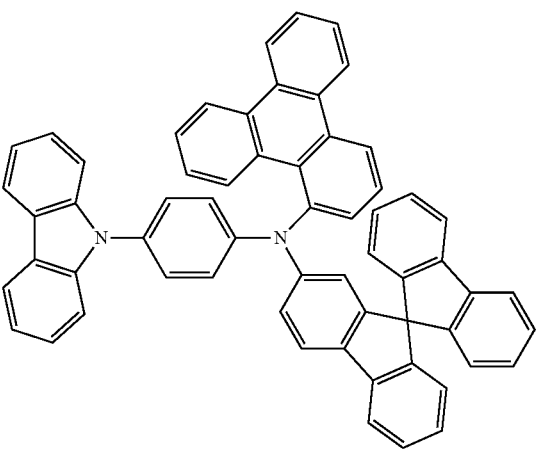

-continued
253
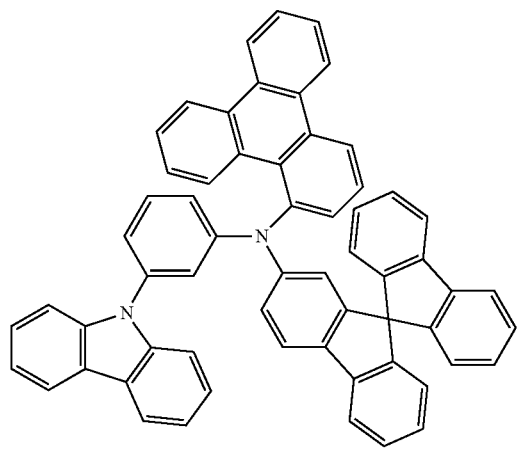
254
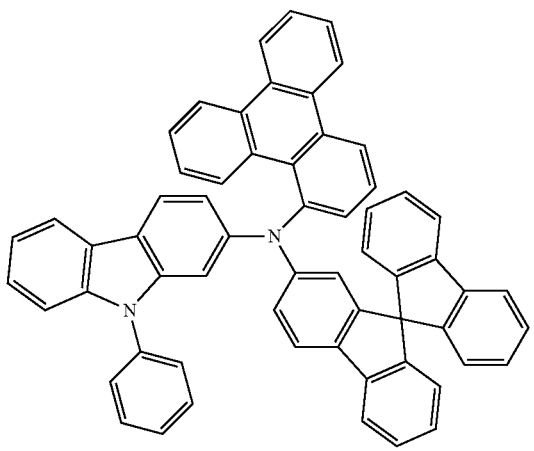
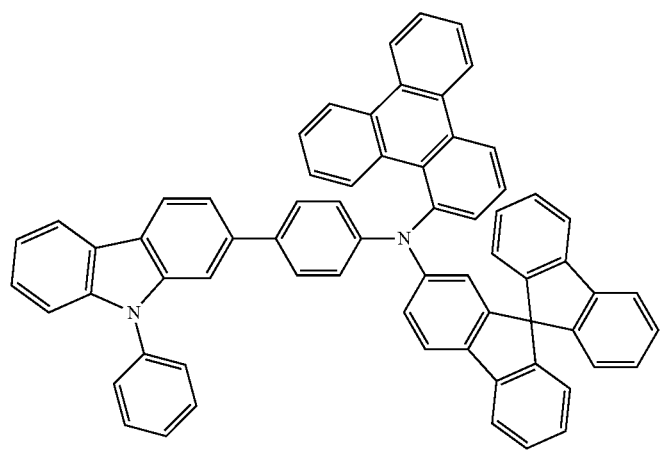
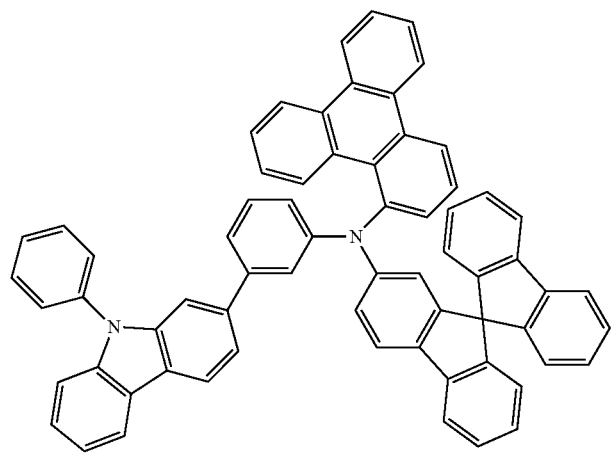
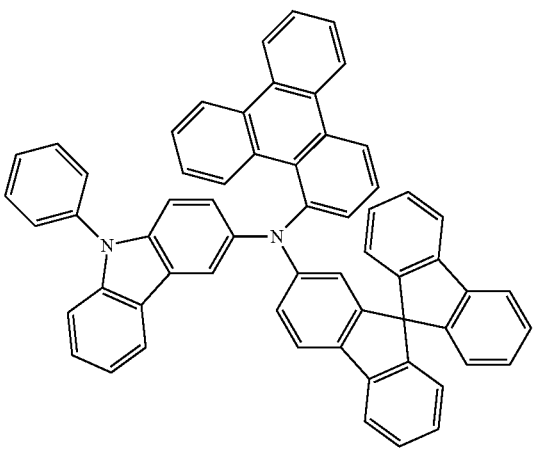

-continued
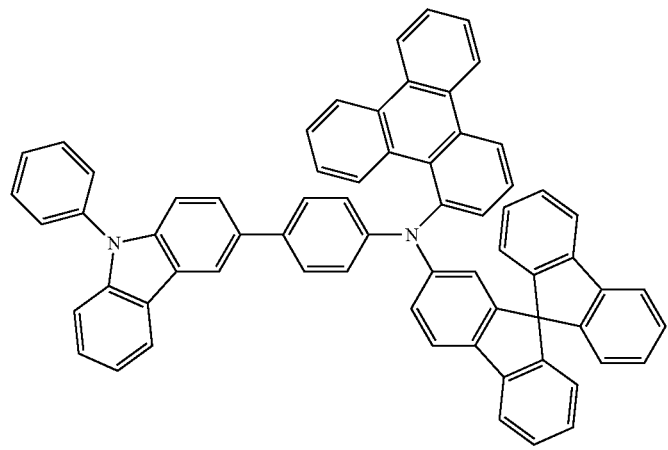
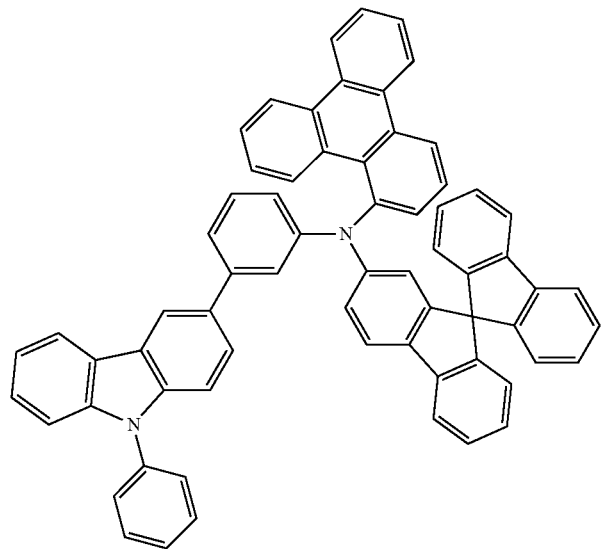
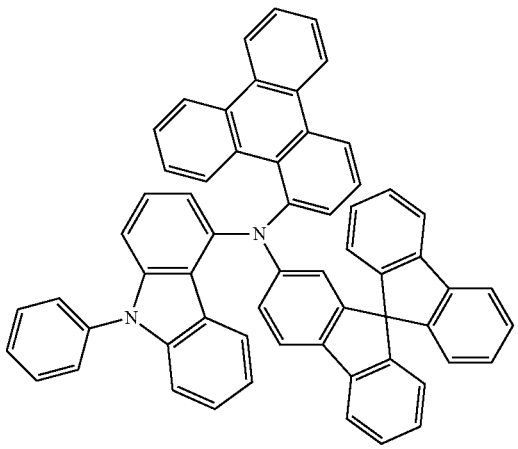
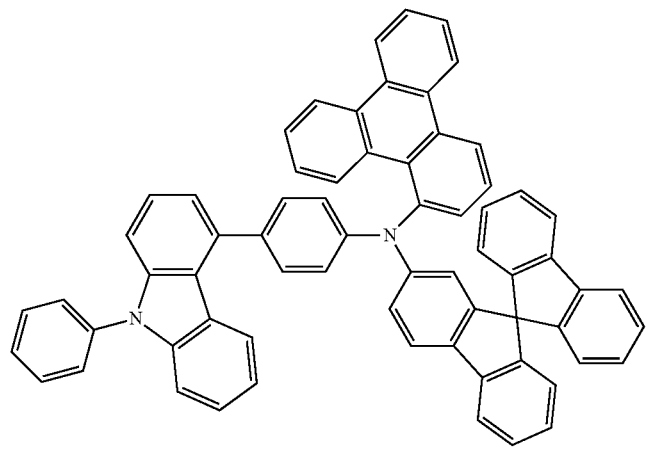
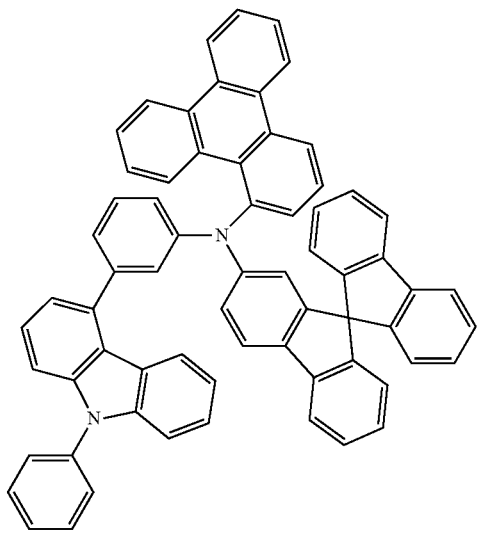

-continued
257
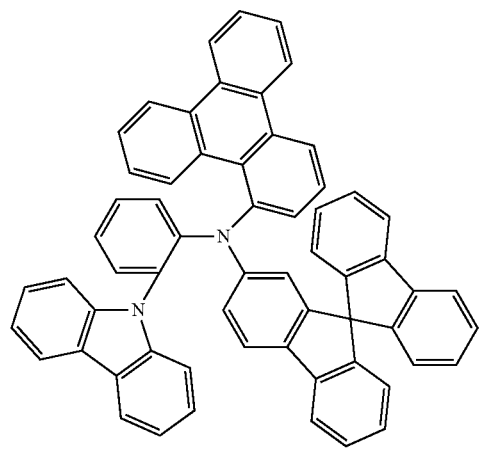
258
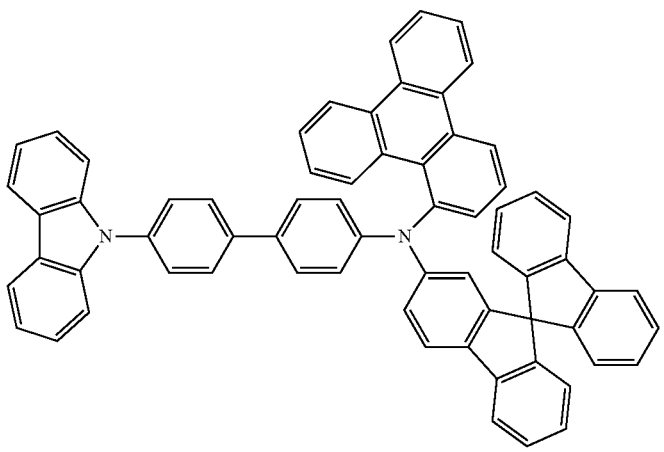
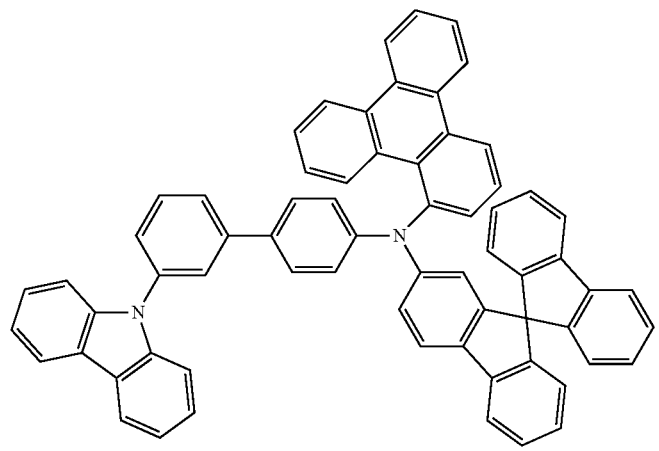
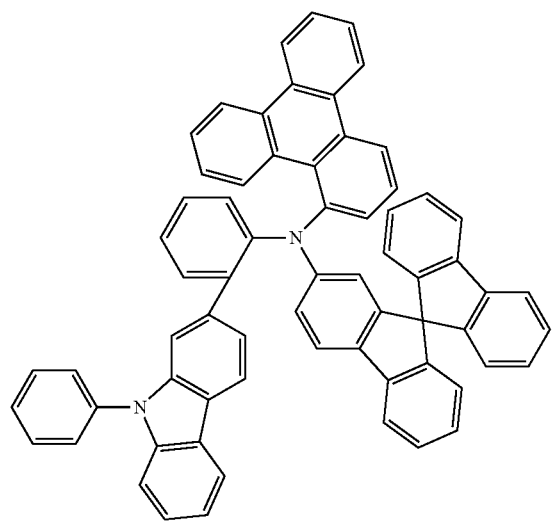

-continued
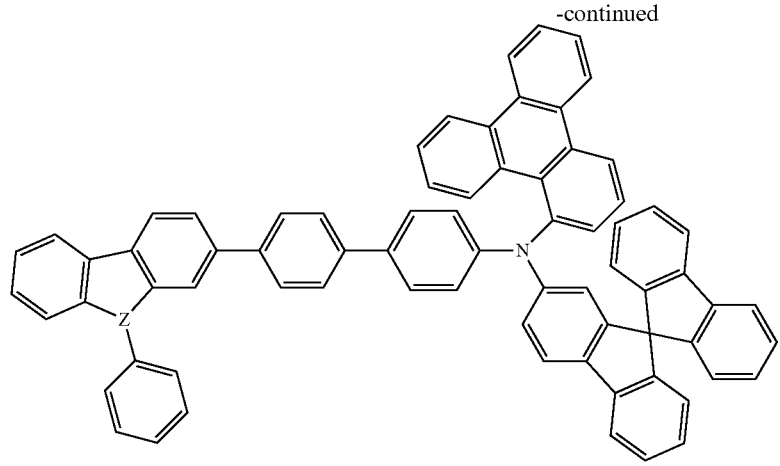
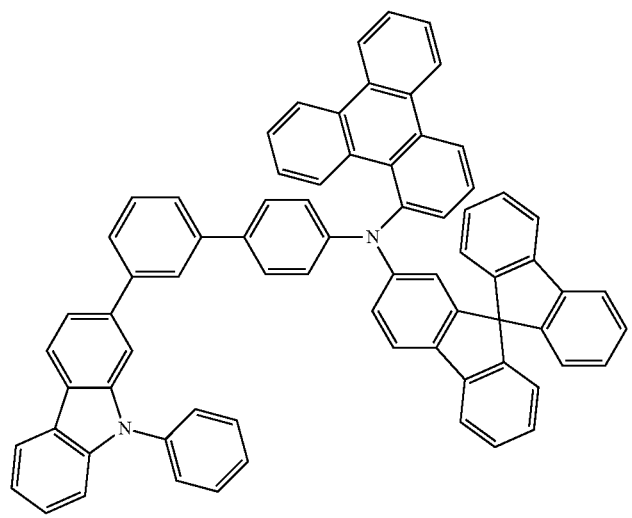
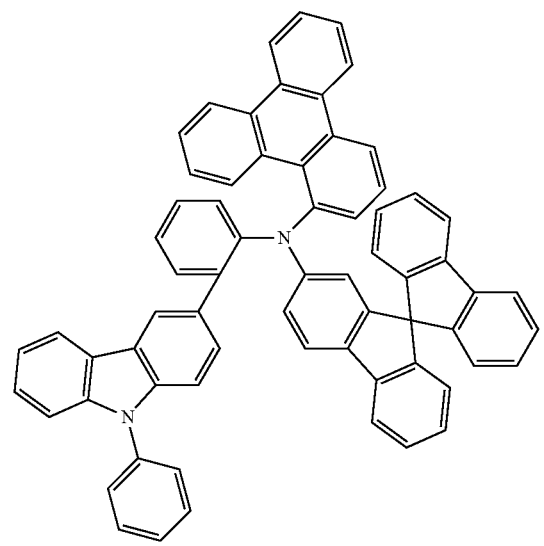

-continued
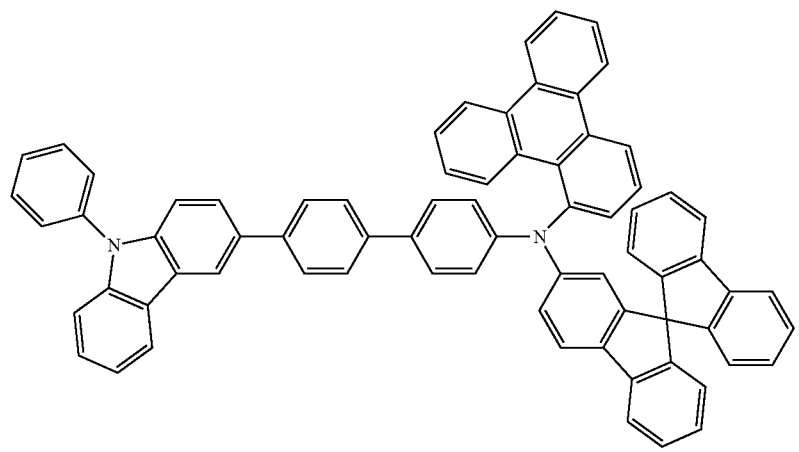
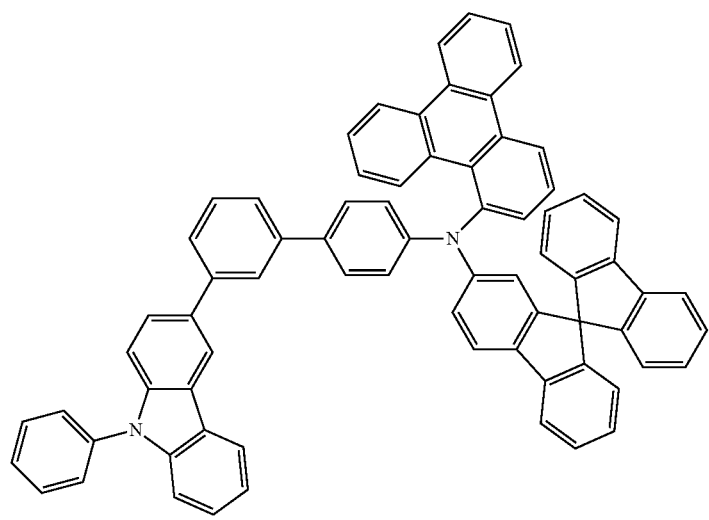
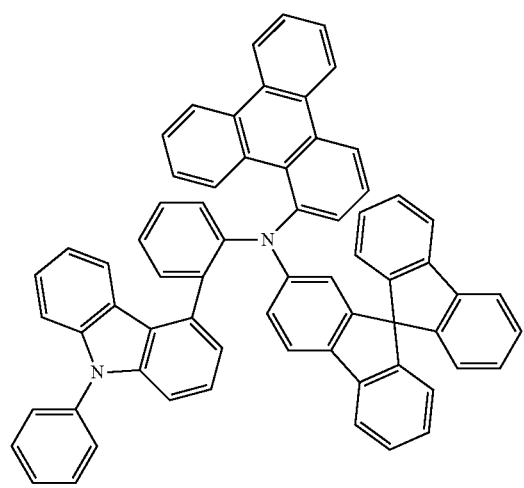

-continued
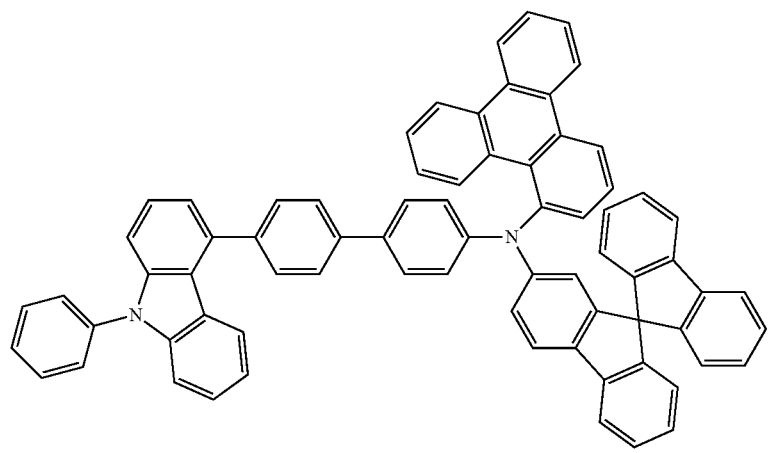
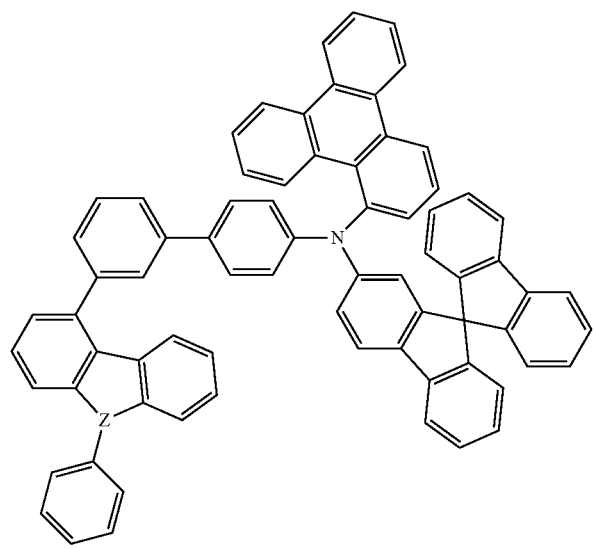
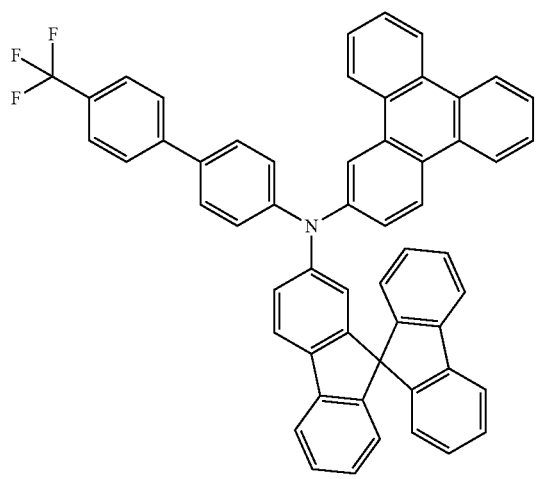
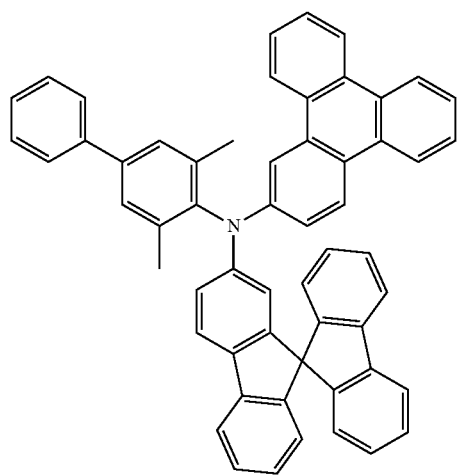
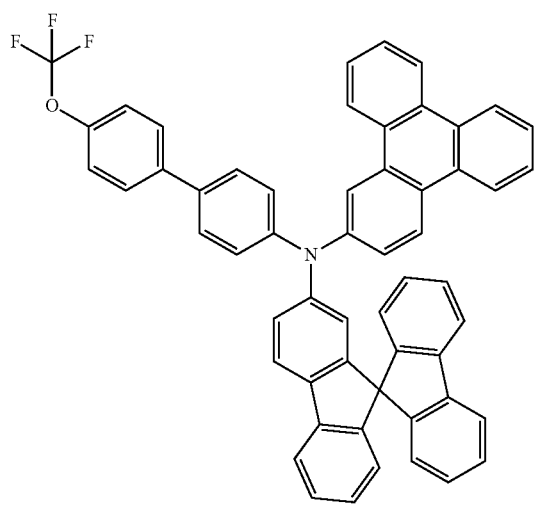

| 265 | 266 |
|---|---|
| 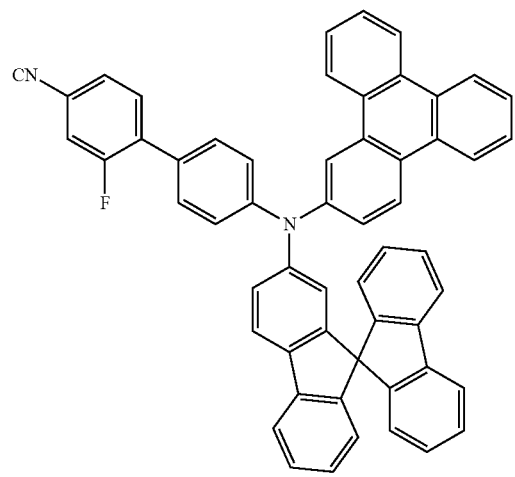 | 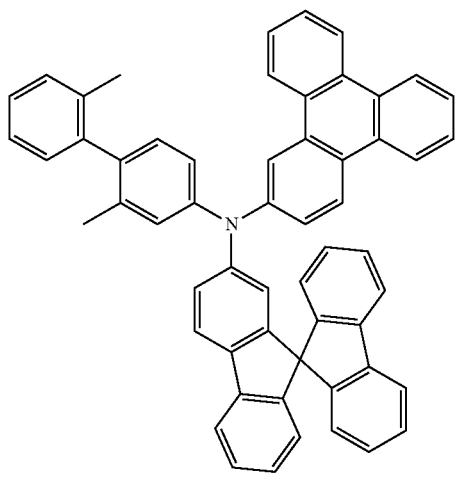 |
| 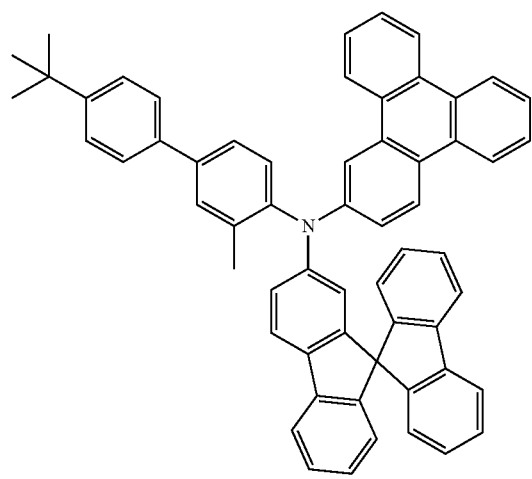 | 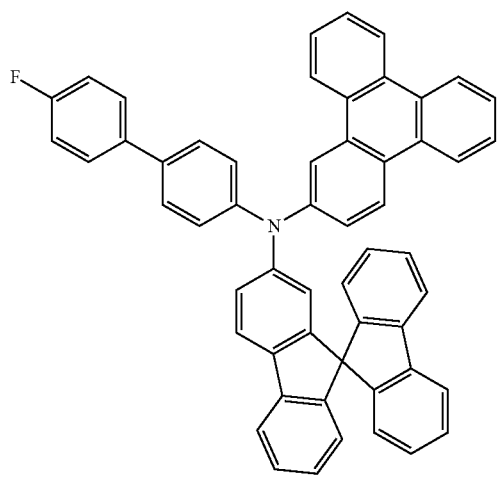 |
| 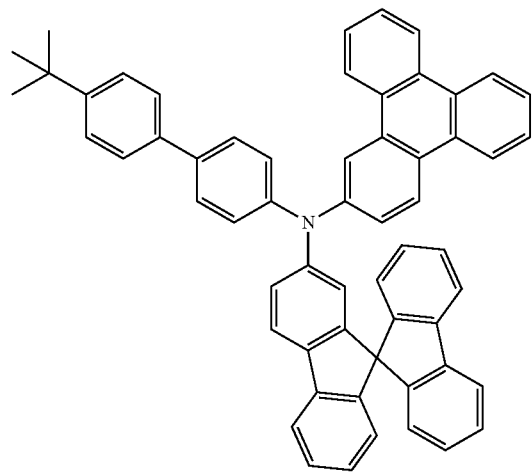 | 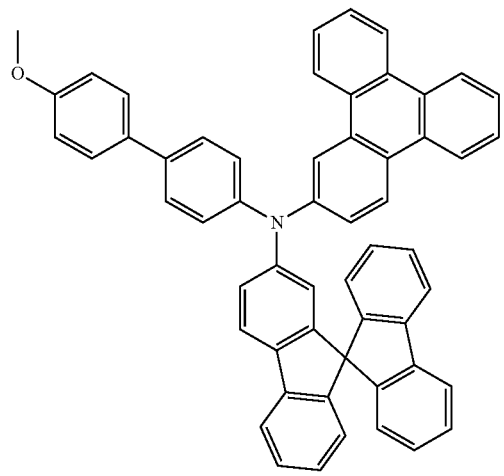 |

-continued
| 267 | 268 |
|---|---|
| 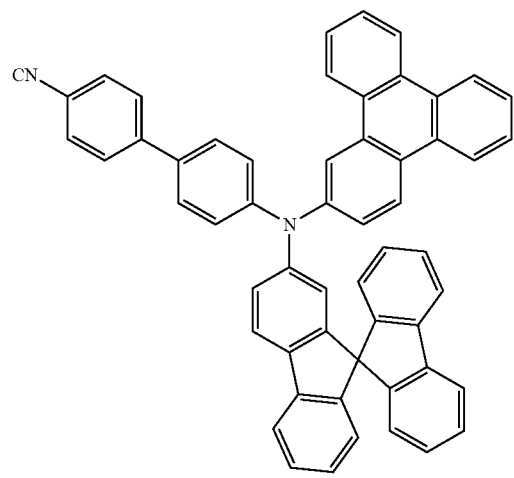 | 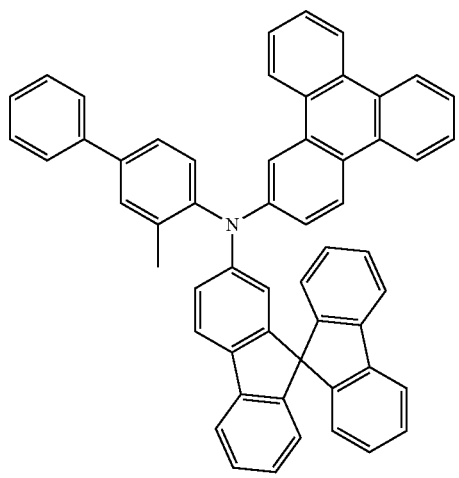 |
| 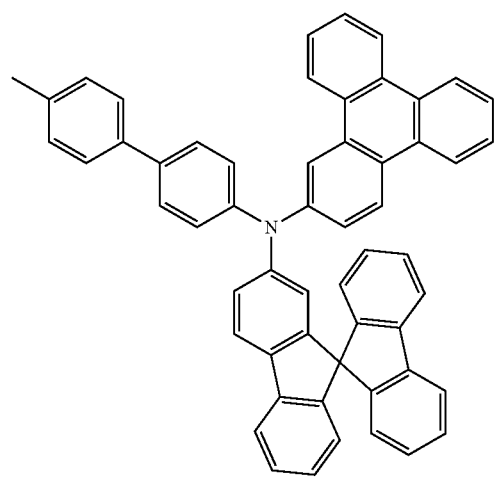 | 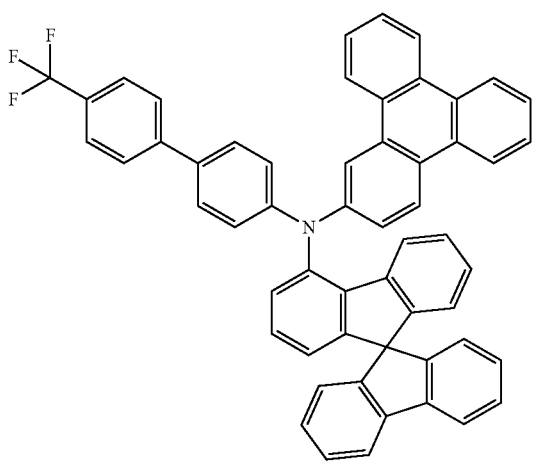 |
| 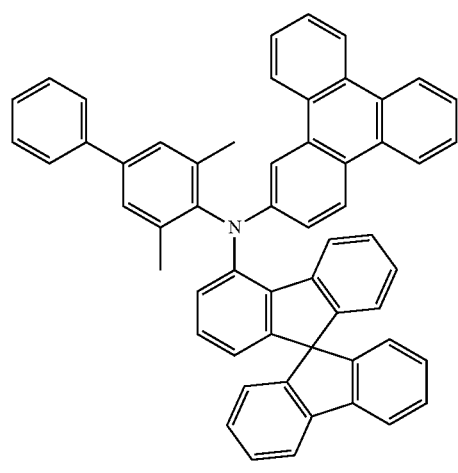 | 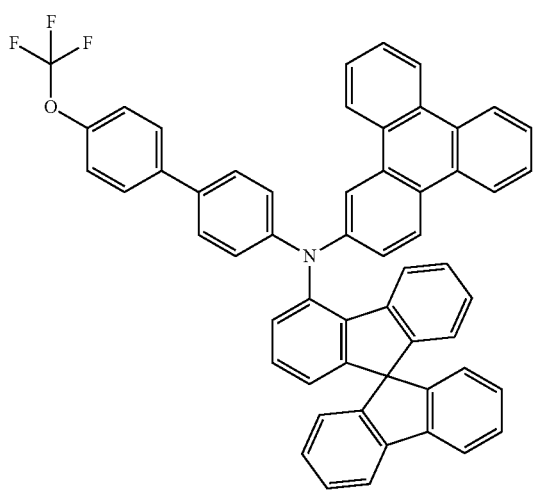 |

-continued
269
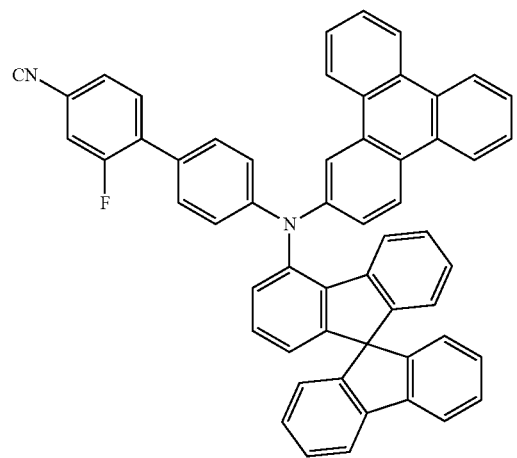
270
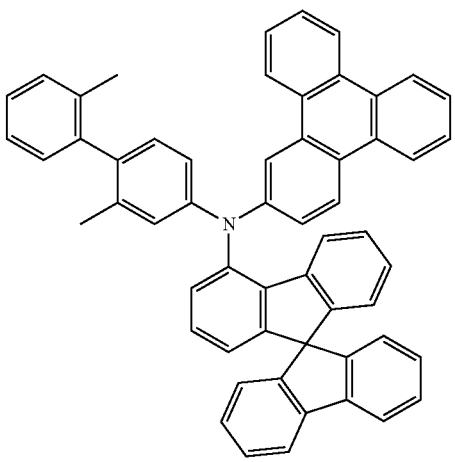
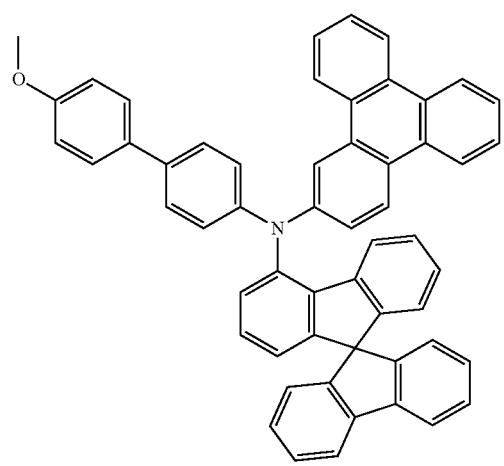
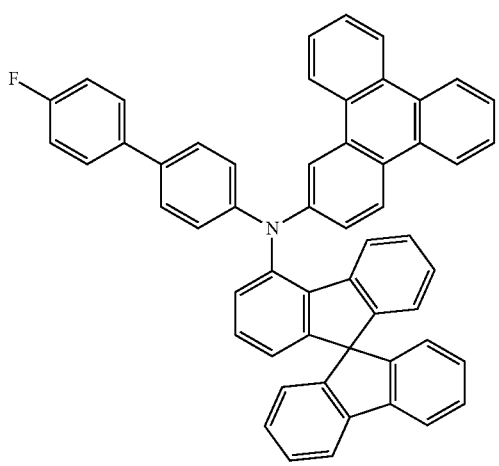
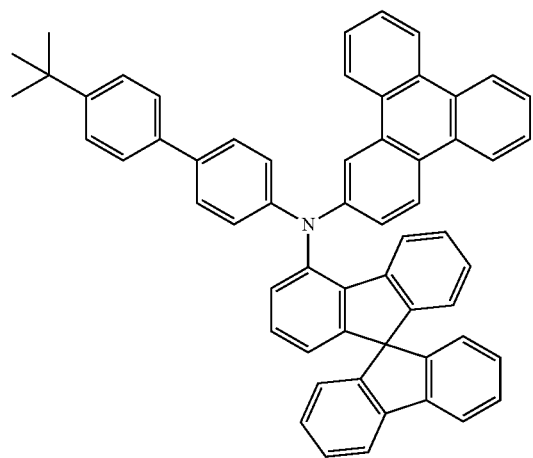
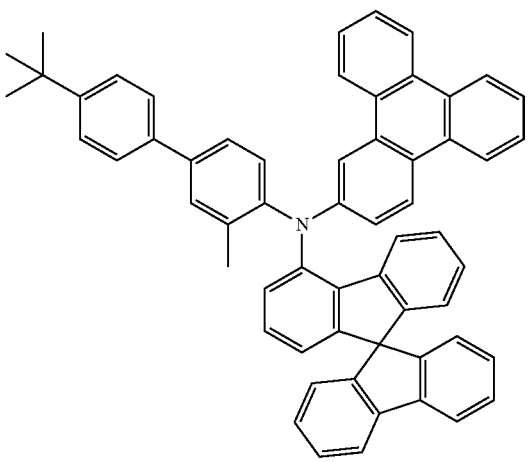

-continued
271
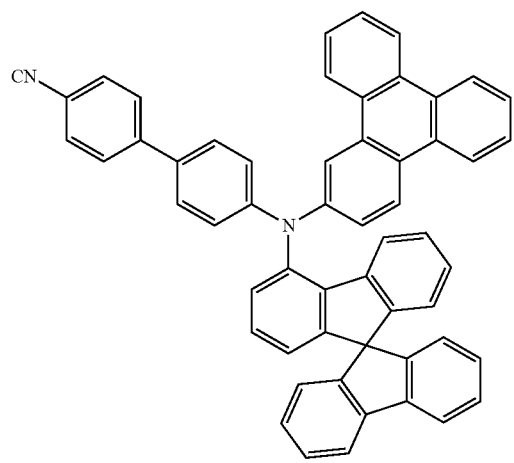
272
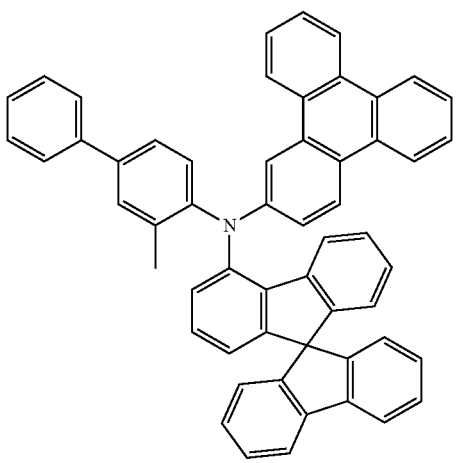
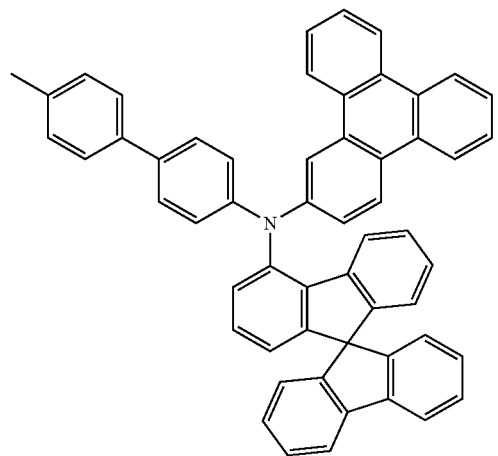
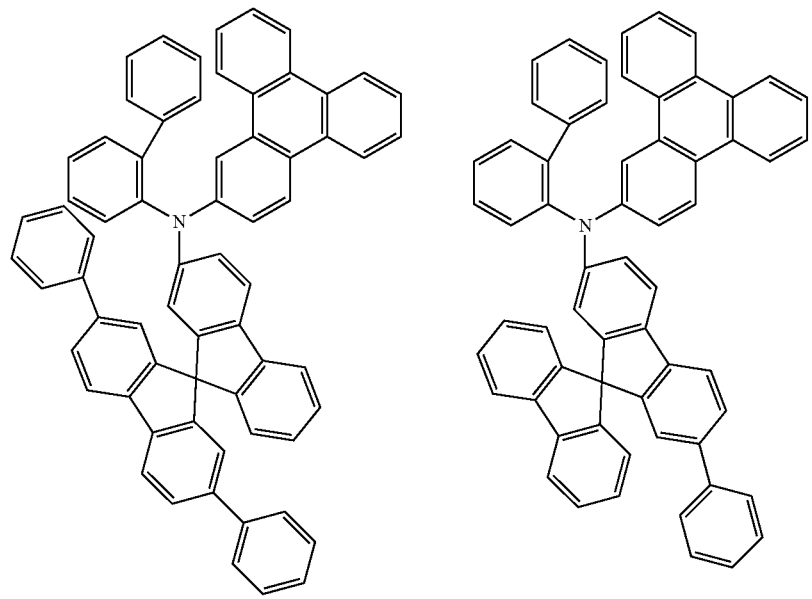

273
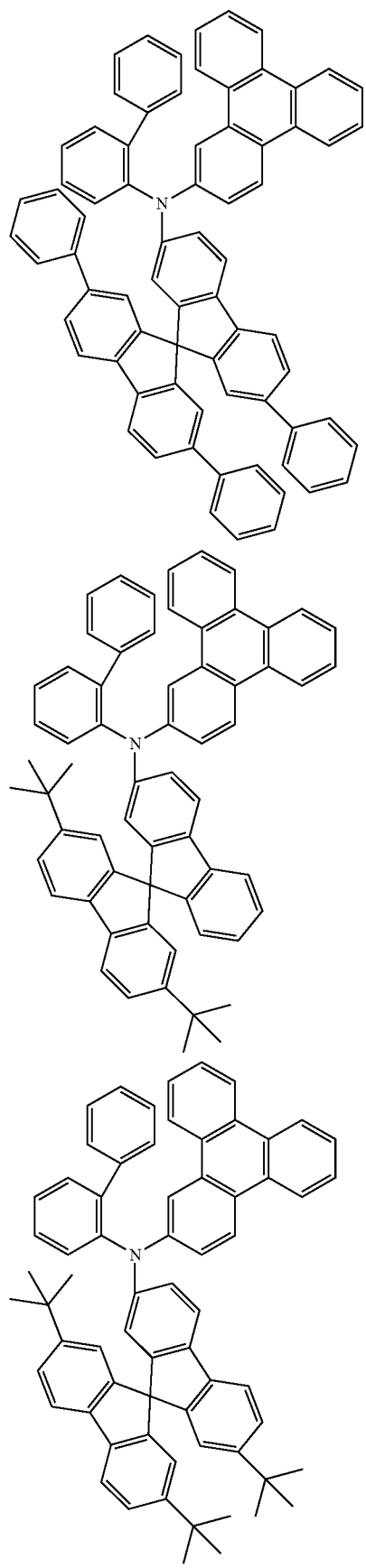
274
-continued
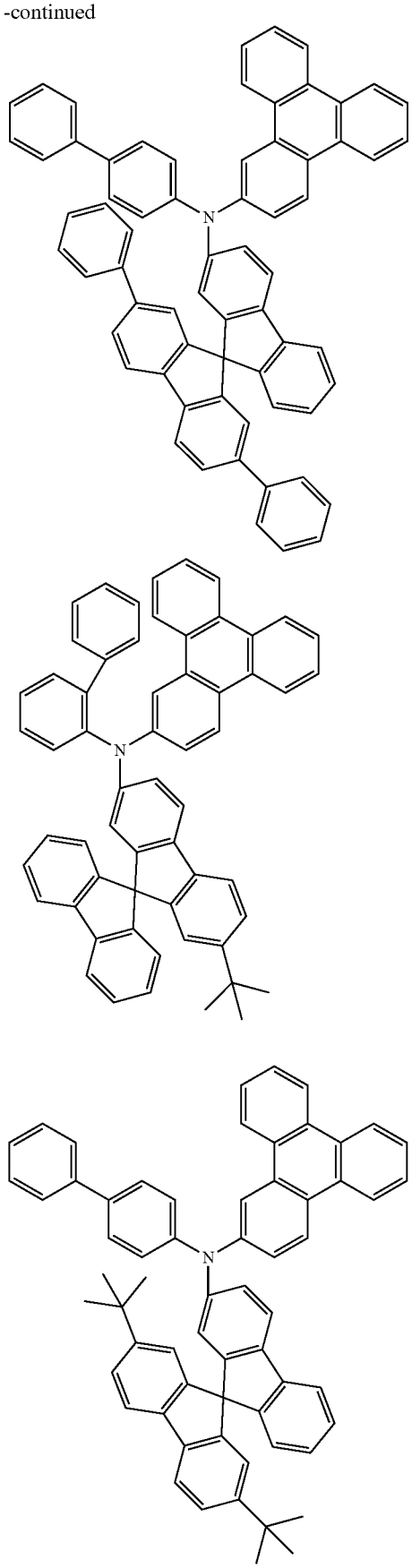

275
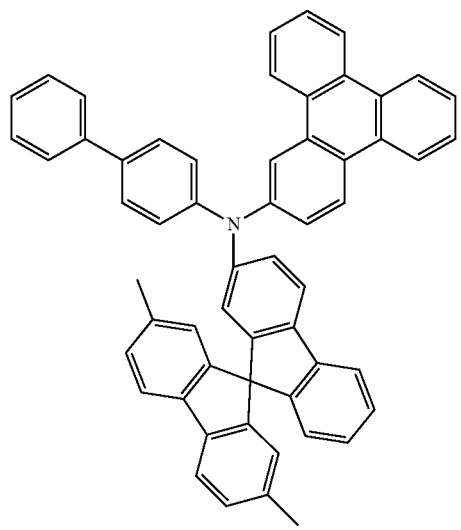
276
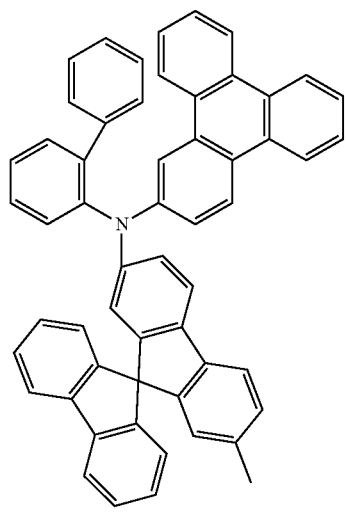
-continued
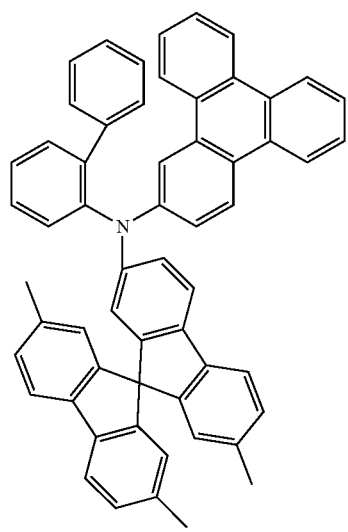
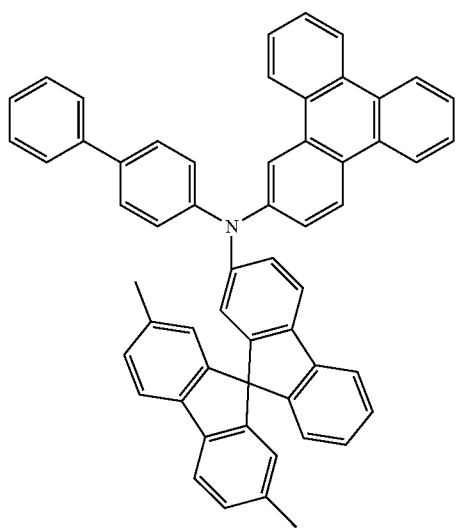
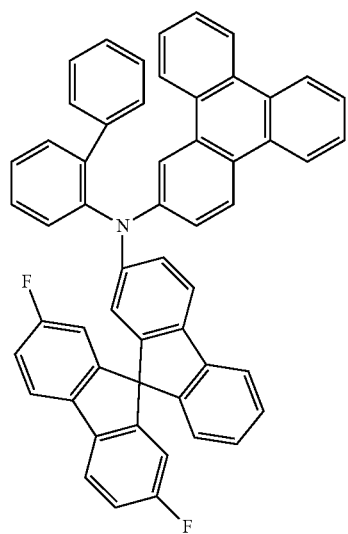
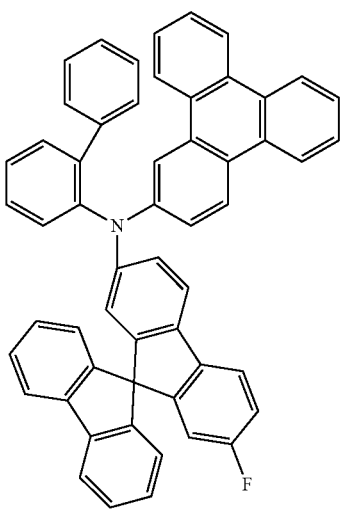
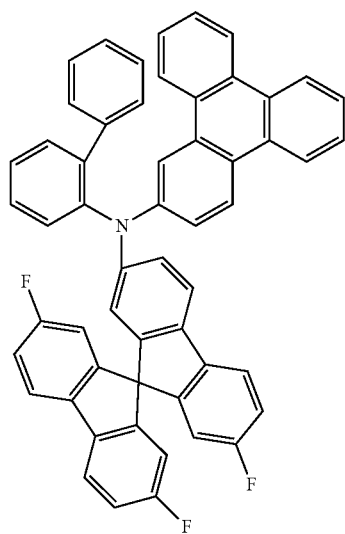

-continued
277
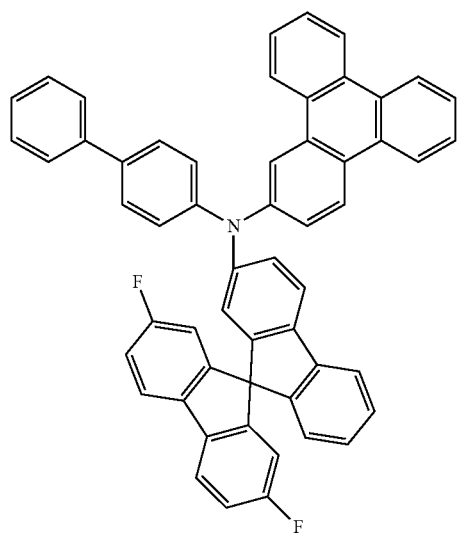
278
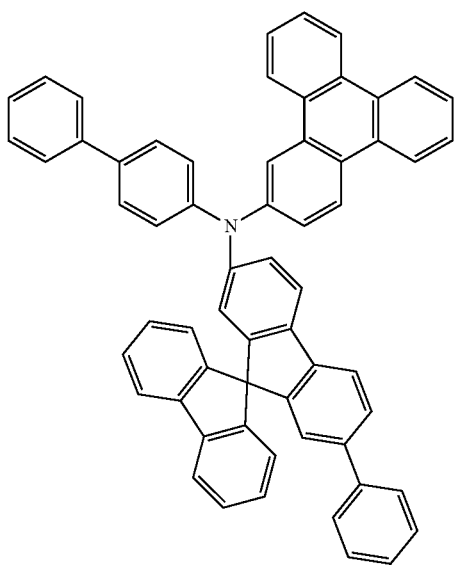
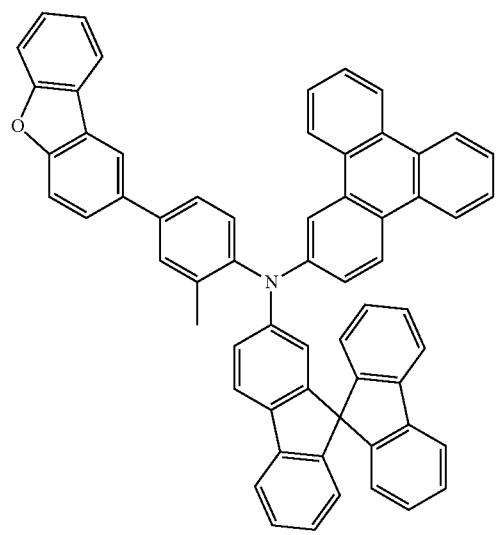
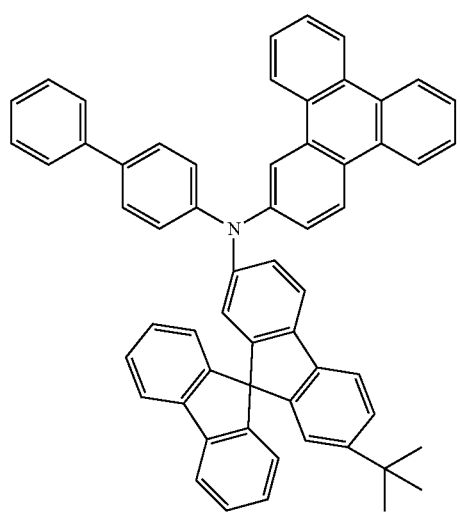
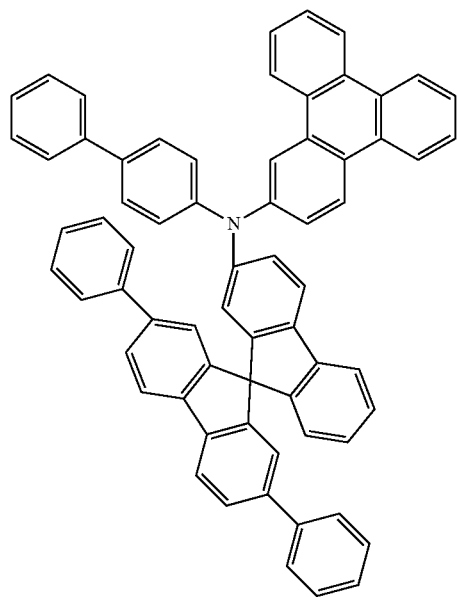 [SMILES: c1ccc(-c2ccc(N(c3ccc4c(c3)C3(c5ccccc5-4)c4cc(-c5ccccc5)ccc4-c4ccc(-c5ccccc5)cc43)c3ccc4c5ccccc5c5ccccc5c4c3)cc2)cc1]

279
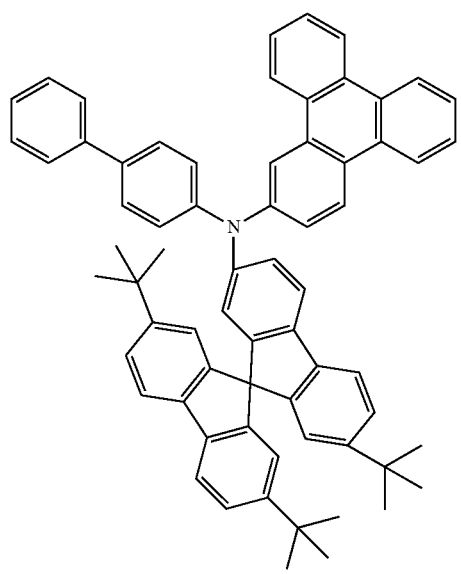
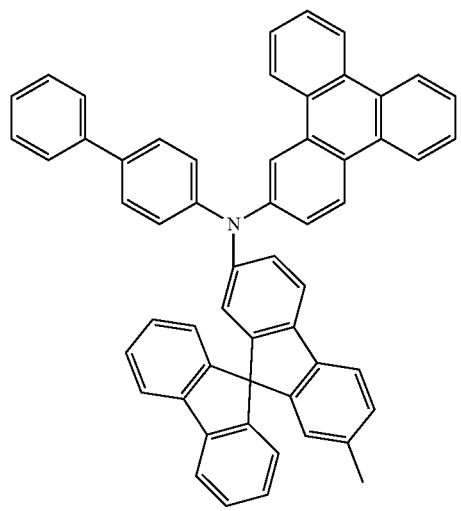
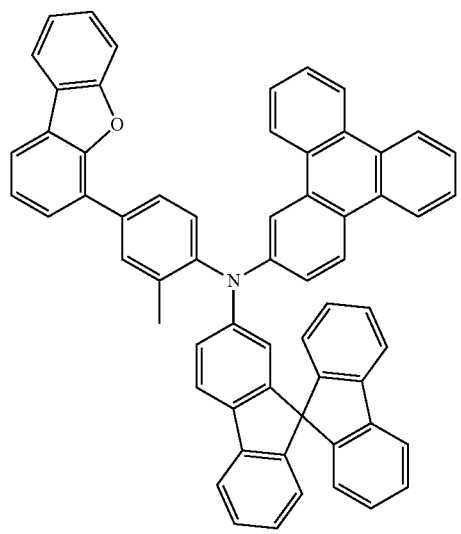
280
-continued
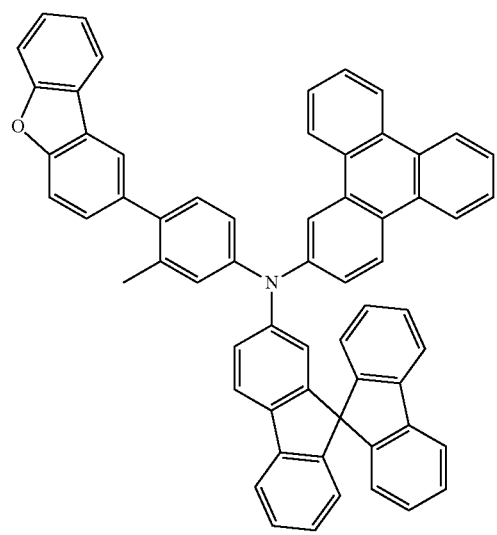
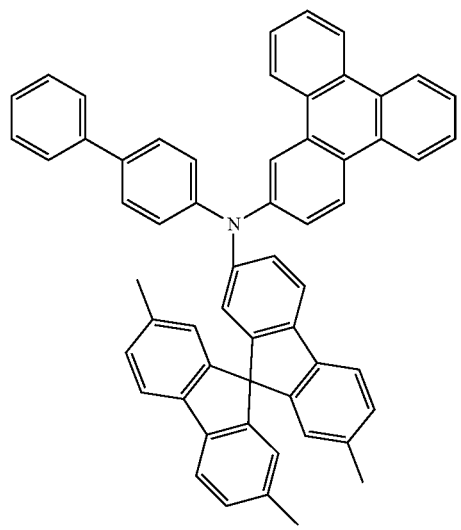
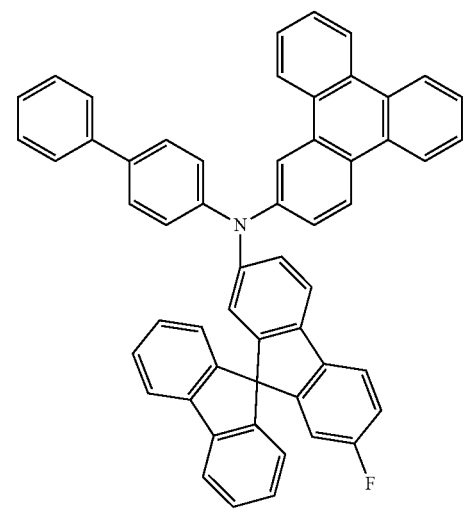

-continued
281
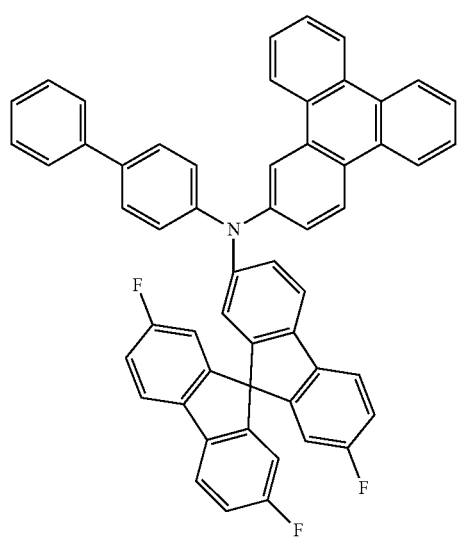
282
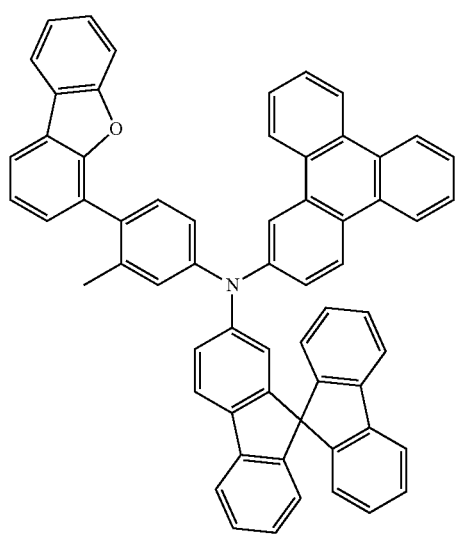
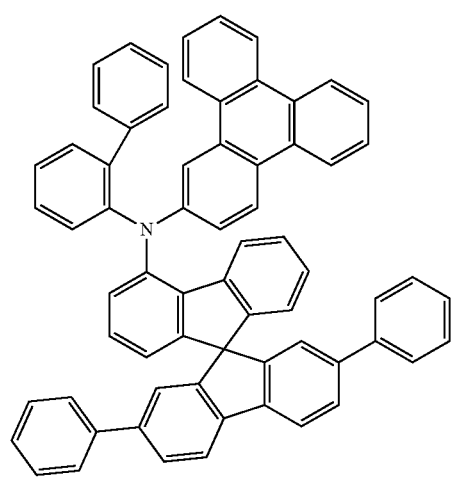
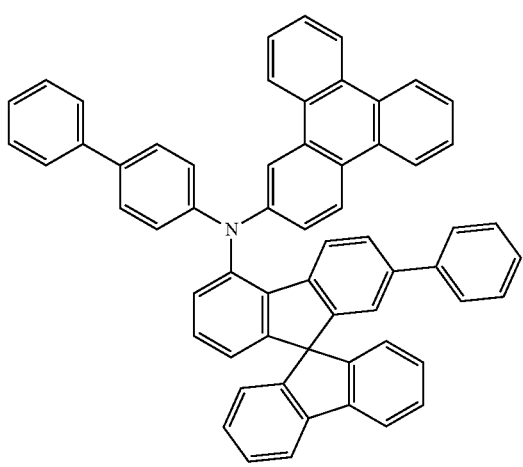
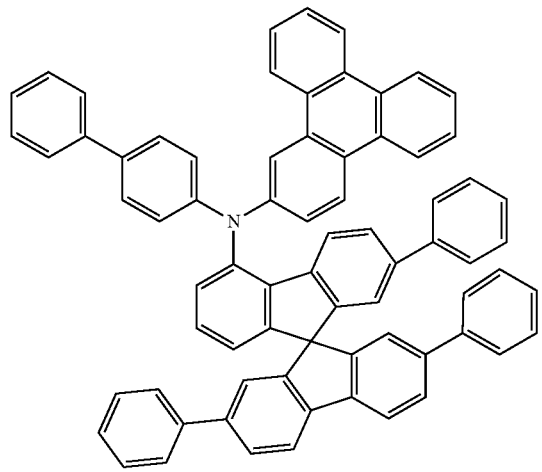
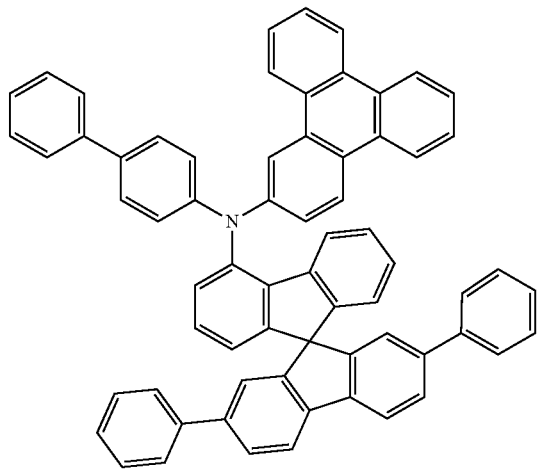

283
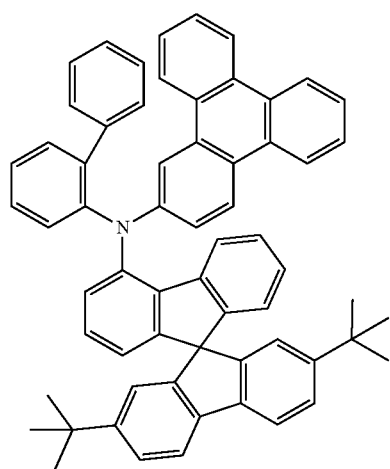
284
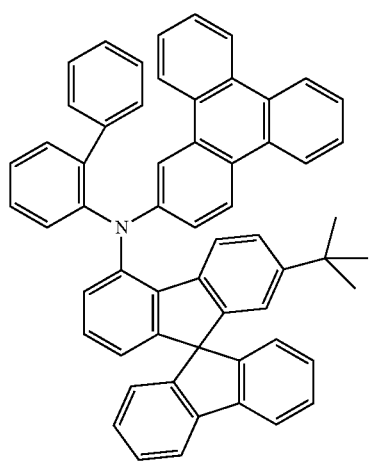
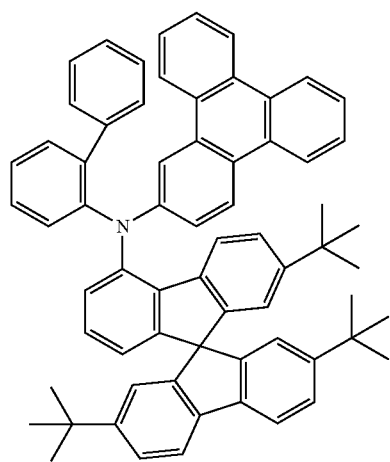
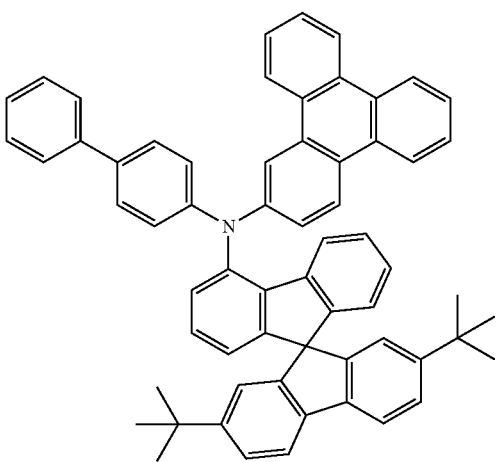
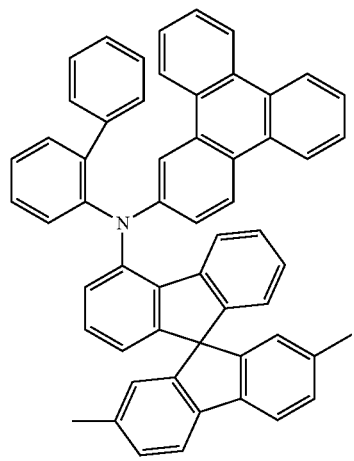
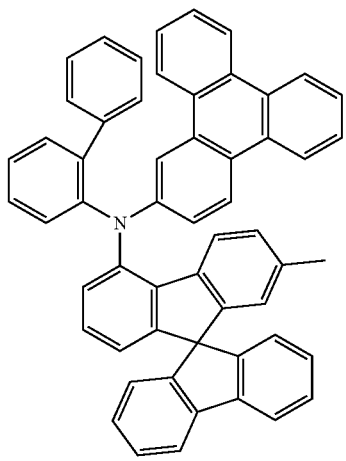
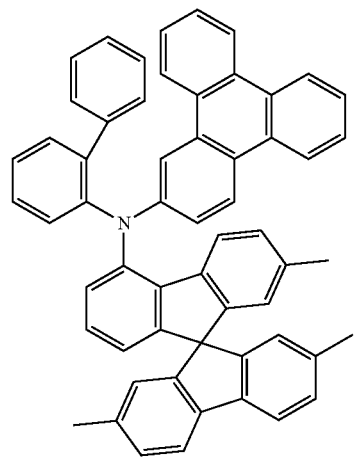

285
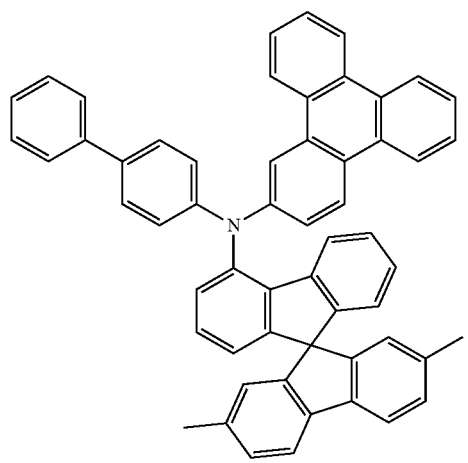
286
-continued
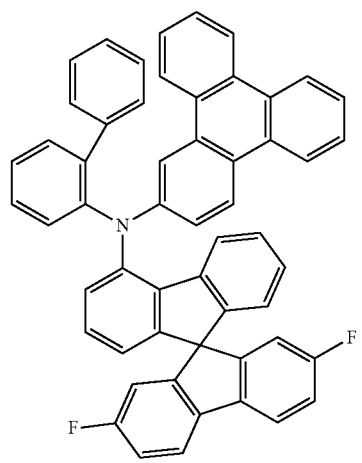
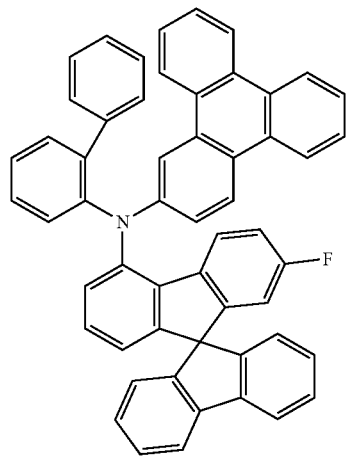
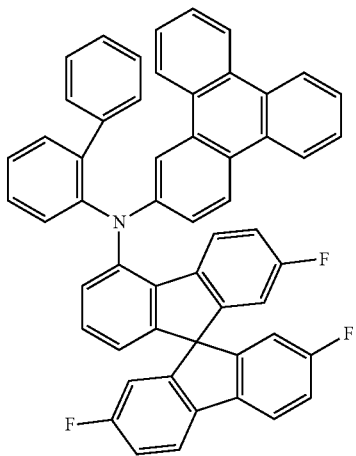
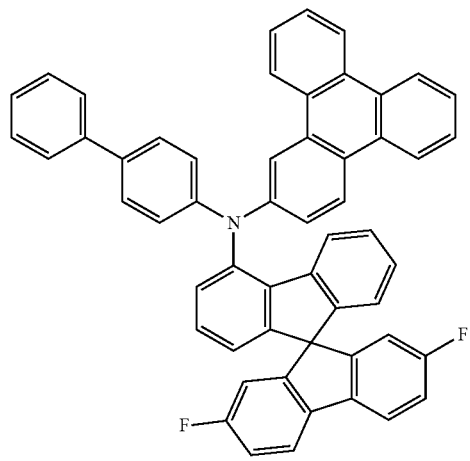
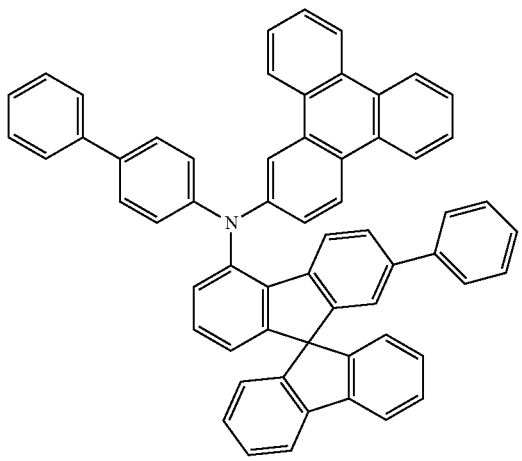

287
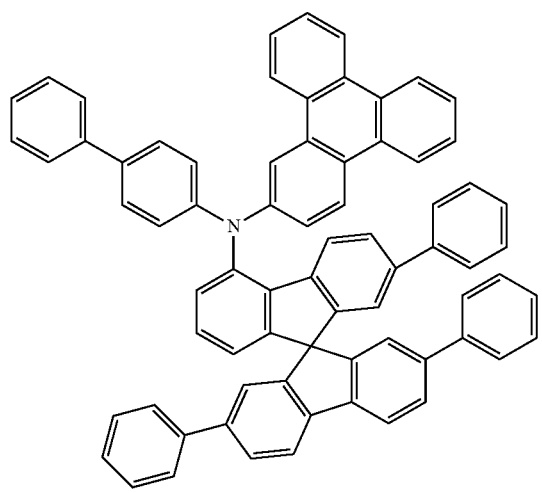
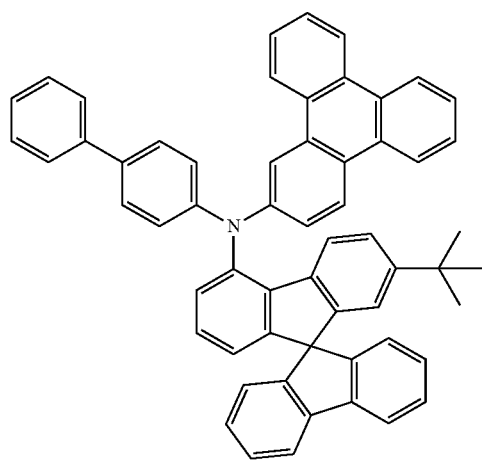
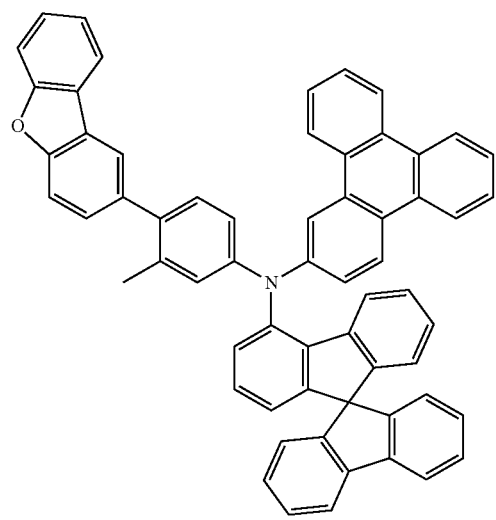
288
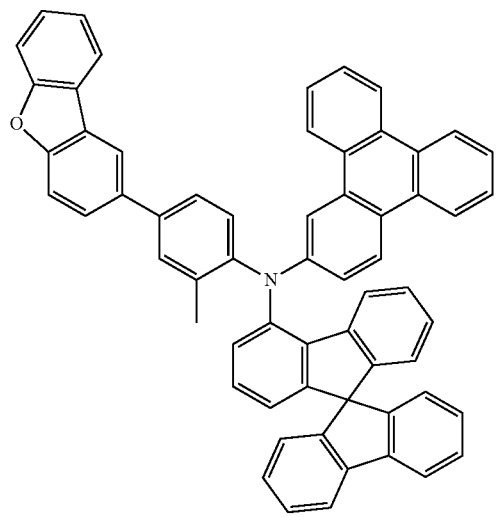
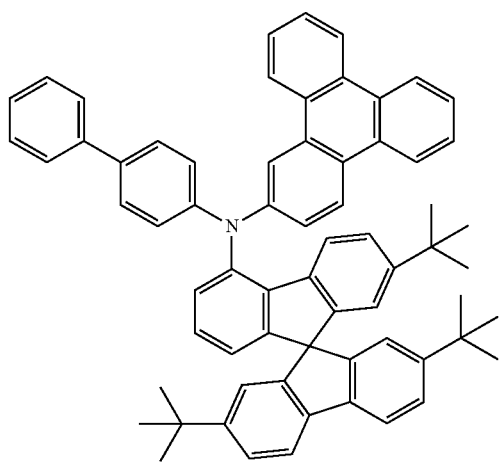
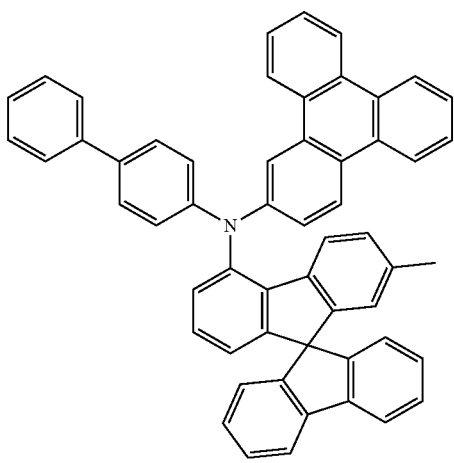

289
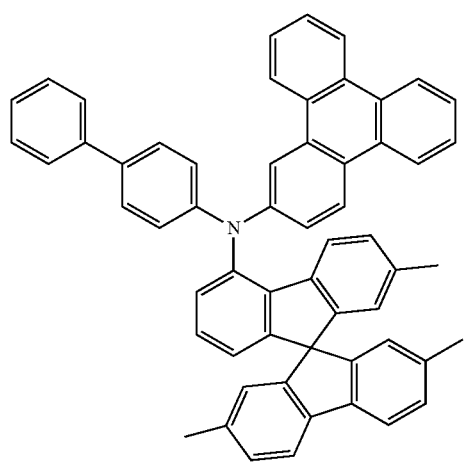
290
-continued
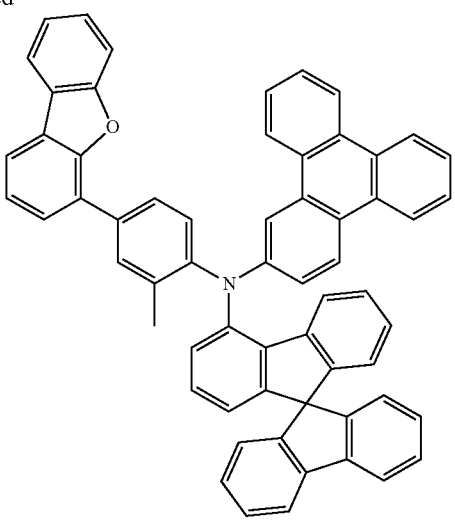
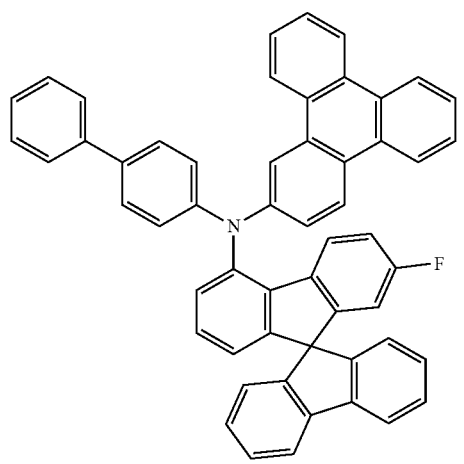
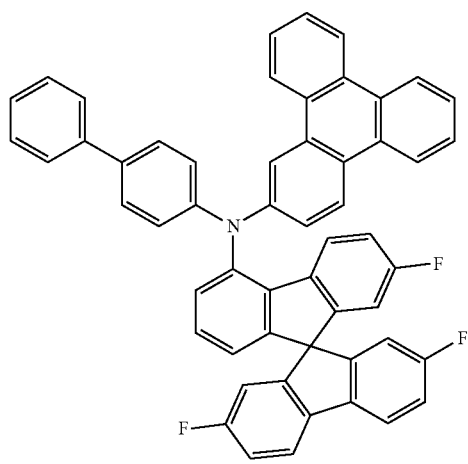
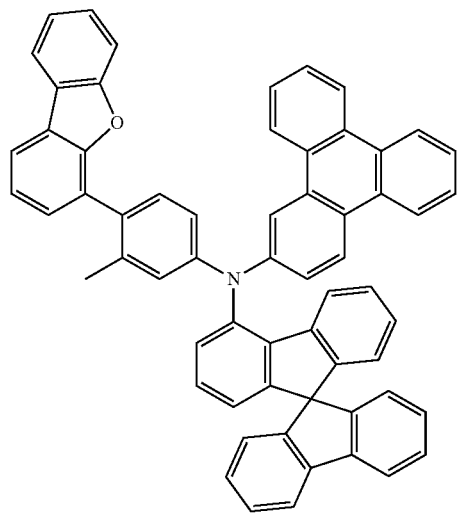
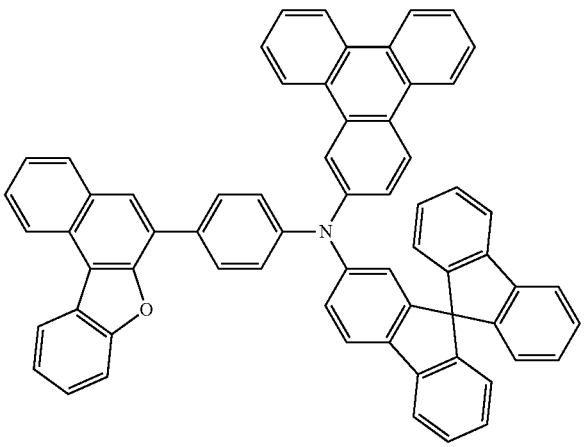

-continued
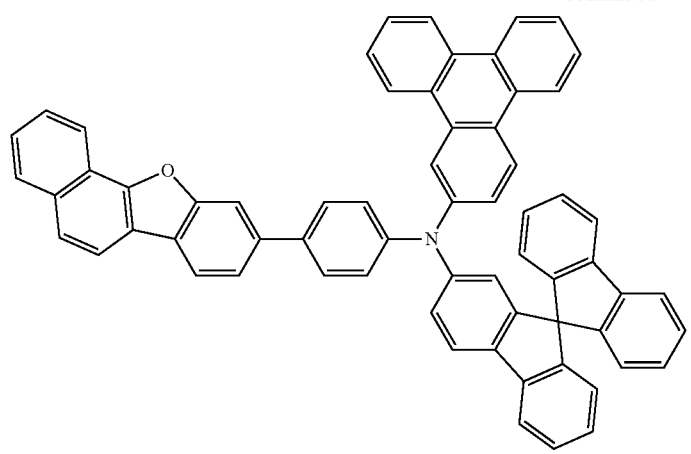
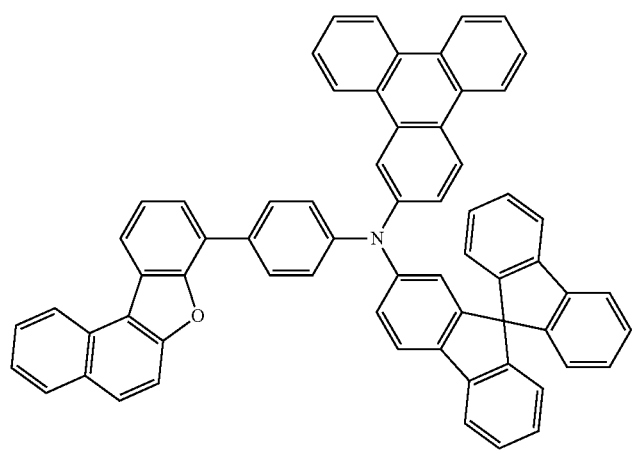
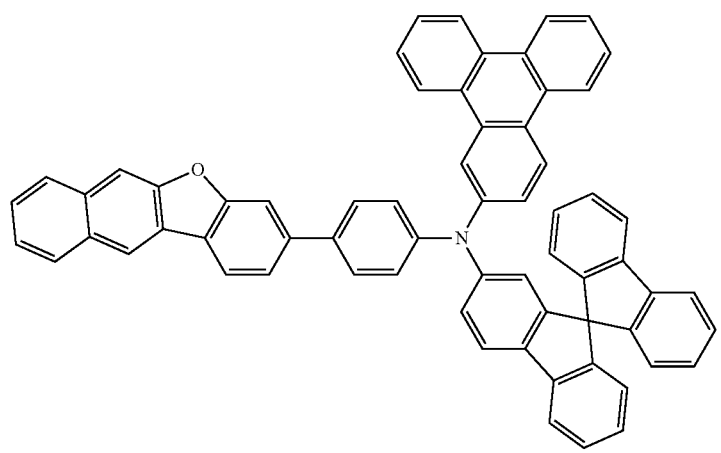

293
294
-continued
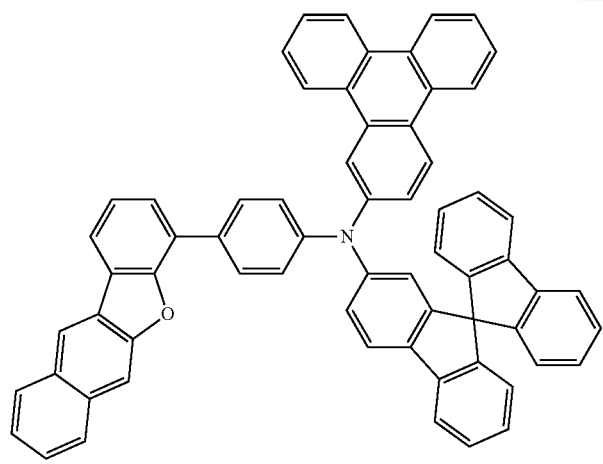
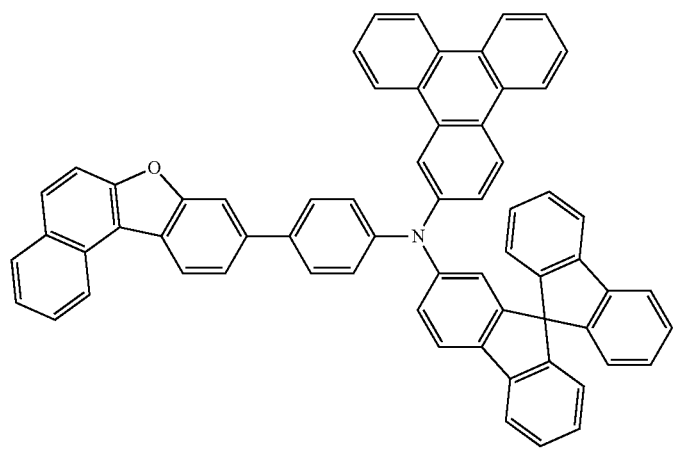
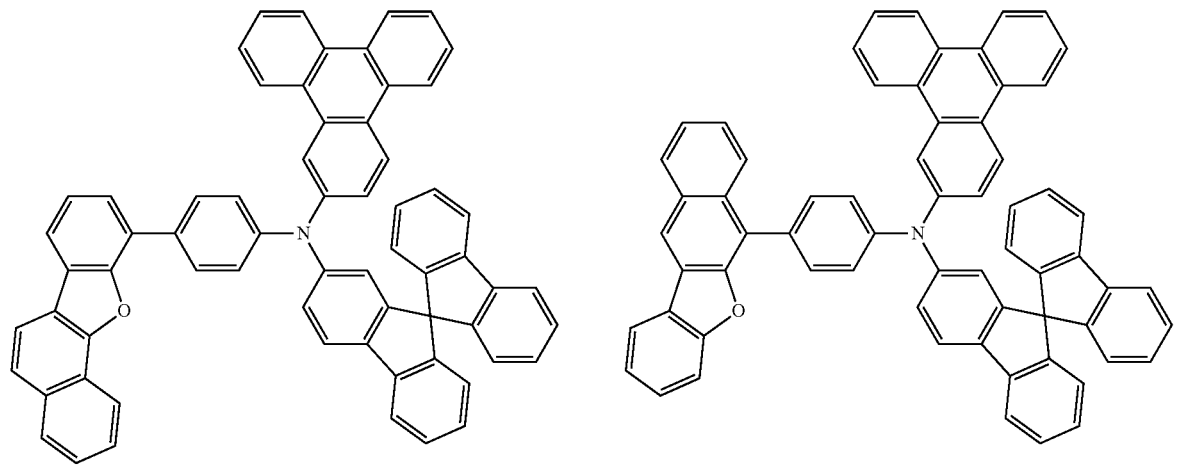

-continued
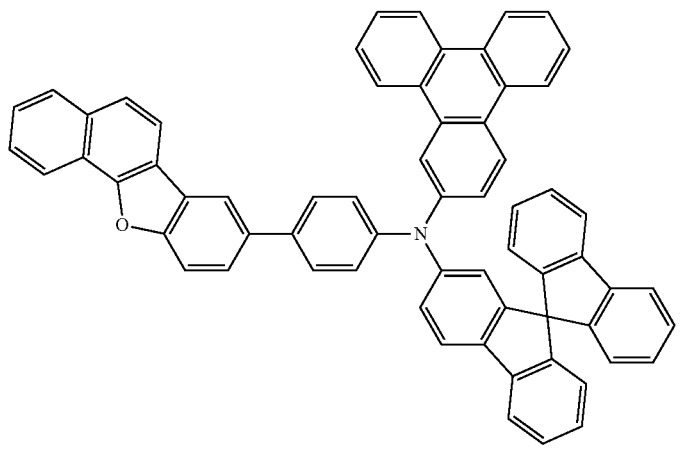
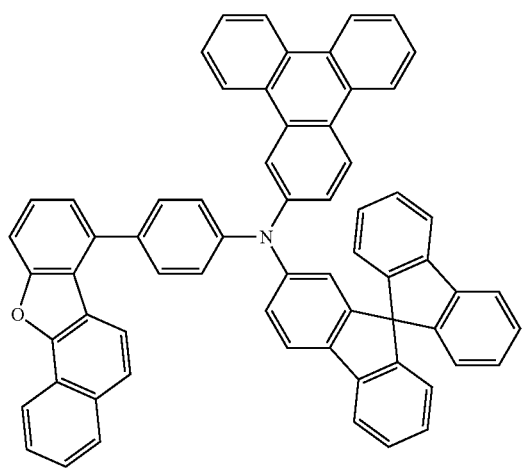
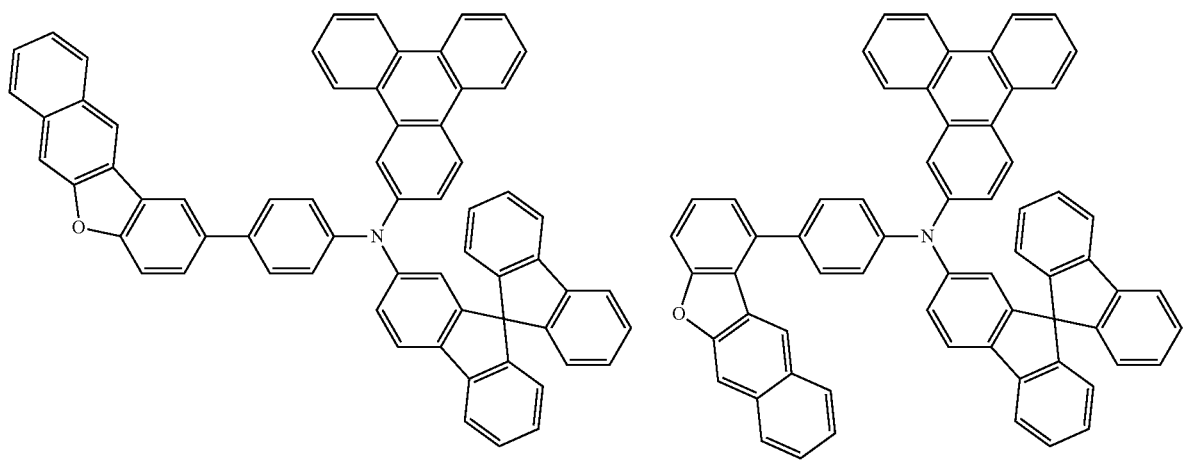

297
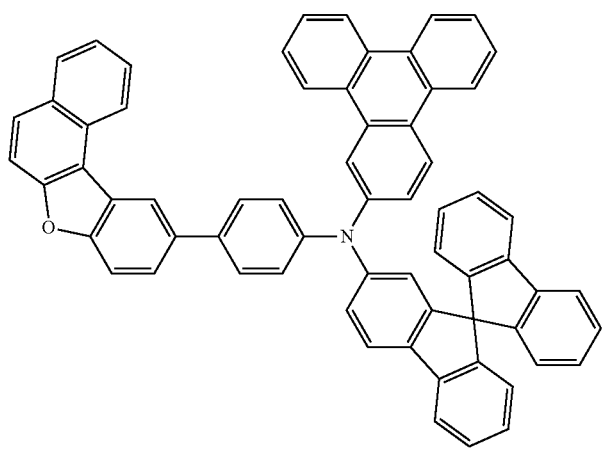
298
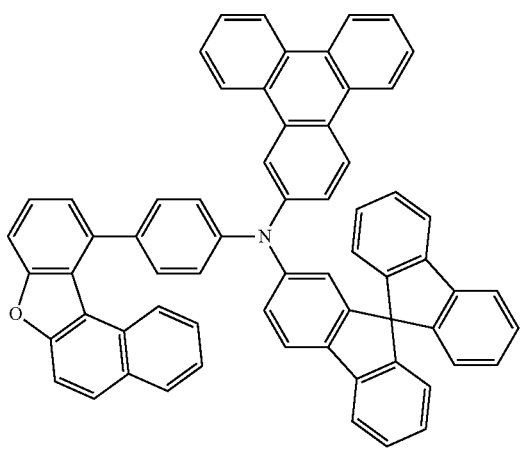
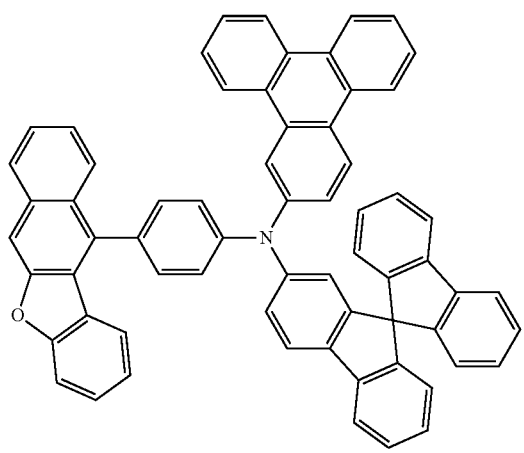
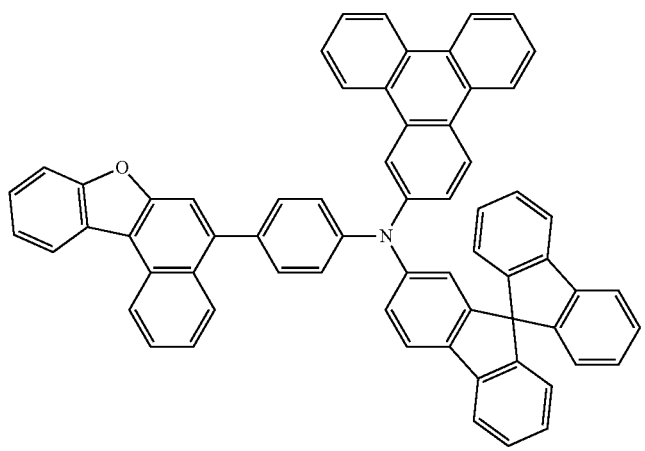

-continued
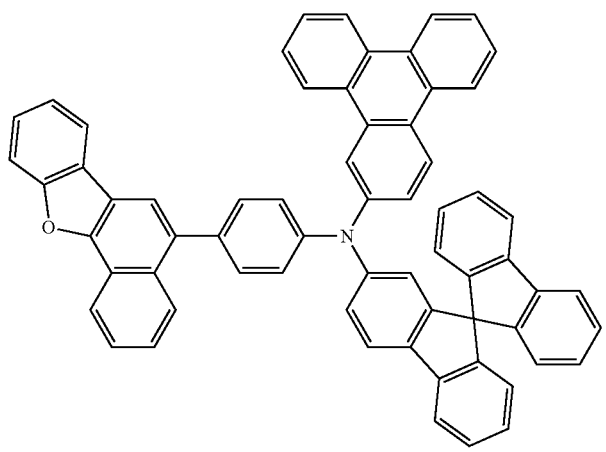
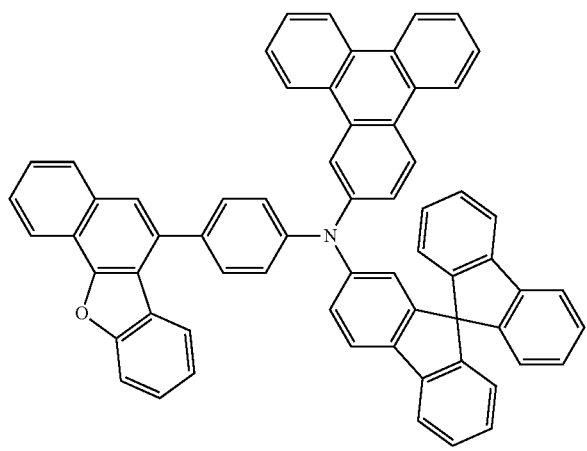
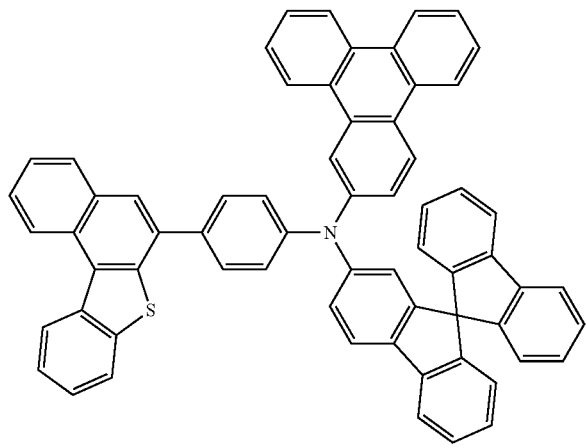

-continued
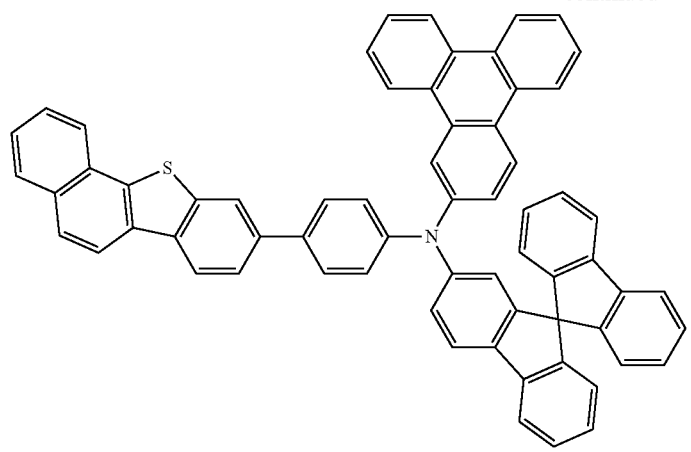
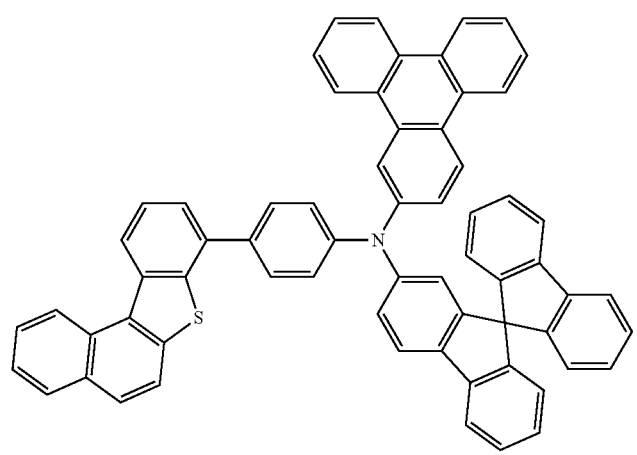
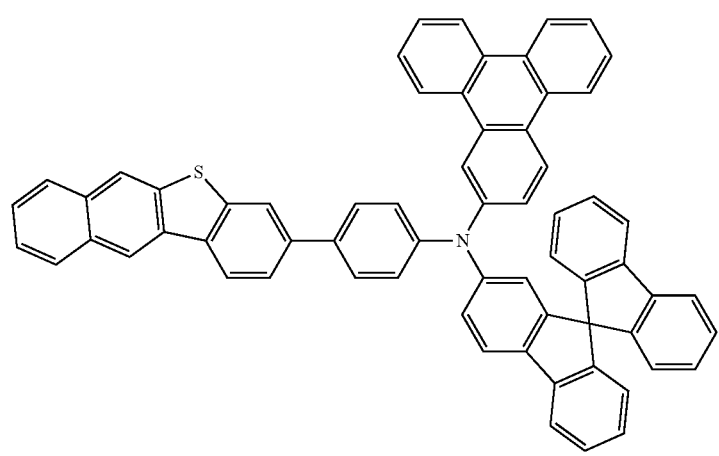

-continued
303
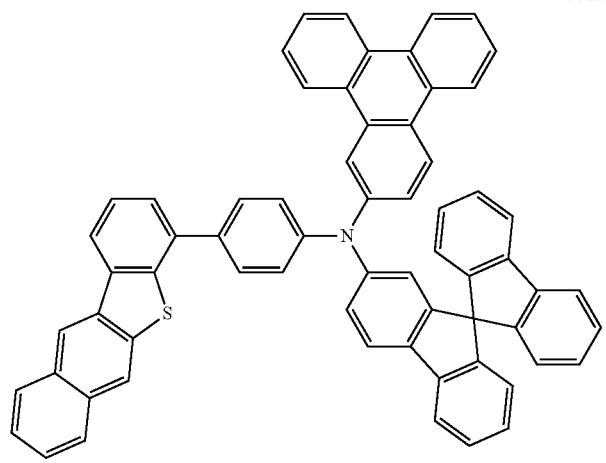
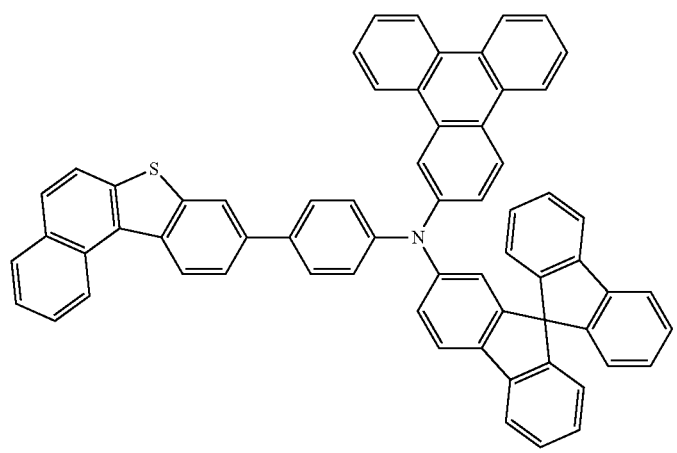
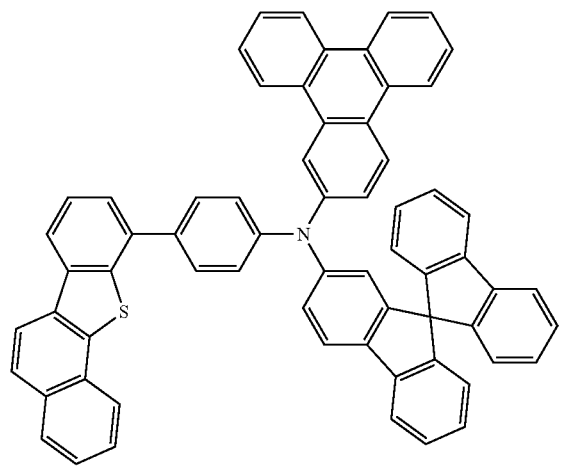
304
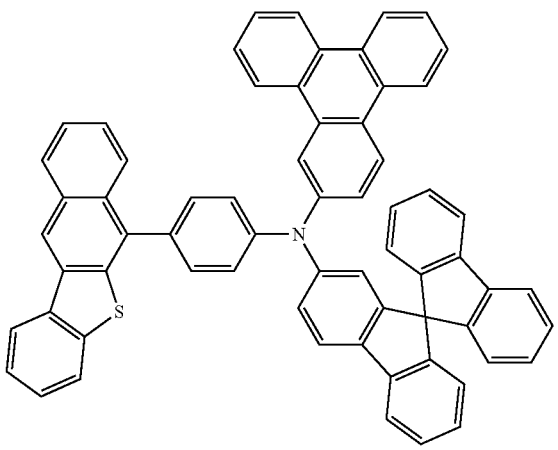

-continued
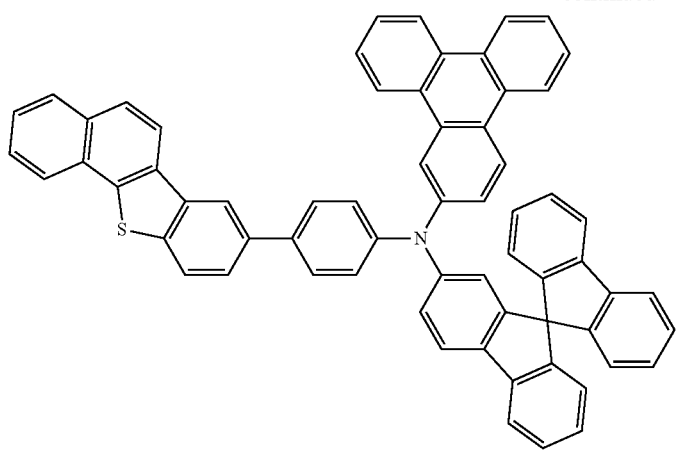
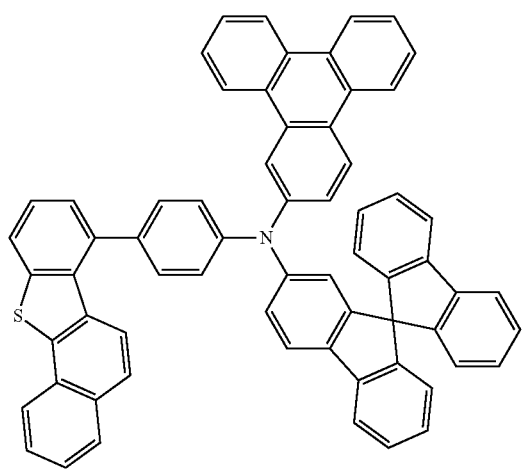
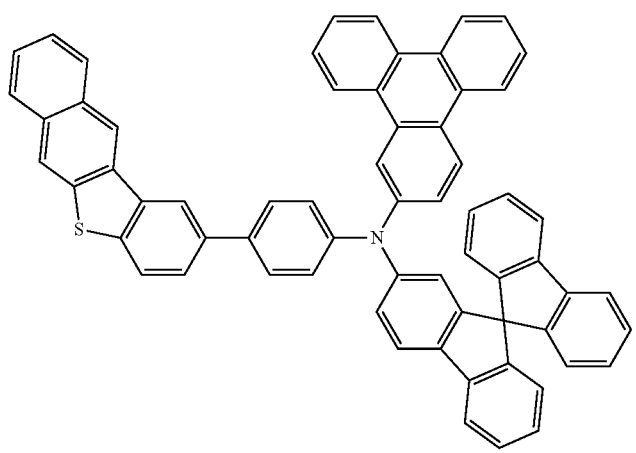

307
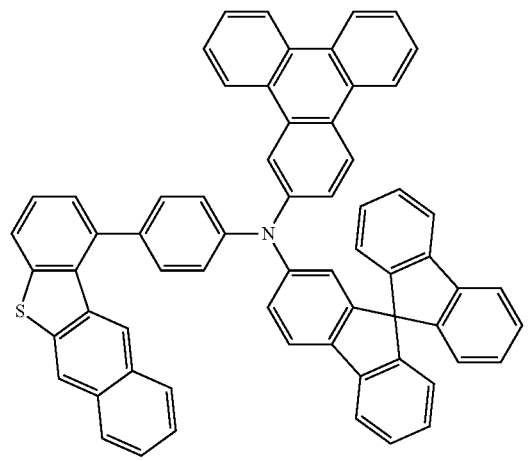
308
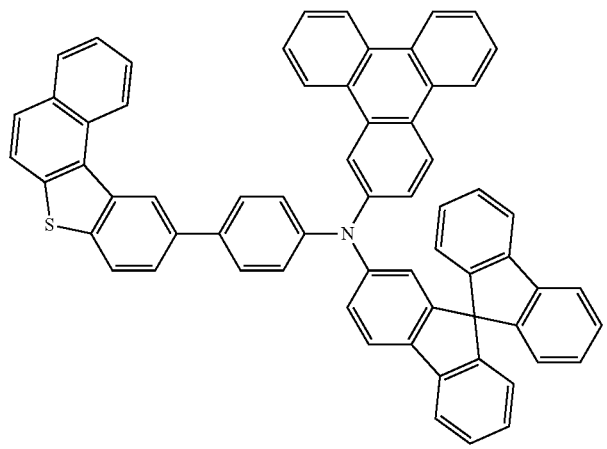
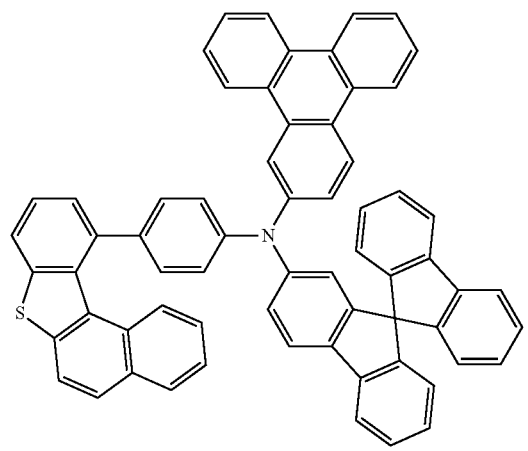
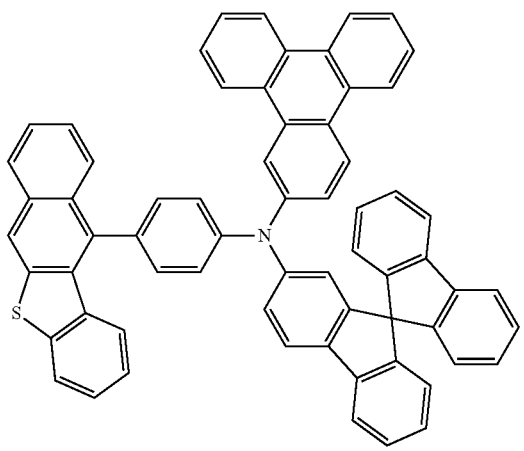
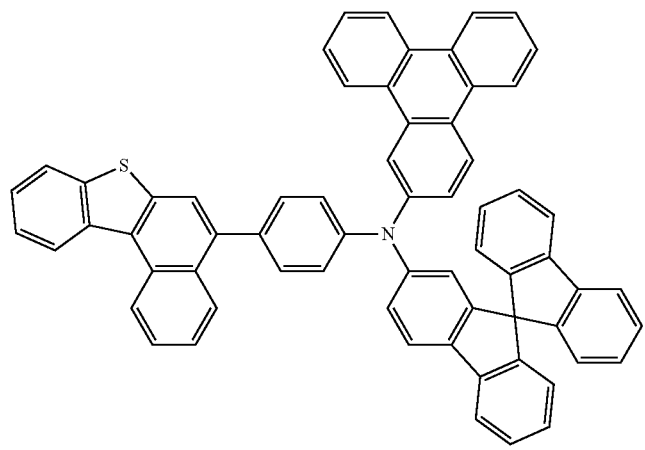

-continued
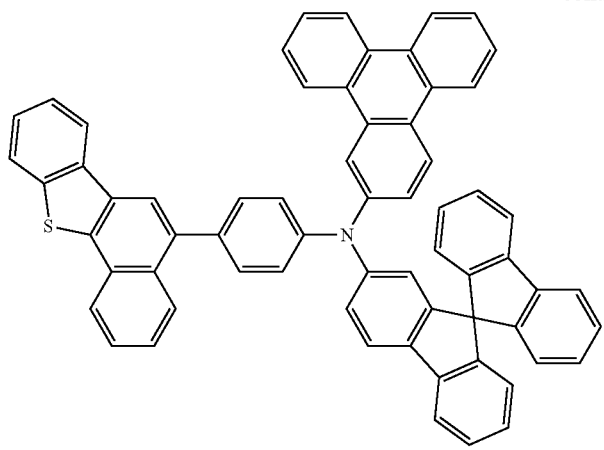
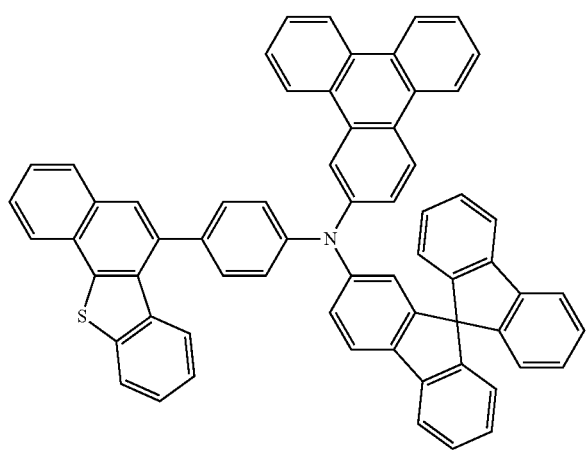
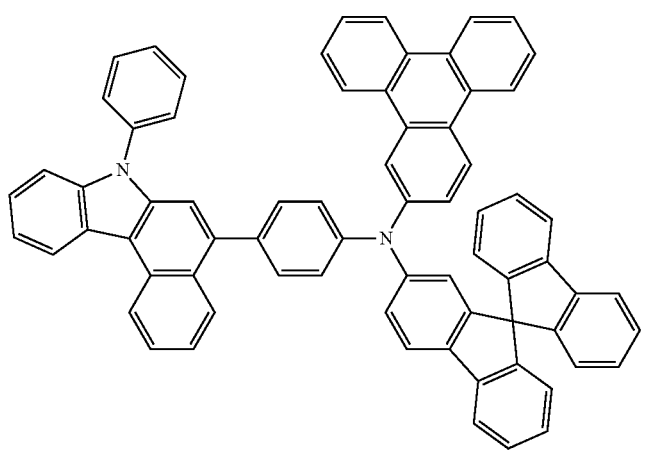

-continued
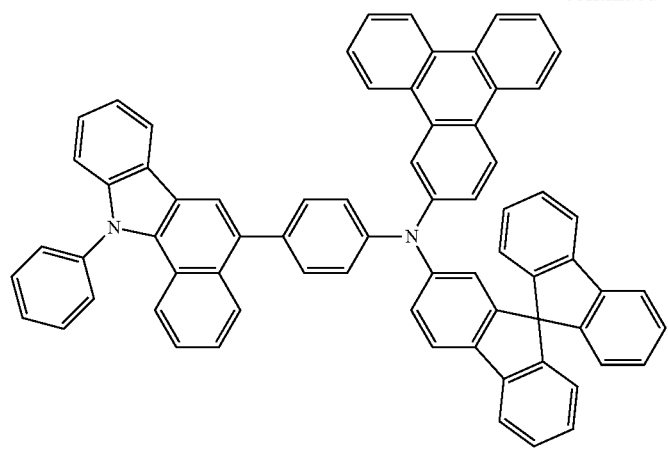
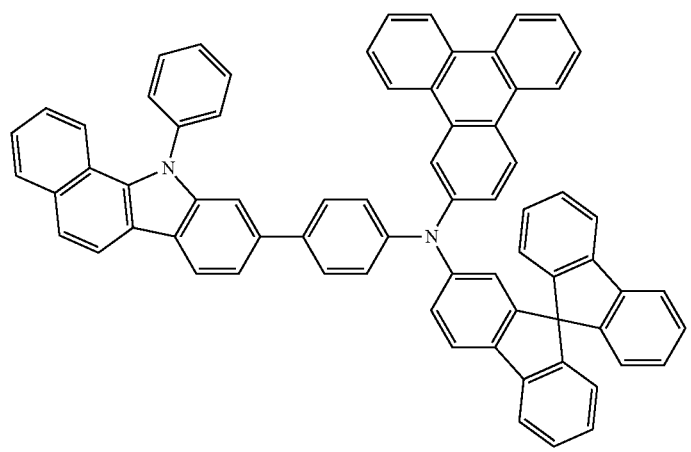
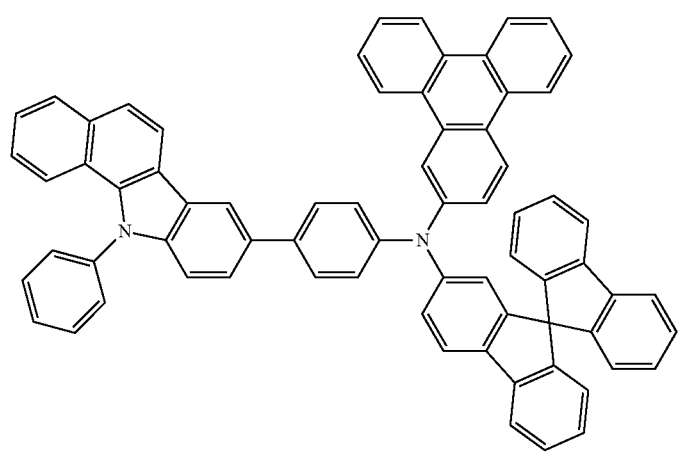

-continued
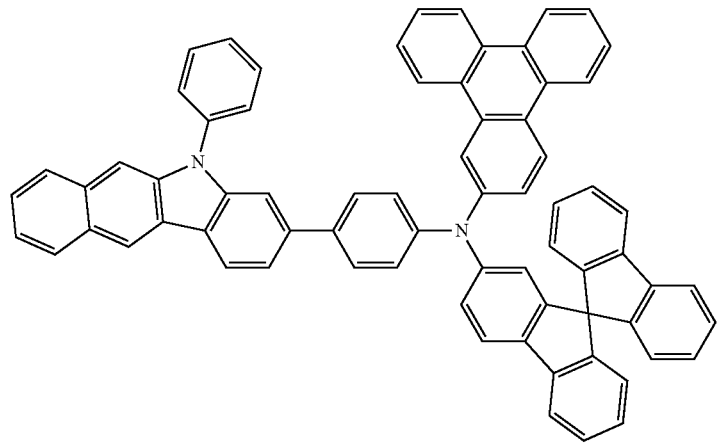
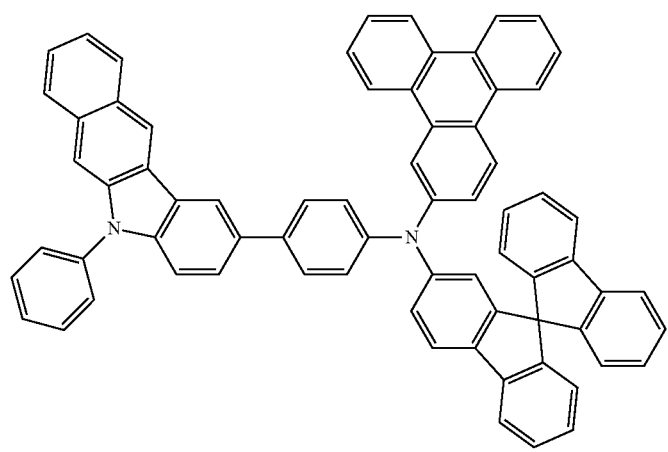
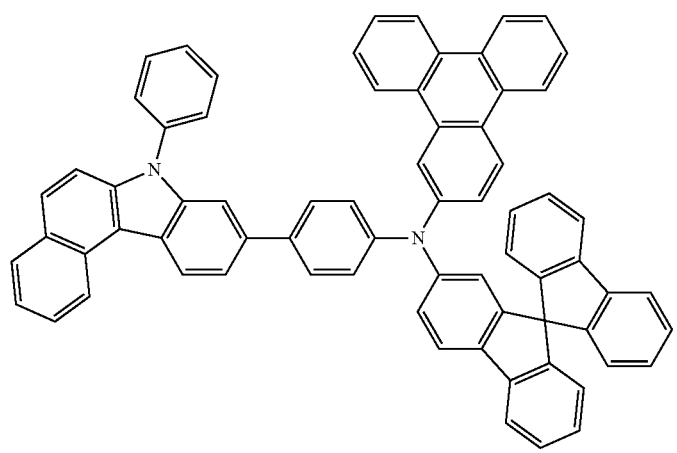

-continued
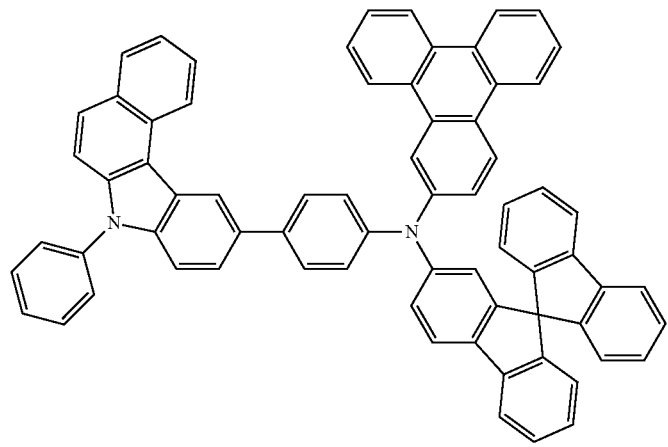
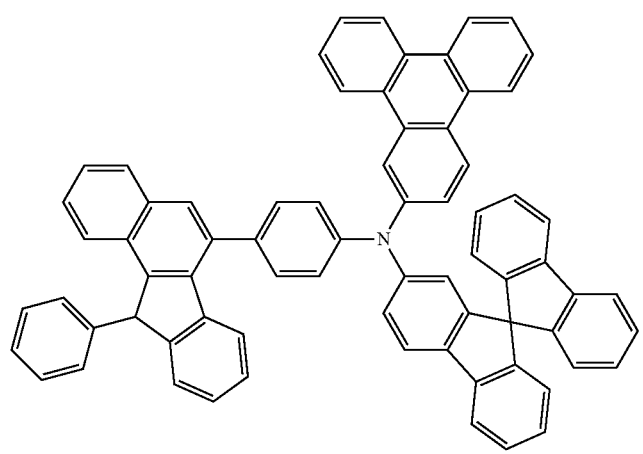
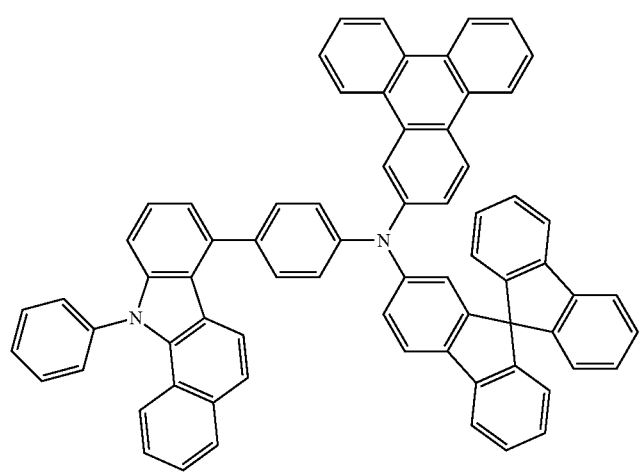

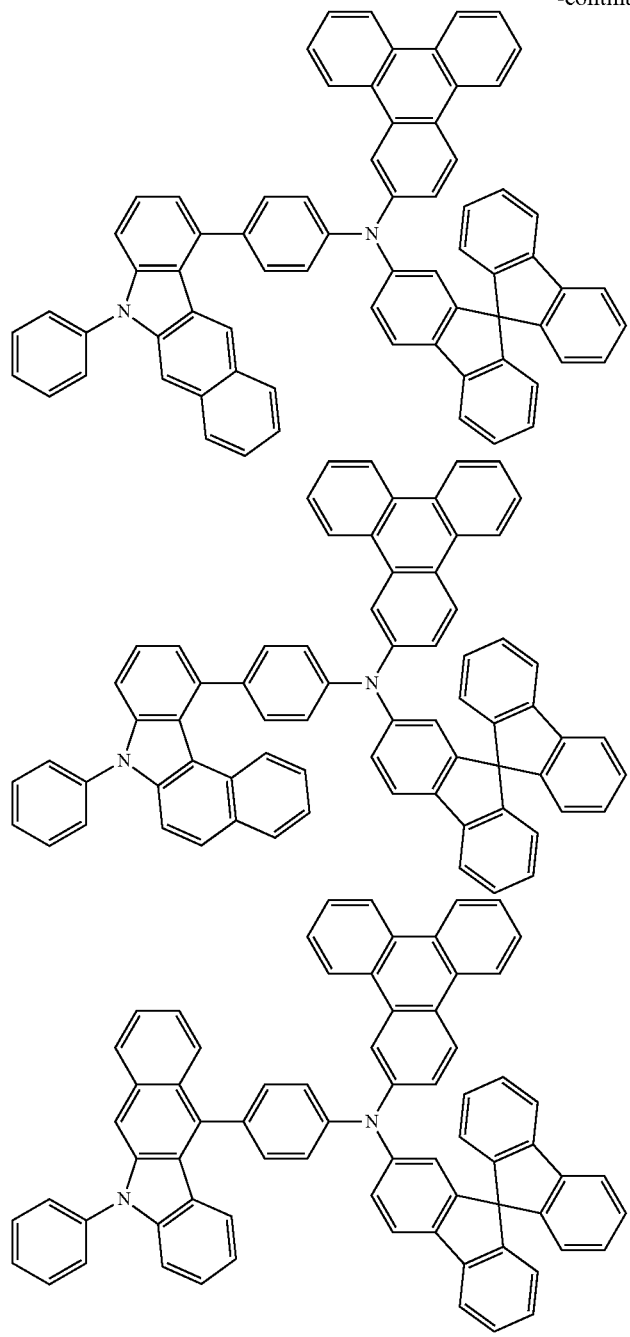

Organic Electroluminescence Device

The organic EL device in an aspect of the invention will be described below.

The organic EL device comprises an organic thin film layer between a cathode and an anode. The organic thin film layer comprises one or more layers and a light emitting layer, and at least one layer of the organic thin film layer comprises the compound represented by formula (1) (compound (1)).

Examples of the organic thin film layer which comprises the compound (1) include an anode-side organic thin film layer formed between an anode and a light emitting layer (hole transporting layer, hole injecting layer, etc.), a light emitting layer, a space layer, and a blocking layer, although not limited thereto. The compound (1) is usable in a fluorescent emission unit as, for example, a host material or a dopant material in a light emitting layer, a hole injecting layer material, and a hole transporting layer material. The compound (1) is also usable in a phosphorescent emission unit as a host material in a light emitting layer, a hole injecting layer material and a hole transporting layer material.

The organic EL device in an aspect of the invention may be any of a fluorescent or phosphorescent single color emitting device, a white-emitting device of fluorescent-phosphorescent hybrid type, a simple-type emitting device having a single emission unit, and a tandem emitting device having two or more emission units, with a fluorescent device being preferred. The "emission unit" referred to herein is the smallest unit for emitting light by the recombination of injected holes and injected electrons, which comprises an organic thin film layer comprising one or more layers, wherein at least one layer is a light emitting layer.

Representative device structures of the simple-type organic EL device are shown below:
(1) Anode/Emission Unit/Cathode The emission unit may be a laminated unit comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below:
(a) (hole injecting layer/) hole transporting layer/fluorescent emitting layer (/electron transporting layer);
(b) (hole injecting layer/) hole transporting layer/first fluorescent emitting layer/second fluorescent emitting layer (/electron transporting layer);
(c) (hole injecting layer/) hole transporting layer/phosphorescent emitting layer/space layer/fluorescent emitting layer (/electron transporting layer);
(d) (hole injecting layer/) hole transporting layer/first phosphorescent emitting layer/second phosphorescent emitting layer/space layer/fluorescent emitting layer (/electron transporting layer);
(e) (hole injecting layer/) hole transporting layer/first phosphorescent emitting layer/space layer/second phosphorescent emitting layer/space layer/fluorescent emitting layer (/electron transporting layer);
(f) (hole injecting layer/) hole transporting layer/phosphorescent emitting layer/space layer/first fluorescent emitting layer/second fluorescent emitting layer (/electron transporting layer);
(g) (hole injecting layer/) hole transporting layer/electron blocking layer/fluorescent emitting layer (/electron transporting layer);
(h) (hole injecting layer/) hole transporting layer/fluorescent emitting layer/hole blocking layer (/electron transporting layer); and
(i) (hole injecting layer/) hole transporting layer/fluorescent emitting layer/triplet blocking layer (/electron transporting layer).

The emission color of the fluorescent emitting layer and that of the phosphorescent emitting layer may be different. For example, the layered structure of the laminated emission unit (d) may be (hole injecting layer/) hole transporting layer/first phosphorescent emitting layer (red emission)/second phosphorescent emitting layer (green emission)/space layer/fluorescent emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:

(2) Anode/First Emission Unit/Intermediate Layer/Second Emission Unit/Cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials which can supply electrons to the first emission unit and holes to the second emission unit.

A schematic structure of an example of the organic EL device is shown in FIG. 1, wherein the organic EL device 1 comprises a substrate 2, an anode 3, a cathode 4, and an emission unit 10 disposed between the anode 3 and the cathode 4. The emission unit 10 comprises a light emitting layer 5. A hole injecting/transporting layer 6 (anode-side organic thin film layer) may be disposed between the light emitting layer 5 and the anode 3, and an electron injecting/transporting layer 7 (cathode-side organic thin film layer) may be disposed between the light emitting layer 5 and the cathode 4. An electron blocking layer (not shown) may be disposed on the side of anode 3 of the light emitting layer 5, and a hole blocking layer (not shown) may be disposed on the side of cathode 4 of the light emitting layer 5. With these blocking layers, electrons and holes are confined in the light emitting layer 5 to increase the exciton generation in the light emitting layer 5.

In the present specification, a host is referred to as a fluorescent host when combinedly used with a fluorescent dopant (fluorescent emitting material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of polycarbonate, polyarylate, polyether sulfone, polypropylene, polyester, polyvinyl fluoride, and polyvinyl chloride. An inorganic deposition film is also usable.

Anode

The anode is formed on the substrate preferably from a metal, an alloy, an electrically conductive compound, and a mixture thereof, each having a large work function, for example, 4.5 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), and a nitride of the above metal (for example, titanium nitride) are also usable.

These materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally known as an electrode material, for example, a metal, an alloy, an electroconductive compound, a mixture thereof, and a group 1 element and a group 2 element of the periodic table.

A material having a small work function, for example, the group 1 element and the group 2 element of the periodic table, i.e., an alkali metal, such as lithium (Li) and cesium (Cs), an alkaline earth metal, such as magnesium (Mg), calcium (Ca), and strontium (Sr), and an alloy thereof, such as MgAg and AlLi, are also usable. In addition, a rare earth metal, such as europium (Eu) and ytterbium (Yb), and an alloy thereof are also usable. The alkali metal, the alkaline earth metal, and the alloy thereof can be made into the anode by a vacuum vapor deposition or a sputtering method. When a silver paste, etc. is used, a coating method and an inkjet method are usable.

Hole Injecting Layer

The hole injecting layer comprises a highly hole injecting material (hole injecting material). The compound (1) may be used in a hole injecting layer solely or in combination with the material mentioned below.

Examples of the hole injecting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable as the hole injecting material: 4,4',4"-tris(N, N-diphenylamino)triphenylamine (TDATA), 4,4',4"-tris[N-(3-methylphenyl)-N-phenylamino]triphenylamine (MT-DATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A macromolecular compound, such as an oligomer, a dendrimer, a polymer, is also usable. Examples thereof include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide] (PTPDMA), and poly[N,N'-bis(4-butylphenyl)-N,N'-bis(phenyl)benzidine] (Poly-TPD). An acid-added macromolecular compound, such as poly(3,4-ethylene dioxythiophene)/poly(styrene sulfonic acid) (PEDOT/PSS) and polyaniline/poly(styrenesulfonic acid) (PAni/PSS), is also usable.

In addition, an acceptor material, such as a hexaazatriphenylene (HAT) compound represented by formula (K), is preferably used in combination with the compound (1):

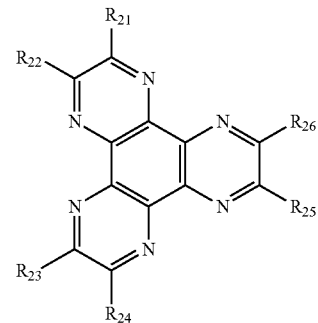

(K)

wherein $R_{21}$ to $R_{26}$ may be the same or different and each of $R_{21}$ to $R_{26}$ is independently a cyano group, —$CONH_2$, a carboxyl group, or —$COOR_{27}$ wherein $R_{27}$ is an alkyl group having 1 to 20 carbon atoms or a cycloalkyl group having 3 to 20 carbon atoms, or $R_{21}$ and $R_{22}$, $R_{23}$ and $R_{24}$, or $R^{25}$ and $R_{26}$ may be bonded to each other to form a group represented by —CO—O—CO—.

Examples of $R_{27}$ include a methyl group, an ethyl group, a n-propyl group, an isopropyl group, a n-butyl group, an isobutyl group, a t-butyl group, a cyclopentyl group, and a cyclohexyl group.

Hole Transporting Layer

The hole transporting layer comprises a highly hole transporting material (hole transporting material). The compound (1) may be used in the hole transporting layer solely or in combination with the compound mentioned below.

Examples of the hole transporting material include an aromatic amine compound, a carbazole derivative, and an anthracene derivative. Examples of the aromatic amine compound are 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluoren-9-yl)triphenylamine (BAFLP), 4,4'-bis[N-(9,9-dimethylfluorene-2-yl)-N-phenylamino]biphenyl (DFLDPBi), 4,4',4"-tris(N,N-diphenylamino)triphenylamine (TDATA), 4,4',4"-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of mainly $10^{-6}$ $cm^2/Vs$ or more.

The hole transporting layer may comprise a carbazole derivative, such as 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA); an anthracene derivative, such as 2-t-butyl-9,10-di(2-naphthyl)anthracene (t-BuDNA), 9,10-di(2-naphthyl)anthracene (DNA), and 9,10-diphenylanthracene (DPAnth); and a macromolecular compound, such as poly (N-vinylcarbazole) (PVK) and poly(4-vinyltriphenylamine) (PVTPA).

Compounds other than those mentioned above are also usable if their hole transporting ability is higher than their electron transporting ability. The layer comprising a highly hole-transporting material may be a single layer or a laminate of two or more layers each comprising the compound mentioned above. For example, the hole transporting layer may be a two-layered structure of a first hole transporting layer (anode side) and a second hole transporting layer (cathode side). In this case, the compound (1) may be used in either of the first hole transporting layer and the second hole transporting layer.

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound capable of emitting light from a singlet excited state, and the phosphorescent emitting material is a compound capable of emitting light from a triplet excited state.

Examples of blue fluorescent emitting material for use in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material for use in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N, N, 9-triphenylanthracene-9-amine (DPhAPhA).

Examples of red fluorescent emitting material for use in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material for use in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIrG), bis[2-(4',6'-difluorophenyl)pyridinato-N,C2']iridium(III) picolinato (FIrpic), bis[2-(3',5'-bistrifluoromethylphenyl)pyridinato-N,C2']iridium(III) picolinato (Ir(CF$_3$ppy)$_2$(pic)), and bis[2-(4',6'-difluorophenyl)pyridinato-N,C2']iridium(III) acetylacetonato (FIracac).

Examples of green phosphorescent emitting material for use in the light emitting layer include an iridium complex, such as tris(2-phenylpyridinato-N, C2')iridium(III) (Ir(ppy)$_3$), bis(2-phenylpyridinato-N,C2')iridium(III) acetylacetonato (Ir(ppy)$_2$(acac)), bis(1,2-diphenyl-1H-benzimidazolato)iridium(III) acetylacetonato (Ir(pbi)$_2$(acac)), and bis(benzo[h]quinolinato)iridium(III) acetylacetonato (Ir(bzq)$_2$(acac)).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)$_2$(acac)), bis(1-phenylisoquinolinato-N,C2')iridium(III) acetylacetonato (Ir(piq)$_2$(acac)), (acetylacetonato)bis[2,3-bis(4-fluorophenyl)quinoxalinato]iridium(III) (Ir(Fdpq)$_2$(acac)), and 2,3,7,8,12,13,17,18-octaethyl-21H,23H-porphyrin platinum(II) (PtOEP).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium (III) acetylacetonato (Ir(btp)$_2$(acac)), bis(1-phenylisoquinolinato-N,C2')iridium(III) acetylacetonato (Ir(piq)$_2$(acac)), (acetylacetonato)bis[2,3-bis(4-fluorophenyl) quinoxalinato]iridium(III) (Ir(Fdpq)$_2$(acac)), and 2,3,7,8,12,13,17,18-octaethyl-21H,23H-porphyrin platinum(II) (PtOEP).

A rare earth metal complex, such as tris(acetylacetonato)(monophenanthroline)terbium(III) (Tb(acac)$_3$(Phen)), tris(1,3-diphenyl-1,3-propanedionato)(monophenanthroline)europium(III) (Eu(DBM)$_3$(Phen)), and tris[1-(2-thenoyl)-3,3,3-trifluoroacetonato](monophenanthroline)europium(III) (Eu(TTA)$_3$(Phen)), emits light from the rare earth metal ion (electron transition between different multiple states), and therefore, usable as a phosphorescent emitting compound.

Host Material for Light Emitting Layer

The light emitting layer may be formed by dispersing the dopant material mentioned above in another material (host material). The host material may be selected from various kinds of materials and is preferably a material having a lowest unoccupied molecular orbital level (LUMO level) higher than that of the dopant material and a highest occupied molecular orbital level (HOMO level) lower than that of the dopant material.

The host material may include, for example, (1) a metal complex, such as an aluminum complex, a beryllium complex, and a zinc complex;

(2) a heterocyclic compound, such as an oxadiazole derivative, a benzimidazole derivative, and a phenanthroline derivative;

(3) a fused aromatic compound, such as a carbazole derivative, an anthracene derivative, a phenanthrene derivative, a pyrene derivative, and a chrysene derivative; and (4) an aromatic amine compound, such as a triarylamine derivative and a fused aromatic polycyclic amine derivative.

Examples thereof include:

a metal complex, such as tris(8-quinolinolato)aluminum (III) (Alq), tris(4-methyl-8-quinolinolato)aluminum(III) (Almqs$_3$), bis(10-hydroxybenzo[h]quinolinato)beryllium(II) (BeBq$_2$), bis(2-methyl-8-quinolinolato)(4-phenylphenolato) aluminum(III) (BAlq), bis(8-quinolinolato)zinc(II) (Znq), bis[2-(2-benzoxazolyl)phenolato]zinc(II) (ZnPBO), and bis [2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazol-2-yl]benzene (OXD-7), 3-(4-biphenylyl)-4-phenyl 5-(4-tert-butylphenyl)-1,2,4-triazole (TAZ), 2,2',2''-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3''-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-anthryl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dimethylfluorene-2-yl)-N-phenylamino]biphenyl (DFLDPBi), and 4,4'-bis[N-(spiro-9,9'-bifluorene-2-yl)-N-phenylamino]biphenyl (BSPB). The host material may be used alone or in combination of two or more.

Electron Transporting Layer

The electron transporting layer comprises a highly electron-transporting material (electron transporting material). Examples thereof are:
(1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative; and
(3) a macromolecular compound.

Examples of the metal complex include tris(8-quinolinolato)aluminum (III) (Alq), tris(4-methyl-8-quinolinolato)aluminum (Almq$_3$), bis(10-hydroxybenzo[h]quinolinato)beryllium (BeBq$_2$), bis(2-methyl-8-quinolinato)(4-phenylphenolato)aluminum (III)(BAlq), bis(8-quinolinato)zinc(II) (Znq), bis[2-(2-benzoxazolyl)phenolato]zinc(II) (ZnPBO), and bis[2-(2-benzothiazolyl)phenolato]zinc(II) (ZnBTZ).

Examples of the heteroaromatic compound include 2-(4-biphenylyl)-5-(4-tert-butylphenyl)-1,3,4-oxadiazole (PBD), 1,3-bis[5-(ptert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

Examples of the macromolecular compound include poly[(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

The above compounds have an electron mobility of mainly $10^{-6}$ cm$^2$/Vs or more. Materials other than those mentioned above are also usable in the electron transporting layer if their electron transporting ability is higher than their hole transporting ability. The electron transporting layer may be a single layer or a laminate of two or more layers each comprising the material mentioned above.

Electron Injecting Layer

The electron injecting layer comprises a highly electron-injecting material, for example, an alkali metal, an alkaline earth metal, and a compound of these metals, such as lithium (Li), cesium (Cs), calcium (Ca), lithium fluoride (LiF), cesium fluoride (CsF), calcium fluoride (CaF2), and lithium oxide (LiOx). In addition, an electron transporting material which is doped with an alkali metal, an alkaline earth metal or a compound thereof, for example, Alq doped with magnesium (Mg), is also usable. By using such a material, electrons are efficiently injected from the cathode.

A composite material obtained by mixing an organic compound and an electron donor is also usable in the electron injecting layer. Such a composite material is excellent in the electron injecting ability and the electron transporting ability, because the organic compound receives electrons from the electron donor. The organic compound is preferably a material excellent in transporting the received electrons. Examples thereof are the materials for the electron transporting layer mentioned above, such as the metal complex and the aromatic heterocyclic compound. Any material capable of giving its electron to another organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include a metal of the group 1 or 2 of the periodic table, for example, an alkali metal, such as lithium (Li) and cesium (Cs), an alkaline earth metal, such as magnesium (Mg), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof can be made into the cathode by a vacuum vapor deposition or a sputtering method. When a silver paste, etc. is used, a coating method and an inkjet method are usable.

When the electron injecting layer is formed, the material for the cathode can be selected independently from the work function and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating thin film layer is preferably interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be made into laminated layers.

Space Layer

For example, in an organic EL device wherein a fluorescent emitting layer and a phosphorescent emitting layer are laminated, a space layer is disposed between the fluorescent emitting layer and the phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

In the organic EL device, a blocking layer, such as an electron blocking layer, a hole blocking layer, and a triplet blocking layer, may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The triplet blocking layer prevents the diffusion of excitons generated in the light emitting layer to adjacent layers and has a function of confining the excitons in the light emitting layer.

Each layer of the organic EL device can be formed by a known method, such as a vapor deposition method and a coating method. For example, each layer can be formed by a known vapor deposition method, such as a vacuum vapor deposition method and a molecular beam evaporation method (MBE method), and a known coating method using a solution of the compound for forming the layer, such as a dipping method, a spin coating method, a casting method, a bar coating method, and a roll coating method.

The thickness of each layer is not particularly limited and preferably 5 nm to 10 μm, more preferably 10 nm to 0.2 μm, because an excessively small thickness may cause defects such as pin holes and an excessively large thickness may require a high driving voltage.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The invention will be described in more detail with reference to the examples and comparative examples. It should be noted that the scope of the invention is not limited to the following examples.

Intermediate Synthesis Example 1-1: Synthesis of Intermediate 1-1

Under argon atmosphere, to a mixture of 28.3 g of 4-iodobromobenzene (100.0 mmol), 22.3 g of dibenzofuran-4-boronic acid (105.0 mmol), and 2.31 g of Pd[PPh$_3$]$_4$ (2.00 mmol), 150 ml of toluene, 150 ml of dimethoxyethane, and 150 ml of a 2 M aqueous solution of Na$_2$CO$_3$ (300.0 mmol) were added. The resultant mixture was stirred for 10 h while refluxing under heating.

After the reaction, the reaction mixture was cooled to room temperature and extracted with dichloromethane in a separating funnel. The organic layer was dried over MgSO$_4$, filtered, and then concentrated. The concentrated residue was purified by a silica gel column chromatography to obtain 26.2 g of a white solid, which was identified as the following intermediate 1-1 by FD-MS (field desorption mass spectrometry) analysis (yield: 81%).

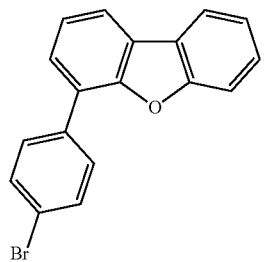

Intermediate 1-1

Intermediate Synthesis Example 1-2: Synthesis of Intermediate 1-2

In the same manner as in Intermediate Synthesis Example 1-1 except for using 22.3 g of dibenzofuran-2-boronic acid in place of dibenzofuran-4-boronic acid, 27.4 g of a white solid was obtained, which was identified as the following intermediate 1-2 by FD-MS analysis (yield: 85%).

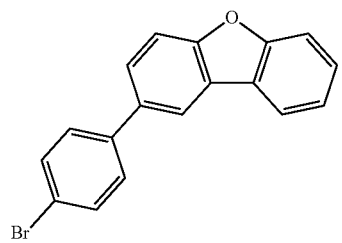

Intermediate 1-2

Intermediate Synthesis Example 1-3: Synthesis of Intermediate 1-3

Under argon atmosphere, to a mixture of 28.3 g of 4-iodobromobenzene (100.0 mmol), 23.9 g of dibenzothiophene-4-boronic acid (105.0 mmol), and 2.31 g of Pd[PPh$_3$]$_4$ (2.00 mmol), 150 ml of toluene, 150 ml of dimethoxyethane, and 150 ml of a 2 M aqueous solution of Na$_2$CO$_3$ (300.0 mmol) were added. The resultant mixture was stirred for 10 h while refluxing under heating.

After the reaction, the reaction mixture was cooled to room temperature and extracted with dichloromethane in a separating funnel. The organic layer was dried over MgSO$_4$, filtered, and then concentrated. The concentrated residue was purified by a silica gel column chromatography to obtain 27.1 g of a white solid was obtained, which was identified as the following intermediate 1-3 by FD-MS analysis (yield: 80%).

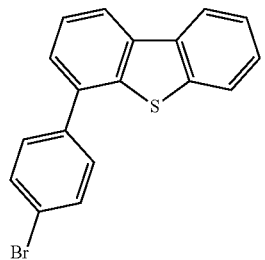

Intermediate 1-3

Intermediate Synthesis Example 1-4: Synthesis of Intermediate 1-4

In the same manner as in Intermediate Synthesis Example 1-3 except for using 23.9 g of dibenzothiophene-2-boronic acid in place of dibenzothiophene-4-boronic acid, 27.2 g of a white solid was obtained, which was identified as the following intermediate 1-4 by FD-MS analysis (yield: 80%).

Intermediate 1-4

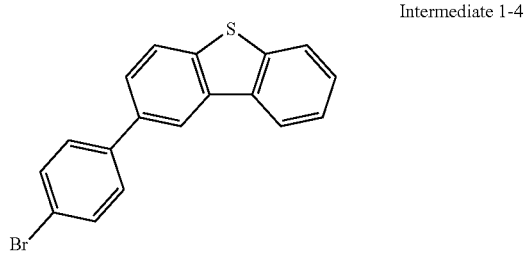 [SMILES: Brc1ccc(-c2ccc3sc4ccccc4c3c2)cc1]

Intermediate Synthesis Example 1-5: Synthesis of Intermediate 1-5

Under argon atmosphere, to a mixture of 28.3 g of 4-iodobromobenzene (100.0 mmol), 30.1 g of 4-(9H-carbazole-9-yl)phenylboronic acid (105.0 mmol), and 2.31 g of Pd[PPh$_3$]$_4$ (2.00 mmol), 150 ml of toluene, 150 ml of dimethoxyethane, and 150 ml of a 2 M aqueous solution of Na$_2$CO$_3$ (300.0 mmol) were added. The resultant mixture was stirred for 10 h while refluxing under heating.

After the reaction, the reaction mixture was cooled to room temperature and extracted with dichloromethane in a separating funnel. The organic layer was dried over MgSO$_4$, filtered, and then concentrated. The concentrated residue was purified by a silica gel column chromatography to obtain 29.9 g of a white solid was obtained, which was identified as the following intermediate 1-5 by FD-MS (field desorption mass spectrometry) analysis (yield: 75%).

Intermediate 1-5

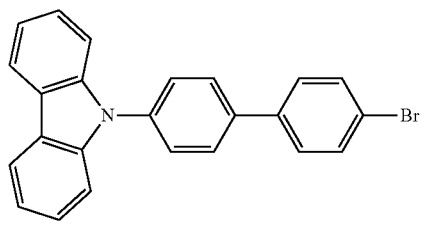

Intermediate Synthesis Example 1-6: Synthesis of Intermediate 1-6

In the same manner as in Intermediate Synthesis Example 1-5 except for using 30.1 g of 3-(9H-carbazole-9-yl)phenylboronic acid in place of 4-(9H-carbazole-9-yl)phenylboronic acid, 27.2 g of a white solid was obtained, which was identified as the following intermediate 1-6 by FD-MS analysis (yield: 68%).

Intermediate 1-6

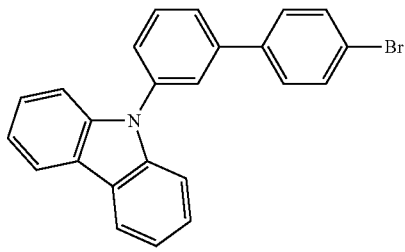

Intermediate Synthesis Example 1-7: Synthesis of Intermediate 1-7

In the same manner as in Intermediate Synthesis Example 1-5 except for using 30.1 g of 9-phenylcarbazole-3-boronic acid in place of 4-(9H-carbazole-9-yl)phenylboronic acid, 31.5 g of a white solid was obtained, which was identified as the following intermediate 1-7 by FD-MS analysis (yield: 79%).

Intermediate 1-7

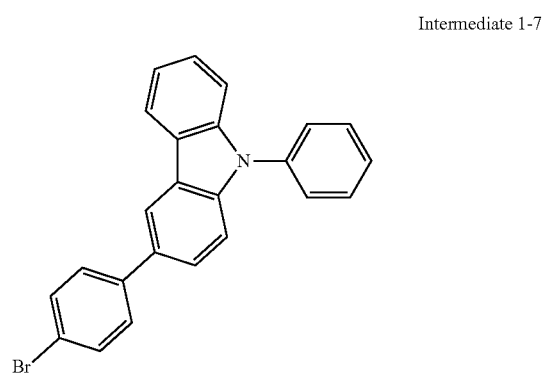 [SMILES: Brc1ccc(-c2ccc3c(c2)c2ccccc2n3-c2ccccc2)cc1]

Intermediate Synthesis Example 2-1: Synthesis of Intermediate 2-1

Under argon atmosphere, a mixture of 12.2 g of 2-aminotriphenylene (50.0 mmol), 19.8 g of 2-bromo-9,9'-spirobifluorene (50.0 mmol), and 9.6 g of sodium t-butoxide (100.0 mmol) in 250 ml of dehydrated toluene was stirred. After adding 225 mg of palladium acetate (1.0 mmol) and 202 mg of tri-t-butylphosphine (1.0 mmol), the reaction was allowed to proceed at 80° C. for 8 h.

After cooling, the reaction mixture was filtered through Celite/silica gel and the filtrate was concentrated under reduced pressure. The obtained residue was recrystallized from toluene, and the crystal collected by filtration was dried to obtain 18.1 g of a white solid, which was identified as the following intermediate 2-1 by FD-MS analysis (yield: 65%).

Intermediate 2-1

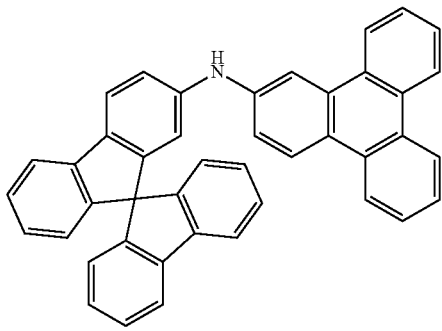

Intermediate Synthesis Example 2-2: Synthesis of Intermediate 2-2

In the same manner as in Intermediate Synthesis Example 2-1 except for using 19.8 g of 4-bromo-9,9'-spirobifluorene in place of 2-bromo-9,9'-spirobifluorene, 16.7 g of a white crystal was obtained, which was identified as the following intermediate 2-2 by FD-MS analysis (yield: 60%).

Intermediate 2-2

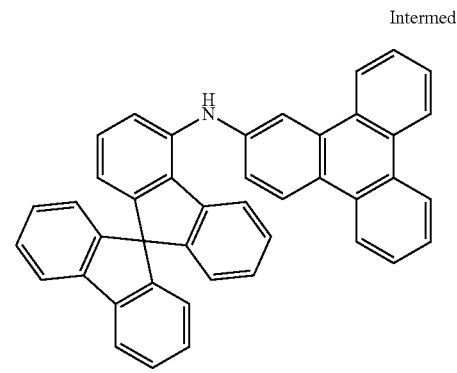

Intermediate Synthesis Example 2-3: Synthesis of Intermediate 2-3

In the same manner as in Intermediate Synthesis Example 2-1 except for using 19.8 g 3-bromo-9,9'-spirobifluorene in place of 2-bromo-9,9'-spirobifluorene, 19.5 g of a white crystal was obtained, which was identified as the following intermediate 2-3 by FD-MS analysis (yield: 70%).

Intermediate 2-3

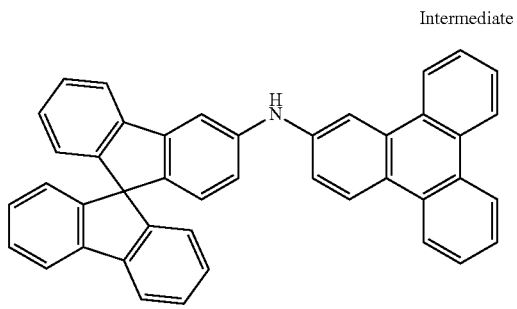

Intermediate Synthesis Example 2-4: Synthesis of Intermediate 2-4

In the same manner as in Intermediate Synthesis Example 2-1 except for using 19.8 g of 1-bromo-9,9'-spirobifluorene in place of 2-bromo-9,9'-spirobifluorene, 9.8 g of a white crystal was obtained, which was identified as the following intermediate 2-4 by FD-MS analysis (yield: 35%).

Intermediate 2-4

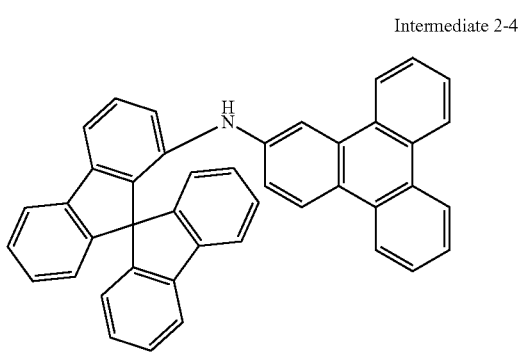 [SMILES: c1ccc2c(c1)-c1ccccc1C21c2ccccc2-c2cccc(Nc3ccc4c5ccccc5c5ccccc5c4c3)c21]

Intermediate Synthesis Example 2-5: Synthesis of Intermediate 2-5

In the same manner as in Intermediate Synthesis Example 2-1 except for using 12.2 g of 1-aminotriphenylene in place of 2-aminotriphenylene, 11.2 g of a white crystal was obtained, which was identified as the following intermediate 2-5 by FD-MS analysis (yield: 40%).

Intermediate 2-5

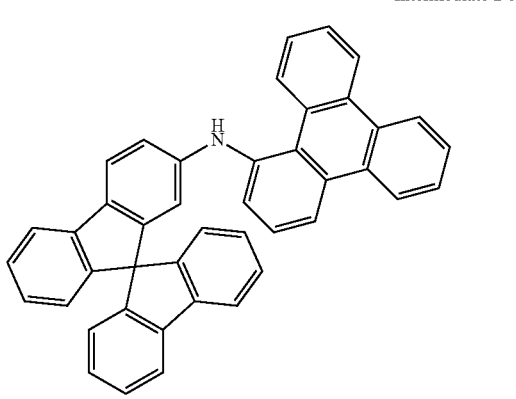

Synthesis Example 1: Production of Aromatic Amine Derivative H1

Under argon atmosphere, to a mixture of 2.3 g of 2-bromobiphenyl (10.0 mmol), 6.5 g of the intermediate 2-1 (10.0 mmol), 0.14 g of $Pd_2(dba)_3$ (0.15 mmol), 0.087 g of $P(tBu)_3HBF_4$ (0.3 mmol), and 1.9 g of sodium t-butoxide (20.0 mmol), 50 ml of dehydrated xylene was added. The resultant mixture was refluxed for 8 h under heating.

After the reaction, the reaction liquid was cooled to 50° C. and filtered through Celite/silica gel. The filtrate was concentrated. The obtained concentrated residue was purified by a silica gel column chromatography to obtain a white solid.

The obtained crude product was recrystallized from toluene to obtain 2.5 g of a white crystal, which was identified as the following aromatic amine derivative H1 by FD-MS analysis (yield: 35).

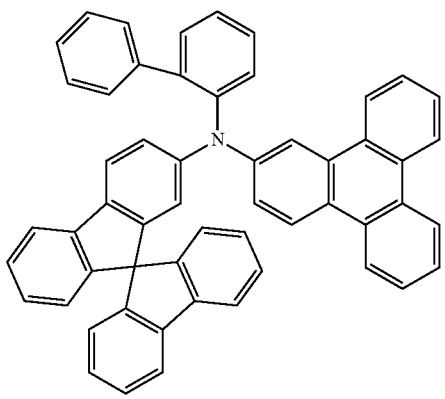

H1

Synthesis Example 2: Production of Aromatic Amine Derivative H2

In the same manner as in Synthesis Example 1 except for using 2.3 g of 4-bromobiphenyl in place of 2-bromobiphenyl, 2.8 g of a white crystal was obtained, which was identified as the following aromatic amine derivative H2 by FD-MS analysis (yield: 40%).

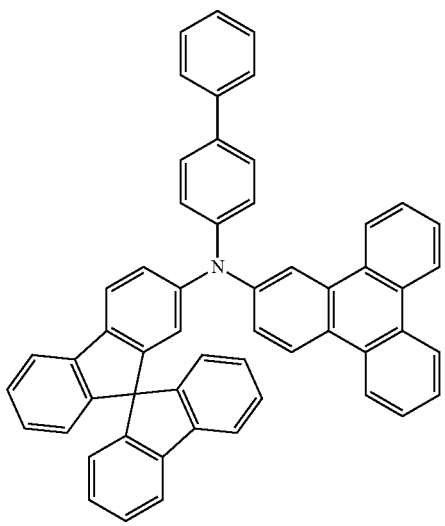

H2

Synthesis Example 3: Production of Aromatic Amine Derivative H3

In the same manner as in Synthesis Example 1 except for using 3.1 g of 2-bromo-1,1':4',1''-terphenyl in place of 2-bromobiphenyl, 2.4 g of a white crystal was obtained, which was identified as the following aromatic amine derivative H3 by FD-MS analysis (yield: 30%).

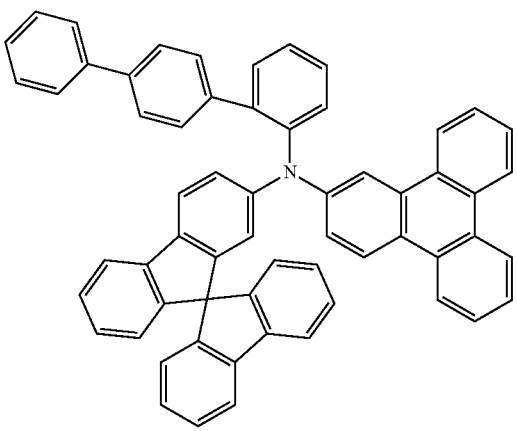

H3

Synthesis Example 4: Production of Aromatic Amine Derivative H4

In the same manner as in Synthesis Example 1 except for using 3.1 g of 4-bromo-1,1':4',1''-terphenyl in place of 2-bromobiphenyl, 3.3 g of a white crystal was obtained, which was identified as the following aromatic amine derivative H4 by FD-MS analysis (yield: 42%).

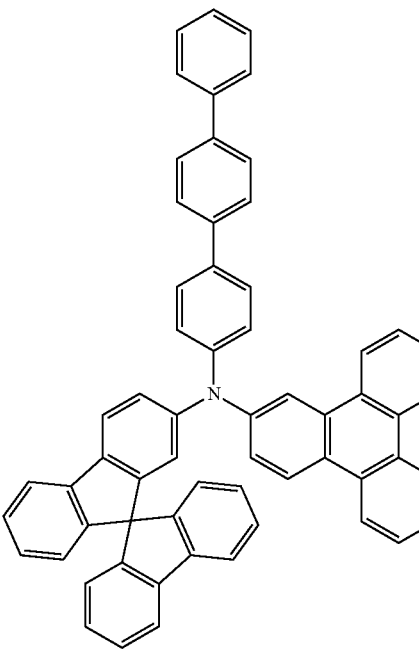

H4

Synthesis Example 5: Production of Aromatic Amine Derivative H5

In the same manner as in Synthesis Example 1 except for using 2.7 g of 2-bromo-9,9-dimethylfluorene in place of 2-bromobiphenyl, 3.4 g of a white crystal was obtained, which was identified as the following aromatic amine derivative H5 by FD-MS analysis (yield: 46%).

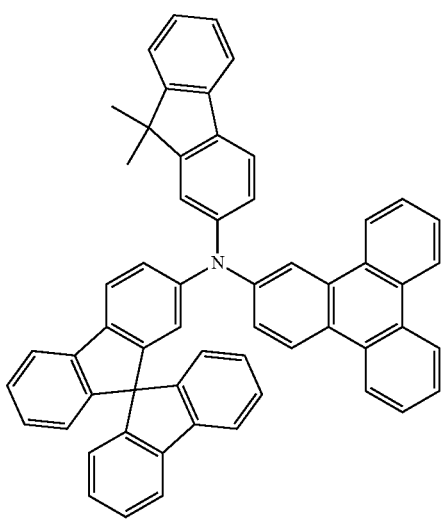

H5

Synthesis Example 6: Production of Aromatic Amine Derivative H6

In the same manner as in Synthesis Example 1 except for using 4.0 g of 2-bromo-9,9-diphenylfluorene in place of 2-bromobiphenyl, 3.3 g of a white crystal was obtained, which was identified as the following aromatic amine derivative H6 by FD-MS analysis (yield: 38%).

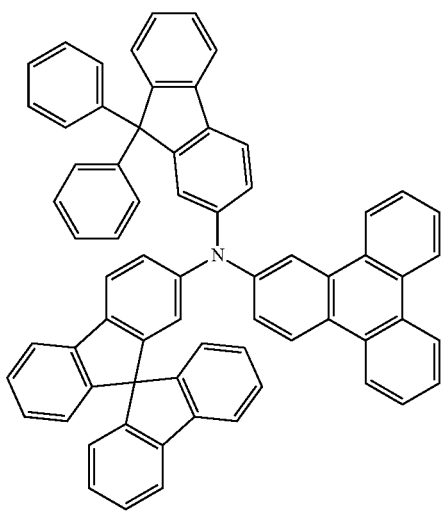

H6

Synthesis Example 7: Production of Aromatic Amine Derivative H7

In the same manner as in Synthesis Example 1 except for using 4.0 g of 2-bromo-9,9-spirobifluorene in place of 2-bromobiphenyl, 3.5 g of a white crystal was obtained, which was identified as the following aromatic amine derivative H7 by FD-MS analysis (yield: 40%).

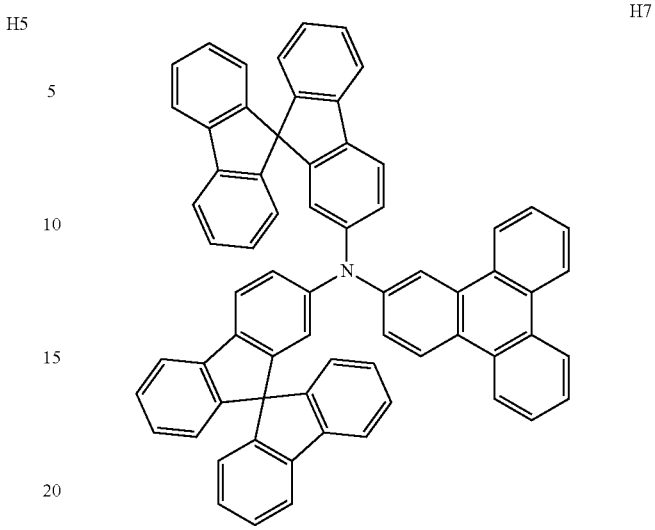

H7

Synthesis Example 8: Production of Aromatic Amine Derivative H8

In the same manner as in Synthesis Example 1 except for using 3.2 g of the intermediate 1-1 in place of 2-bromobiphenyl, 3.6 g of a white crystal was obtained, which was identified as the following aromatic amine derivative H8 by FD-MS analysis (yield: 45%).

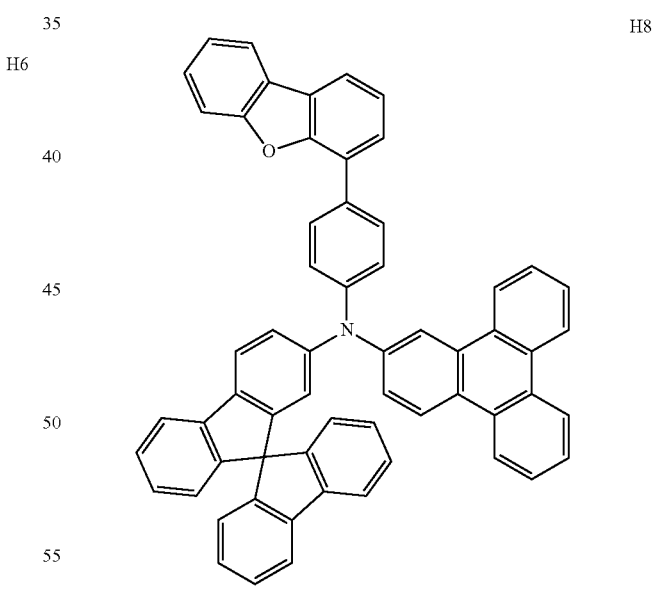

H8

Synthesis Example 9: Production of Aromatic Amine Derivative H9

In the same manner as in Synthesis Example 1 except for using 3.2 g of the intermediate 1-2 in place of 2-bromobiphenyl, 3.4 g of a white crystal was obtained, which was identified as the following aromatic amine derivative H9 by FD-MS analysis (yield: 42%).

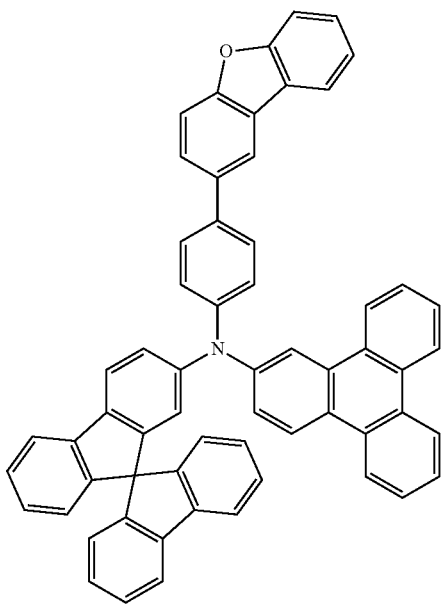

H9

Synthesis Example 10: Production of Aromatic Amine Derivative H10

In the same manner as in Synthesis Example 1 except for using 3.4 g of the intermediate 1-3 in place of 2-bromobiphenyl, 3.7 g of a white crystal was obtained, which was identified as the following aromatic amine derivative H10 by FD-MS analysis (yield: 45%).

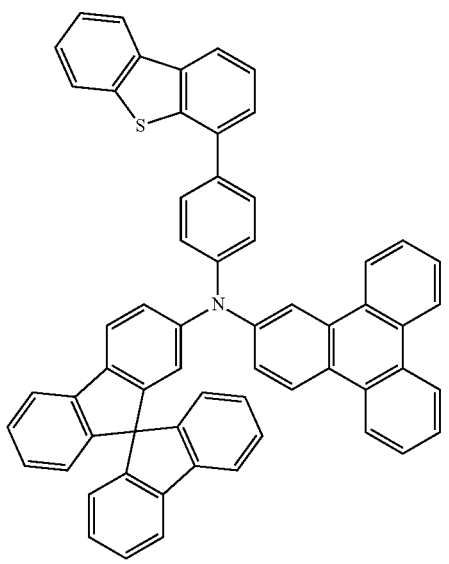

H10

Synthesis Example 11: Production of Aromatic Amine Derivative H11

In the same manner as in Synthesis Example 1 except for using 3.4 g of the intermediate 1-4 in place of 2-bromobiphenyl, 3.3 g of a white crystal was obtained, which was identified as the following aromatic amine derivative H11 by FD-MS analysis (yield: 40%).

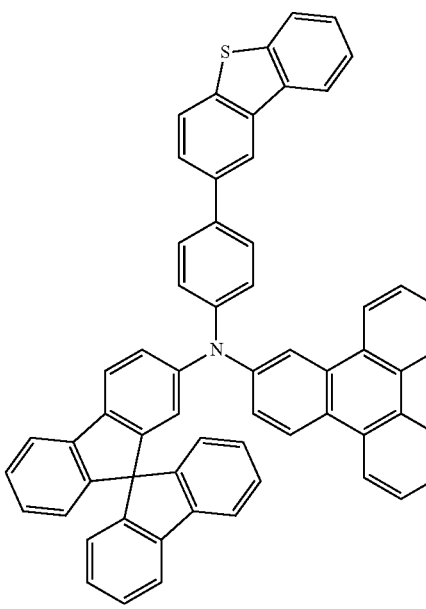

H11

Synthesis Example 12: Production of Aromatic Amine Derivative H12

In the same manner as in Synthesis Example 1 except for using 3.2 g of 9-(4-bromophenyl)carbazole in place of 2-bromobiphenyl, 3.6 g of a white crystal was obtained, which was identified as the following aromatic amine derivative H12 by FD-MS analysis (yield: 45%).

H12

Synthesis Example 13: Production of Aromatic Amine Derivative H13

In the same manner as in Synthesis Example 1 except for using 4.0 g of the intermediate 1-5 in place of 2-bromobiphenyl, 4.4 g of a white crystal was obtained, which was identified as the following aromatic amine derivative H13 by FD-MS analysis (yield: 50%).

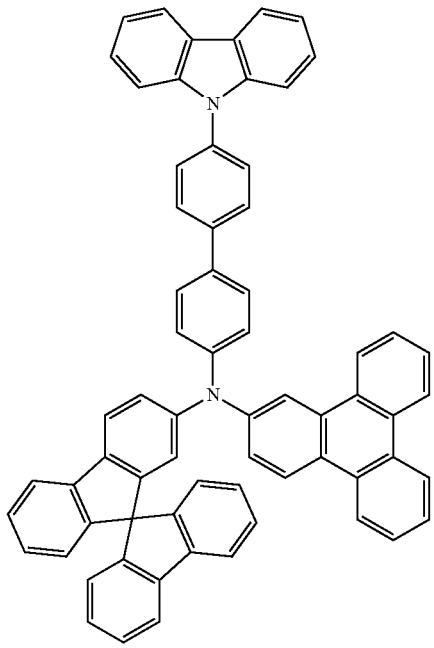

H13

Synthesis Example 14: Production of Aromatic Amine Derivative H14

In the same manner as in Synthesis Example 1 except for using 4.0 g of the intermediate 1-6 in place of 2-bromobiphenyl, 4.2 g of a white crystal was obtained, which was identified as the following aromatic amine derivative H14 by FD-MS analysis (yield: 48%).

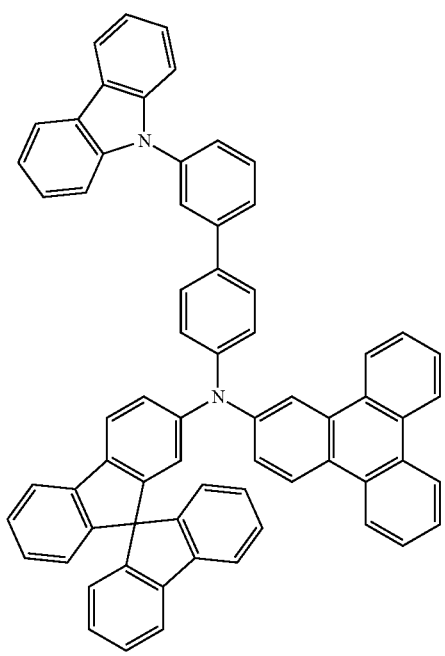

H14

Synthesis Example 15: Production of Aromatic Amine Derivative H15

In the same manner as in Synthesis Example 1 except for using 4.0 g of the intermediate 1-7 in place of 2-bromobiphenyl, 4.1 g of a white crystal was obtained, which was identified as the following aromatic amine derivative H15 by FD-MS analysis (yield: 47%).

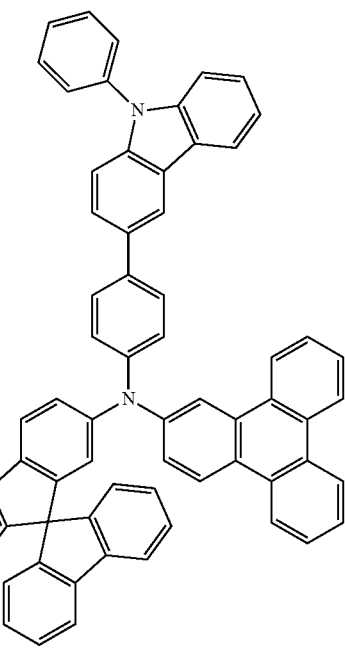

H15

Synthesis Example 16: Production of Aromatic Amine Derivative H16

In the same manner as in Synthesis Example 1 except for using 4.0 g of 9-(4-bromophenyl)-9-phenylfluorene in place of 2-bromobiphenyl, 3.2 g of a white crystal was obtained, which was identified as the following aromatic amine derivative H16 by FD-MS analysis (yield: 37%).

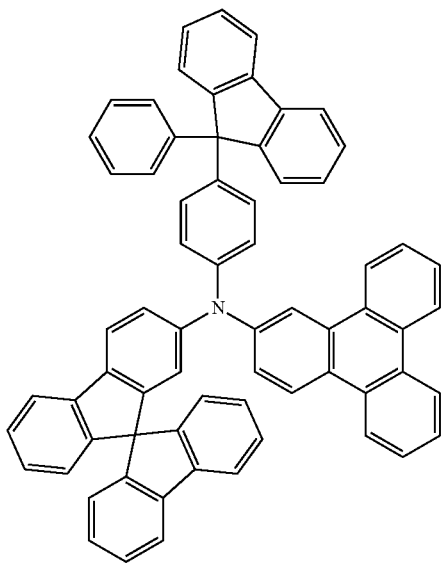

Synthesis Example 17: Production of Aromatic Amine Derivative H17

In the same manner as in Synthesis Example 1 except for using 3.2 g of 2-(4-bromophenyl)-5-phenylthiophene in place of 2-bromobiphenyl, 3.5 g of a white crystal was obtained, which was identified as the following aromatic amine derivative H17 by FD-MS analysis (yield: 44%).

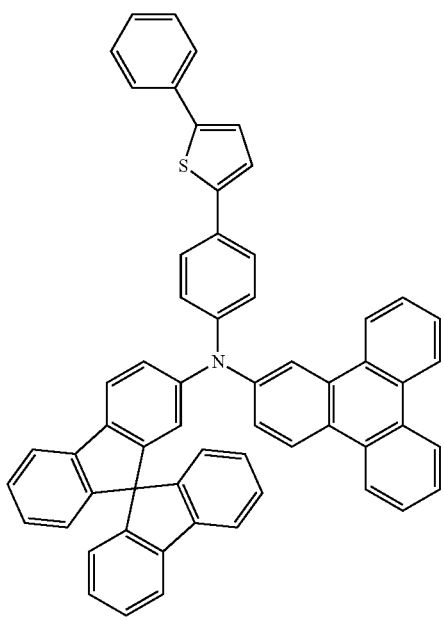

Synthesis Example 18: Production of Aromatic Amine Derivative H18

Under argon atmosphere, to a mixture of 5.6 g of the intermediate 2-2 (10.0 mmol), 2.3 g of 2-bromobiphenyl (10.0 mmol), 0.14 g of $Pd_2(dba)_3$ (0.15 mmol), 0.087 g of $P(tBu)_3HBF_4$ (0.3 mmol), and 1.9 g of sodium t-butoxide (20.0 mmol), 50 ml of dehydrated xylene was added. The resultant mixture was refluxed for 8 h under heating.

After the reaction, the reaction liquid was cooled to 50° C. and filtered through Celite/silica gel. The filtrate was concentrated. The obtained concentrated residue was purified by a silica gel column chromatography to obtain a white solid. The obtained crude product was recrystallized from toluene to obtain 2.3 g of a white crystal, which was identified as the following aromatic amine derivative H18 by FD-MS analysis (yield: 33%).

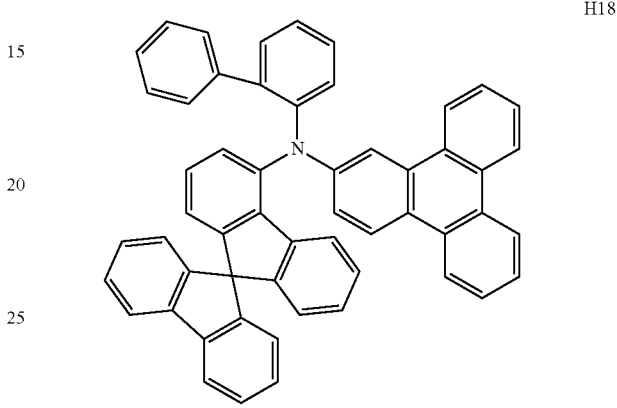

Synthesis Example 19: Production of Aromatic Amine Derivative H19

In the same manner as in Synthesis Example 18 except for using 2.3 g 4-bromobiphenyl in place of 2-bromobiphenyl, 3.2 g of a white crystal was obtained, which was identified as the following aromatic amine derivative H19 by FD-MS analysis (yield: 45%).

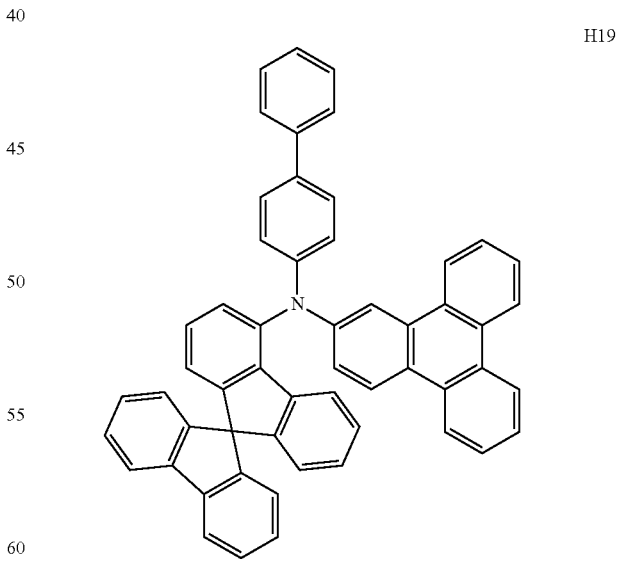

Synthesis Example 20: Production of Aromatic Amine Derivative H20

In the same manner as in Synthesis Example 18 except for using 3.1 g of 4-bromo-1,1':4',1''-terphenyl in place of 2-bromobiphenyl, 3.1 g of a white crystal was obtained, which was identified as the following aromatic amine derivative H20 by FD-MS analysis (yield: 40%).

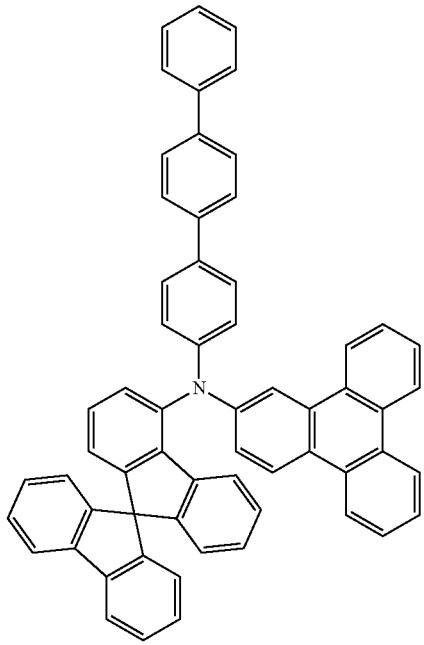

H20

Synthesis Example 21: Production of Aromatic Amine Derivative H21

In the same manner as in Synthesis Example 18 except for using 2.7 g of 2-bromo-9,9-dimethylfluorene in place of 2-bromobiphenyl, 3.0 g of a white crystal was obtained, which was identified as the following aromatic amine derivative H21 by FD-MS analysis (yield: 40%).

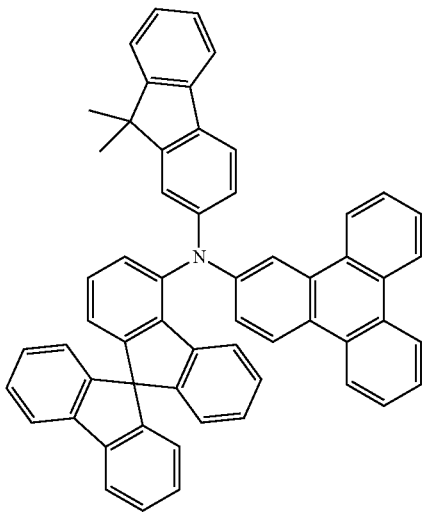

H21

Synthesis Example 22: Production of Aromatic Amine Derivative H22

In the same manner as in Synthesis Example 18 except for using 4.0 g of 2-bromo-9,9-diphenylfluorene in place of 2-bromobiphenyl, 3.8 g of a white crystal was obtained, which was identified as the following aromatic amine derivative H22 by FD-MS analysis (yield: 43%).

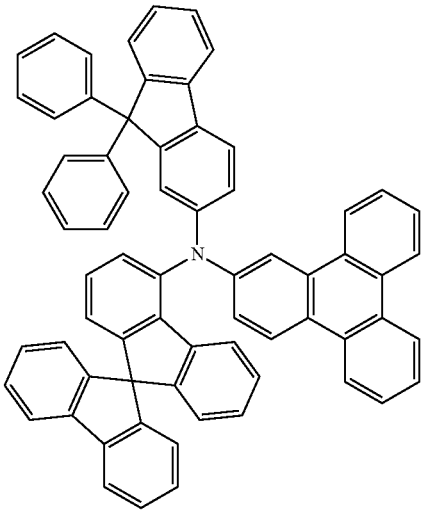

H22

Synthesis Example 23: Production of Aromatic Amine Derivative H23

In the same manner as in Synthesis Example 18 except for using 4.0 g of 2-bromo-9,9-spirobifluorene in place of 2-bromobiphenyl, 3.5 g of a white crystal was obtained, which was identified as the following aromatic amine derivative H23 by FD-MS analysis (yield: 40%).

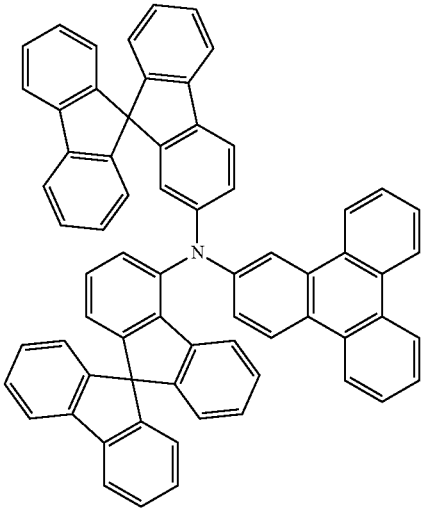

H23

Synthesis Example 24: Production of Aromatic Amine Derivative H24

In the same manner as in Synthesis Example 18 except for using 4.0 g of the intermediate 1-7 in place of 2-bromobiphenyl, 3.9 g of a white crystal was obtained, which was identified as the following aromatic amine derivative H24 by FD-MS analysis (yield: 45%).

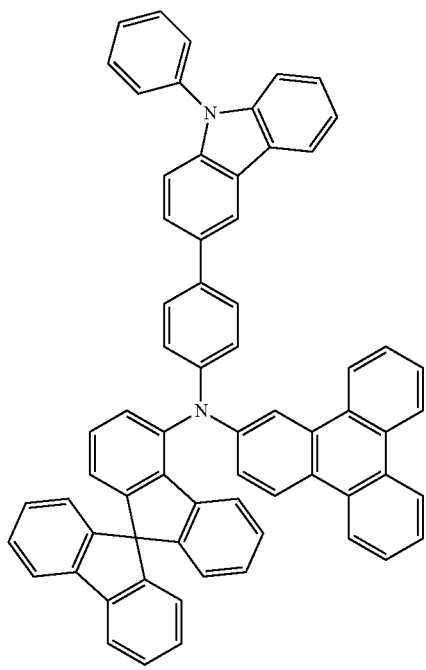

H24

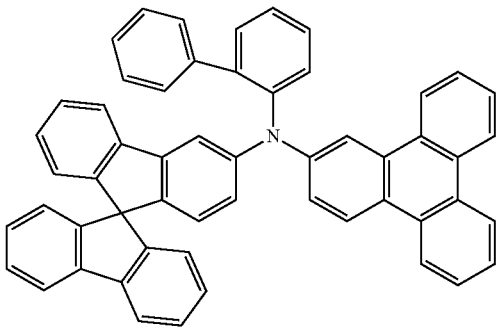

H25

Synthesis Example 25: Production of Aromatic Amine Derivative H25

Under argon atmosphere, to a mixture of 5.6 g of the intermediate 2-3 (10.0 mmol), 2.3 g of 2-bromobiphenyl (10.0 mmol), 0.14 g of $Pd_2(dba)_3$ (0.15 mmol), 0.087 g of $P(tBu)_3HBF_4$ (0.3 mmol), and 1.9 g of sodium t-butoxide (20.0 mmol), 50 ml of dehydrated xylene was added. The resultant mixture was refluxed for 8 h under heating.

After the reaction, the reaction liquid was cooled to 50° C. and filtered through Celite/silica gel. The filtrate was concentrated. The obtained concentrated residue was purified by a silica gel column chromatography to obtain a white solid. The obtained crude product was recrystallized from toluene to obtain 2.4 g of a white crystal, which was identified as the following aromatic amine derivative H25 by FD-MS analysis (yield: 34%).

Synthesis Example 26: Production of Aromatic Amine Derivative H26

In the same manner as in Synthesis Example 25 except for using 2.3 g of 4-bromobiphenyl in place of 2-bromobiphenyl, 3.5 g of a white crystal was obtained, which was identified as the following aromatic amine derivative H26 by FD-MS analysis (yield: 50%).

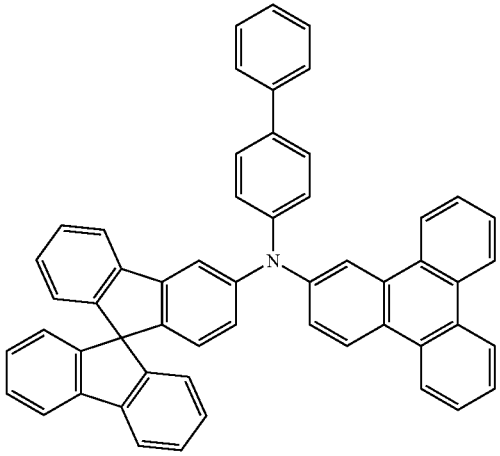

H26

Synthesis Example 27: Production of Aromatic Amine Derivative H27

In the same manner as in Synthesis Example 25 except for using 3.1 g of 4-bromo-1,1':4',1"-terphenyl in place of 2-bromobiphenyl, 3.5 g of a white crystal was obtained, which was identified as the following aromatic amine derivative H27 by FD-MS analysis (yield: 45%).

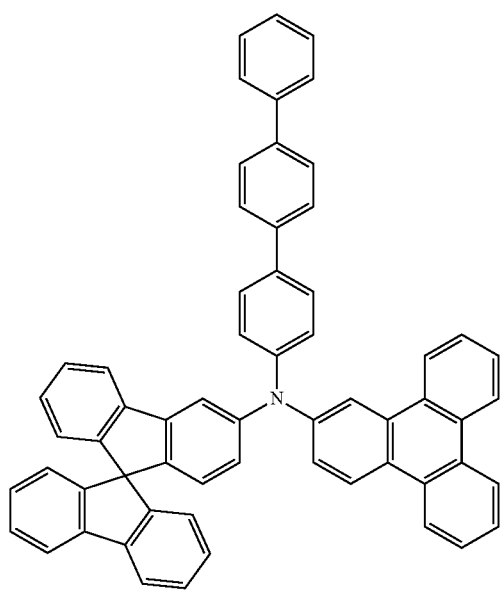

H27

Synthesis Example 28: Production of Aromatic Amine Derivative H28

In the same manner as in Synthesis Example 25 except for using 2.7 g of 2-bromo-9,9-dimethylfluorene in place of 2-bromobiphenyl, 3.4 g of a white crystal was obtained, which was identified as the following aromatic amine derivative H28 by FD-MS analysis (yield: 45%).

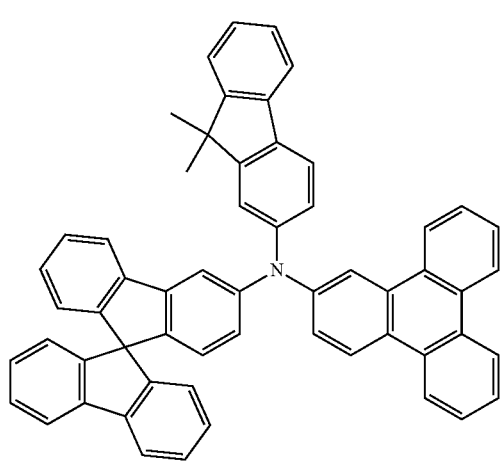

H28

Synthesis Example 29: Production of Aromatic Amine Derivative H29

In the same manner as in Synthesis Example 25 except for using 4.0 g of 2-bromo-9,9-diphenylfluorene in place of 2-bromobiphenyl, 4.1 g of a white crystal was obtained, which was identified as the following aromatic amine derivative H29 by FD-MS analysis (yield: 47%).

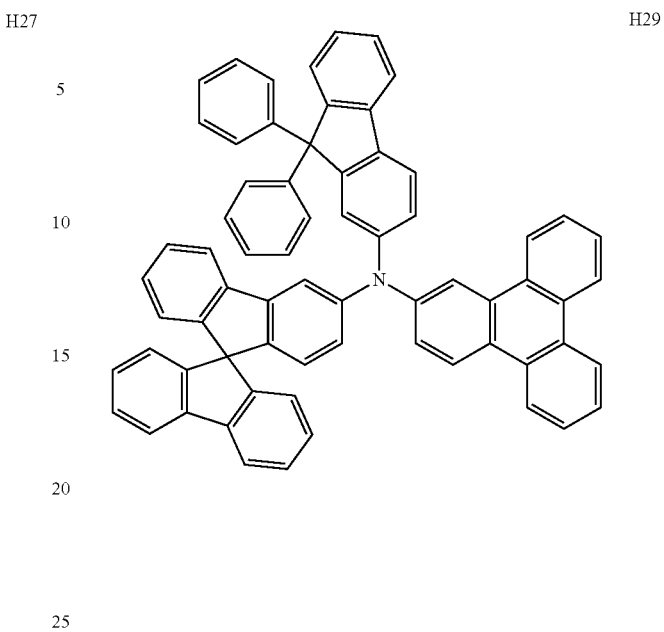

H29

Synthesis Example 30: Production of Aromatic Amine Derivative H30

In the same manner as in Synthesis Example 25 except for using 4.0 g of 2-bromo-9,9-spirobifluorene in place of 2-bromobiphenyl, 3.5 g of a white crystal was obtained, which was identified as the following aromatic amine derivative H30 by FD-MS analysis (yield: 40%).

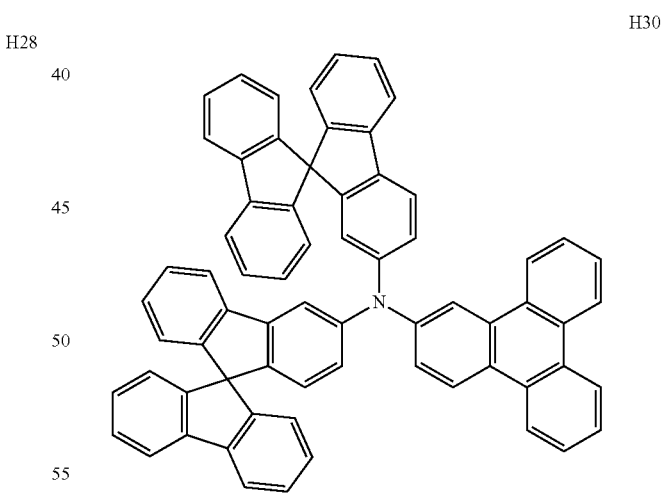

H30

Synthesis Example 31: Production of Aromatic Amine Derivative H31

In the same manner as in Synthesis Example 25 except for using 4.0 g of the intermediate 1-7 in place of 2-bromobiphenyl, 3.3 g of a white crystal was obtained, which was identified as the following aromatic amine derivative H31 by FD-MS analysis (yield: 38%).

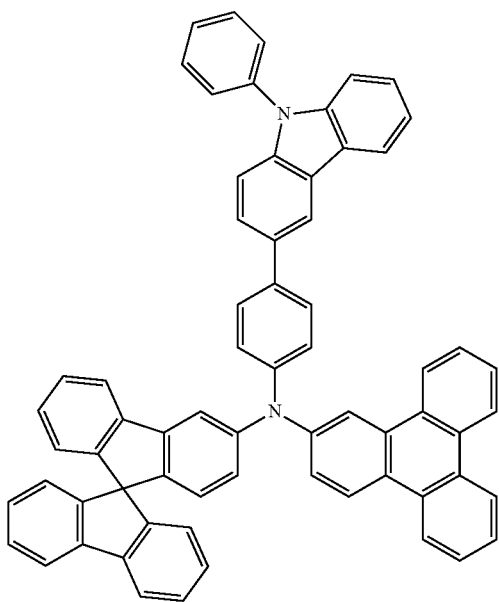

H31

Synthesis Example 32: Production of Aromatic Amine Derivative H32

Under argon atmosphere, to a mixture of 5.6 g of the intermediate 2-4 (10.0 mmol), 2.3 g of 2-bromobiphenyl (10.0 mmol), 0.14 g of Pd$_2$(dba)$_3$ (0.15 mmol), 0.087 g of P(tBu)$_3$HBF$_4$ (0.3 mmol), and 1.9 g of sodium t-butoxide (20.0 mmol), 50 ml of dehydrated xylene were added. The resultant mixture was refluxed for 8 h under heating.

After the reaction, the reaction liquid was cooled to 50° C. and filtered through Celite/silica gel. The filtrate was concentrated. The obtained concentrated residue was purified by a silica gel column chromatography to obtain a white solid. The obtained crude product was recrystallized from toluene to obtain 1.1 g of a white crystal, which was identified as the following aromatic amine derivative H32 by FD-MS analysis (yield: 15%).

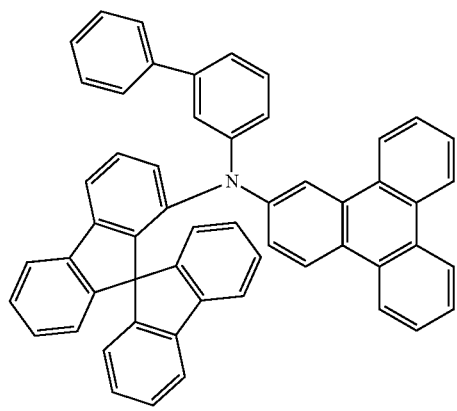

H32

Synthesis Example 33: Production of Aromatic Amine Derivative H33

In the same manner as in Synthesis Example 32 except for using 2.3 g of 4-bromobiphenyl in place of 2-bromobiphenyl, 1.4 g of a white crystal was obtained, which was identified as the following aromatic amine derivative H33 by FD-MS analysis (yield: 20%).

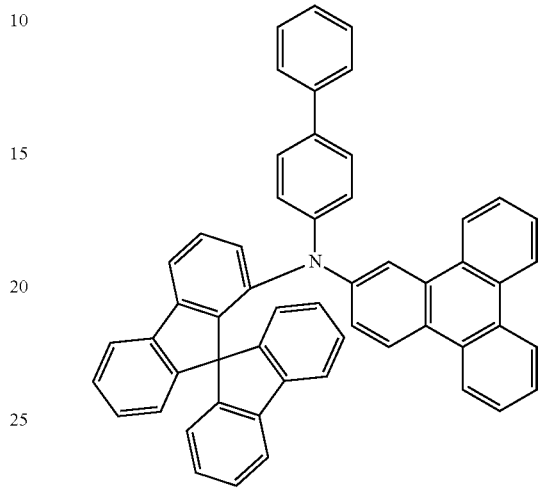

H33

Synthesis Example 34: Production of Aromatic Amine Derivative H34

Under argon atmosphere, to a mixture of 5.6 g of the intermediate 2-5 (10.0 mmol), 2.3 g of 4-bromobiphenyl (10.0 mmol), 0.14 g of Pd$_2$(dba)$_3$ (0.15 mmol), 0.087 g of P(tBu)$_3$HBF$_4$ (0.3 mmol), and 1.9 g of sodium t-butoxide (20.0 mmol), 50 ml of dehydrated xylene was added. The resultant mixture was refluxed for 8 h under heating.

After the reaction, the reaction liquid was cooled to 50° C. and filtered through Celite/silica gel. The filtrate was concentrated. The obtained concentrated residue was purified by a silica gel column chromatography to obtain a white solid. The obtained crude product was recrystallized from toluene to obtain 1.8 g of a white crystal, which was identified as the following aromatic amine derivative H34 by FD-MS analysis (yield: 25%).

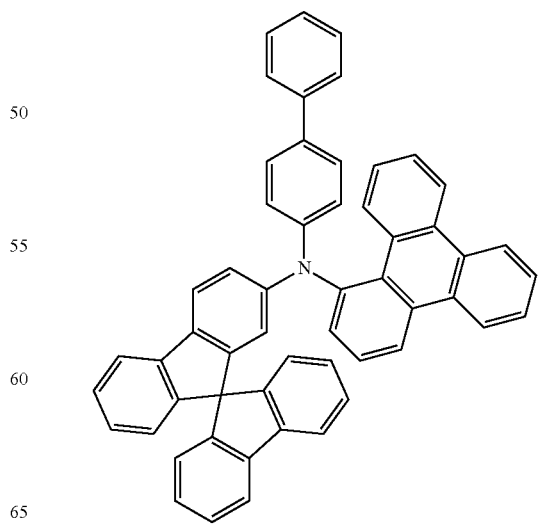

H34

Example 1-1: Production of Organic EL Device

A glass substrate of 25 mm×75 mm×1.1 mm having an ITO transparent electrode (product of Geomatec Company) was cleaned by ultrasonic cleaning in isopropyl alcohol for 5 min and then UV (ultraviolet)/ozone cleaning for 30 min.

The cleaned glass substrate having a transparent electrode line was mounted to a substrate holder of a vacuum vapor deposition apparatus. First, the following electron injecting compound A was vapor-deposited on the surface having the transparent electrode line so as to cover the transparent electrode to form a film A with a thickness of 5 nm.

On the film A, the following aromatic amine derivative H1 obtained in Synthesis Example 1 (first hole transporting material) was vapor-deposited to form a first hole transporting layer with a thickness of 80 nm. Successively after forming the first hole transporting layer, the following aromatic amide derivative Y1 (second hole transporting material) was vapor-deposited to form a second hole transporting layer with a thickness of 10 nm.

On the hole transporting layer, the following host compound BH and the following dopant compound BD were vapor co-deposited to form a light emitting layer with a thickness of 25 nm. The concentration of the dopant compound BD in the light emitting layer was 4% by mass.

Thereafter, on the light emitting layer, the following compound ET1 was vapor-deposited into a thickness of 10 nm, next the following compound ET2 was vapor-deposited into a thickness of 15 nm, and then the Li F was vapor-deposited into a thickness of 1 nm to form an electron transporting/injecting layer. Further, metallic Al was vorpor-deposited into a thickness of 80 nm to form a cathode, thereby producing an organic EL device.

A

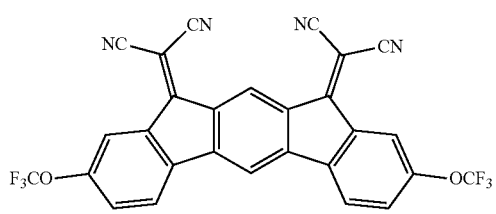

Y1

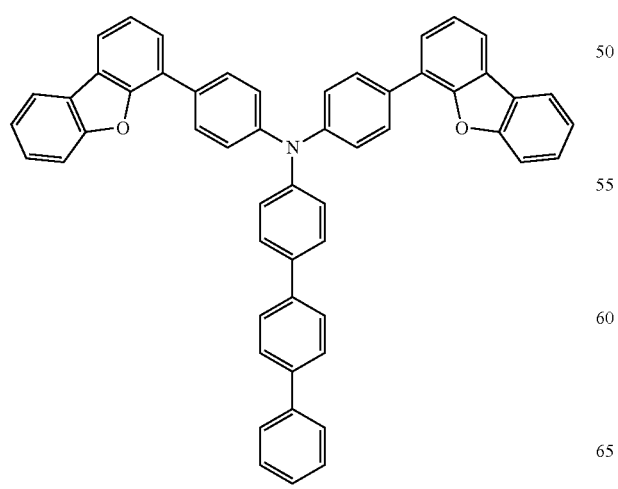

H1

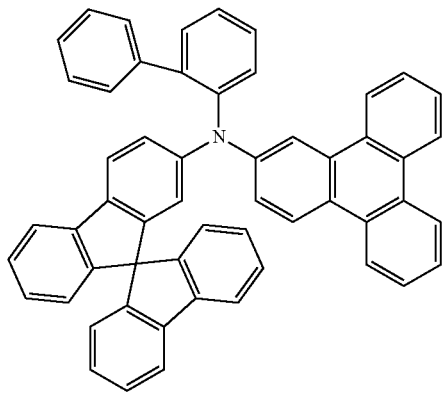

BH

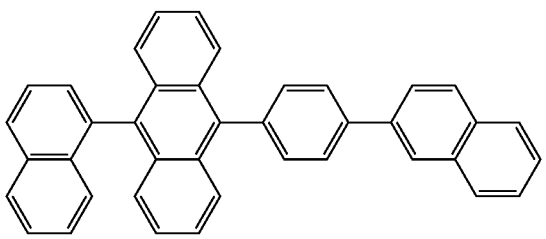

BD

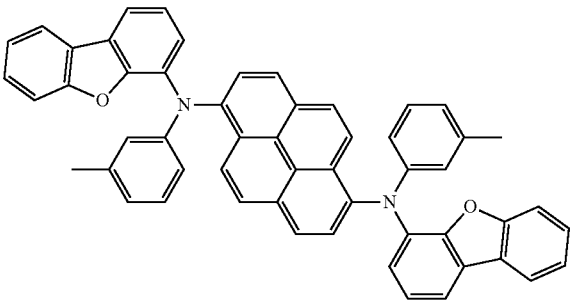

ET1

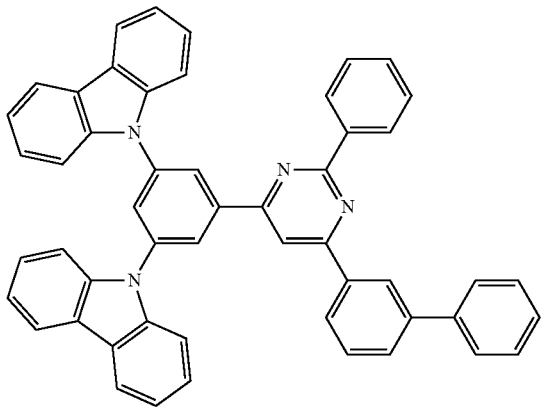

ET2

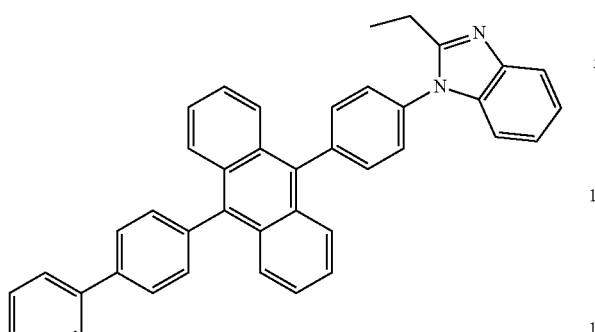

Examples 1-2 to 1-34

In the same manner as in Example 1-1 except for using each of the aromatic amine derivatives H2 to H34 obtained in Synthesis Examples 2 to 34 as a first hole transporting material, each organic EL device of Examples 1-2 to 1-34 was produced.

Comparative Examples 1-1 and 1-2

In the same manner as in Example 1-1 except for using each of the following comparative compound 1 (compound described in Patent Literature 1) and the comparative compound 2 (compound described in Patent Literature 3), each organic EL device was produced.

Comparative Compound 1

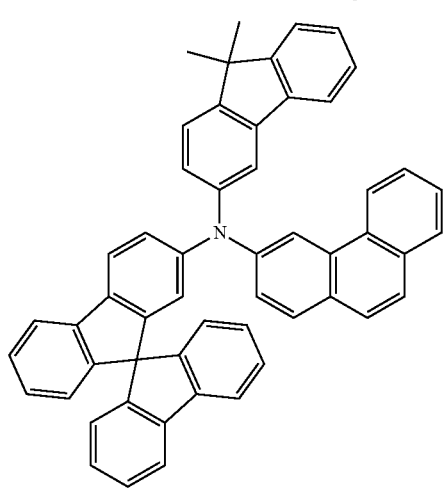

Comparative Compound 2

Evaluation of Emission Performance of Organic EL Device

Each organic EL device thus produced was allowed to emit light by driving at a constant current to measure the luminance (L) and the current density. From the measured results, the emission efficiency (EQE) and the driving voltage (V) at a current density of 10 mA/cm$^2$ were determined. In addition, the 90% lifetime was measured at a current density of 50 mA/cm$^2$. The 90% lifetime is the time taken until the luminance is reduced to 90% of the initial luminance when driving at a constant current. The results are shown in Table 1.

TABLE 1

| | | | Measured Results | | |
|---|---|---|---|---|---|
| | First hole transporting material | Second hole transporting material | emission efficiency (EQE, %) @10 mA/cm$^2$ | driving voltage (V) @10 mA/cm$^2$ | 90% lifetime (h) |
| Examples | | | | | |
| 1-1 | H1 | Y1 | 9.6 | 3.7 | 240 |
| 1-2 | H2 | Y1 | 9.3 | 3.8 | 240 |
| 1-3 | H3 | Y1 | 9.8 | 3.7 | 270 |
| 1-4 | H4 | Y1 | 9.6 | 3.7 | 270 |
| 1-5 | H5 | Y1 | 10.3 | 3.7 | 240 |
| 1-6 | H6 | Y1 | 10.0 | 3.8 | 300 |
| 1-7 | H7 | Y1 | 10.0 | 3.7 | 320 |
| 1-8 | H8 | Y1 | 9.8 | 3.7 | 230 |
| 1-9 | H9 | Y1 | 9.9 | 3.7 | 380 |
| 1-10 | H10 | Y1 | 9.8 | 3.7 | 230 |
| 1-11 | H11 | Y1 | 9.9 | 3.7 | 380 |
| 1-12 | H12 | Y1 | 9.4 | 3.9 | 230 |
| 1-13 | H13 | Y1 | 9.5 | 3.8 | 380 |
| 1-14 | H14 | Y1 | 10.0 | 4.0 | 380 |
| 1-15 | H15 | Y1 | 9.3 | 3.7 | 350 |
| 1-16 | H16 | Y1 | 9.8 | 3.8 | 350 |
| 1-17 | H17 | Y1 | 9.0 | 3.6 | 270 |
| 1-18 | H18 | Y1 | 8.7 | 4.0 | 280 |
| 1-19 | H19 | Y1 | 9.1 | 3.9 | 350 |
| 1-20 | H20 | Y1 | 9.4 | 3.8 | 360 |
| 1-21 | H21 | Y1 | 9.8 | 3.7 | 280 |
| 1-22 | H22 | Y1 | 9.6 | 3.9 | 340 |
| 1-23 | H23 | Y1 | 9.7 | 3.9 | 340 |
| 1-24 | H24 | Y1 | 9.5 | 3.9 | 350 |
| 1-25 | H25 | Y1 | 9.6 | 3.7 | 360 |
| 1-26 | H26 | Y1 | 9.9 | 3.7 | 310 |
| 1-27 | H27 | Y1 | 10.2 | 3.7 | 340 |
| 1-28 | H28 | Y1 | 9.7 | 3.6 | 300 |
| 1-29 | H29 | Y1 | 10.0 | 3.7 | 350 |
| 1-30 | H30 | Y1 | 10.0 | 3.7 | 340 |

TABLE 1-continued

|  | First hole transporting material | Second hole transporting material | emission efficiency (EQE, %) @10 mA/cm² | driving voltage (V) @10 mA/cm² | 90% lifetime (h) |
|---|---|---|---|---|---|
| 1-31 | H31 | Y1 | 9.5 | 3.7 | 350 |
| 1-32 | H32 | Y1 | 9.2 | 4.0 | 300 |
| 1-33 | H33 | Y1 | 9.4 | 4.0 | 340 |
| 1-34 | H34 | Y1 | 9.8 | 3.8 | 270 |
| Comparative Examples | | | | | |
| 1-1 | Comparative compound 1 | Y1 | 9.0 | 4.3 | 180 |
| 1-2 | Comparative compound 2 | Y1 | 8.2 | 3.8 | 200 |

As seen from Table 1, it can be found that the compounds H1 to H34 which fall within formula (1) of the invention provide organic EL devices, each of which can be operated at a low driving voltage and has a long lifetime while keeping the emission efficiency at high level.

Example 2-1: Production of Organic EL Device

A glass substrate of 25 mm×75 mm×1.1 mm having an ITO transparent electrode (product of Geomatec Company) was cleaned by ultrasonic cleaning in isopropyl alcohol for 5 min and then UV (ultraviolet)/ozone cleaning for 30 min.

The cleaned glass substrate having a transparent electrode line was mounted to a substrate holder of a vacuum vapor deposition apparatus. First, the following electron injecting compound A was vapor-deposited on the surface having the transparent electrode line so as to cover the transparent electrode to form a film A with a thickness of 5 nm.

On the film A, the following aromatic amine derivative X1 (first hole transporting material) was vapor-deposited to form a first hole transporting layer with a thickness of 80 nm. Successively after forming the first hole transporting layer, the following aromatic amide derivative H1 obtained in Synthesis Example 1 (second hole transporting material) was vapor-deposited to form a second hole transporting layer with a thickness of 10 nm.

On the hole transporting layer, the following host compound BH and the following dopant compound BD were vapor co-deposited to form a light emitting layer with a thickness of 25 nm. The concentration of the dopant compound BD in the light emitting layer was 4% by mass.

Thereafter, on the light emitting layer, the following compound ET1 was vapor-deposited into a thickness of 10 nm, next the following compound ET2 was vapor-deposited into a thickness of 15 nm, and then the Li F was vapor-deposited into a thickness of 1 nm to form an electron transporting/injecting layer. Further, metallic Al was vapor-deposited into a thickness of 80 nm to form a cathode, thereby producing an organic EL device.

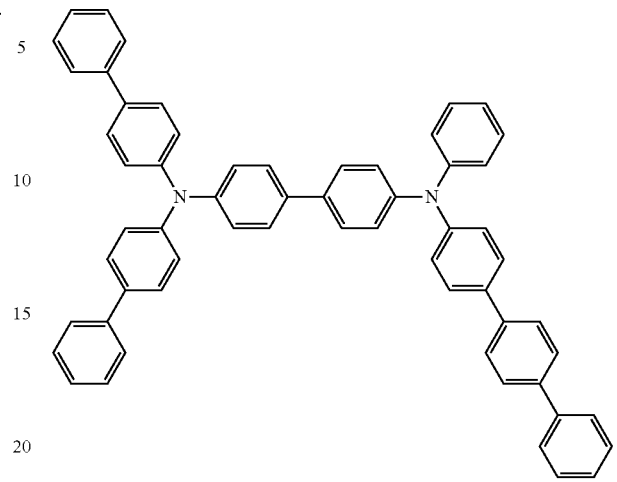

X1

Examples 2-2 to 2-10

In the same manner as in Example 2-1 except for using each aromatic amine derivative shown in Table 2 as the second hole transporting material, each organic EL device was produced.

Comparative Examples 2-1 and 2-2

In the same manner as in Example 2-1 except for using each of the comparative compounds 1 and 2 mentioned above as the second hole transporting material, each organic EL device was produced.

Evaluation of Emission Performance of Organic EL Device

In the same manner as mentioned above, each organic EL device thus produced was measured for the emission efficiency (EQE) and the driving voltage (V) each at a current density of 10 mA/cm², and the 90% lifetime at a current density of 50 mA/cm². The results are shown in Table 2.

TABLE 2

|  | First hole transporting material | Second hole transporting material | emission efficiency (EQE, %) @10 mA/cm² | driving voltage (V) @10 mA/cm² | 90% lifetime (h) |
|---|---|---|---|---|---|
| Examples | | | | | |
| 2-1 | X1 | H1 | 10.0 | 3.7 | 100 |
| 2-2 | X1 | H2 | 9.0 | 3.7 | 125 |
| 2-3 | X1 | H4 | 9.2 | 3.6 | 140 |
| 2-4 | X1 | H9 | 9.7 | 3.6 | 95 |
| 2-5 | X1 | H10 | 9.5 | 3.6 | 80 |
| 2-6 | X1 | H13 | 10.0 | 3.7 | 118 |
| 2-7 | X1 | H14 | 10.6 | 3.9 | 106 |
| 2-8 | X1 | H15 | 10.6 | 4.0 | 100 |
| 2-9 | X1 | H19 | 9.9 | 3.9 | 45 |
| 2-10 | X1 | H20 | 10.1 | 3.8 | 77 |

TABLE 2-continued

| | First hole transporting material | Second hole transporting material | Measured Results | | |
|---|---|---|---|---|---|
| | | | emission efficiency (EQE, %) @10 mA/cm² | driving voltage (V) @10 mA/cm² | 90% lifetime (h) |
| Comparative Examples | | | | | |
| 2-1 | X1 | Comparative compound 1 | 9.5 | 3.9 | 30 |
| 2-2 | X1 | Comparative compound 2 | 9.0 | 3.7 | 65 |

As seen from Table 2, in can be found that the aromatic amine derivatives which fall within formula (1) provide organic EL devices, each of which can be operated at a low driving voltage and has a long lifetime while keeping the emission efficiency at high level.

REFERENCE SIGNS LIST

1: Organic EL device
2: Substrate
3: Anode
4: Cathode
5: Light emitting layer
6: Anode-side organic thin film layer
7: Cathode-side organic thin film layer
10: Emission unit

The invention claimed is:

1. A compound represented by formula (1):

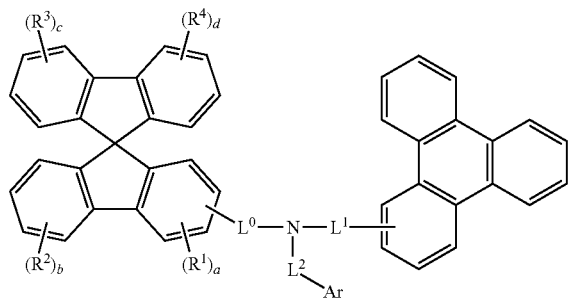

(1)

wherein:
each of $R^1$ to $R^4$ is independently a substituted or unsubstituted alkyl group having 1 to 20 carbon atoms, a substituted or unsubstituted aryl group having 6 to 10 ring carbon atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 10 ring carbon atoms, or a cyano group;
a is an integer of 0 to 3 and each of b, c, and d is independently an integer of 0 to 4, wherein each of $(R^1)_0$, $(R^2)_0$, $(R^3)_0$, and $(R^4)_0$ means that $R^1$, $R^2$, $R^3$, or $R^4$ does not exist, and when a, b, c, or d is an integer of 2 or more, two or three $R^1$'s, two to four $R^2$'s, two to four $R^3$'s, and two to four $R^4$'s may be respectively the same or different, and adjacent two $R^1$'s, adjacent two $R^2$'s, adjacent two $R^3$'s, and adjacent two $R^4$'s may be bonded to each other to form a ring structure, respectively;
each of $L^0$ to $L^2$ is independently a single bond, a substituted or unsubstituted arylene group having 6 to 50 ring carbon atoms, or a substituted or unsubstituted heteroarylene group having 5 to 50 ring atoms;
Ar is a substituted or unsubstituted aryl group having 6 to 50 ring carbon atoms or a substituted or unsubstituted heteroaryl group having 5 to 50 ring atoms; and
an optional substituent referred to by "substituted or unsubstituted" is at least one group selected from the group consisting of an alkyl group having 1 to 20 carbon atoms; a cycloalkyl group having 3 to 50 ring carbon atoms; an aryl group having 6 to 10 ring carbon atoms; an aralkyl group having 7 to 30 carbon atoms which comprises an aryl group having 6 to 10 ring carbon atoms; an alkoxy group having 1 to 20 carbon atoms; an aryloxy group having 6 to 10 ring carbon atoms; a mono-, di-, or tri-substituted silyl group, wherein the substituent is selected from an alkyl group having 1 to 20 carbon atoms and an aryl group having 6 to 10 ring carbon atoms; a haloalkyl group having 1 to 20 carbon atoms; a haloalkoxy group having 1 to 20 carbon atoms; a halogen atom; a cyano group; and a nitro group.

2. The compound according to claim 1, wherein the compound is represented by formula (1-1),

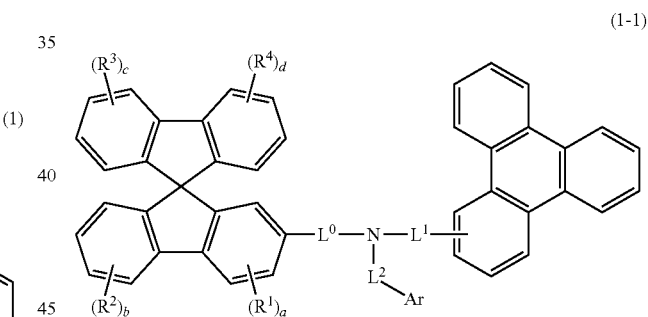

(1-1)

wherein $R^1$ to $R^4$, a to d, $L^0$ to $L^2$, and Ar are as defined in formula (1).

3. The compound according to claim 1, wherein the compound is represented by formula (1-2):

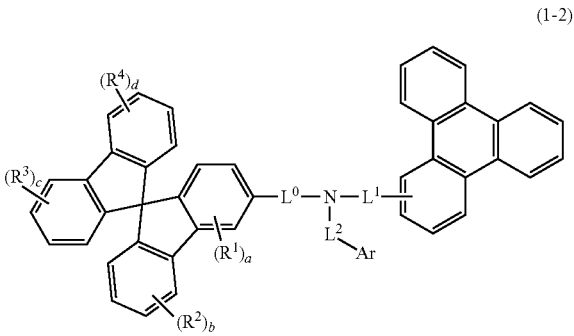

(1-2)

wherein $R^1$ to $R^4$, a to d, $L^0$ to $L^2$, and Ar are as defined in formula (1).

4. The compound according to claim 1, wherein the compound is represented by formula (1-3):

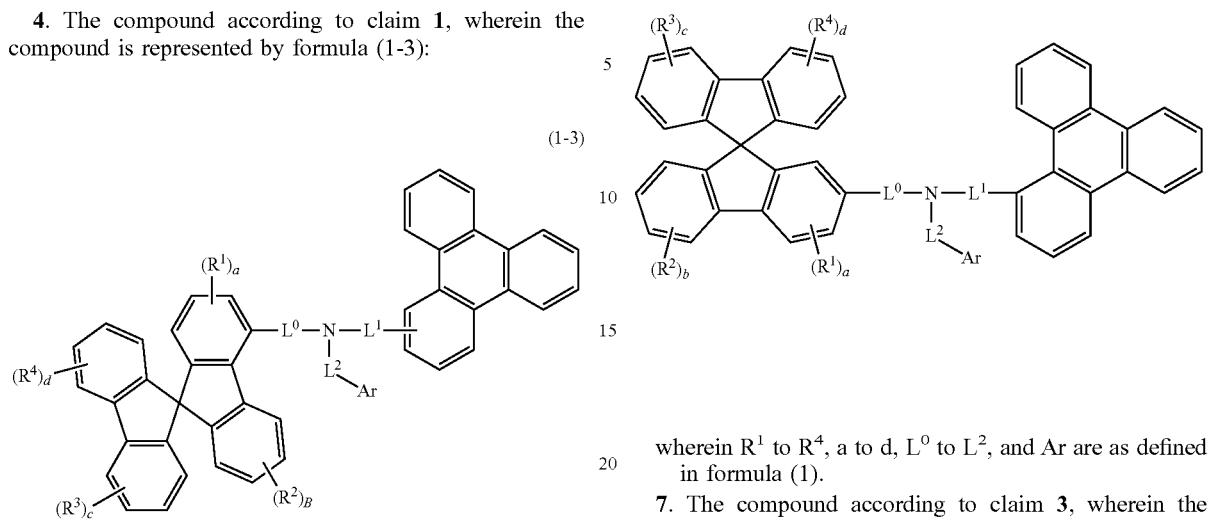

(1-3)

wherein $R^1$ to $R^4$, a to d, $L^0$ to $L^2$, and Ar are as defined in formula (1).

5. The compound according to claim 1, wherein the compound is represented by formula (1-4):

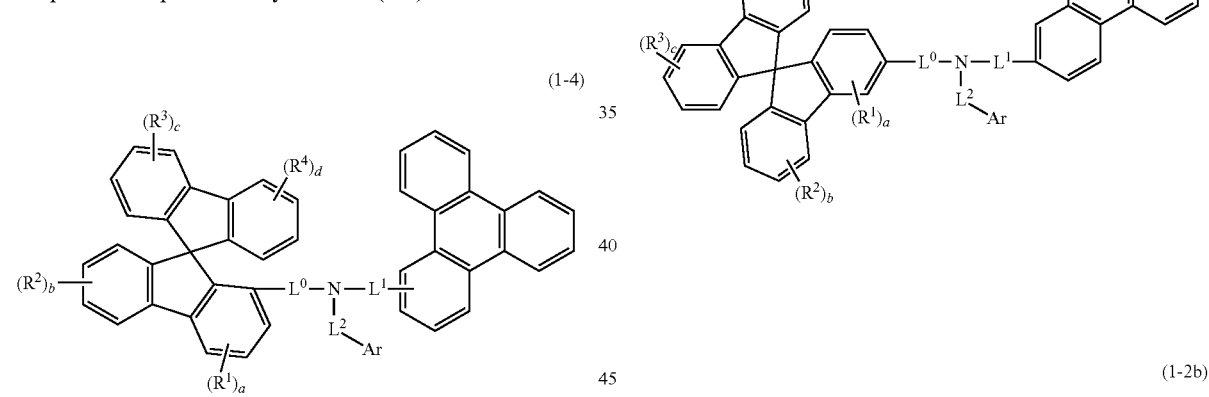

(1-4)

wherein $R^1$ to $R^4$, a to d, $L^0$ to $L^2$, and Ar are as defined in formula (1).

6. The compound according to claim 2, wherein the compound is represented by formula (1-1a) or (1-1b):

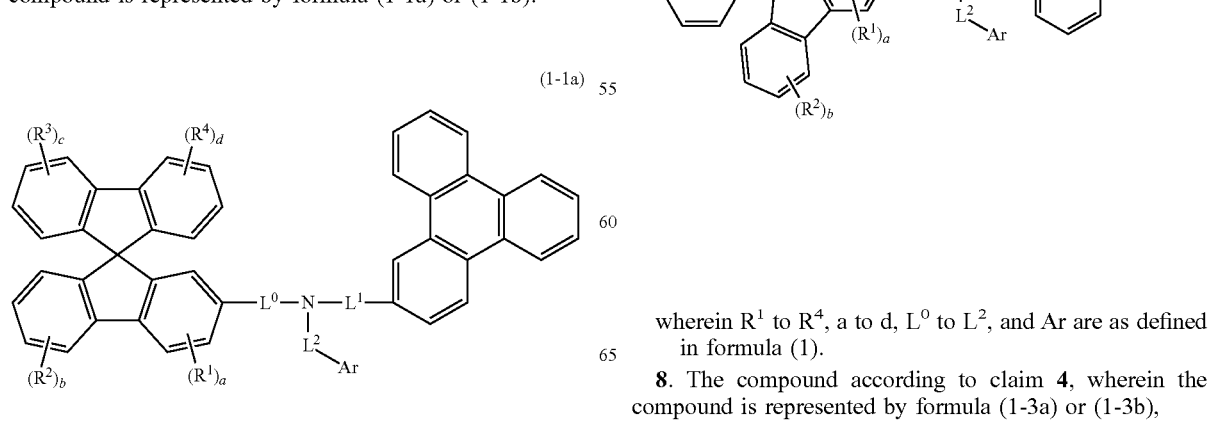

(1-1a)

(1-1b)

wherein $R^1$ to $R^4$, a to d, $L^0$ to $L^2$, and Ar are as defined in formula (1).

7. The compound according to claim 3, wherein the compound is represented by formula (1-2a) or (1-2b):

(1-2a)

(1-2b)

wherein $R^1$ to $R^4$, a to d, $L^0$ to $L^2$, and Ar are as defined in formula (1).

8. The compound according to claim 4, wherein the compound is represented by formula (1-3a) or (1-3b), (1-3a)

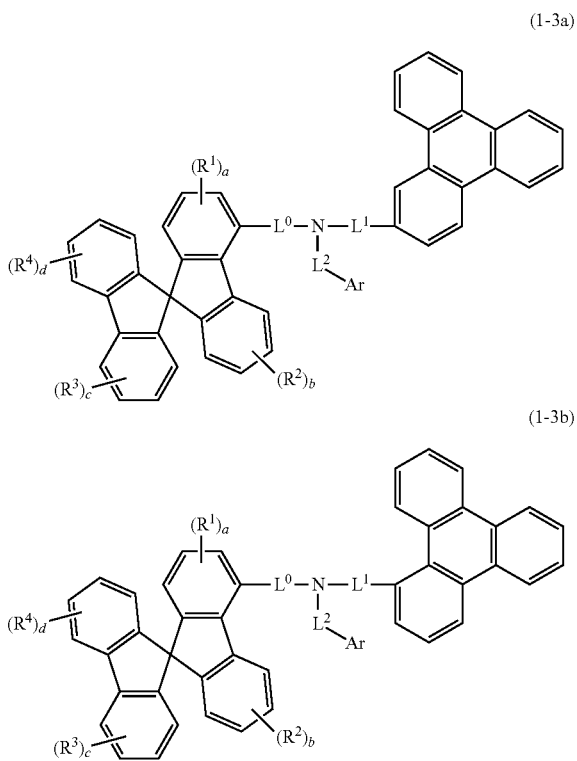

(1-3b)

wherein R¹ to R⁴, a to d, L⁰ to L², and Ar are as defined in formula (1).

9. The compound according to claim 5, wherein the compound is represented by formula (1-4a) or (1-4b):

(1-4a)

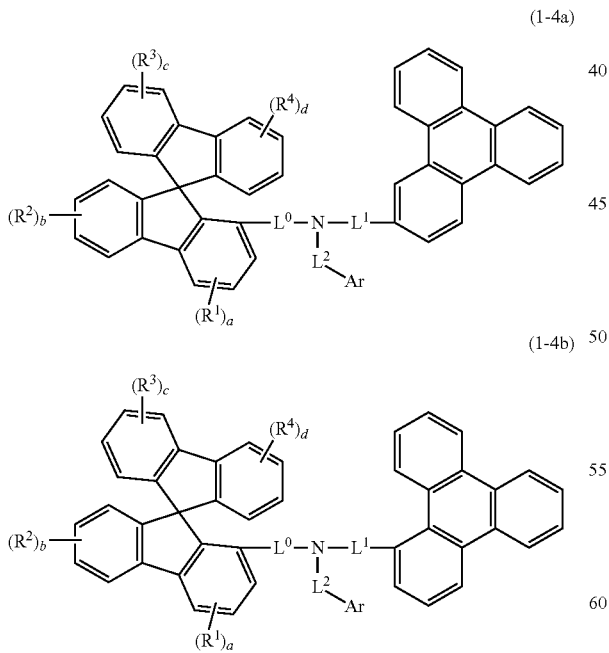

(1-4b)

wherein R¹ to R⁴, a to d, L⁰ to L², and Ar are as defined in formula (1).

10. The compound according to claim 1, wherein the aryl group in the substituted or unsubstituted aryl group having 6 to 50 ring carbon atoms for Ar is selected from the group consisting of a phenyl group, a biphenylyl group, a terphenylyl group, a biphenylenyl group, a naphthyl group, an acenaphthylenyl group, an anthryl group, a benzanthryl group, an aceanthryl group, a benzophenanthryl group, a triphenylenyl group, a phenalenyl group, a fluorenyl group, a pentacenyl group, a picenyl group, a pentaphenyl group, a pyrenyl group, a chrysenyl group, a benzochrysenyl group, a s-indanyl group, an as-indanyl group, a fluoranthenyl group, and a perylenyl group.

11. The compound according to claim 1, wherein the heteroaryl group in the substituted or unsubstituted heteroaryl group having 5 to 50 ring atoms for Ar is selected from the group consisting of a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a naphthobenzofuranyl group, a dibenzothiophenyl group, a naphthobenzothiophenyl group, a N-carbazolyl group, a benzo-N-carbazolyl group, a C-carbazolyl group, a benzo-C-carbazolyl group, a phenanthridinyl group, an acridinyl group, a phenanthrolinyl group, a phenazinyl group, a phenothiazinyl group, a phenoxazinyl group, and a xanthenyl group.

12. The compound according to claim 1, wherein Ar is represented by any of formulae (a) to (n):

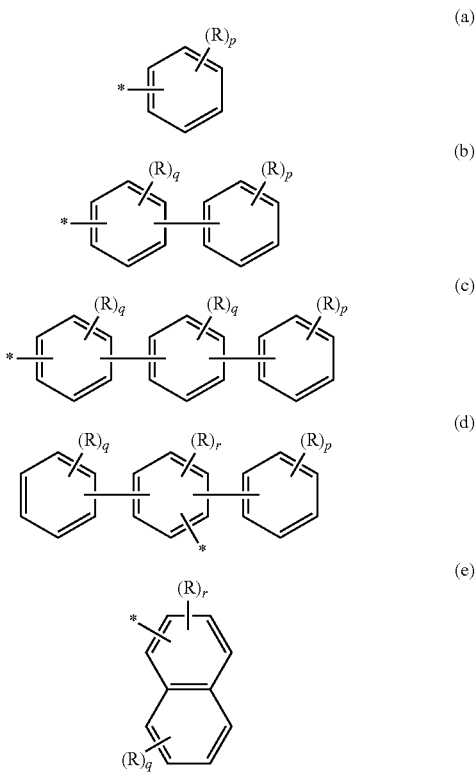

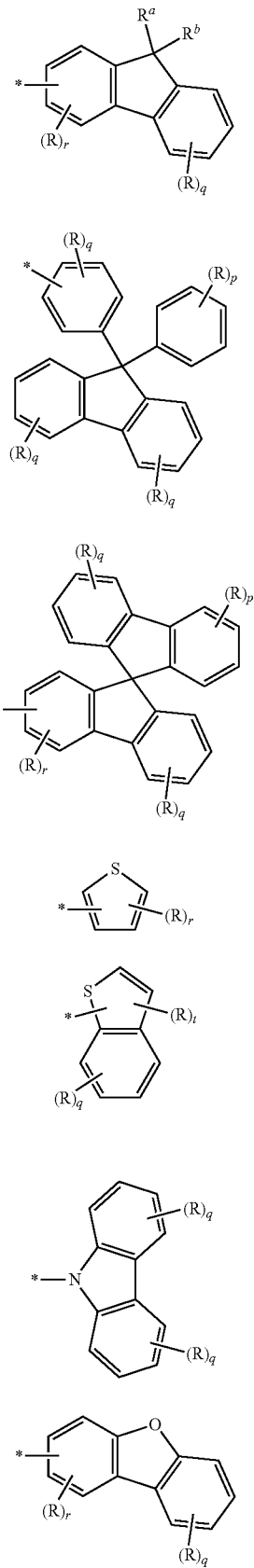

in formulae (a) to (n):
each R is independently a substituted or unsubstituted alkyl group having 1 to 20 carbon atoms, a substituted or unsubstituted cycloalkyl group having 3 to 50 ring carbon atoms, a substituted or unsubstituted aryl group having 6 to 10 ring carbon atoms, a substituted or unsubstituted aralkyl group having 7 to 30 carbon atoms which comprises a substituted or unsubstituted aryl group having 6 to 10 ring carbon atoms, a substituted or unsubstituted alkoxy group having 1 to 20 carbon atoms, a substituted or unsubstituted aryloxy group having 6 to 10 ring carbon atoms, a mono-, di-, or tri-substituted silyl group, wherein the substituent is selected from a substituted or unsubstituted alkyl group having 1 to 20 carbon atoms and a substituted or unsubstituted aryl group having 6 to 10 ring carbon atoms, a substituted or unsubstituted haloalkyl group having 1 to 20 carbon atoms, a substituted or unsubstituted haloalkoxy group having 1 to 20 carbon atoms, a halogen atom, a cyano group, and a nitro group;

in each of formulae (a) to (n), adjacent two Rs may be bonded to each other to from a benzene ring together with two ring carbon atoms to which the two Rs are bonded;

each p is independently an integer of 0 to 5, each q is independently an integer of 0 to 4, each r is independently an integer of 0 to 3, s is 0 or 1, wherein $(R)_0$ means that R does not exist and when p, q, or r is an integer of 2 or more, two to five Rs, two to four Rs, and two to three Rs may be the same or different, and adjacent two Rs may be bonded to each other to form a ring structure;

in formula (f), each of $R^a$ and $R^b$ is independently a substituted or unsubstituted alkyl group having 1 to 20 carbon atoms, a substituted or unsubstituted aryl group having 6 to 10 ring carbon atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 10 ring carbon atoms, or a cyano group, wherein two selected from R, $R^a$, and $R^b$ may be bonded to each other to form a ring structure;

in formula (n), $R^c$ is a hydrogen atom, a substituted or unsubstituted alkyl group having 1 to 20 carbon atoms, or a substituted or unsubstituted aryl group having 6 to 10 ring carbon atoms; and

* is a bond to $L^2$ of formula (1).

13. The compound according to claim 1, wherein the arylene group in the substituted or unsubstituted arylene group having 6 to 50 ring carbon atoms for $L^0$ to $L^2$ is selected from the group consisting of divalent groups obtained by removing one hydrogen atom from an aryl group selected from a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a triphenylenyl group, a benzophenanthryl group, a phenalenyl group, a fluorenyl group, a pentacenyl group, a picenyl group, a pentaphenyl group, a pyrenyl group, a chrysenyl group, a benzochrysenyl group, a s-indanyl group, an as-indanyl group, a fluoranthenyl group, and a perylenyl group.

14. The compound according to claim 1, wherein the heteroarylene group in the substituted or unsubstituted heteroarylene group having 5 to 50 ring atoms for $L^0$ to $L^2$ is selected from the group consisting of divalent groups obtained by removing one hydrogen atom from a heteroaryl group selected from a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a N-carbazolyl group, a C-carbazolyl group, a phenanthridinyl group, an acridinyl group, a phenanthrolinyl group, a phenazinyl group, a phenothiazinyl group, a phenoxazinyl group, and a xanthenyl group.

15. The compound according to claim 1, wherein each of $L^0$ to $L^2$ is independently a single bond or an arylene group represented by formula (ii) or (iii):

(ii)

(iii)

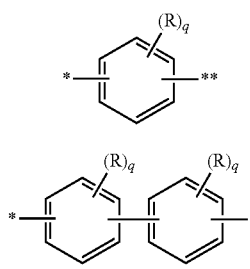

wherein:
R and q are as defined above with respect to formulae (a) to (n);
when $L^0$ is represented by formula (ii) or (iii), one of * and ** is a bond to the spirobifluorene structure, and the other is a bond to the nitrogen atom;
when $L^1$ is represented by formula (ii) or (iii), one of * and ** is a bond to the triphenylene, and the other is a bond to the nitrogen atom; and
when $L^2$ is represented by formula (ii) or (iii), one of * and ** is a bond to Ar, and the other is a bond to the nitrogen atom.

16. The compound according to claim 1, wherein each of $L^0$ to $L^2$ is a single bond and Ar is represented by any of formulae (a) to (h):

(a)
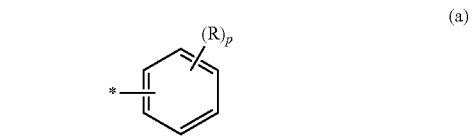

(b)
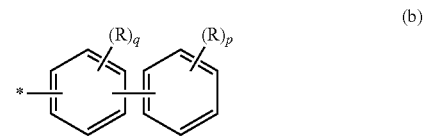

(c)
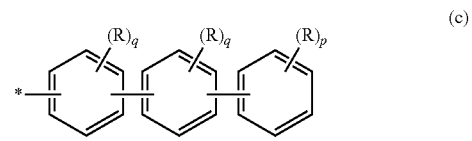

(d)
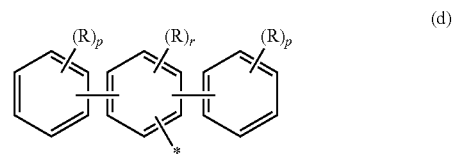

(e)
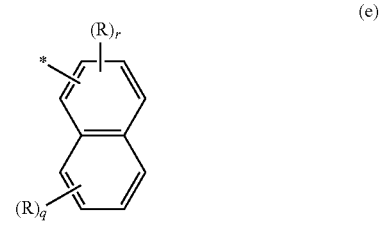

(f)
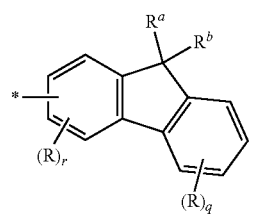

(g)
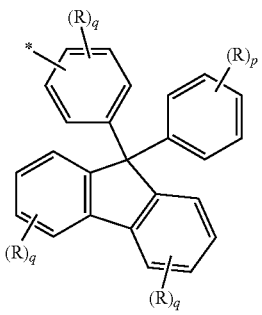

-continued

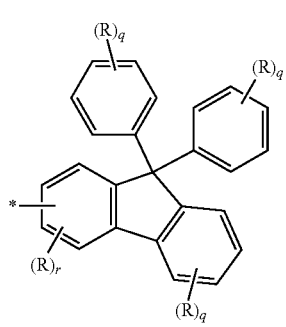
(h)

wherein R, $R^a$, $R^b$, p, q, r and * are as defined above.

17. The compound according to claim 1, wherein Ar is represented by any of formulae (b-1), (b-2), (c-1), (c-2), and (d-1):

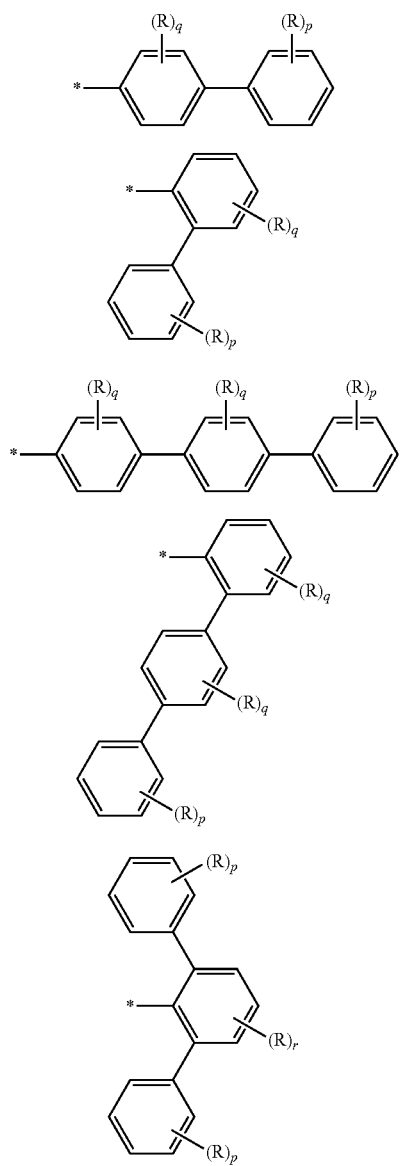

wherein R, p, q, r and * are as defined above.

18. The compound according to claim 1, wherein each of $L^0$ and $L^1$ is a single bond, $L^2$ is a substituted or unsubstituted arylene group having 6 to 50 ring carbon atoms or a substituted or unsubstituted heteroarylene group having 5 to 50 ring atoms, and Ar is represented by any of formulae (i) to (n):

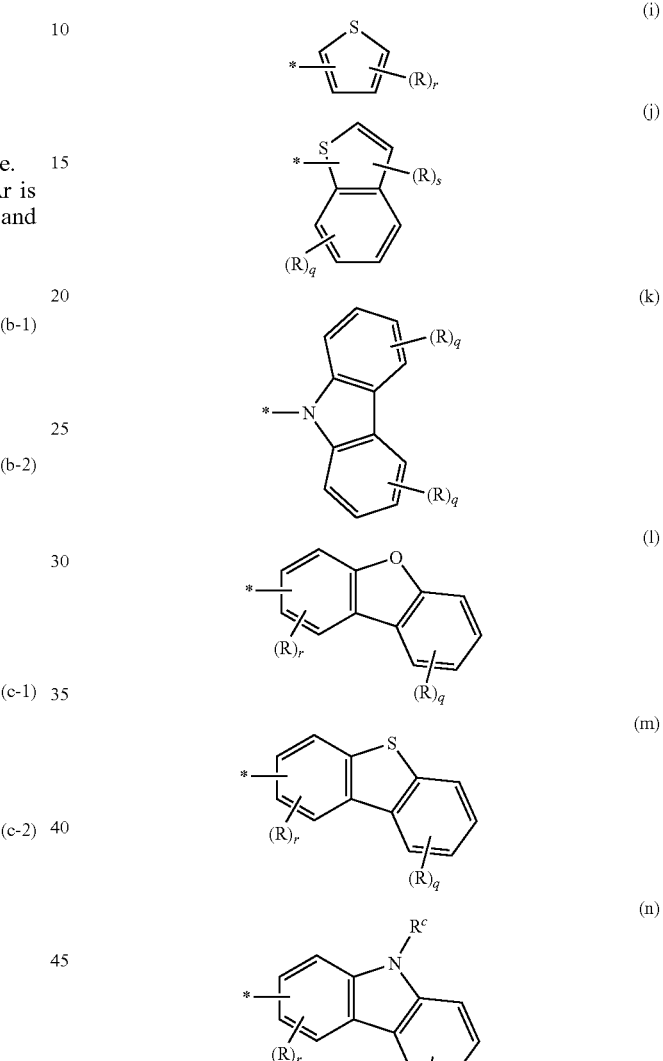

wherein R, $R^c$, a, r, s and * are as defined above.

19. A material for organic electroluminescence devices comprising the compound according to claim 1.

20. An organic electroluminescence device which comprises a cathode, an anode, and an organic thin film layer disposed between the cathode and the anode, wherein the organic thin film layer comprises one or more layers, the organic thin film layer comprises a light emitting layer, and at least one layer of the organic thin film layer comprises the compound according to claim 1.

21. The organic electroluminescence device according to claim 20, wherein the organic electroluminescence device comprises an anode-side organic thin film layer which comprises at least one layer, and at least one layer of the anode-side organic thin film layer comprises the compound.

22. The organic electroluminescence device according to claim 21, wherein the anode-side organic thin film layer comprises a hole injecting layer at a side of the anode and a hole transporting layer at a side of the light emitting layer, and at least one selected from the hole injecting layer and the hole transporting layer comprises the compound.

23. An electronic device comprising the organic electroluminescence device according to claim 20.

* * * * *